US011352662B2

(12) United States Patent
Jensen et al.

(10) Patent No.: US 11,352,662 B2
(45) Date of Patent: Jun. 7, 2022

(54) SEQUENCE ADAPTER MANUFACTURE AND USE

(71) Applicant: Sequenom, Inc., San Diego, CA (US)

(72) Inventors: Taylor Jensen, San Diego, CA (US); Christopher Ellison, San Diego, CA (US)

(*) Notice: Subject to any disclaimer, the term of this patent is extended or adjusted under 35 U.S.C. 154(b) by 0 days.

(21) Appl. No.: 16/479,473

(22) PCT Filed: Jan. 22, 2018

(86) PCT No.: PCT/US2018/014710
§ 371 (c)(1),
(2) Date: Jul. 19, 2019

(87) PCT Pub. No.: WO2018/136881
PCT Pub. Date: Jul. 26, 2018

(65) Prior Publication Data
US 2019/0390265 A1 Dec. 26, 2019

Related U.S. Application Data

(60) Provisional application No. 62/448,601, filed on Jan. 20, 2017.

(51) Int. Cl.
*C12Q 1/6855* (2018.01)
*C12N 15/10* (2006.01)
*C12Q 1/6869* (2018.01)
*G16B 30/00* (2019.01)

(52) U.S. Cl.
CPC ....... *C12Q 1/6855* (2013.01); *C12N 15/1068* (2013.01); *C12Q 1/6869* (2013.01); *G16B 30/00* (2019.02)

(58) Field of Classification Search
CPC .................................................. C12Q 1/6855
See application file for complete search history.

(56) References Cited

U.S. PATENT DOCUMENTS

| | | | | |
|---|---|---|---|---|
| 6,287,825 B1 * | 9/2001 | Weissman | .......... | C12N 15/1096 |
| | | | | 435/6.13 |
| 2015/0044687 A1 * | 2/2015 | Schmitt et al. | ...... | C12Q 1/6876 |
| | | | | 435/6.12 |

FOREIGN PATENT DOCUMENTS

| | | | | |
|---|---|---|---|---|
| WO | 2013142389 | | 9/2013 | |
| WO | WO-2013142389 A1 * | 9/2013 | ........... | C12Q 1/6876 |
| WO | 2014151117 | | 9/2014 | |
| WO | WO-2014151117 A1 * | 9/2014 | ........... | C12Q 1/6806 |
| WO | 2016201142 | | 12/2016 | |
| WO | WO-2016201142 A1 * | 12/2016 | ........... | C12Q 1/6827 |

OTHER PUBLICATIONS

Koon Ho Wong, Multiplex Illumina Sequencing Using DNA barcoding, Jan. 2013, Wiley Online Library (Year: 2013).*
Horecka et al., "Identifying tagged transposon insertion sites in yeast by direct genomic sequencing," Yeast 2000, 16:967-970. (Year: 2000).*
PCT/US2018/014710 , "International Search Report and Written Opinion", dated Jun. 26, 2018, 24 pages.
PCT/US2018/014710 , "Invitation to Pay Add'l Fees and Partial Search Report", dated Apr. 25, 2018, 22 pages.
PCT/US2018/014710, "International Preliminary Report on Patentability," dated Aug. 1, 2019, 18 pages.

* cited by examiner

*Primary Examiner* — Kaijiang Zhang
(74) *Attorney, Agent, or Firm* — Kilpatrick Townsend & Stockton LLP

(57) ABSTRACT

Technology provided herein relates in part to methods, processes, machines and apparatuses for determining sequences of nucleotides for nucleic acid templates in a nucleic acid sample. The technology provide herein also relates in part to methods, processes, machines and apparatuses for counting nucleic acid templates. Nucleic acid templates of a sample are tagged with nonrandom oligonucleotide adapters that include predetermined non-randomly generated sequences. The use of these nonrandom oligonucleotide adapters provides an efficient method to reduce sequencing errors, and increase the sensitivity of detection of low-frequency single nucleotide alterations.

41 Claims, 17 Drawing Sheets

Specification includes a Sequence Listing.

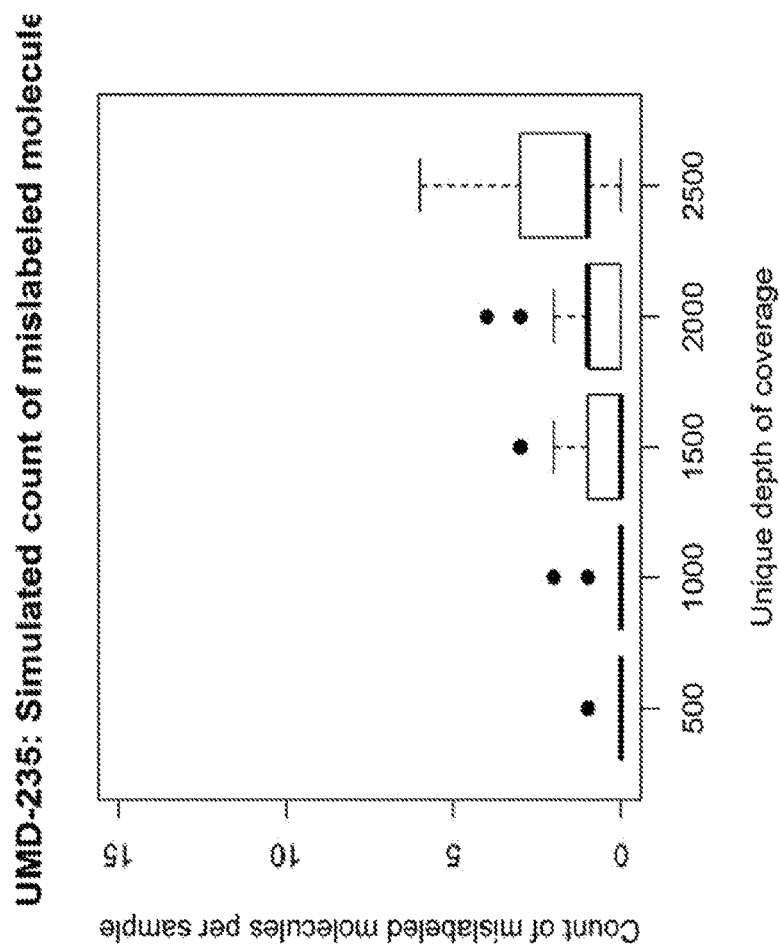
FIG. 16

SEQUENCE LISTING

<160> NUMBER OF SEQ ID NOS: 576

<210> SEQ ID NO 1
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
acactctttc cctacacgac gctcttccga tctcctttgg ctgact           46

<210> SEQ ID NO 2
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
gtcagccaaa ggagatcgga agagcacacg tctgaactcc agtcacac         48

<210> SEQ ID NO 3
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
acactctttc cctacacgac gctcttccga tctttgggta ctgact           46

<210> SEQ ID NO 4
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
gtcagtaccc aaagatcgga agagcacacg tctgaactcc agtcacac         48

<210> SEQ ID NO 5
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
acactctttc cctacacgac gctcttccga tctttcaata gtgact           46

<210> SEQ ID NO 6
<211> LENGTH: 48
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 6
gtcactattg aaagatcgga agagcacacg tctgaactcc agtcacac            48

<210> SEQ ID NO 7
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
acactctttc cctacacgac gctcttccga tcttcgcgca atgact             46

<210> SEQ ID NO 8
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gtcattgcgc gaagatcgga agagcacacg tctgaactcc agtcacac            48

<210> SEQ ID NO 9
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
acactctttc cctacacgac gctcttccga tctaggctcc atgact             46

<210> SEQ ID NO 10
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
gtcatggagc ctagatcgga agagcacacg tctgaactcc agtcacac            48

<210> SEQ ID NO 11
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
acactctttc cctacacgac gctcttccga tctcggtgga atgact             46

<210> SEQ ID NO 12
```

```
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
gtcattccac cgagatcgga agagcacacg tctgaactcc agtcacac                 48

<210> SEQ ID NO 13
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
acactctttc cctacacgac gctcttccga tcttcgctac atgact                   46

<210> SEQ ID NO 14
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
gtcatgtagc gaagatcgga agagcacacg tctgaactcc agtcacac                 48

<210> SEQ ID NO 15
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
acactctttc cctacacgac gctcttccga tctaagatcg ttgact                   46

<210> SEQ ID NO 16
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
gtcaacgatc ttagatcgga agagcacacg tctgaactcc agtcacac                 48

<210> SEQ ID NO 17
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
```

```
acactctttc cctacacgac gctcttccga tcttcgtaag ctgact          46
```

<210> SEQ ID NO 18
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18

```
gtcagcttac gaagatcgga agagcacacg tctgaactcc agtcacac        48
```

<210> SEQ ID NO 19
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19

```
acactctttc cctacacgac gctcttccga tctattaccc atgact          46
```

<210> SEQ ID NO 20
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20

```
gtcatgggta atagatcgga agagcacacg tctgaactcc agtcacac        48
```

<210> SEQ ID NO 21
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21

```
acactctttc cctacacgac gctcttccga tctgtcgtcc atgact          46
```

<210> SEQ ID NO 22
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22

```
gtcatggacg acagatcgga agagcacacg tctgaactcc agtcacac        48
```

<210> SEQ ID NO 23
<211> LENGTH: 46
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 23
acactctttc cctacacgac gctcttccga tcttcaggcg ttgact          46

<210> SEQ ID NO 24
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
gtcaacgcct gaagatcgga agagcacacg tctgaactcc agtcacac        48

<210> SEQ ID NO 25
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
acactctttc cctacacgac gctcttccga tctcggtacc ttgact          46

<210> SEQ ID NO 26
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
gtcaaggtac cgagatcgga agagcacacg tctgaactcc agtcacac        48

<210> SEQ ID NO 27
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
acactctttc cctacacgac gctcttccga tctcagcttc gtgact          46

<210> SEQ ID NO 28
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
gtcacgaagc tgagatcgga agagcacacg tctgaactcc agtcacac        48
```

```
<210> SEQ ID NO 29
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
acactctttc cctacacgac gctcttccga tcttctggaa ctgact          46

<210> SEQ ID NO 30
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
gtcagttcca gaagatcgga agagcacacg tctgaactcc agtcacac        48

<210> SEQ ID NO 31
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
acactctttc cctacacgac gctcttccga tctagcgaga atgact          46

<210> SEQ ID NO 32
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
gtcattctcg ctagatcgga agagcacacg tctgaactcc agtcacac        48

<210> SEQ ID NO 33
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
acactctttc cctacacgac gctcttccga tctaaccgat gtgact          46

<210> SEQ ID NO 34
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 34
gtcacatcgg ttagatcgga agagcacacg tctgaactcc agtcacac         48

<210> SEQ ID NO 35
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
acactctttc cctacacgac gctcttccga tctttacccg ctgact            46

<210> SEQ ID NO 36
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
gtcagcgggt aaagatcgga agagcacacg tctgaactcc agtcacac         48

<210> SEQ ID NO 37
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
acactctttc cctacacgac gctcttccga tctttctctc gtgact            46

<210> SEQ ID NO 38
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
gtcacgagag aaagatcgga agagcacacg tctgaactcc agtcacac         48

<210> SEQ ID NO 39
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
acactctttc cctacacgac gctcttccga tctctttccc ttgact            46

<210> SEQ ID NO 40
<211> LENGTH: 48
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 40
gtcaagggaa agagatcgga agagcacacg tctgaactcc agtcacac            48

<210> SEQ ID NO 41
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
acactctttc cctacacgac gctcttccga tctgtgcgag gtgact             46

<210> SEQ ID NO 42
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
gtcacctcgc acagatcgga agagcacacg tctgaactcc agtcacac            48

<210> SEQ ID NO 43
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
acactctttc cctacacgac gctcttccga tctgacaggt ttgact             46

<210> SEQ ID NO 44
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
gtcaaacctg tcagatcgga agagcacacg tctgaactcc agtcacac            48

<210> SEQ ID NO 45
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
acactctttc cctacacgac gctcttccga tctcggtgac ctgact             46
```

<210> SEQ ID NO 46
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
gtcaggtcac cgagatcgga agagcacacg tctgaactcc agtcacac         48

<210> SEQ ID NO 47
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
acactctttc cctacacgac gctcttccga tcttaatctc gtgact              46

<210> SEQ ID NO 48
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
gtcacgagat taagatcgga agagcacacg tctgaactcc agtcacac         48

<210> SEQ ID NO 49
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
acactctttc cctacacgac gctcttccga tctcgatcga atgact              46

<210> SEQ ID NO 50
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
gtcattcgat cgagatcgga agagcacacg tctgaactcc agtcacac         48

<210> SEQ ID NO 51
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
acactctttc cctacacgac gctcttccga tctacagttg ttgact                          46

<210> SEQ ID NO 52
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
gtcaacaact gtagatcgga agagcacacg tctgaactcc agtcacac                        48

<210> SEQ ID NO 53
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
acactctttc cctacacgac gctcttccga tctggcacga atgact                          46

<210> SEQ ID NO 54
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
gtcattcgtg ccagatcgga agagcacacg tctgaactcc agtcacac                        48

<210> SEQ ID NO 55
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
acactctttc cctacacgac gctcttccga tctgccaatc ctgact                          46

<210> SEQ ID NO 56
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
gtcaggattg gcagatcgga agagcacacg tctgaactcc agtcacac                        48

<210> SEQ ID NO 57
<211> LENGTH: 46
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
acactctttc cctacacgac gctcttccga tctacccgtt gtgact                    46

<210> SEQ ID NO 58
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
gtcacaacgg gtagatcgga agagcacacg tctgaactcc agtcacac                  48

<210> SEQ ID NO 59
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
acactctttc cctacacgac gctcttccga tctccgacca gtgact                    46

<210> SEQ ID NO 60
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
gtcactggtc ggagatcgga agagcacacg tctgaactcc agtcacac                  48

<210> SEQ ID NO 61
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
acactctttc cctacacgac gctcttccga tctccttcaa ttgact                    46

<210> SEQ ID NO 62
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
gtcaattgaa ggagatcgga agagcacacg tctgaactcc agtcacac                  48
```

<210> SEQ ID NO 63
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
acactctttc cctacacgac gctcttccga tctatccgca gtgact        46

<210> SEQ ID NO 64
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
gtcactgcgg atagatcgga agagcacacg tctgaactcc agtcacac        48

<210> SEQ ID NO 65
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
acactctttc cctacacgac gctcttccga tctgttggcg ttgact        46

<210> SEQ ID NO 66
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
gtcaacgcca acagatcgga agagcacacg tctgaactcc agtcacac        48

<210> SEQ ID NO 67
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
acactctttc cctacacgac gctcttccga tctttgcgtt atgact        46

<210> SEQ ID NO 68
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:

```
                Synthetic oligonucleotide"

<400> SEQUENCE: 68
gtcataacgc aaagatcgga agagcacacg tctgaactcc agtcacac            48

<210> SEQ ID NO 69
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
acactctttc cctacacgac gctcttccga tctgatgtca ttgact              46

<210> SEQ ID NO 70
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
gtcaatgaca tcagatcgga agagcacacg tctgaactcc agtcacac            48

<210> SEQ ID NO 71
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
acactctttc cctacacgac gctcttccga tctgtgtggc atgact              46

<210> SEQ ID NO 72
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
gtcatgccac acagatcgga agagcacacg tctgaactcc agtcacac            48

<210> SEQ ID NO 73
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
acactctttc cctacacgac gctcttccga tctgtagtag atgact              46

<210> SEQ ID NO 74
<211> LENGTH: 48
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
gtcatctact acagatcgga agagcacacg tctgaactcc agtcacac         48

<210> SEQ ID NO 75
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
acactctttc cctacacgac gctcttccga tctggcttac ttgact           46

<210> SEQ ID NO 76
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
gtcaagtaag ccagatcgga agagcacacg tctgaactcc agtcacac         48

<210> SEQ ID NO 77
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
acactctttc cctacacgac gctcttccga tcttacctgt gtgact           46

<210> SEQ ID NO 78
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
gtcacacagg taagatcgga agagcacacg tctgaactcc agtcacac         48

<210> SEQ ID NO 79
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
```

```
acactctttc cctacacgac gctcttccga tctgctcgaa gtgact          46
```

<210> SEQ ID NO 80
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80

```
gtcacttcga gcagatcgga agagcacacg tctgaactcc agtcacac        48
```

<210> SEQ ID NO 81
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81

```
acactctttc cctacacgac gctcttccga tctactgccc gtgact          46
```

<210> SEQ ID NO 82
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82

```
gtcacgggca gtagatcgga agagcacacg tctgaactcc agtcacac        48
```

<210> SEQ ID NO 83
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83

```
acactctttc cctacacgac gctcttccga tctttacaca atgact          46
```

<210> SEQ ID NO 84
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84

```
gtcattgtgt aaagatcgga agagcacacg tctgaactcc agtcacac        48
```

<210> SEQ ID NO 85
<211> LENGTH: 46
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 85
acactctttc cctacacgac gctcttccga tcttagcacc ttgact                  46

<210> SEQ ID NO 86
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
gtcaaggtgc taagatcgga agagcacacg tctgaactcc agtcacac                48

<210> SEQ ID NO 87
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
acactctttc cctacacgac gctcttccga tctctaattc ttgact                  46

<210> SEQ ID NO 88
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
gtcaagaatt agagatcgga agagcacacg tctgaactcc agtcacac                48

<210> SEQ ID NO 89
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
acactctttc cctacacgac gctcttccga tctgaggacc atgact                  46

<210> SEQ ID NO 90
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
gtcatggtcc tcagatcgga agagcacacg tctgaactcc agtcacac                48

<210> SEQ ID NO 91
```

```
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
acactctttc cctacacgac gctcttccga tcttacttgc ctgact                    46

<210> SEQ ID NO 92
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
gtcaggcaag taagatcgga agagcacacg tctgaactcc agtcacac                  48

<210> SEQ ID NO 93
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
acactctttc cctacacgac gctcttccga tctaatacgt ctgact                    46

<210> SEQ ID NO 94
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
gtcagacgta ttagatcgga agagcacacg tctgaactcc agtcacac                  48

<210> SEQ ID NO 95
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
acactctttc cctacacgac gctcttccga tctagatgat ctgact                    46

<210> SEQ ID NO 96
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
```

```
gtcagatcat ctagatcgga agagcacacg tctgaactcc agtcacac              48
```

<210> SEQ ID NO 97
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97

```
acactctttc cctacacgac gctcttccga tctgtacatg ttgact                46
```

<210> SEQ ID NO 98
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98

```
gtcaacatgt acagatcgga agagcacacg tctgaactcc agtcacac              48
```

<210> SEQ ID NO 99
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99

```
acactctttc cctacacgac gctcttccga tcttgcggga ttgact                46
```

<210> SEQ ID NO 100
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100

```
gtcaatcccg caagatcgga agagcacacg tctgaactcc agtcacac              48
```

<210> SEQ ID NO 101
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101

```
acactctttc cctacacgac gctcttccga tctcatatag ctgact                46
```

<210> SEQ ID NO 102
<211> LENGTH: 48
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 102
gtcagctata tgagatcgga agagcacacg tctgaactcc agtcacac        48

<210> SEQ ID NO 103
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
acactctttc cctacacgac gctcttccga tctaacgcga atgact        46

<210> SEQ ID NO 104
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
gtcattcgcg ttagatcgga agagcacacg tctgaactcc agtcacac        48

<210> SEQ ID NO 105
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
acactctttc cctacacgac gctcttccga tctatggctg ttgact        46

<210> SEQ ID NO 106
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
gtcaacagcc atagatcgga agagcacacg tctgaactcc agtcacac        48

<210> SEQ ID NO 107
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
acactctttc cctacacgac gctcttccga tctatgttta gtgact        46

```
<210> SEQ ID NO 108
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
gtcactaaac atagatcgga agagcacacg tctgaactcc agtcacac            48

<210> SEQ ID NO 109
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
acactctttc cctacacgac gctcttccga tctaccaaca gtgact             46

<210> SEQ ID NO 110
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
gtcactgttg gtagatcgga agagcacacg tctgaactcc agtcacac            48

<210> SEQ ID NO 111
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
acactctttc cctacacgac gctcttccga tcttccgagt ctgact             46

<210> SEQ ID NO 112
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
gtcagactcg gaagatcgga agagcacacg tctgaactcc agtcacac            48

<210> SEQ ID NO 113
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 113
acactctttc cctacacgac gctcttccga tcttgcccat ctgact     46

<210> SEQ ID NO 114
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
gtcagatggg caagatcgga agagcacacg tctgaactcc agtcacac     48

<210> SEQ ID NO 115
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
acactctttc cctacacgac gctcttccga tctattggac atgact     46

<210> SEQ ID NO 116
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
gtcatgtcca atagatcgga agagcacacg tctgaactcc agtcacac     48

<210> SEQ ID NO 117
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
acactctttc cctacacgac gctcttccga tctgcgttct atgact     46

<210> SEQ ID NO 118
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
gtcatagaac gcagatcgga agagcacacg tctgaactcc agtcacac     48

<210> SEQ ID NO 119
<211> LENGTH: 46
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 119
acactctttc cctacacgac gctcttccga tctaagtgtg gtgact          46

<210> SEQ ID NO 120
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
gtcaccacac ttagatcgga agagcacacg tctgaactcc agtcacac       48

<210> SEQ ID NO 121
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
acactctttc cctacacgac gctcttccga tcttccattt ctgact          46

<210> SEQ ID NO 122
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
gtcagaaatg gaagatcgga agagcacacg tctgaactcc agtcacac       48

<210> SEQ ID NO 123
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
acactctttc cctacacgac gctcttccga tcttcatcac gtgact          46

<210> SEQ ID NO 124
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
gtcacgtgat gaagatcgga agagcacacg tctgaactcc agtcacac       48
```

```
<210> SEQ ID NO 125
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
acactctttc cctacacgac gctcttccga tctttcccga atgact                    46

<210> SEQ ID NO 126
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
gtcattcggg aaagatcgga agagcacacg tctgaactcc agtcacac                  48

<210> SEQ ID NO 127
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
acactctttc cctacacgac gctcttccga tctggacttc ctgact                    46

<210> SEQ ID NO 128
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
gtcaggaagt ccagatcgga agagcacacg tctgaactcc agtcacac                  48

<210> SEQ ID NO 129
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
acactctttc cctacacgac gctcttccga tctgacgcac ttgact                    46

<210> SEQ ID NO 130
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 130
gtcaagtgcg tcagatcgga agagcacacg tctgaactcc agtcacac        48

<210> SEQ ID NO 131
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
acactctttc cctacacgac gctcttccga tctgtgtatc gtgact        46

<210> SEQ ID NO 132
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gtcacgatac acagatcgga agagcacacg tctgaactcc agtcacac        48

<210> SEQ ID NO 133
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
acactctttc cctacacgac gctcttccga tctcaagact gtgact        46

<210> SEQ ID NO 134
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
gtcacagtct tgagatcgga agagcacacg tctgaactcc agtcacac        48

<210> SEQ ID NO 135
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
acactctttc cctacacgac gctcttccga tcttgcgttc ttgact        46

<210> SEQ ID NO 136
<211> LENGTH: 48
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
gtcaagaacg caagatcgga agagcacacg tctgaactcc agtcacac          48

<210> SEQ ID NO 137
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
acactctttc cctacacgac gctcttccga tcttggcact gtgact            46

<210> SEQ ID NO 138
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
gtcacagtgc caagatcgga agagcacacg tctgaactcc agtcacac          48

<210> SEQ ID NO 139
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
acactctttc cctacacgac gctcttccga tctcacctgt atgact            46

<210> SEQ ID NO 140
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
gtcatacagg tgagatcgga agagcacacg tctgaactcc agtcacac          48

<210> SEQ ID NO 141
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
acactctttc cctacacgac gctcttccga tctagaatcc atgact            46
```

<210> SEQ ID NO 142
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 142
gtcatggatt ctagatcgga agagcacacg tctgaactcc agtcacac         48

<210> SEQ ID NO 143
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 143
acactctttc cctacacgac gctcttccga tctaatccat gtgact           46

<210> SEQ ID NO 144
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 144
gtcacatgga ttagatcgga agagcacacg tctgaactcc agtcacac         48

<210> SEQ ID NO 145
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 145
acactctttc cctacacgac gctcttccga tctgagtcga ttgact           46

<210> SEQ ID NO 146
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 146
gtcaatcgac tcagatcgga agagcacacg tctgaactcc agtcacac         48

<210> SEQ ID NO 147
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 147
acactctttc cctacacgac gctcttccga tctgtggata atgact            46

<210> SEQ ID NO 148
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
gtcattatcc acagatcgga agagcacacg tctgaactcc agtcacac          48

<210> SEQ ID NO 149
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
acactctttc cctacacgac gctcttccga tcttcagcgc ctgact            46

<210> SEQ ID NO 150
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
gtcaggcgct gaagatcgga agagcacacg tctgaactcc agtcacac          48

<210> SEQ ID NO 151
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
acactctttc cctacacgac gctcttccga tctgcactgg ctgact            46

<210> SEQ ID NO 152
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
gtcagccagt gcagatcgga agagcacacg tctgaactcc agtcacac          48

<210> SEQ ID NO 153
<211> LENGTH: 46

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
acactctttc cctacacgac gctcttccga tctcattatg gtgact                46

<210> SEQ ID NO 154
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
gtcaccataa tgagatcgga agagcacacg tctgaactcc agtcacac             48

<210> SEQ ID NO 155
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
acactctttc cctacacgac gctcttccga tctacacgac ttgact                46

<210> SEQ ID NO 156
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
gtcaagtcgt gtagatcgga agagcacacg tctgaactcc agtcacac             48

<210> SEQ ID NO 157
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
acactctttc cctacacgac gctcttccga tctgaatcgc ctgact                46

<210> SEQ ID NO 158
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
```

-continued

```
gtcaggcgat tcagatcgga agagcacacg tctgaactcc agtcacac          48
```

<210> SEQ ID NO 159
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 159

```
acactctttc cctacacgac gctcttccga tcttaccggc ttgact            46
```

<210> SEQ ID NO 160
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 160

```
gtcaagccgg taagatcgga agagcacacg tctgaactcc agtcacac          48
```

<210> SEQ ID NO 161
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 161

```
acactctttc cctacacgac gctcttccga tctacacctg ctgact            46
```

<210> SEQ ID NO 162
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 162

```
gtcagcaggt gtagatcgga agagcacacg tctgaactcc agtcacac          48
```

<210> SEQ ID NO 163
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 163

```
acactctttc cctacacgac gctcttccga tctcataccg ttgact            46
```

<210> SEQ ID NO 164
<211> LENGTH: 48
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 164
gtcaacggta tgagatcgga agagcacacg tctgaactcc agtcacac            48

<210> SEQ ID NO 165
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
acactctttc cctacacgac gctcttccga tctgagacag ttgact              46

<210> SEQ ID NO 166
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
gtcaactgtc tcagatcgga agagcacacg tctgaactcc agtcacac            48

<210> SEQ ID NO 167
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
acactctttc cctacacgac gctcttccga tctagtcgct atgact              46

<210> SEQ ID NO 168
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
gtcatagcga ctagatcgga agagcacacg tctgaactcc agtcacac            48

<210> SEQ ID NO 169
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
acactctttc cctacacgac gctcttccga tcttcctagg ttgact              46

<210> SEQ ID NO 170
```

```
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
gtcaacctag gaagatcgga agagcacacg tctgaactcc agtcacac            48

<210> SEQ ID NO 171
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
acactctttc cctacacgac gctcttccga tctgatatga atgact              46

<210> SEQ ID NO 172
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
gtcattcata tcagatcgga agagcacacg tctgaactcc agtcacac            48

<210> SEQ ID NO 173
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
acactctttc cctacacgac gctcttccga tcttaaatca ctgact              46

<210> SEQ ID NO 174
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
gtcagtgatt taagatcgga agagcacacg tctgaactcc agtcacac            48

<210> SEQ ID NO 175
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
```

```
acactctttc cctacacgac gctcttccga tctctctcat atgact          46
```

<210> SEQ ID NO 176
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176

```
gtcatatgag agagatcgga agagcacacg tctgaactcc agtcacac       48
```

<210> SEQ ID NO 177
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177

```
acactctttc cctacacgac gctcttccga tctcatgtgc ttgact          46
```

<210> SEQ ID NO 178
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178

```
gtcaagcaca tgagatcgga agagcacacg tctgaactcc agtcacac       48
```

<210> SEQ ID NO 179
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179

```
acactctttc cctacacgac gctcttccga tcttgcaatg gtgact          46
```

<210> SEQ ID NO 180
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180

```
gtcaccattg caagatcgga agagcacacg tctgaactcc agtcacac       48
```

<210> SEQ ID NO 181
<211> LENGTH: 46
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 181
acactctttc cctacacgac gctcttccga tctccgactc ttgact           46

<210> SEQ ID NO 182
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
gtcaagagtc ggagatcgga agagcacacg tctgaactcc agtcacac         48

<210> SEQ ID NO 183
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
acactctttc cctacacgac gctcttccga tcttcccacg atgact           46

<210> SEQ ID NO 184
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
gtcatcgtgg gaagatcgga agagcacacg tctgaactcc agtcacac         48

<210> SEQ ID NO 185
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
acactctttc cctacacgac gctcttccga tcttctgaat gtgact           46

<210> SEQ ID NO 186
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
gtcacattca gaagatcgga agagcacacg tctgaactcc agtcacac         48
```

```
<210> SEQ ID NO 187
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
acactctttc cctacacgac gctcttccga tctcagcagt ctgact        46

<210> SEQ ID NO 188
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
gtcagactgc tgagatcgga agagcacacg tctgaactcc agtcacac      48

<210> SEQ ID NO 189
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
acactctttc cctacacgac gctcttccga tcttgaatac ctgact        46

<210> SEQ ID NO 190
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
gtcaggtatt caagatcgga agagcacacg tctgaactcc agtcacac      48

<210> SEQ ID NO 191
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
acactctttc cctacacgac gctcttccga tctgattgtg ctgact        46

<210> SEQ ID NO 192
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 192
gtcagcacaa tcagatcgga agagcacacg tctgaactcc agtcacac        48

<210> SEQ ID NO 193
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
acactctttc cctacacgac gctcttccga tctctcccac ttgact        46

<210> SEQ ID NO 194
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
gtcaagtggg agagatcgga agagcacacg tctgaactcc agtcacac        48

<210> SEQ ID NO 195
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
acactctttc cctacacgac gctcttccga tcttcatgtg atgact        46

<210> SEQ ID NO 196
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
gtcatcacat gaagatcgga agagcacacg tctgaactcc agtcacac        48

<210> SEQ ID NO 197
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
acactctttc cctacacgac gctcttccga tcttagtgat gtgact        46

<210> SEQ ID NO 198
<211> LENGTH: 48
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 198
gtcacatcac taagatcgga agagcacacg tctgaactcc agtcacac            48

<210> SEQ ID NO 199
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
acactctttc cctacacgac gctcttccga tctcgatatc atgact              46

<210> SEQ ID NO 200
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
gtcatgatat cgagatcgga agagcacacg tctgaactcc agtcacac            48

<210> SEQ ID NO 201
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
acactctttc cctacacgac gctcttccga tctgcgccga atgact              46

<210> SEQ ID NO 202
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
gtcattcggc gcagatcgga agagcacacg tctgaactcc agtcacac            48

<210> SEQ ID NO 203
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
acactctttc cctacacgac gctcttccga tcttagggag atgact              46
```

<210> SEQ ID NO 204
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 204
gtcatctccc taagatcgga agagcacacg tctgaactcc agtcacac         48

<210> SEQ ID NO 205
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 205
acactctttc cctacacgac gctcttccga tcttcggaca gtgact           46

<210> SEQ ID NO 206
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 206
gtcactgtcc gaagatcgga agagcacacg tctgaactcc agtcacac         48

<210> SEQ ID NO 207
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 207
acactctttc cctacacgac gctcttccga tctgttccgg atgact           46

<210> SEQ ID NO 208
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 208
gtcatccgga acagatcgga agagcacacg tctgaactcc agtcacac         48

<210> SEQ ID NO 209
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 209
acactctttc cctacacgac gctcttccga tctattcggt atgact              46

<210> SEQ ID NO 210
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
gtcataccga atagatcgga agagcacacg tctgaactcc agtcacac            48

<210> SEQ ID NO 211
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
acactctttc cctacacgac gctcttccga tctctacaca gtgact              46

<210> SEQ ID NO 212
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
gtcactgtgt agagatcgga agagcacacg tctgaactcc agtcacac            48

<210> SEQ ID NO 213
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
acactctttc cctacacgac gctcttccga tctgtccgca atgact              46

<210> SEQ ID NO 214
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
gtcattgcgg acagatcgga agagcacacg tctgaactcc agtcacac            48

<210> SEQ ID NO 215
<211> LENGTH: 46
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
acactctttc cctacacgac gctcttccga tctacttcgg atgact                    46

<210> SEQ ID NO 216
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
gtcatccgaa gtagatcgga agagcacacg tctgaactcc agtcacac                  48

<210> SEQ ID NO 217
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
acactctttc cctacacgac gctcttccga tctactgcta ttgact                    46

<210> SEQ ID NO 218
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
gtcaatagca gtagatcgga agagcacacg tctgaactcc agtcacac                  48

<210> SEQ ID NO 219
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
acactctttc cctacacgac gctcttccga tctcctacat gtgact                    46

<210> SEQ ID NO 220
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
gtcacatgta ggagatcgga agagcacacg tctgaactcc agtcacac                  48
```

```
<210> SEQ ID NO 221
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
acactctttc cctacacgac gctcttccga tctgtcagta ttgact              46

<210> SEQ ID NO 222
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
gtcaatactg acagatcgga agagcacacg tctgaactcc agtcacac            48

<210> SEQ ID NO 223
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
acactctttc cctacacgac gctcttccga tcttctacgg ctgact              46

<210> SEQ ID NO 224
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
gtcagccgta gaagatcgga agagcacacg tctgaactcc agtcacac            48

<210> SEQ ID NO 225
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
acactctttc cctacacgac gctcttccga tctacgtatt ctgact              46

<210> SEQ ID NO 226
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
```

```
                      Synthetic oligonucleotide"

<400> SEQUENCE: 226
gtcagaatac gtagatcgga agagcacacg tctgaactcc agtcacac              48

<210> SEQ ID NO 227
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
acactctttc cctacacgac gctcttccga tctagatcta ttgact                46

<210> SEQ ID NO 228
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
gtcaatagat ctagatcgga agagcacacg tctgaactcc agtcacac              48

<210> SEQ ID NO 229
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
acactctttc cctacacgac gctcttccga tctagttcca ctgact                46

<210> SEQ ID NO 230
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
gtcagtggaa ctagatcgga agagcacacg tctgaactcc agtcacac              48

<210> SEQ ID NO 231
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
acactctttc cctacacgac gctcttccga tctttgatcc gtgact                46

<210> SEQ ID NO 232
<211> LENGTH: 48
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
gtcacggatc aaagatcgga agagcacacg tctgaactcc agtcacac            48

<210> SEQ ID NO 233
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
acactctttc cctacacgac gctcttccga tcttgttcgc ctgact              46

<210> SEQ ID NO 234
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
gtcaggcgaa caagatcgga agagcacacg tctgaactcc agtcacac            48

<210> SEQ ID NO 235
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
acactctttc cctacacgac gctcttccga tctgcacacc ttgact              46

<210> SEQ ID NO 236
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
gtcaaggtgt gcagatcgga agagcacacg tctgaactcc agtcacac            48

<210> SEQ ID NO 237
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
```
acactctttc cctacacgac gctcttccga tctgtaagcc ttgact        46

<210> SEQ ID NO 238
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
gtcaaggctt acagatcgga agagcacacg tctgaactcc agtcacac        48

<210> SEQ ID NO 239
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
acactctttc cctacacgac gctcttccga tcttaccaat ctgact        46

<210> SEQ ID NO 240
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
gtcagattgg taagatcgga agagcacacg tctgaactcc agtcacac        48

<210> SEQ ID NO 241
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
acactctttc cctacacgac gctcttccga tctcggtagt ttgact        46

<210> SEQ ID NO 242
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
gtcaaactac cgagatcgga agagcacacg tctgaactcc agtcacac        48

<210> SEQ ID NO 243
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
acactctttc cctacacgac gctcttccga tctgaatata ctgact        46

<210> SEQ ID NO 244
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
gtcagtatat tcagatcgga agagcacacg tctgaactcc agtcacac      48

<210> SEQ ID NO 245
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
acactctttc cctacacgac gctcttccga tctatgccgg ttgact        46

<210> SEQ ID NO 246
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gtcaaccggc atagatcgga agagcacacg tctgaactcc agtcacac      48

<210> SEQ ID NO 247
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
acactctttc cctacacgac gctcttccga tctactagtt gtgact        46

<210> SEQ ID NO 248
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
gtcacaacta gtagatcgga agagcacacg tctgaactcc agtcacac      48

<210> SEQ ID NO 249

```
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
acactctttc cctacacgac gctcttccga tctaatcgta atgact            46

<210> SEQ ID NO 250
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
gtcattacga ttagatcgga agagcacacg tctgaactcc agtcacac          48

<210> SEQ ID NO 251
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
acactctttc cctacacgac gctcttccga tctccaagat ttgact            46

<210> SEQ ID NO 252
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
gtcaaatctt ggagatcgga agagcacacg tctgaactcc agtcacac          48

<210> SEQ ID NO 253
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
acactctttc cctacacgac gctcttccga tctgtaacca ctgact            46

<210> SEQ ID NO 254
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
```
gtcagtggtt acagatcgga agagcacacg tctgaactcc agtcacac         48

<210> SEQ ID NO 255
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 255
acactctttc cctacacgac gctcttccga tctccaaact ctgact         46

<210> SEQ ID NO 256
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 256
gtcagagttt ggagatcgga agagcacacg tctgaactcc agtcacac         48

<210> SEQ ID NO 257
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 257
acactctttc cctacacgac gctcttccga tctgataggg ctgact         46

<210> SEQ ID NO 258
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 258
gtcagcccta tcagatcgga agagcacacg tctgaactcc agtcacac         48

<210> SEQ ID NO 259
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 259
acactctttc cctacacgac gctcttccga tctccaggac atgact         46

<210> SEQ ID NO 260
<211> LENGTH: 48
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 260
gtcatgtcct ggagatcgga agagcacacg tctgaactcc agtcacac        48

<210> SEQ ID NO 261
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
acactctttc cctacacgac gctcttccga tctacgatat gtgact          46

<210> SEQ ID NO 262
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
gtcacatatc gtagatcgga agagcacacg tctgaactcc agtcacac        48

<210> SEQ ID NO 263
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
acactctttc cctacacgac gctcttccga tctacgtggt ttgact          46

<210> SEQ ID NO 264
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
gtcaaaccac gtagatcgga agagcacacg tctgaactcc agtcacac        48

<210> SEQ ID NO 265
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
acactctttc cctacacgac gctcttccga tctcacgatg gtgact          46
```

```
<210> SEQ ID NO 266
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
gtcaccatcg tgagatcgga agagcacacg tctgaactcc agtcacac           48

<210> SEQ ID NO 267
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
acactctttc cctacacgac gctcttccga tctaccgtaa gtgact             46

<210> SEQ ID NO 268
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
gtcacttacg gtagatcgga agagcacacg tctgaactcc agtcacac           48

<210> SEQ ID NO 269
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
acactctttc cctacacgac gctcttccga tctccttgga atgact             46

<210> SEQ ID NO 270
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
gtcattccaa ggagatcgga agagcacacg tctgaactcc agtcacac           48

<210> SEQ ID NO 271
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 271
acactctttc cctacacgac gctcttccga tctagttgag gtgact              46

<210> SEQ ID NO 272
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
gtcacctcaa ctagatcgga agagcacacg tctgaactcc agtcacac            48

<210> SEQ ID NO 273
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
acactctttc cctacacgac gctcttccga tctgtaatgc gtgact              46

<210> SEQ ID NO 274
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
gtcacgcatt acagatcgga agagcacacg tctgaactcc agtcacac            48

<210> SEQ ID NO 275
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
acactctttc cctacacgac gctcttccga tctcgctaat ctgact              46

<210> SEQ ID NO 276
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
gtcagattag cgagatcgga agagcacacg tctgaactcc agtcacac            48

<210> SEQ ID NO 277
<211> LENGTH: 46
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 277
acactctttc cctacacgac gctcttccga tctaaggtca atgact            46

<210> SEQ ID NO 278
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
gtcattgacc ttagatcgga agagcacacg tctgaactcc agtcacac          48

<210> SEQ ID NO 279
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
acactctttc cctacacgac gctcttccga tctgaaagag ttgact            46

<210> SEQ ID NO 280
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
gtcaactctt tcagatcgga agagcacacg tctgaactcc agtcacac          48

<210> SEQ ID NO 281
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
acactctttc cctacacgac gctcttccga tctcggaaac ttgact            46

<210> SEQ ID NO 282
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
gtcaagtttc cgagatcgga agagcacacg tctgaactcc agtcacac          48
```

<210> SEQ ID NO 283
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
acactctttc cctacacgac gctcttccga tctgctggtc ttgact                    46

<210> SEQ ID NO 284
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
gtcaagacca gcagatcgga agagcacacg tctgaactcc agtcacac                  48

<210> SEQ ID NO 285
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
acactctttc cctacacgac gctcttccga tctaccggag ttgact                    46

<210> SEQ ID NO 286
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
gtcaactccg gtagatcgga agagcacacg tctgaactcc agtcacac                  48

<210> SEQ ID NO 287
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
acactctttc cctacacgac gctcttccga tctactccga ttgact                    46

<210> SEQ ID NO 288
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 288
gtcaatcgga gtagatcgga agagcacacg tctgaactcc agtcacac          48

<210> SEQ ID NO 289
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
acactctttc cctacacgac gctcttccga tcttatgacg ttgact            46

<210> SEQ ID NO 290
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
gtcaacgtca taagatcgga agagcacacg tctgaactcc agtcacac          48

<210> SEQ ID NO 291
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
acactctttc cctacacgac gctcttccga tctgcgatca ctgact            46

<210> SEQ ID NO 292
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
gtcagtgatc gcagatcgga agagcacacg tctgaactcc agtcacac          48

<210> SEQ ID NO 293
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
acactctttc cctacacgac gctcttccga tctacgagga gtgact            46

<210> SEQ ID NO 294
<211> LENGTH: 48
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
gtcactcctc gtagatcgga agagcacacg tctgaactcc agtcacac            48

<210> SEQ ID NO 295
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
acactctttc cctacacgac gctcttccga tctctgagct ctgact              46

<210> SEQ ID NO 296
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
gtcagagctc agagatcgga agagcacacg tctgaactcc agtcacac            48

<210> SEQ ID NO 297
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
acactctttc cctacacgac gctcttccga tctagagcgg atgact              46

<210> SEQ ID NO 298
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
gtcatccgct ctagatcgga agagcacacg tctgaactcc agtcacac            48

<210> SEQ ID NO 299
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
acactctttc cctacacgac gctcttccga tctctagtcg ctgact              46
```

<210> SEQ ID NO 300
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
gtcagcgact agagatcgga agagcacacg tctgaactcc agtcacac         48

<210> SEQ ID NO 301
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
acactctttc cctacacgac gctcttccga tctcactttg gtgact           46

<210> SEQ ID NO 302
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
gtcaccaaag tgagatcgga agagcacacg tctgaactcc agtcacac         48

<210> SEQ ID NO 303
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
acactctttc cctacacgac gctcttccga tctagattac atgact           46

<210> SEQ ID NO 304
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
gtcatgtaat ctagatcgga agagcacacg tctgaactcc agtcacac         48

<210> SEQ ID NO 305
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 305
acactctttc cctacacgac gctcttccga tctgcctatg atgact          46

<210> SEQ ID NO 306
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
gtcatcatag gcagatcgga agagcacacg tctgaactcc agtcacac        48

<210> SEQ ID NO 307
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
acactctttc cctacacgac gctcttccga tctcgaacgt ctgact          46

<210> SEQ ID NO 308
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
gtcagacgtt cgagatcgga agagcacacg tctgaactcc agtcacac        48

<210> SEQ ID NO 309
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
acactctttc cctacacgac gctcttccga tctgtttctt gtgact          46

<210> SEQ ID NO 310
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
gtcacaagaa acagatcgga agagcacacg tctgaactcc agtcacac        48

<210> SEQ ID NO 311
<211> LENGTH: 46

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
acactctttc cctacacgac gctcttccga tctaagggcg ctgact          46

<210> SEQ ID NO 312
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
gtcagcgccc ttagatcgga agagcacacg tctgaactcc agtcacac        48

<210> SEQ ID NO 313
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
acactctttc cctacacgac gctcttccga tctcgctctt atgact          46

<210> SEQ ID NO 314
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
gtcataagag cgagatcgga agagcacacg tctgaactcc agtcacac        48

<210> SEQ ID NO 315
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
acactctttc cctacacgac gctcttccga tcttcaaccc gtgact          46

<210> SEQ ID NO 316
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
```

```
gtcacgggtt gaagatcgga agagcacacg tctgaactcc agtcacac          48
```

<210> SEQ ID NO 317
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317

```
acactctttc cctacacgac gctcttccga tcttcggtgt atgact            46
```

<210> SEQ ID NO 318
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318

```
gtcatacacc gaagatcgga agagcacacg tctgaactcc agtcacac          48
```

<210> SEQ ID NO 319
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319

```
acactctttc cctacacgac gctcttccga tctgtccgat ctgact            46
```

<210> SEQ ID NO 320
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320

```
gtcagatcgg acagatcgga agagcacacg tctgaactcc agtcacac          48
```

<210> SEQ ID NO 321
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321

```
acactctttc cctacacgac gctcttccga tcttcccaac ctgact            46
```

<210> SEQ ID NO 322
<211> LENGTH: 48
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 322
gtcaggttgg gaagatcgga agagcacacg tctgaactcc agtcacac            48

<210> SEQ ID NO 323
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
acactctttc cctacacgac gctcttccga tcttcttgcg gtgact             46

<210> SEQ ID NO 324
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
gtcaccgcaa gaagatcgga agagcacacg tctgaactcc agtcacac            48

<210> SEQ ID NO 325
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
acactctttc cctacacgac gctcttccga tctgccggta ctgact             46

<210> SEQ ID NO 326
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
gtcagtaccg gcagatcgga agagcacacg tctgaactcc agtcacac            48

<210> SEQ ID NO 327
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
acactctttc cctacacgac gctcttccga tctttctaga gtgact             46

<210> SEQ ID NO 328
```

```
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
gtcactctag aaagatcgga agagcacacg tctgaactcc agtcacac                48

<210> SEQ ID NO 329
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
acactctttc cctacacgac gctcttccga tctggcctat atgact                  46

<210> SEQ ID NO 330
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
gtcatatagg ccagatcgga agagcacacg tctgaactcc agtcacac                48

<210> SEQ ID NO 331
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
acactctttc cctacacgac gctcttccga tcttgcacgt gtgact                  46

<210> SEQ ID NO 332
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
gtcacacgtg caagatcgga agagcacacg tctgaactcc agtcacac                48

<210> SEQ ID NO 333
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
```
acactctttc cctacacgac gctcttccga tctgccgtct ctgact         46

<210> SEQ ID NO 334
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
gtcagagacg gcagatcgga agagcacacg tctgaactcc agtcacac       48

<210> SEQ ID NO 335
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
acactctttc cctacacgac gctcttccga tctatgcctc gtgact         46

<210> SEQ ID NO 336
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
gtcacgaggc atagatcgga agagcacacg tctgaactcc agtcacac       48

<210> SEQ ID NO 337
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
acactctttc cctacacgac gctcttccga tctcagagct atgact         46

<210> SEQ ID NO 338
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
gtcatagctc tgagatcgga agagcacacg tctgaactcc agtcacac       48

<210> SEQ ID NO 339
<211> LENGTH: 46
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 339
acactctttc cctacacgac gctcttccga tctgcaatag gtgact                        46

<210> SEQ ID NO 340
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
gtcacctatt gcagatcgga agagcacacg tctgaactcc agtcacac                      48

<210> SEQ ID NO 341
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
acactctttc cctacacgac gctcttccga tctgtttgct ctgact                        46

<210> SEQ ID NO 342
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
gtcagagcaa acagatcgga agagcacacg tctgaactcc agtcacac                      48

<210> SEQ ID NO 343
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
acactctttc cctacacgac gctcttccga tctcctcggg ttgact                        46

<210> SEQ ID NO 344
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
gtcaacccga ggagatcgga agagcacacg tctgaactcc agtcacac                      48
```

```
<210> SEQ ID NO 345
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
acactctttc cctacacgac gctcttccga tcttgactaa ttgact           46

<210> SEQ ID NO 346
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
gtcaattagt caagatcgga agagcacacg tctgaactcc agtcacac          48

<210> SEQ ID NO 347
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
acactctttc cctacacgac gctcttccga tctcgtaatt gtgact           46

<210> SEQ ID NO 348
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
gtcacaatta cgagatcgga agagcacacg tctgaactcc agtcacac          48

<210> SEQ ID NO 349
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
acactctttc cctacacgac gctcttccga tctcgaaagc atgact           46

<210> SEQ ID NO 350
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 350
gtcatgcttt cgagatcgga agagcacacg tctgaactcc agtcacac          48

<210> SEQ ID NO 351
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
acactctttc cctacacgac gctcttccga tctaatcacg gtgact            46

<210> SEQ ID NO 352
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
gtcaccgtga ttagatcgga agagcacacg tctgaactcc agtcacac          48

<210> SEQ ID NO 353
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
acactctttc cctacacgac gctcttccga tctactgtac atgact            46

<210> SEQ ID NO 354
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
gtcatgtaca gtagatcgga agagcacacg tctgaactcc agtcacac          48

<210> SEQ ID NO 355
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
acactctttc cctacacgac gctcttccga tctgaggtgg gtgact            46

<210> SEQ ID NO 356
<211> LENGTH: 48
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 356
gtcacccacc tcagatcgga agagcacacg tctgaactcc agtcacac            48

<210> SEQ ID NO 357
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
acactctttc cctacacgac gctcttccga tctcttcgcg gtgact              46

<210> SEQ ID NO 358
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
gtcaccgcga agagatcgga agagcacacg tctgaactcc agtcacac            48

<210> SEQ ID NO 359
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
acactctttc cctacacgac gctcttccga tctatgatga gtgact              46

<210> SEQ ID NO 360
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
gtcactcatc atagatcgga agagcacacg tctgaactcc agtcacac            48

<210> SEQ ID NO 361
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
acactctttc cctacacgac gctcttccga tctccgaacg ttgact              46
```

<210> SEQ ID NO 362
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 362
gtcaacgttc ggagatcgga agagcacacg tctgaactcc agtcacac         48

<210> SEQ ID NO 363
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 363
acactctttc cctacacgac gctcttccga tcttagtggg ttgact           46

<210> SEQ ID NO 364
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 364
gtcaacccac taagatcgga agagcacacg tctgaactcc agtcacac         48

<210> SEQ ID NO 365
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 365
acactctttc cctacacgac gctcttccga tcttaaccga atgact           46

<210> SEQ ID NO 366
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 366
gtcattcggt taagatcgga agagcacacg tctgaactcc agtcacac         48

<210> SEQ ID NO 367
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

-continued

<400> SEQUENCE: 367
acactctttc cctacacgac gctcttccga tctgagctaa gtgact        46

<210> SEQ ID NO 368
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
gtcacttagc tcagatcgga agagcacacg tctgaactcc agtcacac      48

<210> SEQ ID NO 369
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
acactctttc cctacacgac gctcttccga tctagtcaca ttgact        46

<210> SEQ ID NO 370
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
gtcaatgtga ctagatcgga agagcacacg tctgaactcc agtcacac      48

<210> SEQ ID NO 371
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
acactctttc cctacacgac gctcttccga tcttaacctt ctgact        46

<210> SEQ ID NO 372
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
gtcagaaggt taagatcgga agagcacacg tctgaactcc agtcacac      48

<210> SEQ ID NO 373
<211> LENGTH: 46
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
acactctttc cctacacgac gctcttccga tctcgatgct gtgact            46

<210> SEQ ID NO 374
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
gtcacagcat cgagatcgga agagcacacg tctgaactcc agtcacac          48

<210> SEQ ID NO 375
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
acactctttc cctacacgac gctcttccga tctatcagag ctgact            46

<210> SEQ ID NO 376
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
gtcagctctg atagatcgga agagcacacg tctgaactcc agtcacac          48

<210> SEQ ID NO 377
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
acactctttc cctacacgac gctcttccga tctagagtgc ttgact            46

<210> SEQ ID NO 378
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
gtcaagcact ctagatcgga agagcacacg tctgaactcc agtcacac          48
```

<210> SEQ ID NO 379
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
acactctttc cctacacgac gctcttccga tctggtgtga gtgact          46

<210> SEQ ID NO 380
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
gtcactcaca ccagatcgga agagcacacg tctgaactcc agtcacac          48

<210> SEQ ID NO 381
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
acactctttc cctacacgac gctcttccga tctttgccaa gtgact          46

<210> SEQ ID NO 382
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
gtcacttggc aaagatcgga agagcacacg tctgaactcc agtcacac          48

<210> SEQ ID NO 383
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
acactctttc cctacacgac gctcttccga tctgtgcacg atgact          46

<210> SEQ ID NO 384
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 384
gtcatcgtgc acagatcgga agagcacacg tctgaactcc agtcacac        48

<210> SEQ ID NO 385
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
acactctttc cctacacgac gctcttccga tcttagaggc gtgact        46

<210> SEQ ID NO 386
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
gtcacgcctc taagatcgga agagcacacg tctgaactcc agtcacac        48

<210> SEQ ID NO 387
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
acactctttc cctacacgac gctcttccga tctggccaag gtgact        46

<210> SEQ ID NO 388
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
gtcaccttgg ccagatcgga agagcacacg tctgaactcc agtcacac        48

<210> SEQ ID NO 389
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
acactctttc cctacacgac gctcttccga tcttcctcac ttgact        46

<210> SEQ ID NO 390
<211> LENGTH: 48

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
gtcaagtgag gaagatcgga agagcacacg tctgaactcc agtcacac          48

<210> SEQ ID NO 391
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
acactctttc cctacacgac gctcttccga tctacccagt atgact          46

<210> SEQ ID NO 392
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
gtcatactgg gtagatcgga agagcacacg tctgaactcc agtcacac          48

<210> SEQ ID NO 393
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
acactctttc cctacacgac gctcttccga tctgacggct atgact          46

<210> SEQ ID NO 394
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
gtcatagccg tcagatcgga agagcacacg tctgaactcc agtcacac          48

<210> SEQ ID NO 395
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
```
acactctttc cctacacgac gctcttccga tctcgtgtag ttgact            46

<210> SEQ ID NO 396
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
gtcaactaca cgagatcgga agagcacacg tctgaactcc agtcacac           48

<210> SEQ ID NO 397
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
acactctttc cctacacgac gctcttccga tctaagcgta ctgact            46

<210> SEQ ID NO 398
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
gtcagtacgc ttagatcgga agagcacacg tctgaactcc agtcacac           48

<210> SEQ ID NO 399
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
acactctttc cctacacgac gctcttccga tctattatcg ttgact            46

<210> SEQ ID NO 400
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
gtcaacgata atagatcgga agagcacacg tctgaactcc agtcacac           48

<210> SEQ ID NO 401
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 401
acactctttc cctacacgac gctcttccga tctccgcatg atgact        46

<210> SEQ ID NO 402
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 402
gtcatcatgc ggagatcgga agagcacacg tctgaactcc agtcacac        48

<210> SEQ ID NO 403
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 403
acactctttc cctacacgac gctcttccga tctcactaga ctgact        46

<210> SEQ ID NO 404
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 404
gtcagtctag tgagatcgga agagcacacg tctgaactcc agtcacac        48

<210> SEQ ID NO 405
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 405
acactctttc cctacacgac gctcttccga tctaacgtcc ttgact        46

<210> SEQ ID NO 406
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 406
gtcaaggacg ttagatcgga agagcacacg tctgaactcc agtcacac        48

<210> SEQ ID NO 407

```
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
acactctttc cctacacgac gctcttccga tctcttgacg atgact            46

<210> SEQ ID NO 408
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
gtcatcgtca agagatcgga agagcacacg tctgaactcc agtcacac          48

<210> SEQ ID NO 409
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
acactctttc cctacacgac gctcttccga tctgttcttg gtgact            46

<210> SEQ ID NO 410
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
gtcaccaaga acagatcgga agagcacacg tctgaactcc agtcacac          48

<210> SEQ ID NO 411
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
acactctttc cctacacgac gctcttccga tctcaagcta gtgact            46

<210> SEQ ID NO 412
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
```

```
gtcactagct tgagatcgga agagcacacg tctgaactcc agtcacac                    48
```

<210> SEQ ID NO 413
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413

```
acactctttc cctacacgac gctcttccga tctcataagg gtgact                      46
```

<210> SEQ ID NO 414
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414

```
gtcaccctta tgagatcgga agagcacacg tctgaactcc agtcacac                    48
```

<210> SEQ ID NO 415
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415

```
acactctttc cctacacgac gctcttccga tcttatggcc atgact                      46
```

<210> SEQ ID NO 416
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416

```
gtcatggcca taagatcgga agagcacacg tctgaactcc agtcacac                    48
```

<210> SEQ ID NO 417
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417

```
acactctttc cctacacgac gctcttccga tctccgctac gtgact                      46
```

<210> SEQ ID NO 418
<211> LENGTH: 48
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 418
gtcacgtagc ggagatcgga agagcacacg tctgaactcc agtcacac            48

<210> SEQ ID NO 419
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
acactctttc cctacacgac gctcttccga tctttagtac gtgact              46

<210> SEQ ID NO 420
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
gtcacgtact aaagatcgga agagcacacg tctgaactcc agtcacac            48

<210> SEQ ID NO 421
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
acactctttc cctacacgac gctcttccga tcttcttgtt ttgact              46

<210> SEQ ID NO 422
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
gtcaaaacaa gaagatcgga agagcacacg tctgaactcc agtcacac            48

<210> SEQ ID NO 423
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
acactctttc cctacacgac gctcttccga tcttgagtgg ttgact              46
```

```
<210> SEQ ID NO 424
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
gtcaaccact caagatcgga agagcacacg tctgaactcc agtcacac           48

<210> SEQ ID NO 425
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
acactctttc cctacacgac gctcttccga tctcaaccga gtgact             46

<210> SEQ ID NO 426
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
gtcactcggt tgagatcgga agagcacacg tctgaactcc agtcacac           48

<210> SEQ ID NO 427
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
acactctttc cctacacgac gctcttccga tctggacagt gtgact             46

<210> SEQ ID NO 428
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
gtcacactgt ccagatcgga agagcacacg tctgaactcc agtcacac           48

<210> SEQ ID NO 429
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 429
acactctttc cctacacgac gctcttccga tctatagagg ctgact          46

<210> SEQ ID NO 430
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
gtcagcctct atagatcgga agagcacacg tctgaactcc agtcacac        48

<210> SEQ ID NO 431
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
acactctttc cctacacgac gctcttccga tctgtgacgt ttgact          46

<210> SEQ ID NO 432
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
gtcaaacgtc acagatcgga agagcacacg tctgaactcc agtcacac        48

<210> SEQ ID NO 433
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
acactctttc cctacacgac gctcttccga tctggtctcc ttgact          46

<210> SEQ ID NO 434
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
gtcaaggaga ccagatcgga agagcacacg tctgaactcc agtcacac        48

<210> SEQ ID NO 435
<211> LENGTH: 46
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 435
acactctttc cctacacgac gctcttccga tctggaagaa gtgact              46

<210> SEQ ID NO 436
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
gtcacttctt ccagatcgga agagcacacg tctgaactcc agtcacac            48

<210> SEQ ID NO 437
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
acactctttc cctacacgac gctcttccga tctttgaaca atgact              46

<210> SEQ ID NO 438
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
gtcattgttc aaagatcgga agagcacacg tctgaactcc agtcacac            48

<210> SEQ ID NO 439
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
acactctttc cctacacgac gctcttccga tcttgaggac ttgact              46

<210> SEQ ID NO 440
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
gtcaagtcct caagatcgga agagcacacg tctgaactcc agtcacac            48
```

<210> SEQ ID NO 441
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 441
acactctttc cctacacgac gctcttccga tctggaccaa gtgact    46

<210> SEQ ID NO 442
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 442
gtcacttggt ccagatcgga agagcacacg tctgaactcc agtcacac    48

<210> SEQ ID NO 443
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 443
acactctttc cctacacgac gctcttccga tctcctgctt ctgact    46

<210> SEQ ID NO 444
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 444
gtcagaagca ggagatcgga agagcacacg tctgaactcc agtcacac    48

<210> SEQ ID NO 445
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 445
acactctttc cctacacgac gctcttccga tctcctatgc atgact    46

<210> SEQ ID NO 446
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 446
gtcatgcata ggagatcgga agagcacacg tctgaactcc agtcacac         48

<210> SEQ ID NO 447
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 447
acactctttc cctacacgac gctcttccga tctcggtcaa ttgact         46

<210> SEQ ID NO 448
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 448
gtcaattgac cgagatcgga agagcacacg tctgaactcc agtcacac         48

<210> SEQ ID NO 449
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 449
acactctttc cctacacgac gctcttccga tctacaccct atgact         46

<210> SEQ ID NO 450
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 450
gtcatagggt gtagatcgga agagcacacg tctgaactcc agtcacac         48

<210> SEQ ID NO 451
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 451
acactctttc cctacacgac gctcttccga tctggattac gtgact         46

<210> SEQ ID NO 452
<211> LENGTH: 48
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
gtcacgtaat ccagatcgga agagcacacg tctgaactcc agtcacac         48

<210> SEQ ID NO 453
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
acactctttc cctacacgac gctcttccga tcttgttgac gtgact           46

<210> SEQ ID NO 454
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
gtcacgtcaa caagatcgga agagcacacg tctgaactcc agtcacac         48

<210> SEQ ID NO 455
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
acactctttc cctacacgac gctcttccga tctggtgact atgact           46

<210> SEQ ID NO 456
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
gtcatagtca ccagatcgga agagcacacg tctgaactcc agtcacac         48

<210> SEQ ID NO 457
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
acactctttc cctacacgac gctcttccga tcttgcaact ttgact           46

<210> SEQ ID NO 458
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
gtcaaagttg caagatcgga agagcacacg tctgaactcc agtcacac                48

<210> SEQ ID NO 459
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
acactctttc cctacacgac gctcttccga tctgccgttg atgact                  46

<210> SEQ ID NO 460
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
gtcatcaacg gcagatcgga agagcacacg tctgaactcc agtcacac                48

<210> SEQ ID NO 461
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
acactctttc cctacacgac gctcttccga tctacaaggc atgact                  46

<210> SEQ ID NO 462
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
gtcatgcctt gtagatcgga agagcacacg tctgaactcc agtcacac                48

<210> SEQ ID NO 463
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 463
acactctttc cctacacgac gctcttccga tcttatggta ctgact        46

<210> SEQ ID NO 464
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
gtcagtacca taagatcgga agagcacacg tctgaactcc agtcacac        48

<210> SEQ ID NO 465
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
acactctttc cctacacgac gctcttccga tctagctcta gtgact        46

<210> SEQ ID NO 466
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
gtcactagag ctagatcgga agagcacacg tctgaactcc agtcacac        48

<210> SEQ ID NO 467
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
acactctttc cctacacgac gctcttccga tctcctggct gtgact        46

<210> SEQ ID NO 468
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
gtcacagcca ggagatcgga agagcacacg tctgaactcc agtcacac        48

<210> SEQ ID NO 469
<211> LENGTH: 46

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
acactctttc cctacacgac gctcttccga tctggcatta gtgact                46

<210> SEQ ID NO 470
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
gtcactaatg ccagatcgga agagcacacg tctgaactcc agtcacac              48

<210> SEQ ID NO 471
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
acactctttc cctacacgac gctcttccga tctcaatcgg ctgact                46

<210> SEQ ID NO 472
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
gtcagccgat tgagatcgga agagcacacg tctgaactcc agtcacac              48

<210> SEQ ID NO 473
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
acactctttc cctacacgac gctcttccga tctaggtcat ctgact                46

<210> SEQ ID NO 474
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
```

```
gtcagatgac ctagatcgga agagcacacg tctgaactcc agtcacac                    48

<210> SEQ ID NO 475
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
acactctttc cctacacgac gctcttccga tctgagagat ctgact                      46

<210> SEQ ID NO 476
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
gtcagatctc tcagatcgga agagcacacg tctgaactcc agtcacac                    48

<210> SEQ ID NO 477
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
acactctttc cctacacgac gctcttccga tctggagctc ttgact                      46

<210> SEQ ID NO 478
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
gtcaagagct ccagatcgga agagcacacg tctgaactcc agtcacac                    48

<210> SEQ ID NO 479
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
acactctttc cctacacgac gctcttccga tctcctaaac ttgact                      46

<210> SEQ ID NO 480
<211> LENGTH: 48
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 480
gtcaagttta ggagatcgga agagcacacg tctgaactcc agtcacac                  48

<210> SEQ ID NO 481
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
acactctttc cctacacgac gctcttccga tctaccgacg ctgact                    46

<210> SEQ ID NO 482
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
gtcagcgtcg gtagatcgga agagcacacg tctgaactcc agtcacac                  48

<210> SEQ ID NO 483
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
acactctttc cctacacgac gctcttccga tctagactca gtgact                    46

<210> SEQ ID NO 484
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
gtcactgagt ctagatcgga agagcacacg tctgaactcc agtcacac                  48

<210> SEQ ID NO 485
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
acactctttc cctacacgac gctcttccga tcttagtagc atgact                    46

<210> SEQ ID NO 486
```

```
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
gtcatgctac taagatcgga agagcacacg tctgaactcc agtcacac          48

<210> SEQ ID NO 487
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
acactctttc cctacacgac gctcttccga tctgcgctgt ttgact            46

<210> SEQ ID NO 488
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
gtcaaacagc gcagatcgga agagcacacg tctgaactcc agtcacac          48

<210> SEQ ID NO 489
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligoncleotide"

<400> SEQUENCE: 489
acactctttc cctacacgac gctcttccga tctctataga ctgact            46

<210> SEQ ID NO 490
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
gtcagtctat agagatcgga agagcacacg tctgaactcc agtcacac          48

<210> SEQ ID NO 491
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
```

```
acactctttc cctacacgac gctcttccga tctagcggcc ttgact          46
```

<210> SEQ ID NO 492
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492

```
gtcaaggccg ctagatcgga agagcacacg tctgaactcc agtcacac       48
```

<210> SEQ ID NO 493
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493

```
acactctttc cctacacgac gctcttccga tctctcacaa ctgact          46
```

<210> SEQ ID NO 494
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494

```
gtcagttgtg agagatcgga agagcacacg tctgaactcc agtcacac       48
```

<210> SEQ ID NO 495
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495

```
acactctttc cctacacgac gctcttccga tctgtatagt ctgact          46
```

<210> SEQ ID NO 496
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496

```
gtcagactat acagatcgga agagcacacg tctgaactcc agtcacac       48
```

<210> SEQ ID NO 497
<211> LENGTH: 46
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 497
acactctttc cctacacgac gctcttccga tctccatccg ctgact                    46

<210> SEQ ID NO 498
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
gtcagcggat ggagatcgga agagcacacg tctgaactcc agtcacac                  48

<210> SEQ ID NO 499
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
acactctttc cctacacgac gctcttccga tctactaata ctgact                    46

<210> SEQ ID NO 500
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
gtcagtatta gtagatcgga agagcacacg tctgaactcc agtcacac                  48

<210> SEQ ID NO 501
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
acactctttc cctacacgac gctcttccga tctgcgtaga gtgact                    46

<210> SEQ ID NO 502
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
gtcactctac gcagatcgga agagcacacg tctgaactcc agtcacac                  48
```

<210> SEQ ID NO 503
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
acactctttc cctacacgac gctcttccga tctgcctgat ttgact                    46

<210> SEQ ID NO 504
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
gtcaaatcag gcagatcgga agagcacacg tctgaactcc agtcacac                  48

<210> SEQ ID NO 505
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
acactctttc cctacacgac gctcttccga tcttgacaac ctgact                    46

<210> SEQ ID NO 506
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
gtcaggttgt caagatcgga agagcacacg tctgaactcc agtcacac                  48

<210> SEQ ID NO 507
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
acactctttc cctacacgac gctcttccga tctgataatg ttgact                    46

<210> SEQ ID NO 508
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 508
gtcaacatta tcagatcgga agagcacacg tctgaactcc agtcacac                48

<210> SEQ ID NO 509
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
acactctttc cctacacgac gctcttccga tcttaggacg gtgact                  46

<210> SEQ ID NO 510
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
gtcaccgtcc taagatcgga agagcacacg tctgaactcc agtcacac                48

<210> SEQ ID NO 511
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
acactctttc cctacacgac gctcttccga tctcaactag atgact                  46

<210> SEQ ID NO 512
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
gtcatctagt tgagatcgga agagcacacg tctgaactcc agtcacac                48

<210> SEQ ID NO 513
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
acactctttc cctacacgac gctcttccga tctcttccaa ctgact                  46

<210> SEQ ID NO 514
<211> LENGTH: 48
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic oligonucleotide"

<400> SEQUENCE: 514
gtcagttgga agagatcgga agagcacacg tctgaactcc agtcacac         48

<210> SEQ ID NO 515
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
acactctttc cctacacgac gctcttccga tcttagctgg ctgact           46

<210> SEQ ID NO 516
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
gtcagccagc taagatcgga agagcacacg tctgaactcc agtcacac         48

<210> SEQ ID NO 517
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
acactctttc cctacacgac gctcttccga tctgttcctc ctgact           46

<210> SEQ ID NO 518
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
gtcaggagga acagatcgga agagcacacg tctgaactcc agtcacac         48

<210> SEQ ID NO 519
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
acactctttc cctacacgac gctcttccga tctagtgact gtgact           46

<210> SEQ ID NO 520
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
gtcacagtca ctagatcgga agagcacacg tctgaactcc agtcacac         48

<210> SEQ ID NO 521
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
acactctttc cctacacgac gctcttccga tctggccagt ttgact           46

<210> SEQ ID NO 522
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522
gtcaaactgg ccagatcgga agagcacacg tctgaactcc agtcacac         48

<210> SEQ ID NO 523
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
acactctttc cctacacgac gctcttccga tctgcctcag ctgact           46

<210> SEQ ID NO 524
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
gtcagctgag gcagatcgga agagcacacg tctgaactcc agtcacac         48

<210> SEQ ID NO 525
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
acactctttc cctacacgac gctcttccga tctagaacac gtgact            46

<210> SEQ ID NO 526
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 526
gtcacgtgtt ctagatcgga agagcacacg tctgaactcc agtcacac          48

<210> SEQ ID NO 527
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 527
acactctttc cctacacgac gctcttccga tctcctttca ctgact            46

<210> SEQ ID NO 528
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 528
gtcagtgaaa ggagatcgga agagcacacg tctgaactcc agtcacac          48

<210> SEQ ID NO 529
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 529
acactctttc cctacacgac gctcttccga tctttggtct ctgact            46

<210> SEQ ID NO 530
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 530
gtcagagacc aaagatcgga agagcacacg tctgaactcc agtcacac          48

<210> SEQ ID NO 531
<211> LENGTH: 46
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
acactctttc cctacacgac gctcttccga tctggctgca ttgact            46

<210> SEQ ID NO 532
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
gtcaatgcag ccagatcgga agagcacacg tctgaactcc agtcacac          48

<210> SEQ ID NO 533
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
acactctttc cctacacgac gctcttccga tctctcgaaa ttgact            46

<210> SEQ ID NO 534
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
gtcaatttcg agagatcgga agagcacacg tctgaactcc agtcacac          48

<210> SEQ ID NO 535
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
acactctttc cctacacgac gctcttccga tctaatgcgc gtgact            46

<210> SEQ ID NO 536
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
gtcacgcgca ttagatcgga agagcacacg tctgaactcc agtcacac          48
```

<210> SEQ ID NO 537
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 537
acactctttc cctacacgac gctcttccga tctcttgaac ctgact        46

<210> SEQ ID NO 538
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 538
gtcaggttca agagatcgga agagcacacg tctgaactcc agtcacac        48

<210> SEQ ID NO 539
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 539
acactctttc cctacacgac gctcttccga tcttaatacg gtgact        46

<210> SEQ ID NO 540
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 540
gtcaccgtat taagatcgga agagcacacg tctgaactcc agtcacac        48

<210> SEQ ID NO 541
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 541
acactctttc cctacacgac gctcttccga tctgacaatt ctgact        46

<210> SEQ ID NO 542
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 542
gtcagaattg tcagatcgga agagcacacg tctgaactcc agtcacac         48

<210> SEQ ID NO 543
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
acactctttc cctacacgac gctcttccga tcttgtacgg atgact           46

<210> SEQ ID NO 544
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
gtcatccgta caagatcgga agagcacacg tctgaactcc agtcacac         48

<210> SEQ ID NO 545
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
acactctttc cctacacgac gctcttccga tctgccacga ctgact           46

<210> SEQ ID NO 546
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
gtcagtcgtg gcagatcgga agagcacacg tctgaactcc agtcacac         48

<210> SEQ ID NO 547
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
acactctttc cctacacgac gctcttccga tcttccatcg atgact           46

<210> SEQ ID NO 548
<211> LENGTH: 48

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
gtcatcgatg gaagatcgga agagcacacg tctgaactcc agtcacac           48

<210> SEQ ID NO 549
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
acactctttc cctacacgac gctcttccga tctttctcca ttgact             46

<210> SEQ ID NO 550
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
gtcaatggag aaagatcgga agagcacacg tctgaactcc agtcacac           48

<210> SEQ ID NO 551
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
acactctttc cctacacgac gctcttccga tctgtggcct atgact             46

<210> SEQ ID NO 552
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
gtcataggcc acagatcgga agagcacacg tctgaactcc agtcacac           48

<210> SEQ ID NO 553
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
```

```
acactctttc cctacacgac gctcttccga tctctgggag ttgact          46
```

<210> SEQ ID NO 554
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554

```
gtcaactccc agagatcgga agagcacacg tctgaactcc agtcacac       48
```

<210> SEQ ID NO 555
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555

```
acactctttc cctacacgac gctcttccga tctttgctgg atgact          46
```

<210> SEQ ID NO 556
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556

```
gtcatccagc aaagatcgga agagcacacg tctgaactcc agtcacac       48
```

<210> SEQ ID NO 557
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557

```
acactctttc cctacacgac gctcttccga tctcttcaag atgact          46
```

<210> SEQ ID NO 558
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558

```
gtcatcttga agagatcgga agagcacacg tctgaactcc agtcacac       48
```

<210> SEQ ID NO 559
<211> LENGTH: 46
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 559
acactctttc cctacacgac gctcttccga tctcatatcc atgact                    46

<210> SEQ ID NO 560
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
gtcatggata tgagatcgga agagcacacg tctgaactcc agtcacac                  48

<210> SEQ ID NO 561
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
acactctttc cctacacgac gctcttccga tctagacgtt gtgact                    46

<210> SEQ ID NO 562
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
gtcacaacgt ctagatcgga agagcacacg tctgaactcc agtcacac                  48

<210> SEQ ID NO 563
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
acactctttc cctacacgac gctcttccga tctattcgag ctgact                    46

<210> SEQ ID NO 564
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
gtcagctcga atagatcgga agagcacacg tctgaactcc agtcacac                  48

<210> SEQ ID NO 565
```

```
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
acactctttc cctacacgac gctcttccga tctcttgcat atgact            46

<210> SEQ ID NO 566
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
gtcatatgca agagatcgga agagcacacg tctgaactcc agtcacac           48

<210> SEQ ID NO 567
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
acactctttc cctacacgac gctcttccga tctatacaaa ctgact            46

<210> SEQ ID NO 568
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
gtcagtttgt atagatcgga agagcacacg tctgaactcc agtcacac           48

<210> SEQ ID NO 569
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
acactctttc cctacacgac gctcttccga tctatgttcc ttgact            46

<210> SEQ ID NO 570
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
```
gtcaaggaac atagatcgga agagcacacg tctgaactcc agtcacac             48

<210> SEQ ID NO 571
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
acactctttc cctacacgac gctcttccga tcttgcacag ttgact                46

<210> SEQ ID NO 572
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
gtcaactgtg caagatcgga agagcacacg tctgaactcc agtcacac             48

<210> SEQ ID NO 573
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
acactctttc cctacacgac gctcttccga tctacatgca ctgact                46

<210> SEQ ID NO 574
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
gtcagtgcat gtagatcgga agagcacacg tctgaactcc agtcacac             48

<210> SEQ ID NO 575
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
acactctttc cctacacgac gctcttccga tcttacggca gtgact                46

<210> SEQ ID NO 576
<211> LENGTH: 48
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 576
gtcactgccg taagatcgga agagcacacg tctgaactcc agtcacac                    48
```

SEQUENCE ADAPTER MANUFACTURE AND USE

RELATED PATENT APPLICATION

This application is a U.S. national phase of International Application PCT/US2018/014710 filed on Jan. 22, 2018, which claims the benefit of U.S. provisional patent application No. 62/448,601, filed on Jan. 20, 2017. The entire contents of each of which is incorporated herein in its' entirety for all purposes.

REFERENCE TO SUBMISSION OF A SEQUENCE LISTING AS A TEXT FILE

The instant application contains a Sequence Listing which has been submitted electronically in ASCII format and is hereby incorporated by reference in its entirety. Said ASCII copy, created on Feb. 15, 2018, is named 057618-1073669_SL.txt and is 149,245 bytes in size.

FIELD

Technology provided herein relates in part to methods, processes, machines and apparatuses for determining sequences of nucleotides for nucleic acid templates in a nucleic acid sample. The technology provide herein also relates in part to methods, processes, machines and apparatuses for counting nucleic acid templates. Nucleic acid templates of a sample are tagged with nonrandom oligonucleotide adapters that include predetermined non-randomly generated molecular barcode sequences. The use of these nonrandom oligonucleotide adapters provides an efficient method to reduce sequencing errors, and increase the sensitivity of detection of low-frequency single nucleotide alterations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on 24 chromosomes (i.e., 22 autosomes, an X chromosome and a Y chromosome; see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations and/or genetic alterations. Certain genetic variations and/or genetic alterations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung, bladder, stomach, cervix, kidney, prostate, brain, and oesophageal).

Identifying one or more genetic variations and/or genetic alterations (e.g., copy number alterations, copy number variations, single nucleotide alterations, single nucleotide variations, chromosome alterations, translocations, deletions, insertions, and the like) or variances can lead to diagnosis of, or determining predisposition to, a particular medical condition. Identifying a genetic variance can result in facilitating a medical decision and/or employing a helpful medical procedure. In certain embodiments, identification of one or more genetic variations and/or genetic alterations involves the analysis of circulating cell-free nucleic acid. Circulating cell-free nucleic acid (CCF-NA), such as cell-free DNA (CCF-DNA) for example, is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

SUMMARY

Provided herein in certain embodiments are compositions, methods and systems for determining a sequence of nucleotides for one or more nucleic acid templates in a nucleic acid sample.

In certain embodiments, this disclosure provides for a method for determining a sequence of nucleotides for one or more nucleic acid templates in a nucleic acid sample, comprising: contacting double-stranded nucleic acid templates of the nucleic acid sample with partially double-stranded nonrandom oligonucleotide adapter species under ligation conditions, thereby generating adapter-ligated nucleic acid templates, wherein: each of the nonrandom oligonucleotide adapter species comprises a first oligonucleotide species and a second oligonucleotide species, each of the first oligonucleotide species comprises 5' to 3' a polynucleotide A and a polynucleotide B species and each of the second oligonucleotide species comprises 5' to 3' a polynucleotide B' species and a polynucleotide A'; each of the polynucleotide B species and the polynucleotide B' species are predetermined, are non-randomly generated, are the same length, and are about 4 to about 20 consecutive nucleotides in length; there are 300 or fewer polynucleotide B species and each polynucleotide B' species is a reverse complement of a polynucleotide B species; polynucleotide A is not a reverse complement of polynucleotide A'; the ratio of nucleic acid templates to polynucleotide B species is greater than 1,000 to 1; and the polynucleotide B species are annealed to complementary polynucleotide B' species and polynucleotide A' is not annealed to polynucleotide A; and amplifying the adapter-ligated nucleic acid templates, thereby generating amplicons; and sequencing all or a portion of each amplicon, thereby determining a sequence of nucleotides for the one or more nucleic acid templates in the nucleic acid sample.

In certain embodiments the composition may comprise a plurality of double stranded nucleic acid adapters. The individual nonrandom oligonucleotide adapter may comprise a defined first oligonucleotide species and a defined second oligonucleotide species. In certain embodiments each of the first oligonucleotide species may comprises 5' to 3' a polynucleotide A species and a polynucleotide B species where the polynucleotide A is a different sequence than the polynucleotide B. Also in an embodiment, each of the second oligonucleotide species comprises 5' to 3' a polynucleotide B' species, and a polynucleotide A', wherein the polynucleotide B' species are the reverse complement of the polynucleotide B species, but the polynucleotide A species are not the reverse complement of the polynucleotide A' species. In certain embodiments, each of the polynucleotide B species and the polynucleotide B' species are predetermined, non-randomly generated sequences. Also in some embodiments, the polynucleotide B species and the polynucleotide B' species are the same length as each other. In certain embodiments, each of the polynucleotide B and polynucleotide B' species are the same length as other polynucleotide B and B' polynucleotide species of the set. In certain embodiments, the polynucleotide B species and the polynucleotide B' specie are about 4 to about 20 consecutive nucleotides in length. In certain embodiments, the polynucleotide A species and the polynucleotide A' specie are about 4 to about 20 consecutive nucleotides in length. The plurality of adapters, in some embodiments, may comprise 999 or fewer polynucleotide B species. Also, in an embodiment, the adapters are designed such that the polynucleotide B species are positioned 3' to the A species of a first strand, and the polynucleotide B' species are positioned 5' to the polynucleotide A' species of the second strand such that upon annealing, double-stranded adapters having a "Y shape" with annealed polynucleotide B and polynucleotide B' sequences, and non-annealed polynucleotide A and polynucleotide A' sequences are formed.

In some embodiments the method may comprise contacting double-stranded nucleic acid templates of the nucleic acid sample with partially double-stranded nonrandom oligonucleotide adapter species as provided herein under ligation conditions, thereby generating adapter-ligated nucleic acid templates. The method may further comprise having the contacting be under conditions such that the ratio of nucleic acid templates to polynucleotide B species is greater than 1,000 to 1. The method may further comprise having polynucleotide B and B' species be the reverse complement of each other, but the polynucleotide A species designed such that it is not a reverse complement of polynucleotide A'; such that upon annealing the polynucleotide B species are annealed to complementary polynucleotide B' species and polynucleotide A' is not annealed to polynucleotide A. Thus, in an embodiment, the adapters are designed such that the B species are positioned 3' to the A species of a first strand, and the B' species are positioned 5' to the A species of the second (complementary strand) such that upon annealing, double-stranded adapters having a "Y shape" with annealed B and B' sequences, and non-annealed A and A' sequences are formed and annealed to the double-stranded template to form a double-stranded DNA molecule having "Y shaped" adapters on each end. The method may also comprises the step of amplifying the adapter-ligated nucleic acid templates, thereby generating amplicons. Also, in certain embodiments the method may comprise the step of sequencing all or a portion of each amplicon, thereby determining a sequence of nucleotides for the one or more nucleic acid template in the nucleic acid sample.

Also provided in certain aspects are methods for manufacturing a set of nonrandom nucleic acid sequencing adapters, for use in determining a sequence of nucleotides for one or more nucleic acid templates in a nucleic acid sample. The set of adapters may be designed to include 999 or fewer unique adapters such that the adapter set may be used in sequencing DNA from a subject, where the ratio of the nonrandom nucleic acid sequencing adapters to nucleic acid templates of the nucleic acid sample is greater than 50 to 1. The method may comprise the step of providing a set of first oligonucleotide species and a set of second oligonucleotide species, where each of the first oligonucleotide species comprises 5' to 3' a polynucleotide A and a polynucleotide B species and each of the second oligonucleotide species comprises 5' to 3' a polynucleotide B' species and a polynucleotide A'. In an embodiment, each of the polynucleotide B species and the polynucleotide B' species are a predetermined sequence and as such, are non-randomly generated. Also in certain embodiments each paired B and B' species and are the reverse complement of each other. In certain embodiments, each of the B and B' species are the same length as other B and B' species of the set. In certain embodiments, the B and B' species may range from about 4 to about 20 consecutive nucleotides in length. In certain embodiments; there are 999 or fewer polynucleotide B species and each polynucleotide B' species is a reverse complement of a polynucleotide B species; the ratio of nucleic acid templates to polynucleotide B species is greater than 1,000 to 1. In other embodiments; there are 500, or 400, or 300 or fewer polynucleotide B species and each polynucleotide B' species is a reverse complement of a polynucleotide B species; the ratio of nucleic acid templates to polynucleotide B species is greater than 1,000 to 1. In an embodiment, the adapters are configured such that polynucleotide A is not a reverse complement of polynucleotide A'. The method may comprise the step of synthesizing each of the first oligonucleotide species and each of the second oligonucleotide species separately. The method may also comprise the step of contacting each first oligonucleotide species with each second oligonucleotide species in separate pairs comprising the reverse complement polynucleotide B' species under annealing conditions, thereby generating partially double-stranded adapter species; where the polynucleotide B species are annealed to complementary polynucleotide B' species and polynucleotide A' is not annealed to polynucleotide A. Thus, in an embodiment, the adapters are designed such that the polynucleotide B species are positioned 3' to the polynucleotide A species of a first strand, and the polynucleotide B' species are positioned 5' to the polynucleotide A' species of the second strand such that upon annealing, double-stranded adapters having a "Y shape" with annealed polynucleotide B and polynucleotide B' sequences, and non-annealed polynucleotide A and polynucleotide A' sequences are formed Also provided in certain aspects are methods for counting nucleic acid templates for a nucleic acid sample, comprising contacting double-stranded nucleic acid templates of the nucleic acid sample with partially double-stranded nonrandom oligonucleotide adapter species as described herein under ligation conditions, thereby generating adapter-ligated nucleic acid templates, and sequencing the templates. In some embodiments, the adapter-ligated templates may be subjected to amplification prior to sequencing thereby generating amplicons; and identifying a set of amplicon duplicates, where the amplicon duplicates comprise amplified adapter-ligated nucleic acid templates comprising a polynucleotide B species at one end, and determining the number of amplicon duplicates comprising the polynucleotide B species.

Also provided are systems, machines and computer program products that carry out processes, or parts of processes, described herein. Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 16 shows an embodiment of a determination of the number of unique templates indistinguishable from each other on the basis of labeling and fragmentation of simulated samples.

DETAILED DESCRIPTION

Figure 1:
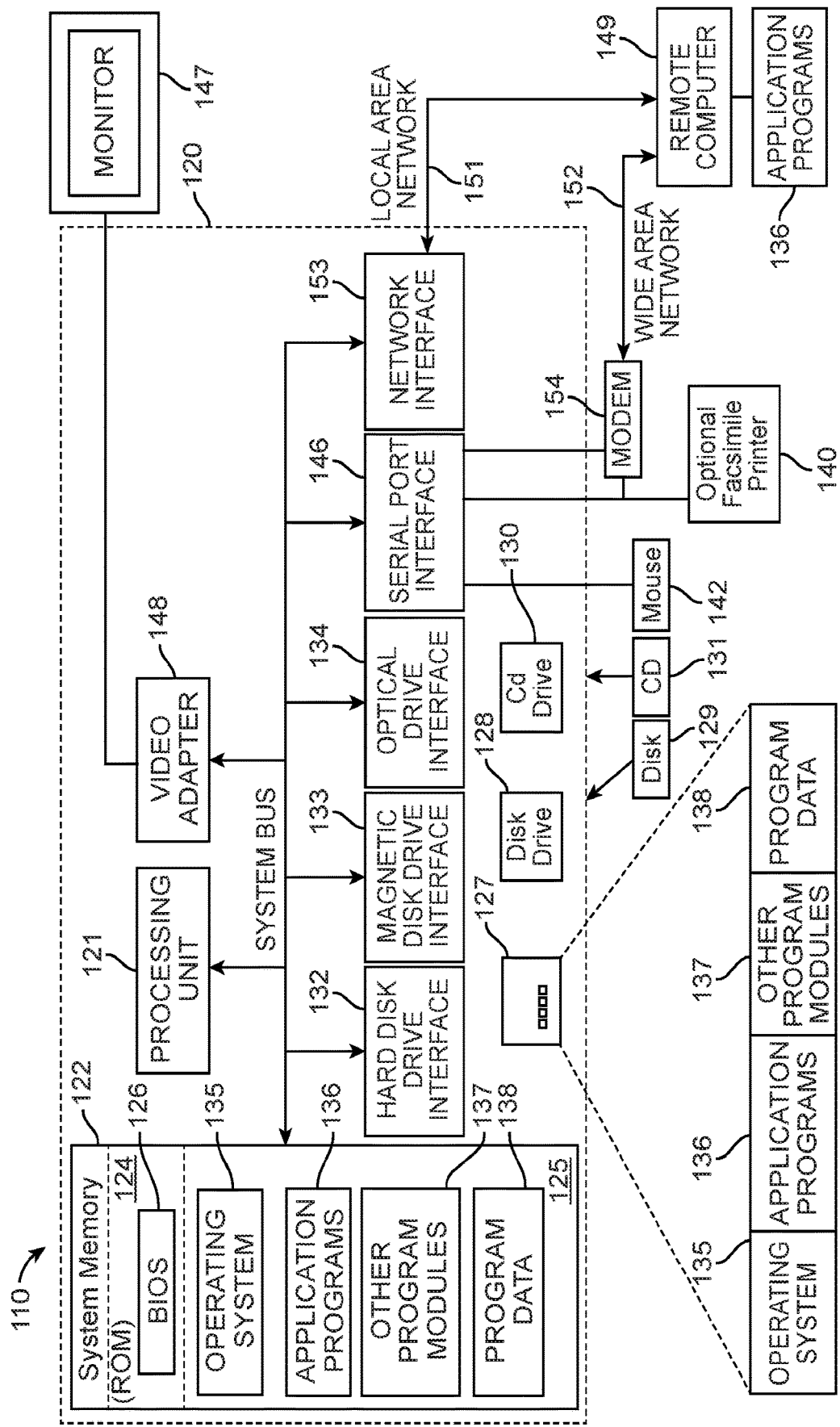
FIG. 1 shows an illustrative embodiment of a system in which certain embodiments of the technology may be implemented.

Provided in certain embodiments herein are methods and compositions for determining nucleotide sequences for a nucleic acid sample. The methods and compositions herein may be utilized for a variety of nucleic acid templates including, for example, fragmented or cleaved nucleic acid, cellular nucleic acid, and/or cell-free nucleic acid.

Thus, disclosed are nucleotide adapters and methods of using and making such adapters. Also disclosed are systems employing such adapters.

In certain embodiments, nucleic acid templates of a sample may be tagged with oligonucleotide adapters that include predetermined non-randomly generated molecular barcode sequences (nonrandom oligonucleotide adapters). The nonrandom oligonucleotide adapters may be prepared using predetermined barcode sequences, thus eliminating degenerate barcode synthesis and purification steps. Using nonrandom oligonucleotide adapters may allow for a more streamlined approach to automated sequencing of nucleic acid templates, while obtaining a low error rate.

Also provided herein are methods for the use of nonrandom oligonucleotide adapters to reduce sequencing errors, and increase the sensitivity of detection of genetic alterations (e.g., low-frequency single nucleotide alterations). The methods provided herein allow for sequencing of nucleic acid templates using a relatively low number of nonrandom oligonucleotide adapter sequences, or tags. Use of a predetermined discrete set of nonrandom oligonucleotide adapters can provide an additional layer of quality control during sequence analysis. For example, sequences obtained from nucleic acid templates ligated to the nonrandom oligonucleotide adapters described herein may be analyzed in part according to barcode sequences. Sequences obtained containing a barcode not matching a barcode in the predetermined set may be removed from analysis, for example, as being potential spurious sequencing artifacts. Thus, the use of a relatively small number of nonrandom oligonucleotide adapter species may allow for the efficient sequencing of nucleic acid templates for a sample, and provides additional quality control for the sequence analysis.

Also provided are systems, machines and computer program products that, in some embodiments, carry out methods or parts of methods described herein.

Nucleic Acid Templates and Adapters

In some embodiments of the present application, methods and compositions are provided to determine a partial or full sequence of a nucleic acid template. In other embodiments, methods and compositions are provided to count nucleic acid templates for a nucleic acid sample.

By "nucleic acid template" is meant a full length nucleic acid molecule, or a portion, or fragment, of a full length nucleic acid molecule, as provided herein. The nucleic acid template may be obtained by, for example, enzyme digestion, sonication, nebulization, biological fragmentation, degradation, apoptosis, necrosis, or physical shearing of larger nucleic acid molecules for a sample, and for example, by methods provided herein. For some applications, the nucleic acid template may be subjected to end repair, and end modification, such as "A-tailing" by methods provided herein. A nucleic acid template may be, for example, a fragment of a full length chromosome. A nucleic acid template may, for example, be an extracellular DNA or RNA molecule, or a fragment thereof, and may, for example, be about 25 to 1000, 50 to 500, 50 to 400, 50 to 300, or 50 to 100 base pairs in length, or may be at least 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, or 500 base pairs in length. Nucleic acid templates are generally double stranded, for most or all of the length, and may be referred to as template strand 1 and template strand 2. Template strand 1 and template strand 2 generally are complementary to each other. In certain instances, strands in a double stranded nucleic acid molecule may be referred to as a first strand and a second strand, a leading strand and a lagging strand, a forward strand and a reverse strand, a plus strand and a minus strand, or a sense strand and an antisense strand. In some examples, the nucleic acid templates are single stranded, and it is understood that the possible lengths provided herein may refer to bases, rather than base pairs. Where the template nucleic acid is single stranded, a complementary strand may be generated, for example by polymerization and/or reverse transcription, rendering the template nucleic acid double stranded and having a first strand (i.e., template strand 1) and a second strand (i.e., template strand 2). In some embodiments, the nucleic acid templates for a nucleic acid sample comprise cell-free DNA obtained following apoptosis. In some embodiments, the nucleic acid templates for a nucleic acid sample are fragmented or sheared molecules obtained from larger nucleic acid molecules.

A nucleic acid template refers to a nucleic acid template molecule for a sample. Each nucleic acid template for a sample is an individual molecule having a full length nucleotide sequence. A full length sequence refers to the sequence of nucleotides spanning the entire length of the individual template molecule (i.e., from the 5' end to the 3' end). In certain embodiments, the molecule is double stranded, in other embodiments, the molecule is single stranded. In some embodiments, a nucleic acid template has the same full length nucleotide sequence as another nucleic acid template for a sample. In some embodiments, a nucleic acid template has a different, or unique full length nucleotide sequence as other nucleic acid templates for a sample. In some embodiments, a nucleic acid sample comprises at least 1, 2, 3, 4, 5, 6, 7, 8, 9, 10, 20, 30, 40, 50, 60, 70, 80, 90, 100, 200, 300, 400, 500, 600, 700, 800, 900, or 1000 nucleic acid templates having full length nucleotide sequences that differ from each other by at least one nucleotide. In some embodiments, a nucleic acid sample comprises at least 1, 2, 3, 4, 5, 6, 7, 8, 9, 10, 20, 30, 40, 50, 60, 70, 80, 90, 100, 200, 300, 400, 500, 600, 700, 800, 900, or 1000 nucleic acid template molecules having the same full length nucleotide sequence. Copies, or amplicons of an original sample nucleic acid template molecule generally comprise the same full length nucleotide sequence as the original template molecule.

Provided in certain embodiments are methods of determining a sequence of nucleotides for one or more nucleic acid templates in a nucleic acid sample. Such methods may comprise, for example, contacting double-stranded nucleic acid templates of a nucleic acid sample with partially double-stranded nonrandom oligonucleotide adapter species under ligation conditions, thereby generating nonrandom oligonucleotide adapter-ligated nucleic acid templates, where each of the nonrandom oligonucleotide adapter species comprises or comprises or consists of a first oligonucleotide species and a second oligonucleotide species; each of the first oligonucleotide species comprises 5' to 3' a polynucleotide A and a polynucleotide B species and each of the second oligonucleotide species comprises 5' to 3' a polynucleotide B' species and a polynucleotide A'. In an embodiment, each of the polynucleotide B species and the polynucleotide B' species are predetermined, are non-randomly generated, are the same length, and are about 4 to about 20 consecutive nucleotides in length. Also, in an embodiment, there are 999 or fewer, or 900 or fewer, or 800 or fewer, or 700 or fewer, or 600 or fewer, or 500 or fewer, or 400 or fewer, or 300 or fewer, or 200 or fewer, or 100 or fewer or about polynucleotide B species. In certain embodiments, the ratio of nucleic acid templates to polynucleotide B species is greater than 1,000 to 1. Also in certain embodiments, each polynucleotide B' species is a reverse complement of a polynucleotide B species and polynucleotide A is not a reverse complement of polynucleotide A', such that the polynucleotide B species are annealed to complementary polynucleotide B' species and polynucleotide A' is not annealed to polynucleotide A, such that the double-stranded adapters are "Y-shaped" with the non-annealing A sequences at the end of the adapter that is not ligated to the DNA template. The method may further comprise after ligation of the adapters to the DNA template, amplifying the nonrandom oligonucleotide adapter-ligated nucleic acid templates, thereby generating amplicons; and sequencing all or a portion of each amplicon, thereby determining a sequence of nucleotides for the one or more nucleic acid templates in the nucleic acid sample.

As used herein, a polynucleotide B generally refers to a barcode, such as, for example, a barcode described herein (e.g., a nonrandom molecular barcode, a non-randomly generated molecular barcode, or a nondegenerate or non semidegenerate molecular barcode). A polynucleotide B species refers to a polynucleotide having a nucleotide sequence that is different from the nucleotide sequence of another polynucleotide B species. Thus, the nucleotide sequence of B1 is distinct from B2, and B3-Bn, where n=the total number of B species. Similarly, the nucleotide sequence of B1' (which is the reverse complement of B1) is distinct from B2', B3'-Bn'. A polynucleotide B species may be considered unique compared to other polynucleotide B species. By "different" or "unique" in this context is meant that when comparing one polynucleotide B species with another polynucleotide B species, the two polynucleotide B species have a nucleotide sequence that differs by at least one nucleotide identity. In some embodiments, polynucleotide B species in a predetermined set of polynucleotide B species differ from one another by at least 1 nucleotide identity. In some embodiments, polynucleotide B species in a predetermined set of polynucleotide B species differ from one another by at least 2 nucleotide identities. In some embodiments, polynucleotide B species in a predetermined set of polynucleotide B species differ from one another by at least 3 nucleotide identities. A set of polynucleotide B species that differ from one another by 1, 2, 3 or more nucleotide identities may be referred to as a set of unique polynucleotide B species. A polynucleotide B species may refer to the individual sequence of the polynucleotide B species before amplification of the nonrandom oligonucleotide adapter ligated template. Following amplification, there may be, for example, 10, 100, 1000, 10000, 100000, or more nucleic acid molecules, that is, copies of the nonrandom oligonucleotide adapter ligated templates, that have the same nucleotide sequence and therefore the same polynucleotide B species. An adapter species (e.g., double-stranded nonrandom oligonucleotide adapter species, partially double-stranded nonrandom oligonucleotide adapter species) generally comprises a polynucleotide B species and a polynucleotide B' species, where the B' species is the reverse complement of the B species. Amplified copies of each strand of the nonrandom oligonucleotide adapter portion of the nonrandom oligonucleotide adapter ligated template may comprise either a single polynucleotide B or a single polynucleotide B' species. In one non-limiting embodiment, 288 unique B (and B') sequences are used, thus providing the ability to generate 288*288 unique template-adapter constructs In one non-limiting embodiment, 1×10e11 to 2×10e11 molecules of template nucleic acids are used in the ligation reaction in which the number of the adaptor molecules is 10-500 fold in excess of the template nucleic acid molecules.

By nonrandom oligonucleotide adapter species is meant a nonrandom oligonucleotide adapter molecule that differs from another nonrandom oligonucleotide adapter molecule by at least one, at least two, or at least three nucleotide identities. A nonrandom oligonucleotide adapter species typically refers to a nonrandom oligonucleotide adapter comprising a unique polynucleotide B species.

Whereas two nonrandom oligonucleotide adapter species consist of nucleotide sequences that differ by at least one nucleotide, two nucleic acid template molecules may, or may not, have the same nucleotide sequence. For purposes of further explication only, where a ligation reaction comprises a sample having 10,0000 nucleic acid template molecules and 20 nonrandom oligonucleotide adapter species, the 10,0000 nucleic acid templates may also be referred to as 10,0000 nucleic acid molecules, and the 20 nonrandom oligonucleotide adapter species may be referred to as 20 nucleotide sequences. Using the designation "T" for each nucleic acid template molecule, the ligation reaction includes T1, T2, T3, T4, T5 . . . T10.0000 nucleic acid templates. In certain examples, the full length nucleotide sequence of, for example, T1, differs by at least one nucleotide from the full length nucleotide sequences of all of the other nucleic acid templates (T2-T10,000) for the sample. In other examples, the full length nucleotide sequence of, for example, T1 is the same as at least 1, 2, 3, 4, 5, 6, 7, 8, 9, 10, 20, 30, 40, 50, 60, 70, 80, 90, 100, 200, 300, 400, 500, 1000, 5000, or 10,000 other nucleic acid templates for the sample. Regardless of whether two template molecules happen to share identical sequences or not, each template in a sample is considered as an individual molecule.

Each nonrandom oligonucleotide adapter species comprises a B species and the complementary B' species. Using the designation "B" for each B species, the ligation reaction in this example includes nonrandom oligonucleotide adapter species comprising B1 (and B1'), B2 (and B2') . . . B20 (and B20') species. Because each B species (and B' species) refers to a nucleotide sequence, each ligation reaction may comprise many copies of the same B species. Thus, in the ligation reaction where the nonrandom oligonucleotide adapters are provided in stoichiometric excess of the nucleic acid templates, the reaction may comprise 1,000 nonrandom oligonucleotide adapters having the B1 and B1' species, 1,000 having the B2 and B2' species, etc. . . . . Thus, the reaction in this embodiment would include 1,000×20=20,000 nonrandom oligonucleotide adapter molecules, and 10,000 nucleic acid template molecules. Because the reaction includes multiple copies of each nonrandom oligonucleotide adapter species, the reaction comprises 20 nonrandom oligonucleotide adapter species, also referred to as 20 B species, and 10,000 nucleic acid template molecules.

Typically, adapter species are ligated to template molecules at random. In some instances, two different nucleic acid templates may be ligated to adapters comprising the same B species. In these instances, the adapter-ligated nucleic acid templates may be considered unique with respect to the combination of molecular barcode B (or B') sequence and the nucleic acid template sequence; or the combination of molecular barcode B (or B') sequence and the mapped genomic coordinates of the nucleic acid template sequence (as determined by mapping the template nucleotide sequence, as described herein). In some embodiments, adapter-ligated nucleic acid templates may be considered unique with respect to the combination of a first molecular barcode B (or B') sequence, a second molecular barcode B (or B') sequence, and the nucleic acid template sequence; or the combination of a first molecular barcode B (or B') sequence, a second molecular barcode B (or B') sequence, and the mapped genomic coordinates of the nucleic acid template sequence. In some embodiments, all or substantially all of the adapter-ligated nucleic acid templates in a sample may be considered unique. In some embodiments, at least 90%, 91%, 92%, 93%, 94%, 95%, 96%, 97%, 98%, or 99% of the adapter-ligated nucleic acid templates in a sample may be considered unique.

A double-stranded nonrandom oligonucleotide adapter species may, for example, be in a Y-shape, or in approximate Y-shape, in that polynucleotide A and polynucleotide A' provide the arms of the Y, and annealed polynucleotide B and polynucleotide B' species form the base of the Y shape. These adapters are referred to as Y adapters. Polynucleotides A and A' generally comprise sequencing adapter polynucleotides (e.g., Illumina adapter sequences or other sequencing adapter sequences) and/or sequences for amplifying the template nucleic acid (e.g., universal sequences for amplification primer annealing), and/or other sequences as described herein.

In some embodiments, the adapter is a nonrandom oligonucleotide adapter and the nonrandom oligonucleotide adapter species may, for example, be in a hairpin-shape, or in approximate hairpin-shape, collectively referred to as the hairpin adapter. The hairpin adapters may comprise polynucleotide A and polynucleotide A', which form the non-complementary portion (also known as the loop of the hairpin adapter); and polynucleotide B and polynucleotide B', which are annealed to form the complementary region (also known as the duplex region or the stem of the hairpin adapter). Polynucleotides A and A' are joined in one DNA strand. In some cases, polynucleotides A and A' are adjacent to each other. In some cases, polynucleotides A and A' are separated by 1-50 nucleotides, e.g., 1-30, 1-15, 1-10, 2-5 nucleotides. Polynucleotides A and A' generally comprise sequencing adapter polynucleotides (e.g., Illumina adapter sequences) and/or sequences for amplifying the template nucleic acid (e.g., universal sequences for amplification primer annealing), and/or other sequences as described herein.

In some embodiments, the polynucleotide B species and the polynucleotide B' species are non-degenerate. A non-degenerate set of polynucleotide species comprises a set of polynucleotides where each polynucleotide sequence is different, but the set does not represent examples of all potential nucleotide combinations. In some embodiments, the polynucleotide B species and the polynucleotide B' species are non-semidegenerate, that is, the set of polynucleotides includes positions where all possible nucleotide combinations are included. That is, in the example where A, C. T, and G are the possible nucleotides, in the set of polynucleotides, there are examples at one or more positions, of each of the possible nucleotides. Where a polynucleotide species is referred to as "non-degenerate" it is understood that the polynucleotide species is part of a non-degenerate set of polynucleotide species.

In contrast, a set of degenerate polynucleotide species, for example, is a set of polynucleotide species where each nucleotide position may be any nucleotide, such as, for example, A, C, G, T, or U, or any nucleotide analog with base pairing properties. Degenerate polynucleotide sets cover all possible nucleotide combinations at each position. For purposes of this example, where A, C, T, and G are the only nucleotides considered for the set, a polynucleotide species that is 10 nucleotides in length would include $4^{10}$ polynucleotides, representing examples of different polynucleotides at each position. Thus, where one degenerate polynucleotide adapter species is ligated to each nucleic acid template, for example, the number of degenerate polynucleotide species in a set of species for a 10 nucleotide nonrandom molecular barcode of an adapter would be $4^{10}$. For sequencing in methods where an adapter is ligated to each end of a nucleic acid template, the number of pairs of adapter species would be $4^{10} \times 4^{10} = 4^{20}$. Where a polynucleotide species is referred to as "degenerate" it is understood that the polynucleotide species is part of a degenerate set of polynucleotide species. In some examples, the degenerate polynucleotide species may be part of a degenerate set of polynucleotide species where not every possible degenerate polynucleotide has been physically synthesized during the course of the synthesis reaction.

Using the non-degenerate, nonrandom oligonucleotide adapters discussed herein, nucleic acid templates may be counted, and/or may be sequenced, following contacting nonrandom oligonucleotide adapters under ligation conditions. Ligation conditions may include nonrandom oligonucleotide adapter molecules provided in stoichiometric excess of nucleic acid templates, while including an excess of nucleic acid templates to nonrandom oligonucleotide adapter species. In an embodiment, the A species are the same for each of the adapters and the 288 species are defined by the B species. In one example, a pool of nonrandom oligonucleotide adapters includes 288 species. That is, while there may be thousands of nonrandom oligonucleotide adapter molecules in the ligation reaction, there are only 288 possible sequences for the nonrandom oligonucleotide adapters. Thus, theoretically, if one nonrandom oligonucleotide adapter is ligated to each nucleic acid template, one of 288 possible nonrandom oligonucleotide adapter species will ligate to each template molecule. For adapter-ligated nucleic acid templates comprising two nonrandom oligonucleotide adapter species (i.e., one adapter at each end of the template molecule), the number of possible paired combinations of nonrandom oligonucleotide adapter species would be 288×288=82,944.

As noted above, double-stranded nucleic acid templates may be provided in excess of the double-stranded nonrandom oligonucleotide adapter species. That is, the ratio of the nucleic acid templates to the nonrandom oligonucleotide adapter species provided in the ligation reaction may be, for example, greater than 10 to 1, greater than 100 to 1, greater than 1,000 to 1, greater than 10,000 to 1, greater than 100,000 to 1, greater than 500,000 to 1, greater than 600,000 to 1, greater than 700,000 to 1, greater than 800,000 to 1, greater than 900,000 to 1, or greater than 1,000,000 to 1.

The concentration of the non-random oligonucleotide adapter used for ligating the nucleic acid templates may vary, in some embodiments, it is between 20-600 nM, e.g., 50-500 nM, 50-400 nM, 70-200 nM, or about 100 nM. The concentration of the nucleic acid templates used in the ligation may also vary, in some embodiments, the nucleic acid templates are 20-40 ng, e.g., 25-30 ng.

In some embodiments, each of the first oligonucleotide species comprises a polynucleotide C species between the polynucleotide A and the polynucleotide B species; each of the second oligonucleotide species comprises a polynucleotide C' species between polynucleotide A' and the polynucleotide B' species. In certain embodiments, each polynucleotide C' species is the reverse complement of the polynucleotide C species, and the polynucleotide C species are able to anneal to the complementary polynucleotide C' species. In some embodiments, each of the polynucleotide C species comprises or consists of the same nucleotide sequence. In some embodiments, the polynucleotide C species comprise universal sequences, i.e., common sequences shared by different adapters, and the polynucleotide C' species comprise universal sequences. In some embodiments, the polynucleotide C species and/or the polynucleotide C' species may comprise an identifier, such as, for example, an index polynucleotide or a barcode polynucleotide. In some embodiments, each of polynucleotide C species comprises or consists of at least two different nucleotide sequences. The polynucleotide C and/or C' species may comprise, for example, an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, the like or combinations thereof.

In some embodiments, the double-stranded nucleic acid templates are double-stranded DNA templates. In some embodiments, the double-stranded nucleic acid templates are double-stranded RNA templates. In some embodiments, the oligonucleotide adapters are DNA adapters. In some embodiments, the adapters are RNA adapters. In some cases, the adapters comprise both DNA and RNA.

In certain embodiments, amplifying the adapter-ligated nucleic acid templates generates double-stranded amplicons, and sequencing comprises sequencing all or a portion of each strand of the amplicons. In some embodiments, the adapter-ligated nucleic acid templates are amplified by a process comprising linear amplification. In some embodiments, the adapter-ligated nucleic acid templates are amplified by a process comprising exponential amplification. In some embodiments, the adapter-ligated nucleic acid templates are amplified by a process comprising isothermal amplification. In some embodiments, the adapter-ligated nucleic acid templates are amplified by a process comprising a single primer extension reaction. In some embodiments, amplification is not performed prior to a clustering reaction on an instrument capable of next generation sequencing.

In certain embodiments, the double-stranded nucleic acid templates are blunt-ended. In some embodiments, the nucleic acid templates comprise at least one blunt end. In some embodiments, the nucleic acid templates are sheared double-stranded DNA templates. In some embodiments, the nucleic acid templates are restriction enzyme-digested double-stranded DNA templates. In some embodiments, the method comprises blunt-ending the nucleic acid templates before contacting the nucleic acid templates with the non-random oligonucleotide adapter species. In some embodiments, the nonrandom oligonucleotide adapter species comprise a blunt end. In some embodiments, the double-stranded nucleic acid templates comprise a ligation linker.

In some embodiments, the method comprises joining a ligation linker to the blunt end of a nucleic acid template. In some embodiments, the ligation linker is comprises at least one of an A-overhang, T-overhang, a CG-overhang, a blunt end, or any ligatable nucleic acid sequence. In some embodiments, the ligation linker is an A-overhang. In some embodiments, the double-stranded nonrandom oligonucleotide adapter species comprises a ligation linker. In some embodiments, the ligation linker is selected from the group consisting of an A-overhang, T-overhang, a CG-overhang, a blunt end, or any ligatable nucleic acid sequence. In some embodiments, the ligation linker is a T-overhang. In some embodiments, both ends of a nucleic acid template include the same type of ligation linker. In some embodiments, both ends of a nucleic acid template include different types of ligation linkers.

In certain embodiments, the nucleic acid sample is obtained from a subject. In some embodiments, the nucleic acid is cell-free nucleic acid. In some embodiments, the nucleic acid sample is blood plasma, blood serum, or urine. In some embodiments, the nucleic acid sample is circulating cell-free nucleic acid. In some embodiments, the nucleic acid sample is isolated from blood plasma, blood serum, or urine. In some embodiments, the nucleic acid sample is isolated from a sample of tissue, cells, or fluid obtained from a subject. In some embodiments, the subject is human.

In certain embodiments, the nucleic acid sample is isolated from a sample of tissue, cells, or fluid obtained from a subject. In certain embodiments, the nucleic acid sample is partially purified from a sample of tissue, cells, or fluid obtained from a subject. In some embodiments, the sequence of nucleotides for one or more nucleic acid templates in a nucleic acid sample is determined in situ. In some embodiment, the nucleic acid templates are enriched. In some embodiments, the method comprises capturing a subset of the nucleic acid templates by hybridization to capture probes under hybridization conditions, thereby generated captured target nucleic acid templates. In some embodiments, the method comprises: enriching for target nucleic acid templates representing one or more selected genes by means of amplifying target nucleic acid templates in the nucleic acid sample that are complementary to selected genes. In some embodiments, the method of obtaining the nucleic acid sample comprises eluting captured target nucleic acid templates from the capture probes. In some embodiments, the capture probes are in an array. In some embodiments, the capture probes are attached to beads.

In certain embodiments of the method, the sequencing depth is at about 100 fold to about 200,000 fold. In some embodiments, the sequencing depth is at about 1,000 fold to about 150,000 fold. In some embodiments, the sequencing depth is at about 5,000 fold to about 100,000 fold. In some embodiments, the sequencing depth is at about 10,000 fold to about 70,000 fold. In some embodiments, the sequencing depth is at about 20,000 fold to about 60,000 fold. In some embodiments, the sequencing depth is at about 30,000 fold to about 50,000 fold. In some embodiments, the sequencing depth is about 100; 200; 300; 400; 500; 600; 700; 800; 900; 1,000; 1,250; 1,500; 1,750 2,000; 2,250; 2,500, 2, 750; 3,000; 3,500; 4,000; 4,500; 5,000; 5,500; 6,000; 6,500; 7,000; 7,500; 8,000; 8,500; 9,000; 9,500; 10,000; 15,000; 20,000; 25,000; 30,000; 35,000; 40,000; 45,000; 50,000; 55,000; 60,000; 65,000; 70,000; 75,000; 80,000; 85,000; 90,000; 95,000; 100,000, 110,000; 120,000; 130,000; 140,000; 150,000; 160,000; 170,000; 180,000; 190,000; or 200,000 fold.

Template Preparation for Sequencing

In certain embodiments, the disclosed sequencing adapters are ligated to each end of a nucleic acid templates. Either one, or both of the adapters may comprise nonrandom molecular barcode sequences. A sequencing adapter that comprises a nonrandom molecular barcode sequence may be referred to herein as a "nonrandom oligonucleotide adapter." Provided in certain embodiments of the methods herein are sequencing methods where each of the nucleic acid templates is ligated to one nonrandom oligonucleotide adapter. In certain embodiments, each adapter-ligated nucleic acid template, having a first end and a second end, comprises one nonrandom oligonucleotide adapter at one of the first and second ends. In certain embodiments, each adapter-ligated nucleic acid template comprises a nonrandom oligonucleotide adapter at a first end and a standard sequencing adapter at a second end. In certain embodiments, each adapter-ligated nucleic acid template comprises or consists of one nonrandom oligonucleotide adapter at one end. In certain embodiments, each adapter-ligated nucleic acid template comprises or consists of one nonrandom oligonucleotide adapter at a first end and a standard sequencing adapter at a second end.

By "standard sequencing adapter" in the context of adapters ligated to more than one nucleic acid template is meant that the adapter provided in the ligation reaction for ligation to a sample of nucleic acid templates comprises or comprises or consists of the same nucleotide sequence. As used herein, a standard sequencing adapter generally does not comprise part of the nonrandom B and B' species oligonucleotide of the disclosed adapters. Standard sequencing adapters may comprise, for example, universal sequences, sample ID sequences, and the like, but where a collection of standard sequencing adapters are provided in a ligation reaction, each standard sequencing adapter comprises or comprises or consists of the same nucleotide sequence. For example, at least 80, 85, 90, 95, 96, 97, 98, or 99% of the standard sequencing adapters ligated to nucleic acid templates in a sample of the present application consist of the same nucleotide sequence. Standard sequencing adapters may include, for example, Illumina sequencing adapters for use with systems such as, for example, MISEQ, NEXTSEQ, and HISEQ systems.

Provided in certain embodiments of the methods herein, are sequencing methods where each nucleic acid template is ligated to two nonrandom oligonucleotide adapters (e.g., one adapter on each end of the template molecule). In certain embodiments, each adapter-ligated nucleic acid template comprises a first nonrandom oligonucleotide adapter at a first end and a second nonrandom oligonucleotide adapter at a second end. The first and second nonrandom oligonucleotide adapters may or may not comprise the same B-species. In some embodiments, the B species at each end of the adapter-ligated nucleic templates are the same or different. Often, the B species at each end of the adapter-ligated nucleic templates are different.

Nonrandom oligonucleotide adapters comprising a particular B species (e.g., "B1") may be ligated to more than one nucleic acid template. Often, nonrandom oligonucleotide adapters comprising a particular B species, e.g., B1, are ligated to more than one nucleic acid template, where each nucleic acid template has a different sequence (e.g., T1, T2, T3 . . . ). In such instances, ligation reactions may produce B1T1, B1T2, B1T3 nonrandom oligonucleotide adapter-ligated nucleic acid templates. In some embodiments, one of the B species for one nonrandom oligonucleotide adapter-ligated nucleic acid template is the same as one of the B species for another nonrandom oligonucleotide adapter-ligated nucleic acid template. In some embodiments, both of the B species for one nonrandom oligonucleotide adapter-ligated nucleic acid template are the same as both of the B species for another nonrandom oligonucleotide adapter-ligated nucleic acid template. In some embodiments, the B species for at least two adapter-ligated nucleic acid templates consist of a different nucleotide sequence. In some embodiments, copies of a first double-stranded adapter species comprising a first B species and a first B' species are ligated to at least two double-stranded nucleic acid templates.

In certain embodiments of the methods herein, copies of a first double-stranded nonrandom oligonucleotide adapter species comprising a first B species and a first B' species (e.g., B1 and B1') are ligated to a first end of at least two double-stranded nucleic acid templates; and copies of a second double-stranded nonrandom oligonucleotide adapter species comprising a second B species and a second B' species (e.g., B2 and B2') are ligated to a second end of at least two double-stranded nucleic acid templates. In some embodiments, the at least two double-stranded nucleic acid templates comprise or consist of nucleotide sequences that differ by at least one nucleotide.

As noted above, the number of nonrandom oligonucleotide adapter DNA molecules provided in the ligation reactions typically is in excess of the amount of nucleic acid template molecules. This excess of nonrandom oligonucleotide adapter DNA molecules helps to ensure that each nucleic acid template is ligated to oligonucleotide adapters. The ratio of nonrandom oligonucleotide adapter molecules to nucleic acid templates provided in the ligation reaction can be, for example, greater than 20 to 1. In some embodiments, the ratio of nonrandom oligonucleotide adapter molecules to nucleic acid templates is, for example, greater than 10 to 1, 15 to 1, 20 to 1, 25 to 1, 30 to 1, 35 to 1, 40 to 1, 45 to 1, 50 to 1, 55 to 1, 60 to 1, 65 to 1, 70 to 1, 75 to 1, 80 to 1, 85 to 1, 90 to 1, 95 to 1, or 100 to 1. In some embodiments, the ratio of nonrandom oligonucleotide adapter molecules to nucleic acid templates is, for example, less than 100 to 1, for example, less than 50 to 1, for example, less than 45 to 1. In some embodiments, the ratio of nonrandom oligonucleotide adapter molecules to nucleic acid templates is about 20 to 1, 30 to 1, 40 to 1, 45 to 1, 50 to 1, 55 to 1, 60 to 1, 65 to 1, or 70 to 1.

In contrast to the ratio of molecules of nonrandom oligonucleotide adapter molecules to molecules of nucleic acid template, the number of unique nucleic acid templates in the ligation reaction is provided in excess of the number of unique nonrandom oligonucleotide adapter species, or nonrandom oligonucleotide adapter sequences, comprising unique molecular barcodes. Multiple copies of a nonrandom oligonucleotide adapter species comprising a unique polynucleotide B species sequence and the reverse complement polynucleotide B' species may be present in the ligation reaction. The number of nonrandom oligonucleotide adapter species is provided in a depleting amount, and as a result of the ligation reaction, each nonrandom oligonucleotide adapter-ligated nucleic acid template may, in some instances, not comprise a unique polynucleotide B nucleotide sequence, or unique molecular barcode. Copies of a nonrandom oligonucleotide adapter comprising the same B species or molecular barcode may be ligated to more than one nucleic acid template. In some embodiments, the ratio of the number of nucleic acid templates to the number of nonrandom oligonucleotide adapter species (each comprising a different B species nucleotide sequence) is about 1,000,000 to 1. In some embodiments, the ratio of nucleic acid templates to the number of nonrandom oligonucleotide adapter species is greater than 100 to 1, 250 to 1, 500 to 1, 750 to 1, 1,000 to 1, 5,000 to 1, 10.000 to 1, 20,000 to 1, 30,000 to 1, 40,000 to 1, 50.000 to 1, 60,000 to 1, 70,000 to 1, 80,000 to 1, 90.000 to 1, 100,000 to 1, 200,000 to 1, 300,000 to 1, 400,000 to 1, 500,000 to 1, 600,000 to 1, 700,000 to 1, 800,000 to 1,900,000 to 1, 1,000,000 to 1, 1,200,000 to 1, 1,400,000 to 1, 1,600,000 to 1, 1,800,000 to 1, or 2,000,000 to 1.

Provided in some embodiments, in a nucleic acid template-nonrandom oligonucleotide adapter ligation reaction, there are 999 or fewer polynucleotide B species. In some embodiments, there are 400 or fewer polynucleotide B species. In some embodiments, there are 300 or fewer polynucleotide B species. In some embodiments, there are about 300 to about 400 polynucleotide B species. In some embodiments, there are about 100 to about 500 polynucleotide B species. In some embodiments, there are about 200 to 300 polynucleotide B species. In some embodiments, there are about 280 to about 290 polynucleotide B species In some embodiments, there are 288 B species. In some embodiments, there are 1000, 750, 500, 475, 450, 425, 400, 375, 350, 325, 300, 275, 250, 225, 200, 175, 150, 125, or 100 or fewer polynucleotide B species.

Thus, in a ligation reaction that comprises, for purposes of this example, 300,000 nucleic acid templates and 300 polynucleotide B species, at a ratio of 1,000 nucleic acid templates per polynucleotide B species, where the nonrandom oligonucleotide adapter molecules are provided in excess (1,000 fold) of the nucleic acid templates, the reaction includes 300,000 nucleic acid templates and 3×10 nonrandom oligonucleotide adapter molecules. The $3 \times 10^8$ nonrandom oligonucleotide adapter molecules represent 300 B species, that is, 300 B sequences. The reaction of this example includes 1,000 nonrandom oligonucleotide adapter molecules comprising the B1 sequence, 1,000 comprising the B2 sequence, etc. . . . to the B300 sequence. And, the reaction of this example includes 300,000 nucleic templates (molecules): T1, T2, T3, T4 . . . T300,000. Nucleic acid templates may or may not have the same nucleotide sequence.

In some embodiments, there may be more than one nonrandom oligonucleotide adapter species that has the same polynucleotide B species present in a ligation reaction. In embodiments, less than 90, 80, 70, 60, 50, 40, 30, 20, 10, 5, 4, 3, 2, or 1% of the nonrandom oligonucleotide adapter-ligated nucleic acid templates comprise a polynucleotide B species that is different from the polynucleotide B species on the other nonrandom oligonucleotide adapter-ligated nucleic acid templates.

As discussed in more detail herein, the use of the disclosed Y adapters can provide for increased specificity and sensitivity in DNA sequencing reactions. The use of double-stranded Y adapters allows for the two strands (i.e., forward and reverse) of each DNA template to be identified as being from the same molecule. In this way, if there is a detected base change at a particular position in the DNA template on one strand that is not replicated for the other strand, it can be inferred that the base change is due to artifactual errors introduced during sample processing including, but not limited to, sequencing errors, and is not a true mutation.

Figure 13:
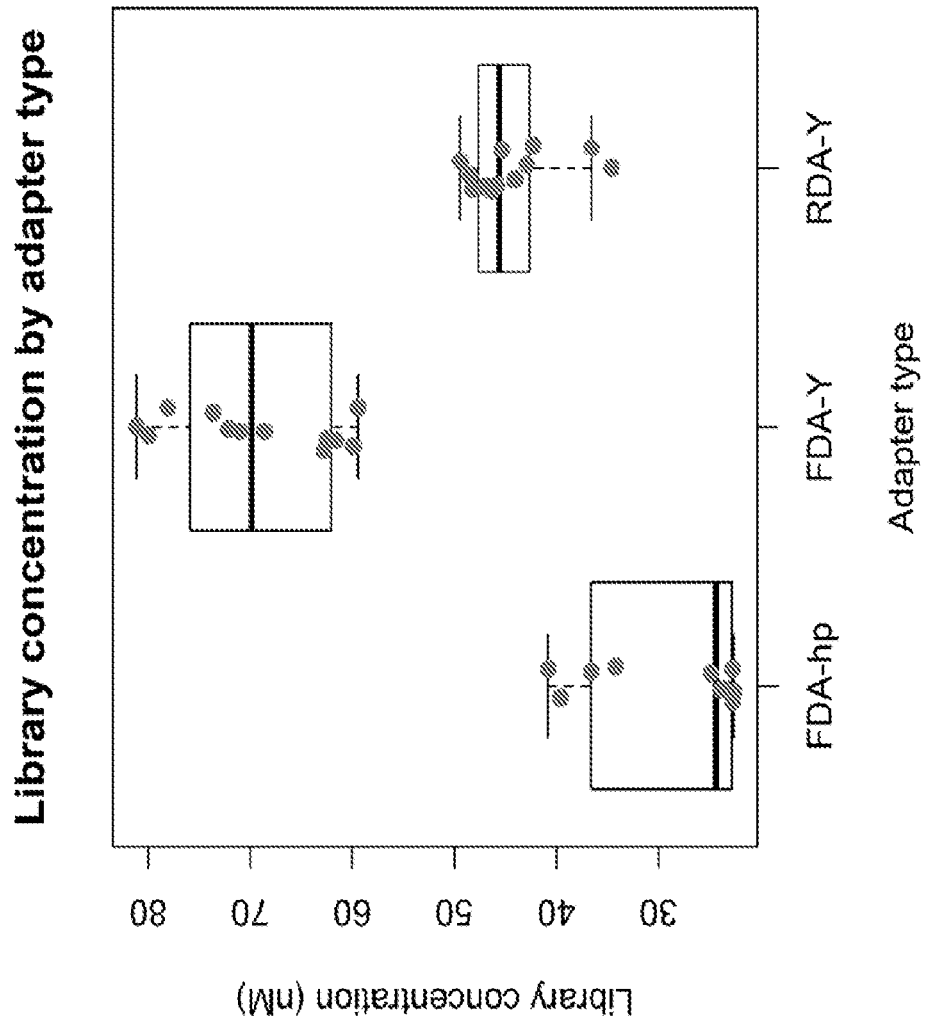
FIG. 13 shows and embodiment of the validation of adapter constructs using library yield for a readout of process efficiency.

The use of nonrandom duplex adapters is more advantageous over the traditional random duplex adaptors. First, manufacture of nonrandom duplex adapters is more direct and streamlined, as it does not require extension and cleavage, but only hybridization of oligonucleotides. Second, through careful design of polynucleotide species, as opposed to randomization, sample processing errors occurring within the polynucleotide motif can be corrected for and eliminated, which is expected to improve the ultimate data quality. Third, nonrandom duplex adapters are significantly more efficient at sampling template molecules than are random duplex adapters; an illustrative examples is shown in FIG. 13, in which nonrandom duplex adapters results in higher library yield than random duplex adapters.

In some embodiments, the presence of a single nucleotide alteration in the nucleic acid template is determined and the single nucleotide alteration is present at a frequency of 5, 4.5, 4, 3.5, 3, 2.5, 2, 1.5, or 1 percent or lower. In some embodiments, the single nucleotide alteration is present at a frequency lower than 1 percent. In some embodiments, the single nucleotide alteration is present at a frequency of 1, 0.75, 0.5, 0.25, 0.1, 0.075, 0.05, 0.025, 0.01, 0.0075, 0.005, 0.0025, 0.001, 0.00075, 0.0005, 0.00025, or 0.0001 percent or lower.

In some embodiments, the ratio of the number of nucleic acid templates for the nucleic acid sample to the number of polynucleotide B species in the nonrandom oligonucleotide adapters is about 1,000,000 to 1, the presence of a single nucleotide alteration in the nucleic acid template is determined and the single nucleotide alteration is present at a frequency of 5, 4.5, 4, 3.5, 3, 2.5, 2, 1.5, or 1 percent or lower. In some embodiments, the single nucleotide alteration is present at a frequency lower than 1 percent. In some embodiments, the single nucleotide alteration is present at a frequency of 1, 0.75, 0.5, 0.25, 0.1, 0.075, 0.05, 0.025, 0.01, 0.0075, 0.005, 0.0025, 0.01, 0.00075, 0.0005, 0.00025, or 0.0001 percent or lower.

In some embodiments, the ratio of the number of nucleic acid templates for the nucleic acid sample to the number of polynucleotide B species in the nonrandom oligonucleotide adapters is about 1,000,000; 900,000; 800,000; 700,000; 600,000; 500,000; 400,000; 300,000; 200,000; 100,000; 50,000; 25,000; or 10,000 to 1, the presence of a single nucleotide alteration in the nucleic acid template is determined and the single nucleotide alteration is present at a frequency of 5, 4.5, 4, 3.5, 3, 2.5, 2, 1.5, or 1 percent or lower. In some embodiments, the single nucleotide alteration is present at a frequency lower than 1 percent. In some embodiments, the single nucleotide alteration is present at a frequency of 1, 0.75, 0.5, 0.25, 0.1, 0.075, 0.05, 0.025, 0.01, 0.0075, 0.005, 0.0025, 0.001, 0.00075, 0.0005, 0.00025, or 0.0001 percent or lower.

In certain embodiments, the method comprises providing a base call, where each base call represents a single nucleotide located at a single nucleotide position in the nucleic acid template. In some embodiments, the frequency of base call errors is $0.9 \times 10^{-3}$, $0.7 \times 10^{-3}$, $0.5 \times 10^{-3}$, $0.25 \times 10^{-3}$, $1 \times 10^{-4}$, $7 \times 10^{-4}$, $5 \times 10^{-5}$, $3 \times 10^{-5}$, $1 \times 10^{-5}$, $7 \times 10^{-6}$, $5 \times 10^{-6}$, $3 \times 10^{-6}$, $1 \times 10^{-6}$, $7 \times 10^{-7}$, $5 \times 10^{-7}$, $3 \times 10^{-7}$, or $1 \times 10^{-7}$ or lower. In some embodiments, the frequency of base call errors is $1 \times 10^{-3}$ or lower. In some embodiments, the frequency of base call errors is lower than $1 \times 10^{-3}$. In some embodiments, the frequency of base call errors is $0.9 \times 10^{-3}$, $0.8 \times 10^{-3}$, $0.7 \times 10^{-3}$, $0.6 \times 10^{-3}$, $0.5 \times 10^{-3}$, $0.4 \times 10^{-3}$, $0.3 \times 10^{-3}$, $0.2 \times 10^{-3}$, $1 \times 10^{-4}$, $0.9 \times 10^{-4}$, $0.8 \times 10^{-4}$, $0.7 \times 10^{-4}$, $0.6 \times 10^{-4}$, $0.5 \times 10^{-4}$, $0.4 \times 10^{-4}$, $0.3 \times 10^{-4}$, $0.2 \times 10^{-4}$, $1 \times 10^{-5}$, $0.9 \times 10^{-5}$, $0.8 \times 10^{-5}$, $0.7 \times 10^{-5}$, $0.6 \times 10^{-5}$, $0.5 \times 10^{-5}$, $0.4 \times 10^{-5}$, $0.3 \times 10^{-5}$, $0.2 \times 10^{-5}$, $1 \times 10^{-6}$, $0.9 \times 10^{-6}$, $0.8 \times 10^{-6}$, $0.7 \times 10^{-6}$, $0.6 \times 10^{-6}$, $0.5 \times 10^{-6}$, $0.4 \times 10^{-6}$, $0.3 \times 10^{-6}$, $0.2 \times 10^{-6}$, or $1 \times 10^{-7}$ or lower.

The ratio of nonrandom oligonucleotide adapter molecules to nucleic acid templates provided in the ligation reaction is, for example, greater than 20 to 1. In some embodiments, the ratio of nonrandom oligonucleotide adapter molecules to nucleic acid templates is, for example, greater than 10, 15, 20, 25, 30, 35, 40, 45, 50, 55, 60, 65, 70, 75, 80, 85, 90, 95, or 100 to 1. In some embodiments, the ratio of nonrandom oligonucleotide adapter molecules to nucleic acid templates is, for example, less than 100 to 1, for example, less than 50 to 1, for example, less than 45 to 1. In some embodiments, the ratio of nonrandom oligonucleotide adapter molecules to nucleic acid templates is about 20, 30, 40, 45, 50, 55, 60, 65, or 70 to 1.

In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $1 \times 10^{-7}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $1 \times 10^{-6}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $0.5 \times 10^{-6}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $1 \times 10^{-5}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $0.8 \times 10^{-5}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $0.5 \times 10^{-5}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $0.3 \times 10^{-5}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $1 \times 10^{-4}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $0.8\times10^{-4}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $0.5\times10^{-4}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $0.3\times10^{-4}$ or lower. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is lower than $1\times10^{-3}$. In some embodiments, the method comprises base calls, where each base call represents a single nucleotide in the nucleic acid template; the ratio of the number of nucleic acid templates for the nucleic acid sample to the number of polynucleotide B species in the nonrandom oligonucleotide adapters is about 1,000,000 to 1; and the frequency of base call errors is $1\times10^{-3}$ or lower.

In some embodiments, the method comprises base calls, where each base call represents a single nucleotide in the nucleic acid template; the ratio of the number of nucleic acid templates to the number of polynucleotide B species (for example, the number of nonrandom oligonucleotide adapter species, each comprising a different polynucleotide B species) is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $1\times10^{-7}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $1\times10^{6}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $0.5\times10^{-6}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $1\times10^{-5}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $0.8\times10^{-5}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $0.5\times10^{-5}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $0.3\times10^{-5}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $1\times10^{-4}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $0.8\times10^{-4}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $0.5\times10^{-4}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $0.3\times10^{-4}$ or lower. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is lower than $1\times10^{-3}$. In some embodiments, the method comprises base calls, where each base call represents a single nucleotide in the nucleic acid template; the ratio of the number of nucleic acid templates to the number of polynucleotide B species is greater than 1,000,000, 900,000, 800,000, 700,000, 600,000, 500,000, 400,000, 300,000, 200,000, 100,000, 80,000, 60,000, 40,000, 20,000, 10,000 to 1; and the frequency of base call errors is $1\times10^{-3}$ or lower.

In some embodiments, the presence of a single nucleotide alteration in the nucleic acid is determined; there are 999 or fewer polynucleotide B species; and the single nucleotide alteration is present at a frequency of 5, 4.5, 4, 3.5, 3, 2.5, 2, 1.5, or 1 percent or lower. In some embodiments, the single nucleotide alteration is present at a frequency lower than 1 percent. In some embodiments, the single nucleotide alteration is present at a frequency of 1, 0.75, 0.5, 0.25, 0.1, 0.075, 0.05, 0.025, 0.01, 0.0075, 0.005, 0.0025, 0.001, 0.00075, 0.0005, 0.00025, or 0.0001 percent or lower. In some embodiments, the presence of a single nucleotide alteration in the nucleic acid is determined; there are 500 or fewer polynucleotide B species; and the single nucleotide alteration is present at a frequency of 5, 4.5, 4, 3.5, 3, 2.5, 2, 1.5, or 1 percent or lower. In some embodiments, the single nucleotide alteration is present at a frequency lower than 1 percent. In some embodiments, the single nucleotide alteration is present at a frequency of 1, 0.75, 0.5, 0.25, 0.1, 0.075, 0.05, 0.025, 0.01, 0.0075, 0.005, 0.0025, 0.001, 0.00075, 0.0005, 0.00025, or 0.0001 percent or lower. In some embodiments, the presence of a single nucleotide alteration in the nucleic acid is determined; there are 400 or fewer polynucleotide B species; and the single nucleotide alteration is present at a frequency of 5, 4.5, 4, 3.5, 3, 2.5, 2, 1.5, or 1 percent or lower. In some embodiments, the single nucleotide alteration is present at a frequency lower than 1 percent. In some embodiments, the single nucleotide alteration is present at a frequency of 1, 0.75, 0.5, 0.25, 0.1, 0.075, 0.05, 0.025, 0.01, 0.0075, 0.005, 0.0025, 0.001, 0.00075, 0.0005, 0.00025, or 0.0001 percent or lower. In some embodiments, the presence of a single nucleotide alteration in the nucleic acid is determined; there are 300 or fewer polynucleotide B species; and the single nucleotide alteration is present at a frequency of 5, 4.5, 4, 3.5, 3, 2.5, 2, 1.5, or 1 percent or lower. In some embodiments, the single nucleotide alteration is present at a frequency lower than 1 percent. In some embodiments, the single nucleotide alteration is present at a frequency of 1, 0.75, 0.5, 0.25, 0.1, 0.075, 0.05, 0.025, 0.01, 0.0075, 0.005, 0.0025, 0.001, 0.00075, 0.0005, 0.00025, or 0.0001 percent or lower. In some embodiments, the presence of a single nucleotide alteration in the nucleic acid is determined; there are about 200 to about 300 polynucleotide B species; and the single nucleotide alteration is present at a frequency of 5, 4.5, 4, 3.5, 3, 2.5, 2, 1.5, or 1 percent or lower. In some embodiments, the single nucleotide alteration is present at a frequency lower than 1 percent. In some embodiments, the single nucleotide alteration is present at a frequency of 1, 0.75, 0.5, 0.25, 0.1, 0.075, 0.05, 0.025, 0.01, 0.0075, 0.005, 0.0025, 0.001, 0.00075, 0.0005, 0.00025, or 0.0001 percent or lower.

In some embodiments, the presence of a single nucleotide alteration in the nucleic acid is determined; there are about 280 to about 290 polynucleotide B species; and the single nucleotide alteration is present at a frequency of 5, 4.5, 4, 3.5, 3, 2.5, 2, 1.5, or 1 percent or lower. In some embodiments, the single nucleotide alteration is present at a frequency lower than 1 percent. In some embodiments, the single nucleotide alteration is present at a frequency of 1, 0.75, 0.5, 0.25, 0.1, 0.075, 0.05, 0.025, 0.01, 0.0075, 0.005, 0.0025, 0.001, 0.00075, 0.0005, 0.00025, or 0.0001 percent or lower.

Error Detection

In some embodiments of the methods and systems provided herein, the sequence of at least one polynucleotide B species and the sequence of at least one polynucleotide B' species are determined and are utilized to identify one or more errors. In some embodiments, the errors are sequencing errors and/or amplification errors. In some embodiments, the sequencing generates sequence reads and the sequence reads are mapped to regions of a reference genome. Thus, as discussed above, the use of the disclosed Y adapters can provide for increased specificity and sensitivity in DNA sequencing reactions. The use of double-stranded Y adapters allows for the two strands (i.e., forward and reverse) of each DNA template to be identified as being from the same molecule. In this way, if there is a detected base change at a particular position in the DNA template on one strand that is not replicated for the other strand, it can be inferred that the base change is due to artifactual errors introduced during sample processing including, but not limited to, sequencing errors, and is not a true mutation.

In certain embodiments, the methods comprise sequencing amplified adapter-ligated nucleic acid templates for a nucleic acid sample. In certain embodiments, the methods and/or systems comprise reviewing sequences obtained for amplified adapter-ligated nucleic acid templates for a nucleic acid sample. Such review may comprise identifying a set of amplicon duplicates, where the amplicon duplicates comprise amplified adapter-ligated nucleic acid templates comprising at least one nonrandom oligonucleotide adapter comprising a polynucleotide B species, and determining the sequence of nucleotides for the template by removing from the determination of the sequence nucleic acid sequences having one or more nucleotide positions that disagree with the nucleotide position determined in about 95% or more of the nucleic acid sequences of the set of amplicon duplicates. In some embodiments, amplicons having the same length are selected for the set of amplicon duplicates.

In some embodiments, the methods and/or systems comprise the steps of and/or software to implement the steps of reviewing the sequence of nucleotides for one or more nucleic acid templates in a nucleic acid sample, comprising (a) identifying a first set of amplicon duplicates, where the amplicon duplicates comprise amplified adapter-ligated nucleic acid templates comprising a first polynucleotide B species at a first end and a second polynucleotide B species at the second end; (b) identifying a second set of amplicon duplicates, where the second set of amplicon duplicates comprise amplified adapter-ligated nucleic acid templates comprising the B' species that are the reverse complement of the first and second B species of step (a); (c) obtaining a first single strand consensus sequence for the first set of amplicon duplicates, and a second single strand consensus sequence for the second set of amplicon duplicates, and (d) determining the sequence of nucleotides for the one or more nucleic acid templates in a nucleic acid sample by removing from the determination of the sequence nucleic acid sequences having one or more nucleotide positions where the first single strand consensus sequence and the second single strand consensus sequence disagree at one or more nucleotide positions. By "disagree" is meant that the nucleotide identified at a position in the first single strand consensus sequence differs from nucleotide identified at the corresponding position in the second single strand consensus sequence. Where the two single strand consensus sequences are complementary, it is understood that by "differ" or "disagree" is meant that the nucleotide identified at a position in the first single strand consensus sequence, is not complementary to the nucleotide identified at the corresponding position in the second single strand consensus sequence.

In some embodiments of the methods, compositions and/or systems provided herein, each of the adapter-ligated nucleic acid templates comprises a first nonrandom oligonucleotide adapter at a first end and a second nonrandom oligonucleotide adapter at a second end, and the methods and/or systems comprise reviewing the sequence of nucleotides for one or more nucleic acid templates in a nucleic acid sample, comprising (a) identifying a first set of amplicon duplicates, where the amplicon duplicates comprise amplified adapter-ligated nucleic acid templates comprising a first polynucleotide B species and a second polynucleotide B species; (b) identifying a second set of amplicon duplicates, where the second set of amplicon duplicates comprise amplified adapter-ligated nucleic acid templates comprising the B' species that are the reverse complement of the first and second B species of step (a); (c) sequencing all or a portion of the sequences of each amplicon of the first set and second set of amplicon duplicates; (d) determining the sequence of nucleotides for the one or more nucleic acid templates in a nucleic acid sample by removing from the determination of the sequence nucleic acid sequences having one or more nucleotide positions where the nucleic acid strand for the first set of amplicon duplicates and the nucleic acid strand for the second set of amplicon duplicates disagree at one or more nucleotide positions. In some embodiments, amplicons having the same length are selected for the first and second set of amplicon duplicates.

In some embodiments, the method and or system further comprises the steps (and/or software to implement such steps) of obtaining a list of B species and B' species of the nonrandom oligonucleotide adapters provided for ligation with the nucleic acid templates; determining the sequence of the B species or B' species of the nonrandom oligonucleotide adapter-ligated nucleic acid templates; comparing the sequence of the B species or B' species to the sequences of the B and B' species on the list; and removing from the determination of the sequence of the nucleic acid templates, adapter-ligated nucleic acid templates that comprise B species or B' species sequences that are not identical to a B species or B' species sequence on the list. By "list" is meant any record of the B or B' species or B or B' species sequences provided in the ligation reaction with the nucleic acid templates, either in the form of a database, or electronic or physical document, and also includes any record of which B or B' species or B or B' species sequences were included in the ligation reaction, such as, for example, a physical sample of the B species. In some embodiments, some of the sequences of adapter-ligated nucleic acid templates that comprise B species or B' species sequences that are not identical to a B species or B' species on the list are not removed from the sequence determination, and are instead assigned a weight, where the assigned weight is considered in the determination of at least one base call. For example, in some embodiments, nonrandom oligonucleotide adapter-ligated nucleic acid sequences comprising a B species sequence or a B' species sequence that is identical to a B species sequence or a B' species sequence provided in the list of step (a) are assigned a weight of 1; nonrandom oligonucleotide adapter-ligated nucleic acid sequences comprising a B species sequence or a B' species sequence that comprises or consists of one nucleotide difference from a B species sequence or B' species sequence provided in the list of step (a) are assigned a weight of less than 1, and greater than 0, for example, 0.5, and nonrandom oligonucleotide adapter-ligated nucleic acid sequences comprising a B species sequence or a B' species sequence that comprise more than one nucleotide difference from a B species sequence or a B' species sequence provided in the list of step (a) are assigned a weight of 0. It is understood that the weights provided herein are provided as examples, and may include, for example, relative weights.

Quantifying DNA Templates

In some embodiments of the methods and/or systems provided herein, the methods comprise steps and/or software to implement such steps to quantifying the nucleic acid templates for the nucleic acid sample. Quantification methods include, for example, quantifying molecules that comprise at least one single nucleotide alteration, and also include methods for quantifying nucleic acid templates, for example, to detect copy number alterations through relative abundance. For some embodiments, accurately counting the number of template molecules can improve the accuracy of the measurement, for example in counting-based methods for the detection of copy number alterations. Such embodiments may be used for detection or monitoring alterations for use in noninvasive prenatal testing (NIPT), cancer, or any disorder where copy number alterations are relevant for the disease. These embodiments may, for example, comprise (a) identifying a set of amplicon duplicates, where the amplicon duplicates comprise amplified adapter-ligated nucleic acid templates comprising a polynucleotide B species; and (b) determining the number of amplicon duplicates comprising the polynucleotide B species. In some embodiments, the methods and/or systems comprise determining a base call of at least one nucleotide of a nucleic acid template, comprising (a) identifying a set of amplicon duplicates, where the amplicon duplicates comprise amplified adapter-ligated nucleic acid templates comprising a polynucleotide B species; (b) identifying the at least one nucleotide in each amplicon of the set of amplicon duplicates; (c) determining the base call of the at least one nucleotide where the identity of the at least one nucleotide is the same in at least 95% of the amplicons in the set of amplicon duplicates. In some embodiments, the methods and/or systems comprise quantifying the nucleic acid templates for the nucleic acid sample that comprise the base call of the at least one nucleotide. In some embodiments, amplicons having the same length are selected for the set of amplicon duplicates.

In some embodiments, methods and/or systems are provided for counting the nucleic acid templates for the nucleic acid sample, comprising identifying a set of amplicon duplicates, where the amplicon duplicates comprise amplified adapter-ligated nucleic acid templates comprising a polynucleotide B species on one strand and determining the number of amplicon duplicates comprising the polynucleotide B species. In some embodiments, the methods and/or systems comprise comparing the number of first amplicon duplicates comprising a first polynucleotide B species with the number of second amplicon duplicates comprising a second polynucleotide B species. In some embodiments, the first amplicon duplicates comprise copies of a first nucleic acid template of a first chromosome and the second amplicon duplicates comprise copies of a second nucleic acid template of a second chromosome.

Also provided are methods and/or systems for implementing such methods comprising counting the number of nucleic acid templates for the nucleic acid sample, comprising identifying the nonrandom oligonucleotide adapter species ligated to each nucleic acid template; and counting the number of nonrandom oligonucleotide adapter species ligated to the nucleic acid templates for the nucleic acid sample. By unique nucleic acid template is meant a nucleic acid templates, that is, for example, a nucleic acid template present in the sample. The nucleic acid template may have, in some embodiments, a particular nucleotide sequence that is not the same as another nucleic acid template nucleotide sequence, or is obtained from a different chromosomal location. For example, two nucleic acid template species include nucleotide sequences that differ by at least one nucleotide, that is, one nucleic acid template species differs from another nucleic acid template species where the nucleic acid templates differ by at least one nucleotide.

In some embodiments, methods and/or systems are provided for counting the nucleic acid templates for the nucleic acid sample, comprising identifying a set of amplicon duplicates, where the amplicon duplicates comprise amplified adapter-ligated nucleic acid templates comprising a first polynucleotide B species and a second polynucleotide B species, where the first and second polynucleotide B species may or may not consist of the same nucleotide sequence; and determining the number of amplicon duplicates comprising both the first and the second polynucleotide B species. In some embodiments, the methods and/or systems comprise comparing the number of first amplicon duplicates comprising the first and second polynucleotide B species on one strand with the number of second amplicon duplicates, where the second amplicon duplicates comprise amplified adapter-ligated nucleic acid templates comprising a third polynucleotide B species and a fourth polynucleotide species on one strand, where the third and fourth polynucleotide B species may or may not consist of the same nucleotide sequence. In some embodiments, the first amplicon duplicates comprise copies of a first nucleic acid template of a first chromosome and the second amplicon duplicates comprise copies of a second nucleic acid template of a second chromosome.

Also provided are methods and/or systems for implementing such methods comprising counting the number of unique nucleic acid templates for the nucleic acid sample, comprising identifying the nonrandom oligonucleotide adapter species pairs, where the nonrandom oligonucleotide adapter species pairs consist of a first nonrandom oligonucleotide adapter ligated to the nucleic acid template and a second nonrandom oligonucleotide adapter ligated to the nucleic acid template; and counting the number of nonrandom oligonucleotide adapter species pairs.

In some embodiments, each of the nonrandom oligonucleotide adapter-ligated nucleic acid templates comprises a first nonrandom oligonucleotide adapter and a second nonrandom oligonucleotide adapter and the methods and/or systems comprise determining a base call of at least one nucleotide of a nucleic acid template, comprising (a) identifying a first set of amplicon duplicates, where the amplicon duplicates comprise amplified adapter-ligated nucleic acid templates comprising a first polynucleotide B species and a second polynucleotide B species on one strand; (b) identifying a second set of amplicon duplicates, where the second set of amplicon duplicates comprise amplified nonrandom oligonucleotide adapter-ligated nucleic acid templates comprising the B' species that are the reverse complement of the first and second B species of step (a); (c) identifying the at least one nucleotide in each amplicon of the first set, and identifying the at least one nucleotide at the complementary position in the second set of amplicon duplicates; (d) determining the base call of the at least one nucleotide where the identity of the at least one nucleotide is the same in at least 95% of the amplicons in the first set or the second set of amplicon duplicates; and the identity of the at least one nucleotide in the first set of amplicon duplicates is the complement to the identity of the at least one nucleotide in the complementary position in the second set of amplicon duplicates. In some embodiments, amplicons having the same length are selected for the first and second set of amplicon duplicates.

As used herein, it is understood that the use of polynucleotide B and polynucleotide B' may be used interchangeably, in that one strand of a double-stranded adapter-ligated nucleic acid template may comprise, for example, a first nonrandom oligonucleotide adapter comprising a first polynucleotide B species and the complementary first polynucleotide B' species, and a second nonrandom oligonucleotide adapter comprising a second polynucleotide B species and the complementary second polynucleotide B' species. A first strand of the adapter-ligated nucleic acid template may therefore comprise the first polynucleotide B species and the second polynucleotide B' species, while the second strand of the adapter-ligated nucleic acid template may comprise the first polynucleotide B' species and the second polynucleotide B species. Thus, in the present methods for counting or sequencing the nucleic acid templates, where the number of first amplicon duplicates comprising the first and second polynucleotide B species on one strand are counted, it is understood that in the context of discussion of one strand, one of the polynucleotide B species may consist of what might otherwise be considered to be a polynucleotide B' species when viewed in the context of the double stranded adapter-ligated nucleic acid template.

In some embodiments of the methods provided herein, each of the nonrandom oligonucleotide adapter-ligated nucleic acid templates comprises a first nonrandom oligonucleotide adapter and a second nonrandom oligonucleotide adapter and the methods comprise determining a base call of at least one nucleotide of a nucleic acid template, comprising (a) identifying a first set of amplicon duplicates, where the amplicon duplicates comprise amplified adapter-ligated nucleic acid templates comprising a first polynucleotide B species and a second polynucleotide B species (for example, a first polynucleotide B species and a first polynucleotide B' species on one strand); (b) identifying a second set of amplicon duplicates, where the second set of amplicon duplicates comprise amplified nonrandom oligonucleotide adapter-ligated nucleic acid templates comprising the B' species that are the reverse complement of the first and second B species of step (a) (for example, the reverse complements of the first polynucleotide B species and the first polynucleotide B' species); (c) identifying the at least one nucleotide in each amplicon of the first set, and identifying the at least one nucleotide at the complementary position in the second set of amplicon duplicates; (d) determining the base call of the at least one nucleotide where the identity of the at least one nucleotide is the same in at least 70, 75, 80, 85, 90, 91, 92, 93, 94, 95, 96, 97, 98, or 99% of the amplicons in the first set or the second set of amplicon duplicates; and the identity of the at least one nucleotide in the first set of amplicon duplicates is the complement to the identity of the at least one nucleotide in the complementary position in the second set of amplicon duplicates. In some embodiments, amplicons having the same length are selected for the first and second set of amplicon duplicates.

In some embodiments, the counting method further comprises the steps of obtaining a list of B species and B' species of the nonrandom oligonucleotide adapters provided for ligation with the nucleic acid templates; determining the sequence of the B species or B' species of the nonrandom oligonucleotide adapter-ligated nucleic acid templates; comparing the sequence of the B species or B' species to the sequences of the B and B' species on the list; and removing from the determination of the count of nucleic acid templates, adapter-ligated nucleic acid templates that comprise B species or B' species sequences that are not identical to a B species or B' species sequence on the list. By "list" is meant any record of the B or B' species or B or B' species sequences provided in the ligation reaction with the nucleic acid templates, either in the form of a database, or electronic or physical document, and also includes any record of which B or B' species or B or B' species sequences were included in the ligation reaction, such as, for example, a physical sample of the B species. In some embodiments, some of the adapter-ligated nucleic acid templates that comprise B species or B' species sequences that are not identical to a B species or B' species on the list are not removed from the sequence determination, and are instead assigned a weight, where the assigned weight is considered in the counting of at least one nucleic acid template. For example, in some embodiments, nonrandom oligonucleotide adapter-ligated nucleic acid templates comprising a B species sequence or a B' species sequence that is identical to a B species sequence or a B' species sequence provided in the list of step (a) are assigned a weight of 1; nonrandom oligonucleotide adapter-ligated nucleic acid templates comprising a B species sequence or a B' species sequence that comprises or consists of one nucleotide difference from a B species sequence or B' species sequence provided in the list of step (a) are assigned a weight of less than 1, and greater than 0, for example, 0.5, and nonrandom oligonucleotide adapter-ligated nucleic acid templates comprising a B species sequence or a B' species sequence that comprise more than one nucleotide difference from a B species sequence or a B' species sequence provided in the list of step (a) are assigned a weight of 0. It is understood that the weights provided herein are provided as examples, and may include, for example, relative weights.

Manufacturing Sets of Nonrandom Nucleic Acid Sequencing Adapters

In certain embodiments, provided herein are methods for manufacturing a set of 999 or fewer, or 900 or fewer, or 800 or fewer, or 700 or fewer, or 600 or fewer, or 500 or fewer, or 400 or fewer, or 300 or fewer (e.g., 288), or 200 or fewer, or 100 or fewer nonrandom nucleic acid sequencing adapters (nonrandom oligonucleotide adapters), for use in determining a sequence of nucleotides for one or more nucleic acid templates in a nucleic acid sample. The set of adapters may be manufactured for use in sequencing where the ratio of the nonrandom nucleic acid sequencing adapter molecules to nucleic acid templates of the nucleic acid sample is greater than 10 to 1, 15 to 1, 20 to 1, 25 to 1, 30 to 1, 35 to 1, 40 to 1, 45 to 1, or 50 to 1. The method may comprise or consisting essentially of: providing first oligonucleotide species and second oligonucleotide species; where: each of the first oligonucleotide species comprises 5' to 3' a polynucleotide A and a polynucleotide B species and each of the second oligonucleotide species comprises 5' to 3' a polynucleotide B' species and a polynucleotide A'; each of the polynucleotide B species and the polynucleotide B' species are predetermined, are non-randomly generated, are the same length, and are about 4 to about 20 consecutive nucleotides in length; there are 999 or fewer polynucleotide B species and each polynucleotide B' species is a reverse complement of a polynucleotide B species; polynucleotide A is not a reverse complement of polynucleotide A'. In certain embodiments each of the first oligonucleotide species and each of the second oligonucleotide species is been synthesized separately; and in separate pairs. The method may further include contacting each first oligonucleotide species with each second oligonucleotide species comprising the reverse complement polynucleotide B' species under annealing conditions, thereby generating partially double-stranded adapter species; where the polynucleotide B species are annealed to complementary polynucleotide B' species and polynucleotide A' is not annealed to polynucleotide A.

In some embodiments, the ratio of the nonrandom oligonucleotide adapter molecules to nucleic acid templates of the nucleic acid sample is designed to be greater than 10 to 1.

In some embodiments, the ratio of the nucleic acid sequencing adapter molecules to nucleic acid templates of the nucleic acid sample is greater than 20 to 1. In some embodiments, the ratio of the nucleic acid sequencing adapter molecules to nucleic acid templates of the nucleic acid sample is greater than 30 to 1.

In some embodiments, the set of nonrandom oligonucleotide adapters are combined in a vessel.

In some embodiments, the polynucleotide B species and the polynucleotide B' species are non-degenerate polynucleotides. In some embodiments, the polynucleotide B species and the polynucleotide B' species are non-degenerate or non-semidegenerate polynucleotides.

In some embodiments, the polynucleotide B species and the polynucleotide B' species are about 6 to about 10 consecutive nucleotide bases in length. In some embodiments, the polynucleotide B species and the polynucleotide B' species are about 8 consecutive nucleotide bases in length.

In some embodiments, there are 999 or fewer polynucleotide B species. In some embodiments, there are 400 or fewer polynucleotide B species. In some embodiments, there are 300 or fewer polynucleotide B species. In some embodiments, there are about 300 to about 400 polynucleotide B species. In some embodiments, there are about 100 to about 500 polynucleotide B species. In some embodiments, there are about 200 to 300 polynucleotide B species. In some embodiments, there are about 280 to about 290 polynucleotide B species. In some embodiments, there are 1000, 750, 500, 475, 450, 425, 400, 375, 350, 325, 300, 275, 250, 225, 200, 175, 150, 125, or 100 or fewer polynucleotide B species.

Samples

Provided herein are systems, methods and products for analyzing nucleic acids. In some embodiments, nucleic acid templates in a mixture of nucleic acid templates are analyzed. A mixture of nucleic acids can comprise two or more nucleic acid templates having the same or different nucleotide sequences, different template lengths, different origins (e.g., genomic origins, fetal vs. maternal origins, cell or tissue origins, cancer vs. non-cancer origin, tumor vs. non-tumor origin, sample origins, subject origins, and the like), or combinations thereof.

Nucleic acid or a nucleic acid mixture utilized in systems, methods and products described herein often is isolated from a sample obtained from a subject (e.g., a test subject). A subject can be any living or non-living organism, including but not limited to a human, a non-human animal, a plant, a bacterium, a fungus, a protest or a pathogen. Any human or non-human animal can be selected, and may include, for example, mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman). A subject may be any age (e.g., an embryo, a fetus, an infant, a child, an adult). A subject may be a cancer patient, a patient suspected of having cancer, a patient in remission, a patient with a family history of cancer, and/or a subject obtaining a cancer screen. In some embodiments, a test subject is a female. In some embodiments, a test subject is a human female. In some embodiments, a test subject is a male. In some embodiments, a test subject is a human male.

Nucleic acid may be isolated from any type of suitable biological specimen or sample (e.g., a test sample). A sample or test sample can be any specimen that is isolated or obtained from a subject or part thereof (e.g., a human subject, a pregnant female, a cancer patient, a fetus, a tumor). Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo; cancer biopsy), celocentesis sample, cells (blood cells, placental cells, embryo or fetal cells, fetal nucleated cells or fetal cellular remnants, normal cells, abnormal cells (e.g., cancer cells)) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a biological sample is a cervical swab from a subject. A fluid or tissue sample from which nucleic acid is extracted may be acellular (e.g., cell-free). In some embodiments, a fluid or tissue sample may contain cellular elements or cellular remnants. In some embodiments, fetal cells or cancer cells may be included in the sample.

A sample can be a liquid sample. A liquid sample can comprise extracellular nucleic acid (e.g., circulating cell-free DNA). Non-limiting examples of liquid samples, include, blood or a blood product (e.g., serum, plasma, or the like), urine, biopsy sample (e.g., liquid biopsy for the detection of cancer), a liquid sample described above, the like or combinations thereof. In certain embodiments, a sample is a liquid biopsy, which generally refers to an assessment of a liquid sample from a subject for the presence, absence, progression or remission of a disease (e.g., cancer). A liquid biopsy can be used in conjunction with, or as an alternative to, a sold biopsy (e.g., tumor biopsy). In certain instances, extracellular nucleic acid is analyzed in a liquid biopsy.

In some embodiments, a biological sample may be blood, plasma or serum. The term "blood" encompasses whole blood, blood product or any fraction of blood, such as serum, plasma, buff coat, or the like as conventionally defined. Blood or fractions thereof often comprise nucleosomes. Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3 to 40 milliliters, between 5 to 50 milliliters) often is collected and can be stored according to standard procedures prior to or after preparation.

An analysis of nucleic acid found in a subject's blood may be performed using, e.g., whole blood, serum, or plasma. An analysis of fetal DNA found in maternal blood, for example, may be performed using, e.g., whole blood, serum, or plasma. An analysis of tumor DNA found in a patient's blood, for example, may be performed using, e.g., whole blood, serum, or plasma. Methods for preparing serum or plasma from blood obtained from a subject (e.g., a maternal subject; cancer patient) are known. For example, a subject's blood (e.g., a pregnant woman's blood; cancer patient's blood) can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for nucleic acid extraction. In addition to the acellular portion of the whole blood, nucleic acid may also be recovered from the cellular fraction, enriched in the buffy coat portion, which can be obtained following centrifugation of a whole blood sample from the subject and removal of the plasma.

A sample may be heterogeneous. For example, a sample may include more than one cell type and/or one or more nucleic acid species. In some instances, a sample may include (i) fetal cells and maternal cells, (ii) cancer cells and non-cancer cells, and/or (iii) pathogenic cells and host cells. In some instances, a sample may include (i) cancer and non-cancer nucleic acid, (ii) pathogen and host nucleic acid, (iii) fetal derived and maternal derived nucleic acid, and/or more generally, (iv) mutated and wild-type nucleic acid. In some instances, a sample may include a minority nucleic acid species and a majority nucleic acid species, as described in further detail below. In some instances, a sample may include cells and/or nucleic acid from a single subject or may include cells and/or nucleic acid from multiple subjects.

Cell Types

As used herein, a "cell type" refers to a type of cell that can be distinguished from another type of cell. Extracellular nucleic acid can include nucleic acid from several different cell types. Non-limiting examples of cell types that can contribute nucleic acid to circulating cell-free nucleic acid include liver cells (e.g., hepatocytes), lung cells, spleen cells, pancreas cells, colon cells, skin cells, bladder cells, eye cells, brain cells, esophagus cells, cells of the head, cells of the neck, cells of the ovary, cells of the testes, prostate cells, placenta cells, epithelial cells, endothelial cells, adipocyte cells, kidney/renal cells, heart cells, muscle cells, blood cells (e.g., white blood cells), central nervous system (CNS) cells, the like and combinations of the foregoing. In some embodiments, cell types that contribute nucleic acid to circulating cell-free nucleic acid analyzed include white blood cells, endothelial cells and hepatocyte liver cells. Different cell types can be screened as part of identifying and selecting nucleic acid loci for which a marker state is the same or substantially the same for a cell type in subjects having a medical condition and for the cell type in subjects not having the medical condition, as described in further detail herein.

A particular cell type sometimes remains the same or substantially the same in subjects having a medical condition and in subjects not having a medical condition. In a non-limiting example, the number of living or viable cells of a particular cell type may be reduced in a cell degenerative condition, and the living, viable cells are not modified, or are not modified significantly, in subjects having the medical condition.

A particular cell type sometimes is modified as part of a medical condition and has one or more different properties than in its original state. In a non-limiting example, a particular cell type may proliferate at a higher than normal rate, may transform into a cell having a different morphology, may transform into a cell that expresses one or more different cell surface markers and/or may become part of a tumor, as part of a cancer condition. In embodiments for which a particular cell type (i.e., a progenitor cell) is modified as part of a medical condition, the marker state for each of the one or more markers assayed often is the same or substantially the same for the particular cell type in subjects having the medical condition and for the particular cell type in subjects not having the medical condition. Thus, the term "cell type" sometimes pertains to a type of cell in subjects not having a medical condition, and to a modified version of the cell in subjects having the medical condition. In some embodiments, a "cell type" is a progenitor cell only and not a modified version arising from the progenitor cell. A "cell type" sometimes pertains to a progenitor cell and a modified cell arising from the progenitor cell. In such embodiments, a marker state for a marker analyzed often is the same or substantially the same for a cell type in subjects having a medical condition and for the cell type in subjects not having the medical condition.

In certain embodiments, a cell type is a cancer cell. Certain cancer cell types include, for example, leukemia cells (e.g., acute myeloid leukemia, acute lymphoblastic leukemia, chronic myeloid leukemia, chronic lymphoblastic leukemia); cancerous kidney/renal cells (e.g., renal cell cancer (clear cell, papillary type 1, papillary type 2, chromophobe, oncocytic, collecting duct), renal adenocarcinoma, hypernephroma, Wilm's tumor, transitional cell carcinoma), brain tumor cells (e.g., acoustic neuroma, astrocytoma (grade I: pilocytic astrocytoma, grade II: low-grade astrocytoma, grade III: anaplastic astrocytoma, grade IV: glioblastoma (GBM)), chordoma, cns lymphoma, craniopharyngioma, glioma (brain stem glioma, ependymoma, mixed glioma, optic nerve glioma, subependymoma), medulloblastoma, meningioma, metastatic brain tumors, oligodendroglioma, pituitary tumors, primitive neuroectodermal (PNET), schwannoma, juvenile pilocytic astrocytoma (JPA), pineal tumor, rhabdoid tumor).

Different cell types can be distinguished by any suitable characteristic, including without limitation, one or more different cell surface markers, one or more different morphological features, one or more different functions, one or more different protein (e.g., histone) modifications and one or more different nucleic acid markers. Non-limiting examples of nucleic acid markers include single-nucleotide polymorphisms (SNPs), methylation state of a nucleic acid locus, short tandem repeats, insertions (e.g., microinsertions), deletions (microdeletions) the like and combinations thereof. Non-limiting examples of protein (e.g., histone) modifications include acetylation, methylation, ubiquitylation, phosphorylation, sumoylation, the like and combinations thereof.

As used herein, the term a "related cell type" refers to a cell type having multiple characteristics in common with another cell type. In related cell types, 75% or more cell surface markers sometimes are common to the cell types (e.g., about 80%, 85%, 90% or 95% or more of cell surface markers are common to the related cell types).

Nucleic Acid

Provided herein are methods for analyzing nucleic acid. The terms "nucleic acid," "nucleic acid molecule," "nucleic acid fragment," and "nucleic acid template" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by a fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, virus, bacterium, autonomously replicating sequence (ARS), mitochondria, centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense," "plus" strand or "minus" strand, "forward" reading frame or "reverse" reading frame) and double-stranded polynucleotides. The term "gene" refers to a section of DNA involved in producing a polypeptide chain, and generally includes regions preceding and following the coding region (leader and trailer) involved in the transcription/translation of the gene product and the regulation of the transcription/translation, as well as intervening sequences (introns) between individual coding regions (exons). A nucleotide or base generally refers to the purine and pyrimidine molecular units of nucleic acid (e.g., adenine (A), thy mine (T), guanine (G), and cytosine (C)). For RNA, the base thymine is replaced with uracil. Nucleic acid length or size may be expressed as a number of bases.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of E. Coli RecA protein and/or by alteration of salt concentration, for example, using methods known in the art.

Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid may be derived from one or more sources (e.g., biological sample, blood, cells, serum, plasma, buffy coat, urine, lymphatic fluid, skin, soil, and the like) by methods known in the art. Any suitable method can be used for isolating, extracting and/or purifying DNA from a biological sample (e.g., from blood or a blood product), non-limiting examples of which include methods of DNA preparation (e.g., described by Sambrook and Russell, Molecular Cloning: A Laboratory Manual 3d ed., 2001), various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany). GenomicPrep™ Blood DNA Isolation Kit (Promega, Madison, Wis.), and GFX™ Genomic Blood DNA Purification Kit (Amersham, Piscataway, N.J.), the like or combinations thereof.

In some embodiments, nucleic acid is extracted from cells using a cell lysis procedure. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. In some instances, a high salt and/or an alkaline lysis procedure may be utilized.

Nucleic acids can include extracellular nucleic acid in certain embodiments. The term "extracellular nucleic acid" as used herein can refer to nucleic acid isolated from a source having substantially no cells and also is referred to as "cell-free" nucleic acid, "circulating cell-free nucleic acid" (e.g., CCF fragments, ccf DNA) and/or "cell-free circulating nucleic acid." Extracellular nucleic acid can be present in and obtained from blood (e.g., from the blood of a human subject). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample. e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder"). In some embodiments, sample nucleic acid from a test subject is circulating cell-free nucleic acid. In some embodiments, circulating cell free nucleic acid is from blood plasma or blood serum from a test subject.

Extracellular nucleic acid can include different nucleic acid species, and therefore is referred to herein as "heterogeneous" in certain embodiments. For example, blood serum or plasma from a person having cancer can include nucleic acid from cancer cells (e.g., tumor, neoplasia) and nucleic acid from non-cancer cells. In another example, blood serum or plasma from a pregnant female can include maternal nucleic acid and fetal nucleic acid. In some instances, cancer or fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is cancer or fetal nucleic acid).

At least two different nucleic acid species can exist in different amounts in extracellular nucleic acid and sometimes are referred to as minority species and majority species. In certain instances, a minority species of nucleic acid is from an affected cell type (e.g., cancer cell, wasting cell, cell attacked by immune system). In certain embodiments, a genetic variation or genetic alteration (e.g., copy number alteration, copy number variation, single nucleotide alteration, single nucleotide variation, chromosome alteration, and translocation) is determined for a minority nucleic acid species. In certain embodiments, a genetic variation or genetic alteration is determined for a majority nucleic acid species. Generally it is not intended that the terms "minority" or "majority" be rigidly defined in any respect. In one aspect, a nucleic acid that is considered "minority," for example, can have an abundance of at least about 0.1% of the total nucleic acid in a sample to less than 50% of the total nucleic acid in a sample. In some embodiments, a minority nucleic acid can have an abundance of at least about 1% of the total nucleic acid in a sample to about 40% of the total nucleic acid in a sample. In some embodiments, a minority nucleic acid can have an abundance of at least about 2% of the total nucleic acid in a sample to about 30% of the total nucleic acid in a sample. In some embodiments, a minority nucleic acid can have an abundance of at least about 3% of the total nucleic acid in a sample to about 25% of the total nucleic acid in a sample. For example, a minority nucleic acid can have an abundance of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% of the total nucleic acid in a sample. In some instances, a minority species of extracellular nucleic acid sometimes is about 1% to about 40%/o of the overall nucleic acid (e.g., about 1%, 2%, 3%, 4%, 5%, 6%, 7%, 8%, 9%, 100%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% of the nucleic acid is minority species nucleic acid). In some embodiments, the minority nucleic acid is extracellular DNA. In some embodiments, the minority nucleic acid is extracellular DNA from apoptotic tissue. In some embodiments, the minority nucleic acid is extracellular DNA from tissue affected by a cell proliferative disorder. In some embodiments, the minority nucleic acid is extracellular DNA from a tumor cell. In some embodiments, the minority nucleic acid is extracellular fetal DNA.

In another aspect, a nucleic acid that is considered "majority," for example, can have an abundance greater than 50% of the total nucleic acid in a sample to about 99.9% of the total nucleic acid in a sample. In some embodiments, a majority nucleic acid can have an abundance of at least about 60% of the total nucleic acid in a sample to about 99% of the total nucleic acid in a sample. In some embodiments, a majority nucleic acid can have an abundance of at least about 70% of the total nucleic acid in a sample to about 98% of the total nucleic acid in a sample. In some embodiments, a majority nucleic acid can have an abundance of at least about 75% of the total nucleic acid in a sample to about 97% of the total nucleic acid in a sample. For example, a majority nucleic acid can have an abundance of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the total nucleic acid in a sample. In some embodiments, the majority nucleic acid is extracellular DNA. In some embodiments, the majority nucleic acid is extracellular maternal DNA. In some embodiments, the majority nucleic acid is DNA from healthy tissue. In some embodiments, the majority nucleic acid is DNA from non-tumor cells.

In some embodiments, a minority species of extracellular nucleic acid is of a length of about 500 base pairs or less (e.g., about 80, 85, 90, 91, 92, 93, 94, 95, 96, 97, 98, 99 or 100% of minority species nucleic acid is of a length of about 500 base pairs or less). In some embodiments, a minority species of extracellular nucleic acid is of a length of about 300 base pairs or less (e.g., about 80, 85, 90, 91, 92, 93, 94, 95, 96, 97, 98, 99 or 100% of minority species nucleic acid is of a length of about 300 base pairs or less). In some embodiments, a minority species of extracellular nucleic acid is of a length of about 250 base pairs or less (e.g., about 80, 85, 90, 91, 92, 93, 94, 95, 96, 97, 98, 99 or 100% of minority species nucleic acid is of a length of about 250 base pairs or less). In some embodiments, a minority species of extracellular nucleic acid is of a length of about 200 base pairs or less (e.g., about 80, 85, 90, 91, 92, 93, 94, 95, 96, 97, 98, 99 or 100% of minority species nucleic acid is of a length of about 200 base pairs or less). In some embodiments, a minority species of extracellular nucleic acid is of a length of about 150 base pairs or less (e.g., about 80, 85, 90, 91, 92, 93, 94, 95, 96, 97, 98, 99 or 100% of minority species nucleic acid is of a length of about 150 base pairs or less). In some embodiments, a minority species of extracellular nucleic acid is of a length of about 100 base pairs or less (e.g., about 80, 85, 90, 91, 92, 93, 94, 95, 96, 97, 98, 99 or 100% of minority species nucleic acid is of a length of about 100 base pairs or less). In some embodiments, a minority species of extracellular nucleic acid is of a length of about 50 base pairs or less (e.g., about 80, 85, 90, 91, 92, 93, 94, 95, 96, 97, 98, 99 or 100% of minority species nucleic acid is of a length of about 50 base pairs or less).

Nucleic acid may be provided for conducting methods described herein with or without processing of the sample(s) containing the nucleic acid. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, small fragments of fetal nucleic acid (e.g., 30 to 500 bp fragments) can be purified, or partially purified, from a mixture comprising both fetal and maternal nucleic acid templates. In certain examples, nucleosomes comprising smaller fragments of fetal nucleic acid can be purified from a mixture of larger nucleosome complexes comprising larger fragments of maternal nucleic acid. In certain examples, cancer cell nucleic acid can be purified from a mixture comprising cancer cell and non-cancer cell nucleic acid. In certain examples, nucleosomes comprising small fragments of cancer cell nucleic acid can be purified from a mixture of larger nucleosome complexes comprising larger fragments of non-cancer nucleic acid. In some embodiments, nucleic acid is provided for conducting methods described herein without prior processing of the sample(s) containing the nucleic acid. For example, nucleic acid may be analyzed directly from a sample without prior extraction, purification, partial purification, and/or amplification.

In some embodiments nucleic acids, such as, for example, cellular nucleic acids, are sheared or cleaved prior to, during or after a method described herein. The term "shearing" or "cleavage" generally refers to a procedure or conditions in which a nucleic acid molecule, such as a nucleic acid template gene molecule or amplified product thereof, may be severed into two (or more) smaller nucleic acid molecules. Such shearing or cleavage can be sequence specific, base specific, or nonspecific, and can be accomplished by any of a variety of methods, reagents or conditions, including, for example, chemical, enzymatic, physical shearing (e.g., physical fragmentation). Sheared or cleaved nucleic acids may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs.

Sheared or cleaved nucleic acids can be generated by a suitable method, non-limiting examples of which include physical methods (e.g., shearing, e.g., sonication, French press, heat, UV irradiation, the like), enzymatic processes (e.g., enzymatic cleavage agents (e.g., a suitable nuclease, a suitable restriction enzyme, a suitable methylation sensitive restriction enzyme)), chemical methods (e.g., alkylation, DMS, piperidine, acid hydrolysis, base hydrolysis, heat, the like, or combinations thereof), processes described in U.S. Patent Application Publication No. 2005/0112590, the like or combinations thereof. The average, mean or nominal length of the resulting nucleic acid fragments can be controlled by selecting an appropriate fragment-generating method.

The term "amplified" as used herein refers to subjecting a nucleic acid in a sample to a process that linearly or exponentially generates amplicon nucleic acids having the same or substantially the same nucleotide sequence as the nucleic acid, or part thereof. In certain embodiments the term "amplified" refers to a method that comprises a polymerase chain reaction (PCR). In certain instances, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule).

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any suitable form useful for conducting a sequence analysis.

Enriching Nucleic Acids

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, cancer nucleic acid, patient nucleic acid, nucleic acid comprising templates of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, cancer or fetal nucleic acid. In certain embodiments, a method for determining fraction of cancer cell nucleic acid or fetal fraction also can be used to enrich for cancer or fetal nucleic acid. In certain embodiments, nucleic acid from normal tissue (e.g., non-cancer cells) is selectively removed (partially, substantially, almost completely or completely) from the sample. In certain embodiments, maternal nucleic acid is selectively removed (partially, substantially, almost completely or completely) from the sample. In certain embodiments, enriching for a particular low copy number species nucleic acid (e.g., cancer or fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639. International Patent Application Publication No. WO2011/034631, International Patent Application Publication No. WO2006/056480, and International Patent Application Publication No. WO2011/143659, the entire content of each is incorporated herein by reference, including all text, tables, equations and drawings.

In some embodiments, nucleic acid is enriched for certain templates and/or reference templates. In certain embodiments, nucleic acid is enriched for a specific nucleic acid template length or range of template lengths using one or more length-based separation methods described below. In certain embodiments, nucleic acid is enriched for templates from a select genomic region (e.g., chromosome) using one or more sequence-based separation methods described herein and/or known in the art.

Non-limiting examples of methods for enriching for a nucleic acid subpopulation in a sample include methods that exploit epigenetic differences between nucleic acid species (e.g., methylation-based fetal nucleic acid enrichment methods described in U.S. Patent Application Publication No. 2010/0105049, which is incorporated by reference herein); restriction endonuclease enhanced polymorphic sequence approaches (e.g., such as a method described in U.S. Patent Application Publication No. 2009/0317818, which is incorporated by reference herein); selective enzymatic degradation approaches; massively parallel signature sequencing (MPSS) approaches; amplification (e.g., PCR)-based approaches (e.g., loci-specific amplification methods, multiplex SNP allele PCR approaches; universal amplification methods); pull-down approaches (e.g., biotinylated ultramer pull-down methods); extension and ligation-based methods (e.g., molecular inversion probe (MIP) extension and ligation); and combinations thereof.

In some embodiments, nucleic acid is enriched for templates from a select genomic region (e.g., chromosome) using one or more sequence-based separation methods described herein. Sequence-based separation generally is based on nucleotide sequences present in the templates of interest (e.g., and/or target or reference templates) and substantially not present in other templates of the sample or present in an insubstantial amount of the other templates (e.g., 5% or less). In some embodiments, sequence-based separation can generate separated target templates and/or separated reference templates. Separated target templates and/or separated reference templates often are isolated away from the remaining templates in the nucleic acid sample. In certain embodiments, the separated target templates and the separated reference templates also are isolated away from each other (e.g., isolated in separate assay compartments). In certain embodiments, the separated target templates and the separated reference templates are isolated together (e.g., isolated in the same assay compartment). In some embodiments, unbound templates can be differentially removed or degraded or digested.

In some embodiments, a selective nucleic acid capture process is used to separate target and/or reference templates away from a nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a part or all of the nucleotide sequence of a target or reference template and can include use of a solid phase (e.g., solid phase array) and/or a solution based platform. Capture oligonucleotides (sometimes referred to as "bait") can be selected or designed such that they preferentially hybridize to nucleic acid templates from selected genomic regions or loci (e.g., one of chromosomes 21, 18, 13, X or Y, or a reference chromosome). In certain embodiments, a hybridization-based method (e.g., using oligonucleotide arrays) can be used to enrich for nucleic acid sequences from certain chromosomes (e.g., a potentially aneuploid chromosome, reference chromosome or other chromosome of interest), genes or regions of interest thereof. Thus, in some embodiments, a nucleic acid sample is optionally enriched by capturing a subset of templates using capture oligonucleotides complementary to, for example, selected genes in sample nucleic acid. In certain instances, captured templates are amplified. For example, captured templates containing adapters may be amplified using primers complementary to the nonrandom oligonucleotide adapters to form collections of amplified templates, indexed according to adapter sequence. In some embodiments, nucleic acid is enriched for templates from a select genomic region (e.g., chromosome, a gene) by amplification of one or more regions of interest using oligonucleotides (e.g., PCR primers) complementary to sequences in templates containing the region(s) of interest, or part(s) thereof.

In some embodiments, nucleic acid is enriched for a particular nucleic acid template length, range of lengths, or lengths under or over a particular threshold or cutoff using one or more length-based separation methods. Nucleic acid template length typically refers to the number of nucleotides in the template. Nucleic acid template length also is sometimes referred to as nucleic acid template size. In some embodiments, a length-based separation method is performed without measuring lengths of individual templates. In some embodiments, a length based separation method is performed in conjunction with a method for determining length of individual templates. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In certain instances, length-based separation approaches can include selective sequence tagging approaches, fragment circularization, chemical treatment (e.g., formaldehyde, polyethylene glycol (PEG) precipitation), mass spectrometry and/or size-specific nucleic acid amplification, for example.

Nucleic Acid Quantification

The amount of nucleic acid (e.g., concentration, relative amount, absolute amount, copy number, and the like) in a sample may be determined. The amount of a minority nucleic acid (e.g., concentration, relative amount, absolute amount, copy number, and the like) in nucleic acid is determined in some embodiments. In certain embodiments, the amount of a minority nucleic acid species in a sample is referred to as "minority species fraction." In some embodiments "minority species fraction" refers to the fraction of a minority nucleic acid species in circulating cell-free nucleic acid in a sample (e.g., a blood sample, a serum sample, a plasma sample, a urine sample) obtained from a subject.

The amount of a minority nucleic acid in extracellular nucleic acid can be quantified and used in conjunction with a method provided herein. Thus, in certain embodiments, methods described herein comprise an additional step of determining the amount of a minority nucleic acid. The amount of a minority nucleic acid can be determined in a sample from a subject before or after processing to prepare sample nucleic acid. In certain embodiments, the amount of a minority nucleic acid is determined in a sample after sample nucleic acid is processed and prepared, which amount is utilized for further assessment. In some embodiments, an outcome comprises factoring the minority species fraction in the sample nucleic acid (e.g., adjusting counts, removing samples, making a call or not making a call).

A determination of minority species fraction can be performed before, during, or at any one point in a method described herein, or after certain methods described herein (e.g., detection of a genetic variation or genetic alteration). For example, to conduct a genetic variation/genetic alteration determination method with a certain sensitivity or specificity, a minority nucleic acid quantification method may be implemented prior to, during or after genetic variation/genetic alteration determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more minority nucleic acid. In some embodiments, samples determined as having a certain threshold amount of minority nucleic acid (e.g., about 15% or more minority nucleic acid; about 4% or more minority nucleic acid) are further analyzed for a genetic variation/genetic alteration, or the presence or absence of a genetic variation/genetic alteration, for example. In certain embodiments, determinations of, for example, a genetic variation or genetic alteration are selected (e.g., selected and communicated to a patient) only for samples having a certain threshold amount of a minority nucleic acid (e.g., about 15% or more minority nucleic acid; about 4% or more minority nucleic acid).

The amount of cancer cell nucleic acid (e.g., concentration, relative amount, absolute amount, copy number, and the like) in nucleic acid is determined in some embodiments. In certain instances, the amount of cancer cell nucleic acid in a sample is referred to as "fraction of cancer cell nucleic acid," and sometimes is referred to as "cancer fraction" or "tumor fraction." In some embodiments "fraction of cancer cell nucleic acid" refers to the fraction of cancer cell nucleic acid in circulating cell-free nucleic acid in a sample (e.g., a blood sample, a serum sample, a plasma sample, a urine sample) obtained from a subject.

The amount of fetal nucleic acid (e.g., concentration, relative amount, absolute amount, copy number, and the like) in nucleic acid is determined in some embodiments. In certain embodiments, the amount of fetal nucleic acid in a sample is referred to as "fetal fraction." In some embodiments "fetal fraction" refers to the fraction of fetal nucleic acid in circulating cell-free nucleic acid in a sample (e.g., a blood sample, a serum sample, a plasma sample, a urine sample) obtained from a pregnant female. Certain methods described herein or known in the art for determining fetal fraction can be used for determining a fraction of cancer cell nucleic acid and/or a minority species fraction.

In certain instances, fetal fraction may be determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation) between mother and fetus, or fetal RNA markers in maternal blood plasma (see e.g., Lo, 2005, Journal of Histochemistry and Cytochemistry 53 (3): 293-296)). Determination of fetal fraction sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample.

In certain embodiments, a minority species fraction can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method for determining fetal fraction, for example, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome.

A minority species fraction can be determined, in some embodiments, using methods that incorporate information derived from chromosomal aberrations as described, for example, in International Patent Application Publication No. WO2014/055774, which is incorporated by reference herein. A minority species fraction can be determined, in some embodiments, using methods that incorporate information derived from sex chromosomes as described, for example, in U.S. Patent Application Publication No. 2013/0288244 and U.S. Patent Application Publication No. 2013/0338933, each of which is incorporated by reference herein.

A minority species fraction can be determined in some embodiments using methods that incorporate fragment length information (e.g., fragment length ratio (FLR) analysis, fetal ratio statistic (FRS) analysis as described in International Patent Application Publication No. WO2013/177086, which is incorporated by reference herein). Cell-free fetal nucleic acid fragments generally are shorter than maternally-derived nucleic acid fragments (see e.g., Chan et al. (2004) Clin. Chem. 50:88-92; Lo et al. (2010) Sci. Transl. Med. 2:61ra91). Thus, fetal fraction can be determined, in some embodiments, by counting templates under a particular length threshold and comparing the counts, for example, to counts from templates over a particular length threshold and/or to the amount of total nucleic acid in the sample. Methods for counting nucleic acid templates of a particular length are described in further detail in International Patent Application Publication No. WO2013/177086.

A minority species fraction can be determined, in some embodiments, according to portion-specific fraction estimates (e.g., as described in International Patent Application Publication No. WO 2014/205401, which is incorporated by reference herein). Without being limited to theory, the amount of reads from fetal CCF fragments (e.g., fragments of a particular length, or range of lengths) often map with ranging frequencies to portions (e.g., within the same sample, e.g., within the same sequencing run). Also, without being limited to theory, certain portions, when compared among multiple samples, tend to have a similar representation of reads from fetal CCF fragments (e.g., fragments of a particular length, or range of lengths), and that the representation correlates with portion-specific fetal fractions (e.g., the relative amount, percentage or ratio of CCF fragments originating from a fetus). Portion-specific fetal fraction estimates generally are determined according to portion-specific parameters and their relation to fetal fraction.

In some embodiments, the determination of minority species fraction (e.g., fraction of cancer cell nucleic acid; fetal fraction) is not required or necessary for identifying the presence or absence of a genetic variation or genetic alteration. In some embodiments, identifying the presence or absence of a genetic variation or genetic alteration does not require a sequence differentiation of a minority nucleic acid versus a majority nucleic acid. In certain embodiments, this is because the summed contribution of both minority and majority sequences in a particular chromosome, chromosome portion or part thereof is analyzed. In some embodiments, identifying the presence or absence of a genetic variation or genetic alteration does not rely on a priori sequence information that would distinguish minority nucleic acid from majority nucleic acid.

Nucleic Acid Library

In some embodiments a nucleic acid library is a plurality of polynucleotide molecules (e.g., a sample of nucleic acids) that are prepared, assembled and/or modified for a specific process, non-limiting examples of which include immobilization on a solid phase (e.g., a solid support, a flow cell, a bead), enrichment, amplification, cloning, detection and/or for nucleic acid sequencing. In certain embodiments, a nucleic acid library is prepared prior to or during a sequencing process. A nucleic acid library (e.g., sequencing library) can be prepared by a suitable method as known in the art. A nucleic acid library can be prepared by a targeted or a non-targeted preparation process.

In some embodiments a library of nucleic acids is modified to comprise a chemical moiety (e.g., a functional group) configured for immobilization of nucleic acids to a solid support. In some embodiments a library of nucleic acids is modified to comprise a biomolecule (e.g., a functional group) and/or member of a binding pair configured for immobilization of the library to a solid support, non-limiting examples of which include thyroxin-binding globulin, steroid-binding proteins, antibodies, antigens, haptens, enzymes, lectins, nucleic acids, repressors, protein A, protein G, avidin, streptavidin, biotin, complement component C1q, nucleic acid-binding proteins, receptors, carbohydrates, oligonucleotides, polynucleotides, complementary nucleic acid sequences, the like and combinations thereof. Some examples of specific binding pairs include, without limitation: an avidin moiety and a biotin moiety; an antigenic epitope and an antibody or immunologically reactive fragment thereof; an antibody and a hapten; a digoxigen moiety and an anti-digoxigen antibody, a fluorescein moiety and an anti-fluorescein antibody: an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; an oligonucleotide or polynucleotide and its corresponding complement; the like or combinations thereof.

In some embodiments, a library of nucleic acids is modified to comprise one or more polynucleotides of known composition, non-limiting examples of which include an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, the like or combinations thereof. Polynucleotides of known sequence can be added at a suitable position, for example on the 5' end, 3' end or within a nucleic acid sequence. Polynucleotides of known sequence can be the same or different sequences. In some embodiments a polynucleotide of known sequence is configured to hybridize to one or more oligonucleotides immobilized on a surface (e.g., a surface in flow cell). For example, a nucleic acid molecule comprising a 5' known sequence may hybridize to a first plurality of oligonucleotides while the 3' known sequence may hybridize to a second plurality of oligonucleotides. In some embodiments a library of nucleic acid can comprise chromosome-specific tags, capture sequences, labels and/or adapters. In some embodiments, a library of nucleic acids comprises one or more detectable labels. In some embodiments one or more detectable labels may be incorporated into a nucleic acid library at a 5' end, at a 3' end, and/or at any nucleotide position within a nucleic acid in the library. In some embodiments a library of nucleic acids comprises hybridized oligonucleotides. In certain embodiments hybridized oligonucleotides are labeled probes. In some embodiments a library of nucleic acids comprises hybridized oligonucleotide probes prior to immobilization on a solid phase.

In some embodiments, a polynucleotide of known sequence comprises a universal sequence. A universal sequence is a specific nucleotide sequence that is integrated into two or more nucleic acid molecules or two or more subsets of nucleic acid molecules where the universal sequence is the same for all molecules or subsets of molecules that it is integrated into. A universal sequence is often designed to hybridize to and/or amplify a plurality of different sequences using a single universal primer that is complementary to a universal sequence. In some embodiments two (e.g., a pair) or more universal sequences and/or universal primers are used. A universal primer often comprises a universal sequence. In some embodiments adapters (e.g., universal adapters) comprise universal sequences. In some embodiments one or more universal sequences are used to capture, identify and/or detect multiple species or subsets of nucleic acids.

In certain embodiments of preparing a nucleic acid library, (e.g., in certain sequencing by synthesis procedures), nucleic acids are size selected and/or fragmented into lengths of several hundred base pairs, or less (e.g., in preparation for library generation). In some embodiments, library preparation is performed without fragmentation (e.g., when using cell-free DNA).

In certain embodiments, a ligation-based library preparation method is used (e.g., ILLUMINA TRUSEQ, Illumina, San Diego Calif.). Ligation-based library preparation methods often make use of an adapter (e.g., a methylated adapter) design which can incorporate an index sequence (e.g., a sample index sequence to identify sample origin for a nucleic acid sequence) at the initial ligation step and often can be used to prepare samples for single-read sequencing, paired-end sequencing and multiplexed sequencing. For example, nucleic acids (e.g., fragmented nucleic acids or cell-free DNA) may be end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides.

In some embodiments nucleic acid library preparation comprises ligating an oligonucleotide adapter. Oligonucleotide adapters are often complementary to flow-cell anchors, and sometimes are utilized to immobilize a nucleic acid library to a solid support, such as the inside surface of a flow cell, for example. In some embodiments, a nonrandom oligonucleotide adapter comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing). In some embodiments, a nonrandom oligonucleotide adapter comprises one or more of primer annealing polynucleotide (e.g., for annealing to flow cell attached oligonucleotides and/or to free amplification primers), an index polynucleotide (e.g., sample index sequence for tracking nucleic acid from different samples), and a barcode polynucleotide (e.g., single molecule barcode (SMB) or duplex barcode (DB) for tracking individual molecules of sample nucleic acid that are amplified prior to sequencing).

An identifier can be a suitable detectable label incorporated into or attached to a nucleic acid (e.g., a polynucleotide) that allows detection and/or identification of nucleic acids that comprise the identifier. In some embodiments an identifier is incorporated into or attached to a nucleic acid during a sequencing method (e.g., by a polymerase). Non-limiting examples of identifiers include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein (e.g., an enzyme, an antibody or part thereof, a linker, a member of a binding pair), the like or combinations thereof. In some embodiments an identifier (e.g., a nucleic acid index or barcode) is a unique, known and/or identifiable sequence of nucleotides or nucleotide analogues. In some embodiments identifiers are six or more contiguous nucleotides. A multitude of fluorophores are available with a variety of different excitation and emission spectra. Any suitable type and/or number of fluorophores can be used as an identifier. In some embodiments 1 or more, 2 or more, 3 or more, 4 or more, 5 or more, 6 or more, 7 or more, 8 or more, 9 or more, 10 or more, 20 or more, 30 or more or 50 or more different identifiers are utilized in a method described herein (e.g., a nucleic acid detection and/or sequencing method). In some embodiments, one or two types of identifiers (e.g., fluorescent labels) are linked to each nucleic acid in a library. Detection and/or quantification of an identifier can be performed by a suitable method, apparatus or machine, non-limiting examples of which include flow cytometry, quantitative polymerase chain reaction (qPCR), gel electrophoresis, a luminometer, a fluorometer, a spectrophotometer, a suitable gene-chip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In some embodiments, a transposon-based library preparation method is used (e.g., EPICENTRE NEXTERA, Epicentre, Madison, Wis.). Transposon-based methods typically use in vitro transposition to simultaneously fragment and tag DNA in a single-tube reaction (often allowing incorporation of platform-specific tags and optional barcodes), and prepare sequencer-ready libraries.

In some embodiments, a nucleic acid library or parts thereof are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by a suitable method. A nucleic acid library can be amplified by a thermocycling method or by an isothermal amplification method. In some embodiments a rolling circle amplification method is used. In some embodiments amplification takes place on a solid support (e.g., within a flow cell) where a nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support. In some embodiments, modified nucleic acid (e.g., nucleic acid modified by addition of adapters) is amplified.

In some embodiments, solid phase amplification comprises a nucleic acid amplification reaction comprising only one species of oligonucleotide primer immobilized to a surface. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WildFire amplification (e.g., U.S. Patent Application Publication No. 2013/0012399), the like or combinations thereof.

Figure 4:
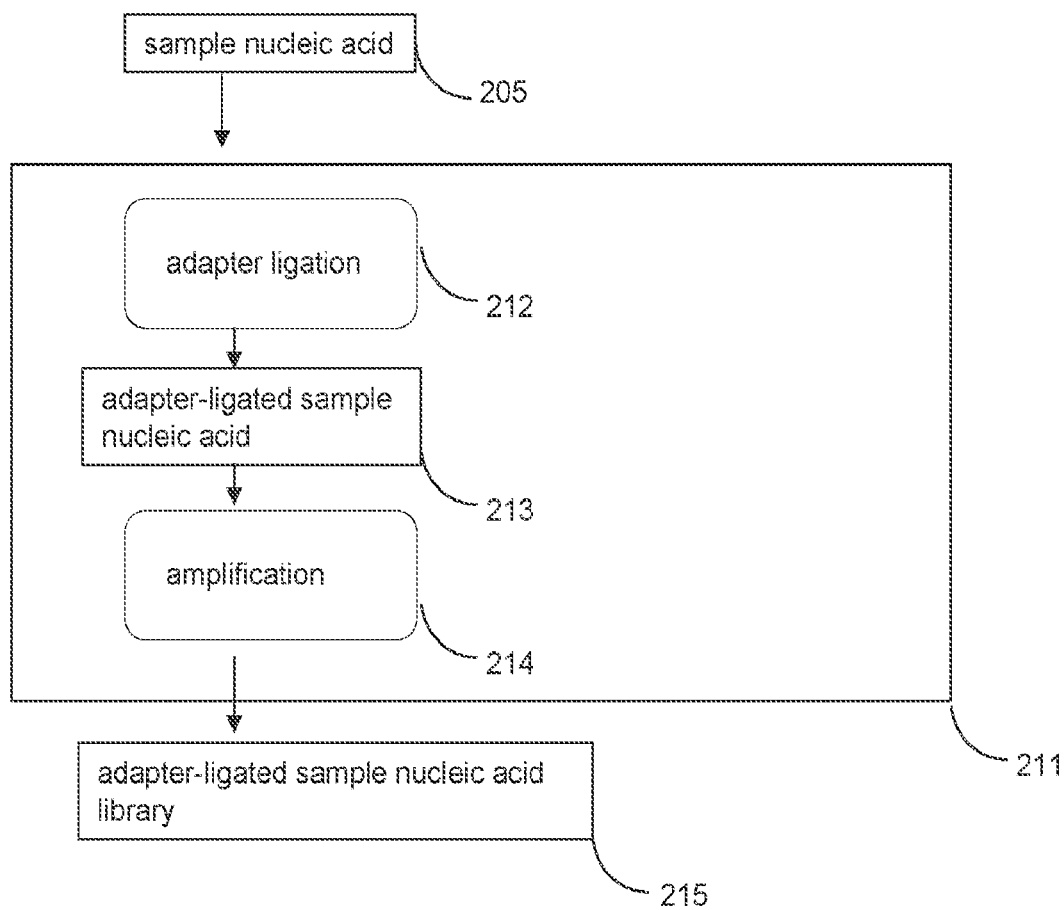
FIG. 4 shows an illustrative embodiment of a process described herein.
Figure 5:
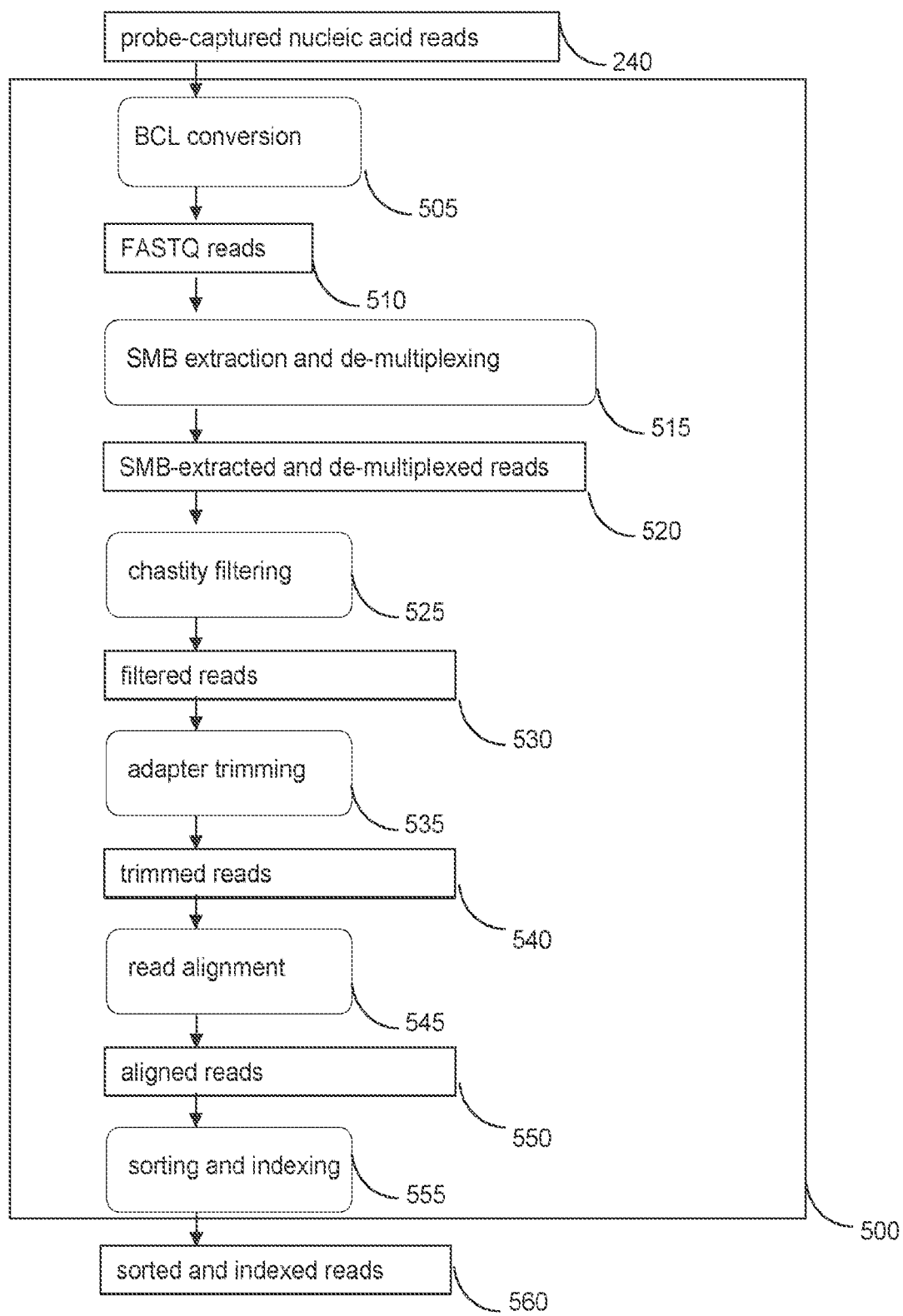
FIG. 5 shows an illustrative embodiment of a process described herein.
Figure 6:
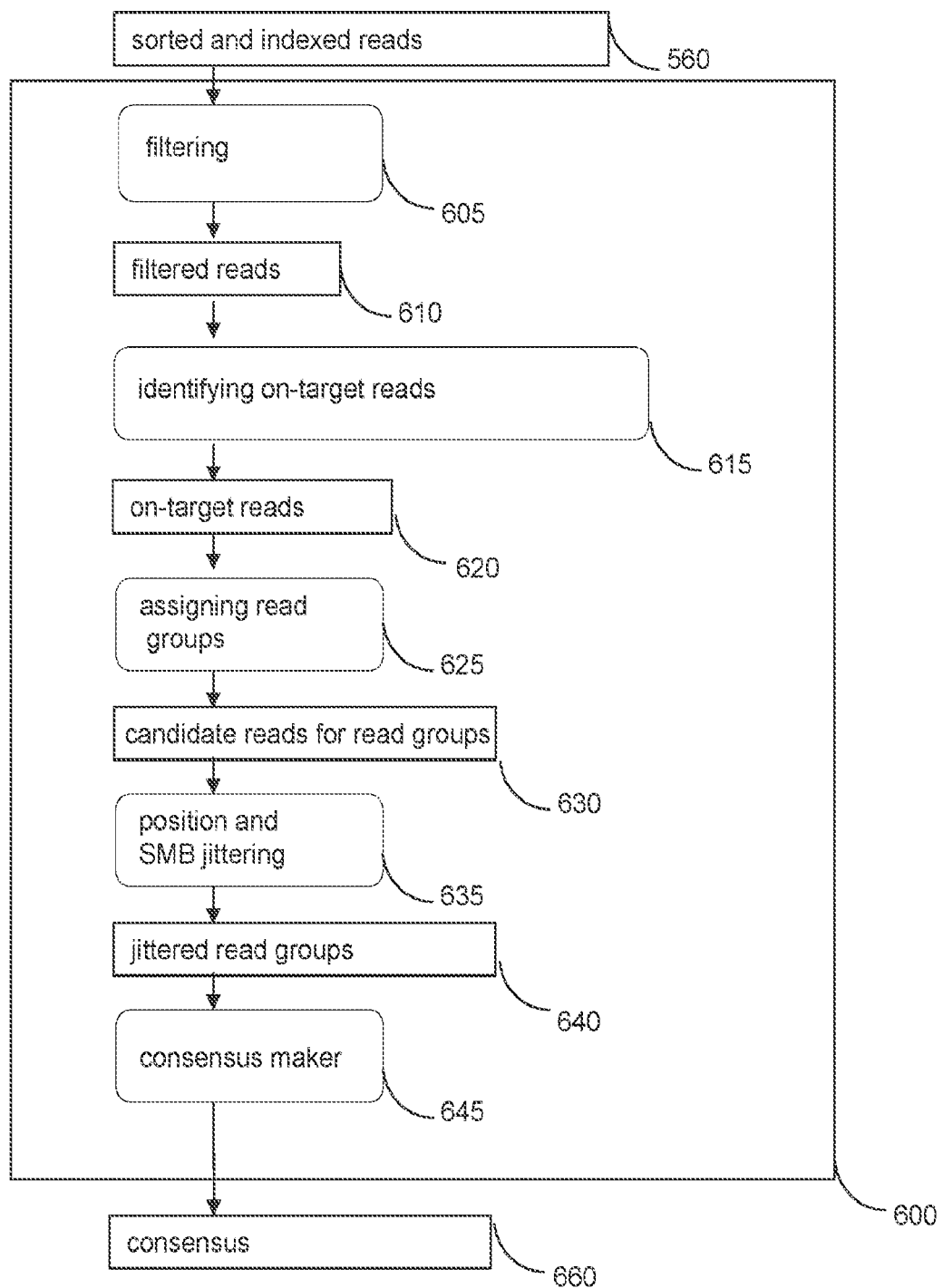
FIG. 6 shows an illustrative embodiment of a process described herein.

An embodiment of nucleic acid library preparation is illustrated in FIG. 4. Sample nucleic acid 205 is subjected to adapter ligation and amplification to generate an adapter-ligated sample nucleic acid library 215. One embodiment of adapter ligation and amplification is illustrated as process 211. Sample nucleic acid 205 is subjected to adapter ligation 212 which generates adapter-ligated sample nucleic acid 213. Adapter-ligated sample nucleic acid 213 is subjected to amplification 214 which generates an adapter-ligated sample nucleic acid library 215.

Nucleic Acid Capture

In some embodiments, a sample nucleic acid (or a sample nucleic acid library) is subjected to a target capture process. Generally a target capture process is performed by contacting sample nucleic acid (or a sample nucleic acid library) with a set of probe oligonucleotides under hybridization conditions. A set of probe oligonucleotides (e.g., capture oligonucleotides or capture probes) generally includes a plurality of probe oligonucleotides having sequences that are complementary to, or substantially complementary to, sequences in sample nucleic acid. A plurality of probe oligonucleotides may include about 10 probe oligonucleotide species, about 50 probe oligonucleotide species, about 100 probe oligonucleotide species, about 5000 probe oligonucleotide species, about 1,000 probe oligonucleotide species, 2,000 probe oligonucleotide species, 3,000 probe oligonucleotide species, 4,000 probe oligonucleotide species, 5000 probe oligonucleotide species, 10,000 probe oligonucleotide species, or more. Generally, a first probe oligonucleotide species has a different nucleotide sequence than a second probe oligonucleotide species, and different species of probe oligonucleotides in a set each have a different nucleotide sequence.

A probe oligonucleotide typically comprises a nucleotide sequence capable of hybridizing or annealing to a nucleic acid template of interest (e.g. target template) or a portion thereof. A probe oligonucleotide may be naturally occurring or synthetic and may be DNA or RNA based. Probe oligonucleotides can allow for specific separation of, for example, a target template away from other templates in a nucleic acid sample. The term "specific" or "specificity," as used herein, refers to the binding or hybridization of one molecule to another molecule, such as an oligonucleotide for a target polynucleotide. "Specific" or "specificity" refers to the recognition, contact, and formation of a stable complex between two molecules, as compared to substantially less recognition, contact, or complex formation of either of those two molecules with other molecules. As used herein, the terms "anneal" and "hybridize" refer to the formation of a stable complex between two molecules. The terms "probe," "probe oligonucleotide," "capture probe," "capture oligonucleotide," "capture oligo," "oligo," or "oligonucleotide" may be used interchangeably throughout the document, when referring to probe oligonucleotides.

A probe oligonucleotide can be designed and synthesized using a suitable process, and may be of any length suitable for hybridizing to a nucleotide sequence of interest and performing separation and/or analysis processes described herein. Oligonucleotides may be designed based upon a nucleotide sequence of interest (e.g., target template sequence, genomic sequence, gene sequence). An oligonucleotide (e.g., a probe oligonucleotide), in some embodiments, may be about 10 to about 300 nucleotides, about 50 to about 200 nucleotides, about 75 to about 150 nucleotides, about 110 to about 130 nucleotides, or about 111, 112, 113, 114, 115, 116, 117, 118, 119, 120, 121, 122, 123, 124, 125, 126, 127, 128, or 129 nucleotides in length. An oligonucleotide may be composed of naturally occurring and/or non-naturally occurring nucleotides (e.g., labeled nucleotides), or a mixture thereof. Oligonucleotides suitable for use with embodiments described herein, may be synthesized and labeled using known techniques. Oligonucleotides may be chemically synthesized according to the solid phase phosphoramidite triester method first described by Beaucage and Caruthers (1981) Tetrahedron Letts. 22:1859-1862, using an automated synthesizer, and/or as described in Needham-VanDevanter et al. (1984) Nucleic Acids Res. 12:6159-6168. Purification of oligonucleotides can be effected by native acrylamide gel electrophoresis or by anion-exchange high-performance liquid chromatography (HPLC), for example, as described in Pearson and Regnier (1983) J. Chrom. 255:137-149.

All or a portion of a probe oligonucleotide sequence (naturally occurring or synthetic) may be substantially complementary to a target sequence or portion thereof, in some embodiments. As referred to herein, "substantially complementary" with respect to sequences refers to nucleotide sequences that will hybridize with each other. The stringency of the hybridization conditions can be altered to tolerate varying amounts of sequence mismatch. Included are target and oligonucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Probe oligonucleotides that are substantially complimentary to a nucleotide sequence of interest (e.g., target sequence) or portion thereof are also substantially similar to the compliment of the target sequence or relevant portion thereof (e.g., substantially similar to the anti-sense strand of the nucleic acid). One test for determining whether two nucleotide sequences are substantially similar is to determine the percent of identical nucleotide sequences shared. As referred to herein, "substantially similar" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other.

Hybridization conditions (e.g., annealing conditions) can be determined and/or adjusted, depending on the characteristics of the oligonucleotides used in an assay. Oligonucleotide sequence and/or length sometimes may affect hybridization to a nucleic acid sequence of interest. Depending on the degree of mismatch between an oligonucleotide and nucleic acid of interest, low, medium or high stringency conditions may be used to effect the annealing. As used herein, the term "stringent conditions" refers to conditions for hybridization and washing. Methods for hybridization reaction temperature condition optimization are known in the art, and may be found in Current Protocols in Molecular Biology, John Wiley & Sons, N.Y., 6.3.1-6.3.6 (1989). Aqueous and non-aqueous methods are described in that reference and either can be used. Non-limiting examples of stringent hybridization conditions are hybridization in 6× sodium chloride/sodium citrate (SSC) at about 45° C. followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C. followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile.

In some embodiments, one or more probe oligonucleotides are associated with an affinity ligand such as a member of a binding pair (e.g., biotin) or antigen that can bind to a capture agent such as avidin, streptavidin, an antibody, or a receptor. For example, a probe oligonucleotide may be biotinylated such that it can be captured onto a streptavidin-coated bead.

In some embodiments, one or more probe oligonucleotides and/or capture agents are effectively linked to a solid support or substrate. A solid support or substrate can be any physically separable solid to which a probe oligonucleotide can be directly or indirectly attached including, but not limited to, surfaces provided by microarrays and wells, and particles such as beads (e.g., paramagnetic beads, magnetic beads, microbeads, nanobeads), microparticles, and nanoparticles. Solid supports also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidenedifluoride (PVDF), and the like), polysaccharides, nylon or nitrocellulose, resins, silica or silica-based materials including silicon, silica gel, and modified silicon, Sephadex®, Sepharoset, carbon, metals (e.g., steel, gold, silver, aluminum, silicon and copper), inorganic glasses, conducting polymers (including polymers such as polypyrole and polyindole); micro or nanostructured surfaces such as nucleic acid tiling arrays, nanotube, nanowire, or nanoparticulate decorated surfaces, or porous surfaces or gels such as methacrylates, acrylamides, sugar polymers, cellulose, silicates, or other fibrous or stranded polymers. In some embodiments, the solid support or substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, the solid phase can be a collection of particles. In some embodiments, the particles can comprise silica, and the silica may comprise silica dioxide. In some embodiments the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of $Fe^{2+}$ and $Fe^{3+}$). The probe oligonucleotides may be linked to the solid support by covalent bonds or by non-covalent interactions and may be linked to the solid support directly or indirectly (e.g., via an intermediary agent such as a spacer molecule or biotin). A probe oligonucleotide may be linked to the solid support before, during or after nucleic acid capture.

Nucleic acid that has been modified, such as modified by the addition of adapter sequences described herein, may be captured. In some embodiments, unmodified nucleic acid is captured. Nucleic acid may be amplified before and/or after capture, in some embodiments, by an amplification process such as PCR. The term "captured nucleic acid" generally includes nucleic acid that has been captured and includes nucleic acid that has been captured and amplified. Captured nucleic acid may be subjected to additional rounds of capture and amplification, in some embodiments. Captured nucleic acid may be sequenced, such as by a sequencing process described herein.

Figure 2:
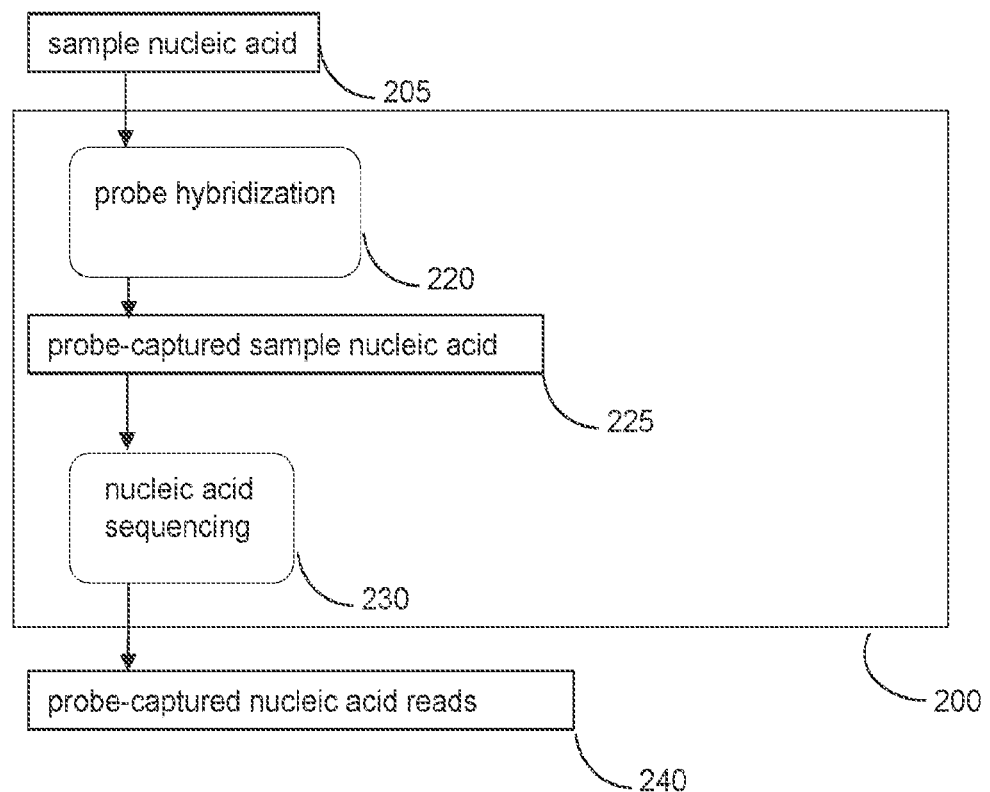
FIG. 2 shows an illustrative embodiment of a process described herein.

An embodiment of a nucleic acid target capture process is illustrated in FIG. 2. Sample nucleic acid 205 is subjected a nucleic acid capture process which generates probe-captured nucleic acid sequence reads 240. One embodiment of a nucleic acid capture process is illustrated as process 200). Sample nucleic acid 205 is subjected to probe hybridization 220 which generates probe-captured sample nucleic acid 225. Probe-captured sample nucleic acid 225 is subjected to nucleic acid sequencing 230 which generates probe-captured nucleic acid sequence reads 240.

Figure 3:
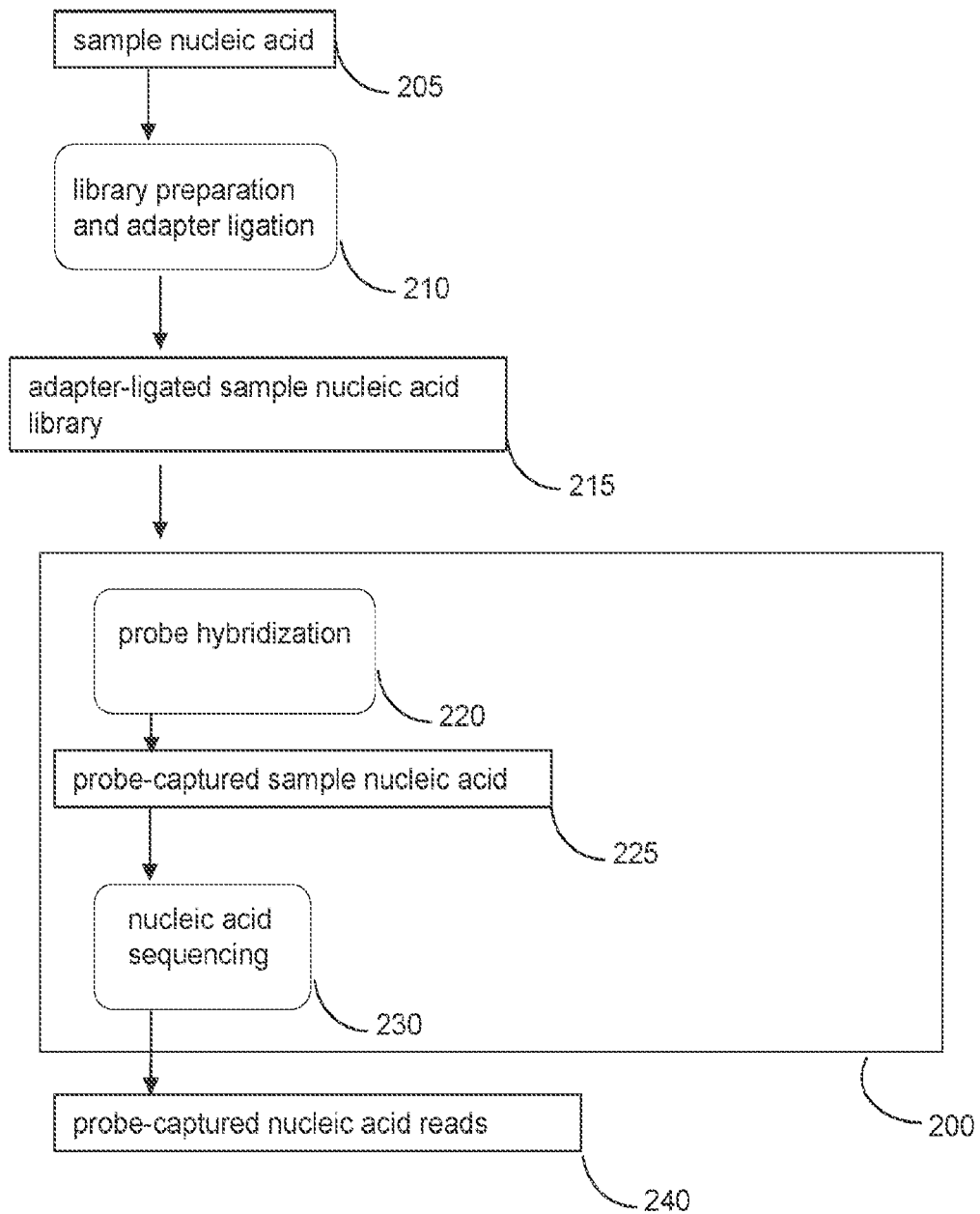
FIG. 3 shows an illustrative embodiment of a process described herein.

In some embodiments, a nucleic acid target capture process comprises probe hybridization to an adapter-ligated sample nucleic acid library. An embodiment of a nucleic acid target capture process comprising probe hybridization to an adapter-ligated sample nucleic acid library is illustrated in FIG. 3. Sample nucleic acid 205 is subjected to library preparation and adapter ligation 210 which generates an adapter-ligated sample nucleic acid library 215. Adapter-ligated sample nucleic acid library 215 is input for a nucleic acid capture process and probe-captured nucleic acid reads 240 are generated. One embodiment of a nucleic acid capture process is illustrated as process 200. An adapter-ligated sample nucleic acid library 215 is subjected to probe hybridization 220 which generates probe-captured sample nucleic acid 225. Probe-captured sample nucleic acid, or "captured target nucleic acid" 225 is subjected to nucleic acid sequencing 230 which generates probe-captured nucleic acid sequence reads 240.

Nucleic Acid Sequencing and Processing

Methods provided herein generally include nucleic acid sequencing and analysis. In some embodiments, nucleic acid is sequenced and the sequencing product (e.g., a collection of sequence reads) is processed prior to, or in conjunction with, an analysis of the sequenced nucleic acid. For example, sequence reads may be processed according to one or more of the following: aligning, mapping, filtering portions, selecting portions, counting, normalizing, weighting, generating a profile, and the like, and combinations thereof. Certain processing steps may be performed in any order and certain processing steps may be repeated. For example, portions may be filtered followed by sequence read count normalization, and, in certain embodiments, sequence read counts may be normalized followed by portion filtering. In some embodiments, a portion filtering step is followed by sequence read count normalization followed by a further portion filtering step. Certain sequencing methods and processing steps are described in further detail below.

Sequencing

In some embodiments, nucleic acid (e.g., nucleic acid fragments, sample nucleic acid, cell-free nucleic acid) is sequenced. In certain instances, a full or substantially full sequence is obtained and sometimes a partial sequence is obtained. Nucleic acid sequencing generally produces a collection of sequence reads. As used herein, "reads" (e.g., "a read," "a sequence read") are short nucleotide sequences produced by any sequencing process described herein or known in the art. Reads can be generated from one end of nucleic acid fragments ("single-end reads"), and sometimes are generated from both ends of nucleic acid fragments (e.g., paired-end reads, double-end reads).

The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length of about 1000 bp or more. In some embodiments sequence reads are of a mean, median, average or absolute length of about 1500, 2000, 2500, 3000, 3500, 4000, 4500, or 5000 bp or more. In some embodiments, sequence reads are of a mean, median, average or absolute length of about 100 bp to about 200 bp. In some embodiments, sequence reads are of a mean, median, average or absolute length of about 140 bp to about 160 bp. For example, sequence reads may be of a mean, median, average or absolute length of about 140, 141, 142, 143, 144, 145, 146, 147, 148, 149, 150, 151, 152, 153, 154, 155, 156, 157, 158, 159 or 160 bp.

In some embodiments the nominal, average, mean or absolute length of single-end reads sometimes is about 10 continuous nucleotides to about 250 or more contiguous nucleotides, about 15 contiguous nucleotides to about 200 or more contiguous nucleotides, about 15 contiguous nucleotides to about 150 or more contiguous nucleotides, about 15 contiguous nucleotides to about 125 or more contiguous nucleotides, about 15 contiguous nucleotides to about 100 or more contiguous nucleotides, about 15 contiguous nucleotides to about 75 or more contiguous nucleotides, about 15 contiguous nucleotides to about 60 or more contiguous nucleotides, 15 contiguous nucleotides to about 50 or more contiguous nucleotides, about 15 contiguous nucleotides to about 40 or more contiguous nucleotides, and sometimes about 15 contiguous nucleotides or about 36 or more contiguous nucleotides. In certain embodiments the nominal, average, mean or absolute length of single-end reads is about 20 to about 30 bases, or about 24 to about 28 bases in length. In certain embodiments the nominal, average, mean or absolute length of single-end reads is about 1, 2, 3, 4, 5, 6, 7, 8, 9, 10, 11, 12, 13, 14, 15, 16, 17, 18, 19, 21, 22, 23, 24, 25, 26, 27, 28 or about 29 bases or more in length. In certain embodiments the nominal, average, mean or absolute length of single-end reads is about 20 to about 200 bases, about 100 to about 200 bases, or about 140 to about 160 to about 28 bases in length. In certain embodiments the nominal, average, mean or absolute length of single-end reads is about 30, 40, 50, 60, 70, 80, 90, 100, 110, 120, 130, 140, 150, 160, 170, 180, 190, or about 200 bases or more in length. In certain embodiments, the nominal, average, mean or absolute length of paired-end reads sometimes is about 10 contiguous nucleotides to about 25 contiguous nucleotides or more (e.g., about 10, 11, 12, 13, 14, 15, 16, 17, 18, 19, 20, 21, 22, 23, 24 or 25 nucleotides in length or more), about 15 contiguous nucleotides to about 20 contiguous nucleotides or more, and sometimes is about 17 contiguous nucleotides or about 18 contiguous nucleotides. In certain embodiments, the nominal, average, mean or absolute length of paired-end reads sometimes is about 25 contiguous nucleotides to about 400 contiguous nucleotides or more (e.g., about 25, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 nucleotides in length or more), about 50 contiguous nucleotides to about 350 contiguous nucleotides or more, about 100 contiguous nucleotides to about 325 contiguous nucleotides, about 150 contiguous nucleotides to about 325 contiguous nucleotides, about 200 contiguous nucleotides to about 325 contiguous nucleotides, 275 contiguous nucleotides to about 310 contiguous nucleotides, about 100 to about 200 contiguous nucleotides, about 100 to about 175 contiguous nucleotides, about 125 to about 175 contiguous nucleotides, and sometimes is about 140 to about 160 contiguous nucleotides. In certain embodiments, the nominal, average, mean, or absolute length of paired-end reads is about 150 contiguous nucleotides, and sometimes is 150 contiguous nucleotides.

In some embodiments, nucleotide sequence reads obtained from a sample are partial nucleotide sequence reads. As used herein, "partial nucleotide sequence reads" refers to sequence reads of any length with incomplete sequence information, also referred to as sequence ambiguity. Partial nucleotide sequence reads may lack information regarding nucleobase identity and/or nucleobase position or order. Partial nucleotide sequence reads generally do not include sequence reads in which the only incomplete sequence information (or in which less than all of the bases are sequenced or determined) is from inadvertent or unintentional sequencing errors. Such sequencing errors can be inherent to certain sequencing processes and include, for example, incorrect calls for nucleobase identity, and missing or extra nucleobases. Thus, for partial nucleotide sequence reads herein, certain information about the sequence is often deliberately excluded. That is, one deliberately obtains sequence information with respect to less than all of the nucleobases or which might otherwise be characterized as or be a sequencing error. In some embodiments, a partial nucleotide sequence read can span a portion of a nucleic acid template. In some embodiments, a partial nucleotide sequence read can span the entire length of a nucleic acid template. Partial nucleotide sequence reads are described, for example, in International Patent Application Publication No. WO2013/052907, the entire content of which is incorporated herein by reference, including all text, tables, equations and drawings.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from a sample from a subject can be reads from a mixture of a minority nucleic acid and a majority nucleic acid. For example, sequence reads obtained from the blood of a cancer patient can be reads from a mixture of cancer nucleic acid and non-cancer nucleic acid. In another example, sequence reads obtained from the blood of a pregnant female can be reads from a mixture of fetal nucleic acid and maternal nucleic acid. A mixture of relatively short reads can be transformed by processes described herein into a representation of genomic nucleic acid present in the subject, and/or a representation of genomic nucleic acid present in a tumor or a fetus. In certain instances, a mixture of relatively short reads can be transformed into a representation of a copy number alteration, a genetic variation/ genetic alteration or an aneuploidy, for example. In one example, reads of a mixture of cancer and non-cancer nucleic acid can be transformed into a representation of a composite chromosome or a part thereof comprising features of one or both cancer cell and non-cancer cell chromosomes. In another example, reads of a mixture of maternal and fetal nucleic acid can be transformed into a representation of a composite chromosome or a part thereof comprising features of one or both maternal and fetal chromosomes.

In some instances, circulating cell free nucleic acid fragments (CCF fragments) obtained from a cancer patient comprise nucleic acid fragments originating from normal cells (i.e., non-cancer fragments) and nucleic acid fragments originating from cancer cells (i.e., cancer fragments). Sequence reads derived from CCF fragments originating from normal cells (i.e., non-cancerous cells) are referred to herein as "non-cancer reads." Sequence reads derived from CCF fragments originating from cancer cells are referred to herein as "cancer reads." CCF fragments from which non-cancer reads are obtained may be referred to herein as non-cancer templates and CCF fragments from which cancer reads are obtained may be referred herein to as cancer templates.

In some instances, circulating cell free nucleic acid fragments (CCF fragments) obtained from a pregnant female comprise nucleic acid fragments originating from fetal cells (i.e., fetal fragments) and nucleic acid fragments originating from maternal cells (i.e., maternal fragments). Sequence reads derived from CCF fragments originating from a fetus are referred to herein as "fetal reads." Sequence reads derived from CCF fragments originating from the genome of a pregnant female (e.g., a mother) bearing a fetus are referred to herein as "maternal reads." CCF fragments from which fetal reads are obtained are referred to herein as fetal templates and CCF fragments from which maternal reads are obtained are referred herein to as maternal templates.

In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, some or all nucleic acids in a sample are enriched and/or amplified (e.g., non-specifically, e.g., by a PCR based method) prior to or during sequencing. In certain embodiments specific nucleic acid species or subsets in a sample are enriched and/or amplified prior to or during sequencing. In some embodiments, a species or subset of a pre-selected pool of nucleic acids is sequenced randomly. In some embodiments, nucleic acids in a sample are not enriched and/or amplified prior to or during sequencing.

In some embodiments, a representative fraction of a genome is sequenced and is sometimes referred to as "coverage" or "fold coverage." For example, a 1-fold coverage indicates that roughly 100% of the nucleotide sequences of the genome are represented by reads. In some instances, fold coverage is referred to as (and is directly proportional to) "sequencing depth." In some embodiments, "fold coverage" is a relative term referring to a prior sequencing run as a reference. For example, a second sequencing run may have 2-fold less coverage than a first sequencing run. In some embodiments a genome is sequenced with redundancy, where a given region of the genome can be covered by two or more reads or overlapping reads (e.g., a "fold coverage" greater than 1, e.g., a 2-fold coverage). In some embodiments, a genome (e.g., a whole genome) is sequenced with about 0.01-fold to about 100-fold coverage, about 0.1-fold to 20-fold coverage, or about 0.1-fold to about 1-fold coverage (e.g., about 0.015-, 0.02-, 0.03-, 0.04-, 0.05-, 0.06-, 0.07-, 0.08-, 0.09-, 0.1-, 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold or greater coverage). In some embodiments, specific parts of a genome (e.g., genomic parts from targeted and/or probe-based methods) are sequenced and fold coverage values generally refer to the fraction of the specific genomic parts sequenced (i.e., fold coverage values do not refer to the whole genome). In some instances, specific genomic parts are sequenced at 1000-fold coverage or more. For example, specific genomic parts may be sequenced at 2000-fold, 5,000-fold, 10,000-fold, 20,000-fold, 30,000-fold, 40,000-fold or 50,000-fold coverage. In some embodiments, sequencing is at about 100 fold to about 200,000 fold coverage. In some embodiments, sequencing is at about 500 fold to about 150,000 fold coverage. In some embodiments, sequencing is at about 1.000-fold to about 100,000-fold coverage. In some embodiments, sequencing is at about 10,000-fold to about 70,000-fold coverage. In some embodiments, sequencing is at about 20,000-fold to about 60,000-fold coverage. In some embodiments, sequencing is at about 30,000-fold to about 50,000-fold coverage.

In some embodiments, one nucleic acid sample from one individual is sequenced. In certain embodiments, nucleic acids from each of two or more samples are sequenced, where samples are from one individual or from different individuals. In certain embodiments, nucleic acid samples from two or more biological samples are pooled, where each biological sample is from one individual or two or more individuals, and the pool is sequenced. In the latter embodiments, a nucleic acid sample from each biological sample often is identified by one or more unique identifiers.

In some embodiments, a sequencing method utilizes identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane is dependent on the number of unique identifiers utilized during library preparation and/or probe design. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments, sequencing technologies that include the use of nucleic acid imaging technologies (e.g., transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments. MPS sequencing methods utilize a targeted approach, where specific chromosomes, genes or regions of interest are sequenced. In certain embodiments, a non-targeted approach is used where most or all nucleic acids in a sample are sequenced, amplified and/or captured randomly.

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

MPS sequencing sometimes makes use of sequencing by synthesis and certain imaging processes. A nucleic acid sequencing technology that may be used in a method described herein is sequencing-by-synthesis and reversible terminator-based sequencing (e.g., Illumina's Genome Analyzer; Genome Analyzer II; HISEQ 2000; HISEQ 2500 (Illumina, San Diego Calif.)). With this technology, millions of nucleic acid (e.g., DNA) templates can be sequenced in parallel. In one example of this type of sequencing technology, a flow cell is used which contains an optically transparent slide with 8 individual lanes on the surfaces of which are bound oligonucleotide anchors (e.g., adapter primers).

Sequencing by synthesis generally is performed by iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof.

Any suitable MPS method, system or technology platform for conducting methods described herein can be used to obtain nucleic acid sequence reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500×1 W and/or 5500×1 W Genetic Analyzer based technologies (e.g., as developed and sold by Life Technologies, U.S. Patent Application Publication No. 2013/0012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing, the like or combinations thereof. Other sequencing methods that may be used to conduct methods herein include digital PCR, sequencing by hybridization, nanopore sequencing, chromosome-specific sequencing (e.g., using DANSR (digital analysis of selected regions) technology.

In some embodiments, sequence reads are generated, obtained, gathered, assembled, manipulated, transformed, processed, and/or provided by a sequence module. A machine comprising a sequence module can be a suitable machine and/or apparatus that determines the sequence of a nucleic acid utilizing a sequencing technology known in the art. In some embodiments a sequence module can align, assemble, fragment, complement, reverse complement, and/or error check (e.g., error correct sequence reads).

Mapping Reads

Sequence reads can be mapped and the number of reads mapping to a specified nucleic acid region (e.g., a chromosome or portion thereof) are referred to as counts. Any suitable mapping method (e.g., process, algorithm, program, software, module, the like or combination thereof) can be used. Certain aspects of mapping processes are described hereafter.

Mapping nucleotide sequence reads (i.e., sequence information from a template whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped," as "a mapped sequence read" or as "a mapped read." In certain embodiments, a mapped sequence read is referred to as a "hit" or "count." In some embodiments, mapped sequence reads are grouped together according to various parameters and assigned to particular genomic portions, which are discussed in further detail below.

The terms "aligned," "alignment," or "aligning" generally refer to two or more nucleic acid sequences that can be identified as a match (e.g., 100% identity) or partial match. Alignments can be done manually or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand (e.g., sense or antisense strand). In certain embodiments a nucleic acid sequence is aligned with the reverse complement of another nucleic acid sequence.

Various computational methods can be used to map each sequence read to a portion. Non-limiting examples of computer algorithms that can be used to align sequences include, without limitation, BLAST, BLITZ, FASTA, BOWTIE 1, BOWTIE 2, ELAND, MAQ, PROBEMATCH, SOAP, BWA or SEQMAP, or variations thereof or combinations thereof. In some embodiments, sequence reads can be aligned with sequences in a reference genome. In some embodiments, sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search identified sequences against a sequence database. Search hits can then be used to sort the identified sequences into appropriate portions (described hereafter), for example.

In some embodiments, a read may uniquely or non-uniquely map to portions in a reference genome. A read is considered as "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at World Wide Web URL ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

In certain embodiments, mappability is assessed for a genomic region (e.g., portion, genomic portion). Mappability is the ability to unambiguously align a nucleotide sequence read to a portion of a reference genome, typically up to a specified number of mismatches, including, for example, 0, 1, 2 or more mismatches. For a given genomic region, the expected mappability can be estimated using a sliding-window approach of a preset read length and averaging the resulting read-level mappability values. Genomic regions comprising stretches of unique nucleotide sequence sometimes have a high mappability value.

For paired-end sequencing, reads may be mapped to a reference genome by use of a suitable mapping and/or alignment program, non-limiting examples of which include BWA (Li H. and Durbin R. (2009) *Bioinformatics* 25, 1754-60), Novoalign [Novocraft (2010)], Bowtie (Langmead B. et al., (2009) *Genome Biol.* 10:R25), SOAP2 (Li R, et al., (2009) *Bioinformatics* 25, 1966-67), BFAST (Homer N, et al., (2009) *PLoS ONE* 4, e7767), GASSST (Rizk, G. and Lavenier, D. (2010) *Bioinformatics* 26, 2534-2540), and MPscan (Rivals E., et al. (2009) *Lecture Notes in Computer Science* 5724, 246-260), and the like. Paired-end reads may be mapped and/or aligned using a suitable short read alignment program. Non-limiting examples of short read alignment programs include BarraCUDA, BFAST, BLASTN, BLAT, Bowtie, BWA, CASHX, CUDA-EC, CUSHAW, CUSHAW2, drFAST, ELAND, ERNE, GNUMAP, GEM, GensearchNGS, GMAP, Geneious Assembler, iSAAC, LAST, MAQ, mrFAST, mrsFAST, MOSAIK, MPscan, Novoalign, NovoalignCS, Novocraft, NextGENe, Omixon, PALMapper, Partek, PASS, PerM, QPalma, RazerS, REAL, cREAL, RMAP, rNA, RTG, Segemehl, SeqMap, Shrec, SHRiMP, SLIDER, SOAP, SOAP2, SOAP3, SOCS, SSAHA, SSAHA2, Stampy, SToRM, Subread, Subjunc, Taipan, UGENE, VelociMapper, TimeLogic, XpressAlign, ZOOM, the like or combinations thereof. Paired-end reads are often mapped to opposing ends of the same polynucleotide fragment, according to a reference genome. In some embodiments, read mates are mapped independently. In some embodiments, information from both sequence reads (i.e., from each end) is factored in the mapping process. A reference genome is often used to determine and/or infer the sequence of nucleic acids located between paired-end read mates. The term "discordant read pairs" as used herein refers to a paired-end read comprising a pair of read mates, where one or both read mates fail to unambiguously map to the same region of a reference genome defined, in part, by a segment of contiguous nucleotides. In some embodiments discordant read pairs are paired-end read mates that map to unexpected locations of a reference genome. Non-limiting examples of unexpected locations of a reference genome include (i) two different chromosomes, (ii) locations separated by more than a predetermined fragment size (e.g., more than 300 bp, more than 500 bp, more than 1000 bp, more than 5000 bp, or more than 10,000 bp), (iii) an orientation inconsistent with a reference sequence (e.g., opposite orientations), the like or a combination thereof. In some embodiments discordant read mates are identified according to a length (e.g., an average length, a predetermined fragment size) or expected length of template polynucleotide fragments in a sample. For example, read mates that map to a location that is separated by more than the average length or expected length of polynucleotide fragments in a sample are sometimes identified as discordant read pairs. Read pairs that map in opposite orientation are sometimes determined by taking the reverse complement of one of the reads and comparing the alignment of both reads using the same strand of a reference sequence. Discordant read pairs can be identified by any suitable method and/or algorithm known in the art or described herein (e.g., SVDetect, Lumpy, BreakDancer, BreakDancerMax, CREST, DELLY, the like or combinations thereof).

Portions

In some embodiments, mapped sequence reads are grouped together according to various parameters and assigned to particular genomic portions (e.g., portions of a reference genome). A "portion" also may be referred to herein as a "genomic section," "bin," "partition," "portion of a reference genome," "portion of a chromosome" or "genomic portion."

A portion often is defined by partitioning of a genome according to one or more features. Non-limiting examples of certain partitioning features include length (e.g., fixed length, non-fixed length) and other structural features. Genomic portions sometimes include one or more of the following features: fixed length, non-fixed length, random length, non-random length, equal length, unequal length (e.g., at least two of the genomic portions are of unequal length), do not overlap (e.g., the 3' ends of the genomic portions sometimes abut the 5' ends of adjacent genomic portions), overlap (e.g., at least two of the genomic portions overlap), contiguous, consecutive, not contiguous, and not consecutive. Genomic portions sometimes are about 1 to about 1,000 kilobases in length (e.g., about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900 kilobases in length), about 5 to about 500 kilobases in length, about 10 to about 100 kilobases in length, or about 40 to about 60 kilobases in length.

Partitioning sometimes is based on, or is based in part on, certain informational features, such as, information content and information gain, for example. Non-limiting examples of certain informational features include speed and/or convenience of alignment, sequencing coverage variability, GC content (e.g., stratified GC content, particular GC contents, high or low GC content), uniformity of GC content, other measures of sequence content (e.g., fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, uncertainty value assigned to individual portions of a reference genome, and/or a targeted search for particular features. In some embodiments, information content may be quantified using a p-value profile measuring the significance of particular genomic locations for distinguishing between groups of confirmed normal and abnormal subjects (e.g. euploid and trisomy subjects, respectively).

In some embodiments, partitioning a genome may eliminate similar regions (e.g., identical or homologous regions or sequences) across a genome and only keep unique regions. Regions removed during partitioning may be within a single chromosome, may be one or more chromosomes, or may span multiple chromosomes. In some embodiments, a partitioned genome is reduced and optimized for faster alignment, often focusing on uniquely identifiable sequences.

In some embodiments, genomic portions result from a partitioning based on non-overlapping fixed size, which results in consecutive, non-overlapping portions of fixed length. Such portions often are shorter than a chromosome and often are shorter than a copy number variation (or copy number alteration) region (e.g., a region that is duplicated or is deleted), the latter of which can be referred to as a segment. A "segment" or "genomic segment" often includes two or more fixed-length genomic portions, and often includes two or more consecutive fixed-length portions (e.g., about 2 to about 100 such portions (e.g., 2, 3, 4, 5, 6, 7, 8, 9, 10, 11, 12, 13, 14, 15, 16, 17, 18, 19, 20, 25, 30, 35, 40, 45, 50, 60, 70, 80, 90 such portions)).

Multiple portions sometimes are analyzed in groups, and sometimes reads mapped to portions are quantified according to a particular group of genomic portions. Where portions are partitioned by structural features and correspond to regions in a genome, portions sometimes are grouped into one or more segments and/or one or more regions. Non-limiting examples of regions include sub-chromosome (i.e., shorter than a chromosome), chromosome, autosome, sex chromosome and combinations thereof. One or more sub-chromosome regions sometimes are genes, gene fragments, regulatory sequences, introns, exons, segments (e.g., a segment spanning a copy number alteration region), microduplications, microdeletions and the like. A region sometimes is smaller than a chromosome of interest or is the same size of a chromosome of interest, and sometimes is smaller than a reference chromosome or is the same size as a reference chromosome.

Filtering and/or Selecting Portions

In some embodiments, one or more processing steps can comprise one or more portion filtering steps and/or portion selection steps. The term "filtering" as used herein refers to removing portions or portions of a reference genome from consideration. In certain embodiments one or more portions are filtered (e.g., subjected to a filtering process) thereby providing filtered portions. In some embodiments a filtering process removes certain portions and retains portions (e.g., a subset of portions). Following a filtering process, retained portions are often referred to herein as filtered portions.

Portions of a reference genome can be selected for removal based on any suitable criteria, including but not limited to redundant data (e.g., redundant or overlapping mapped reads), non-informative data (e.g., portions of a reference genome with zero median counts), portions of a reference genome with over represented or under represented sequences, noisy data, the like, or combinations of the foregoing. A filtering process often involves removing one or more portions of a reference genome from consideration and subtracting the counts in the one or more portions of a reference genome selected for removal from the counted or summed counts for the portions of a reference genome, chromosome or chromosomes, or genome under consideration. In some embodiments, portions of a reference genome can be removed successively (e.g., one at a time to allow evaluation of the effect of removal of each individual portion), and in certain embodiments all portions of a reference genome marked for removal can be removed at the same time. In some embodiments, portions of a reference genome characterized by a variance above or below a certain level are removed, which sometimes is referred to herein as filtering "noisy" portions of a reference genome. In certain embodiments, a filtering process comprises obtaining data points from a data set that deviate from the mean profile level of a portion, a chromosome, or part of a chromosome by a predetermined multiple of the profile variance, and in certain embodiments, a filtering process comprises removing data points from a data set that do not deviate from the mean profile level of a portion, a chromosome or part of a chromosome by a predetermined multiple of the profile variance. In some embodiments, a filtering process is utilized to reduce the number of candidate portions of a reference genome analyzed for the presence or absence of a genetic variation/genetic alteration and/or copy number alteration (e.g., aneuploidy, microdeletion, microduplication). Reducing the number of candidate portions of a reference genome analyzed for the presence or absence of a genetic variation/genetic alteration and/or copy number alteration often reduces the complexity and/or dimensionality of a data set, and sometimes increases the speed of searching for and/or identifying genetic variations/genetic alteration and/or copy number alterations by two or more orders of magnitude.

Portions may be processed (e.g., filtered and/or selected) by any suitable method and according to any suitable parameter. Non-limiting examples of features and/or parameters that can be used to filter and/or select portions include redundant data (e.g., redundant or overlapping mapped reads), non-informative data (e.g., portions of a reference genome with zero mapped counts), portions of a reference genome with over represented or under represented sequences, noisy data, counts, count variability, coverage, mappability, variability, a repeatability measure, read density, variability of read density, a level of uncertainty, guanine-cytosine (GC) content, CCF fragment length and/or read length (e.g., a fragment length ratio (FLR), a fetal ratio statistic (FRS)), DNaseI-sensitivity, methylation state, acetylation, histone distribution, chromatin structure, percent repeats, the like or combinations thereof. Portions can be filtered and/or selected according to any suitable feature or parameter that correlates with a feature or parameter listed or described herein. Portions can be filtered and/or selected according to features or parameters that are specific to a portion (e.g., as determined for a single portion according to multiple samples) and/or features or parameters that are specific to a sample (e.g., as determined for multiple portions within a sample). In some embodiments portions are filtered and/or removed according to relatively low mappability, relatively high variability, a high level of uncertainty, relatively long CCF fragment lengths (e.g., low FRS, low FLR), relatively large fraction of repetitive sequences, high GC content, low GC content, low counts, zero counts, high counts, the like, or combinations thereof. In some embodiments portions (e.g., a subset of portions) are selected according to suitable level of mappability, variability, level of uncertainty, fraction of repetitive sequences, count, GC content, the like, or combinations thereof. In some embodiments portions (e.g., a subset of portions) are selected according to relatively short CCF fragment lengths (e.g., high FRS, high FLR). Counts and/or reads mapped to portions are sometimes processed (e.g., normalized) prior to and/or after filtering or selecting portions (e.g., a subset of portions). In some embodiments counts and/or reads mapped to portions are not processed prior to and/or after filtering or selecting portions (e.g., a subset of portions).

In some embodiments, portions may be filtered according to a measure of error (e.g., standard deviation, standard error, calculated variance, p-value, mean absolute error (MAE), average absolute deviation and/or mean absolute deviation (MAD)). In certain instances, a measure of error may refer to count variability. In some embodiments portions are filtered according to count variability. In certain embodiments count variability is a measure of error determined for counts mapped to a portion (i.e., portion) of a reference genome for multiple samples (e.g., multiple sample obtained from multiple subjects, e.g., 50 or more, 100 or more, 500 or more 1000 or more, 5000 or more or 10,000 or more subjects). In some embodiments, portions with a count variability above a pre-determined upper range are filtered (e.g., excluded from consideration). In some embodiments portions with a count variability below a pre-determined lower range are filtered (e.g., excluded from consideration). In some embodiments, portions with a count variability outside a pre-determined range are filtered (e.g., excluded from consideration). In some embodiments portions with a count variability within a pre-determined range are selected (e.g., used for determining the presence or absence of a copy number alteration). In some embodiments, count variability of portions represents a distribution (e.g., a normal distribution). In some embodiments portions are selected within a quantile of the distribution. In some embodiments portions within a 99% quantile of the distribution of count variability are selected.

Sequence reads from any suitable number of samples can be utilized to identify a subset of portions that meet one or more criteria, parameters and/or features described herein. Sequence reads from a group of samples from multiple subjects sometimes are utilized. In some embodiments, the multiple subjects include pregnant females. In some embodiments, the multiple subjects include healthy subjects. In some embodiments, the multiple subjects include cancer patients. One or more samples from each of the multiple subjects can be addressed (e.g., 1 to about 20 samples from each subject (e.g., about 2, 3, 4, 5, 6, 7, 8, 9, 10, 11, 12, 13, 14, 15, 16, 17, 18 or 19 samples)), and a suitable number of subjects may be addressed (e.g., about 2 to about 10,000 subjects (e.g., about 10, 20, 30, 40, 50, 60, 70, 80, 90, 100, 150, 200, 250, 300, 350, 400, 500, 600, 700, 800, 900, 1000, 2000, 3000, 4000, 5000, 6000, 7000, 8000, 9000 subjects)). In some embodiments, sequence reads from the same test sample(s) from the same subject are mapped to portions in the reference genome and are used to generate the subset of portions.

Portions can be selected and/or filtered by any suitable method. In some embodiments portions are selected according to visual inspection of data, graphs, plots and/or charts. In certain embodiments portions are selected and/or filtered (e.g., in part) by a system or a machine comprising one or more microprocessors and memory. In some embodiments portions are selected and/or filtered (e.g., in part) by a non-transitory computer-readable storage medium with an executable program stored thereon, where the program instructs a microprocessor to perform the selecting and/or filtering.

In some embodiments, sequence reads derived from a sample are mapped to all or most portions of a reference genome and a pre-selected subset of portions are thereafter selected. For example, a subset of portions to which reads from fragments under a particular length threshold preferentially map may be selected. Certain methods for pre-selecting a subset of portions are described in U.S. Patent Application Publication No. 2014/0180594, which is incorporated by reference herein. Reads from a selected subset of portions often are utilized in further steps of a determination of the presence or absence of a genetic variation or genetic alteration, for example. Often, reads from portions not selected are not utilized in further steps of a determination of the presence or absence of a genetic variation or genetic alteration (e.g., reads in the non-selected portions are removed or filtered).

In some embodiments portions associated with read densities (e.g., where a read density is for a portion) are removed by a filtering process and read densities associated with removed portions are not included in a determination of the presence or absence of a copy number alteration (e.g., a chromosome aneuploidy, microduplication, microdeletion). In some embodiments a read density profile comprises and/or comprises or consists of read densities of filtered portions. Portions are sometimes filtered according to a distribution of counts and/or a distribution of read densities. In some embodiments portions are filtered according to a distribution of counts and/or read densities where the counts and/or read densities are obtained from one or more reference samples. One or more reference samples may be referred to herein as a training set. In some embodiments portions are filtered according to a distribution of counts and/or read densities where the counts and/or read densities are obtained from one or more test samples. In some embodiments portions are filtered according to a measure of uncertainty for a read density distribution. In certain embodiments, portions that demonstrate a large deviation in read densities are removed by a filtering process. For example, a distribution of read densities (e.g., a distribution of average mean, or median read densities) can be determined, where each read density in the distribution maps to the same portion. A measure of uncertainty (e.g., a MAD) can be determined by comparing a distribution of read densities for multiple samples where each portion of a genome is associated with measure of uncertainty. According to the foregoing example, portions can be filtered according to a measure of uncertainty (e.g., a standard deviation (SD), a MAD) associated with each portion and a predetermined threshold. In certain instances, portions comprising MAD values within the acceptable range are retained and portions comprising MAD values outside of the acceptable range are removed from consideration by a filtering process. In some embodiments, according to the foregoing example, portions comprising read densities values (e.g., median, average or mean read densities) outside a predetermined measure of uncertainty are often removed from consideration by a filtering process. In some embodiments portions comprising read densities values (e.g., median, average or mean read densities) outside an inter-quartile range of a distribution are removed from consideration by a filtering process. In some embodiments portions comprising read densities values outside more than 2 times, 3 times, 4 times or 5 times an inter-quartile range of a distribution are removed from consideration by a filtering process. In some embodiments portions comprising read densities values outside more than 2 sigma, 3 sigma, 4 sigma, 5 sigma, 6 sigma, 7 sigma or 8 sigma (e.g., where sigma is a range defined by a standard deviation) are removed from consideration by a filtering process.

Sequence Read Quantification

Sequence reads that are mapped or partitioned based on a selected feature or variable can be quantified to determine the amount or number of reads that are mapped to one or more portions (e.g., portion of a reference genome), in some embodiments. In certain embodiments the quantity of sequence reads that are mapped to a portion or segment is referred to as a count or read density.

A count often is associated with a genomic portion. In some embodiments a count is determined from some or all of the sequence reads mapped to (i.e., associated with) a portion. In certain embodiments, a count is determined from some or all of the sequence reads mapped to a group of portions (e.g., portions in a segment or region (described herein)).

A count can be determined by a suitable method, operation or mathematical process. A count sometimes is the direct sum of all sequence reads mapped to a genomic portion or a group of genomic portions corresponding to a segment, a group of portions corresponding to a sub-region of a genome (e.g., copy number variation region, copy number alteration region, copy number duplication region, copy number deletion region, microduplication region, microdeletion region, chromosome region, autosome region, sex chromosome region) and/or sometimes is a group of portions corresponding to a genome. A read quantification sometimes is a ratio, and sometimes is a ratio of a quantification for portion(s) in region a to a quantification for portion(s) in region b. Region a sometimes is one portion, segment region, copy number variation region, copy number alteration region, copy number duplication region, copy number deletion region, microduplication region, microdeletion region, chromosome region, autosome region and/or sex chromosome region. Region b independently sometimes is one portion, segment region, copy number variation region, copy number alteration region, copy number duplication region, copy number deletion region, microduplication region, microdeletion region, chromosome region, autosome region, sex chromosome region, a region including all autosomes, a region including sex chromosomes and/or a region including all chromosomes.

In some embodiments, a count is derived from raw sequence reads and/or filtered sequence reads. In certain embodiments a count is an average, mean or sum of sequence reads mapped to a genomic portion or group of genomic portions (e.g., genomic portions in a region). In some embodiments, a count is associated with an uncertainty value. A count sometimes is adjusted. A count may be adjusted according to sequence reads associated with a genomic portion or group of portions that have been weighted, removed, filtered, normalized, adjusted, averaged, derived as a mean, derived as a median, added, or combination thereof.

A sequence read quantification sometimes is a read density. A read density may be determined and/or generated for one or more segments of a genome. In certain instances, a read density may be determined and/or generated for one or more chromosomes. In some embodiments a read density comprises a quantitative measure of counts of sequence reads mapped to a segment or portion of a reference genome. A read density can be determined by a suitable process. In some embodiments a read density is determined by a suitable distribution and/or a suitable distribution function. Non-limiting examples of a distribution function include a probability function, probability distribution function, probability density function (PDF), a kernel density function (kernel density estimation), a cumulative distribution function, probability mass function, discrete probability distribution, an absolutely continuous univariate distribution, the like, any suitable distribution, or combinations thereof. A read density may be a density estimation derived from a suitable probability density function. A density estimation is the construction of an estimate, based on observed data, of an underlying probability density function. In some embodiments a read density comprises a density estimation (e.g., a probability density estimation, a kernel density estimation). A read density may be generated according to a process comprising generating a density estimation for each of the one or more portions of a genome where each portion comprises counts of sequence reads. A read density may be generated for normalized and/or weighted counts mapped to a portion or segment. In some instances, each read mapped to a portion or segment may contribute to a read density, a value (e.g., a count) equal to its weight obtained from a normalization process described herein. In some embodiments read densities for one or more portions or segments are adjusted. Read densities can be adjusted by a suitable method. For example, read densities for one or more portions can be weighted and/or normalized.

Reads quantified for a given portion or segment can be from one source or different sources. In one example, reads may be obtained from nucleic acid from a subject having cancer or suspected of having cancer. In such circumstances, reads mapped to one or more portions often are reads representative of both healthy cells (i.e., non-cancer cells) and cancer cells (e.g., tumor cells). In certain embodiments, some of the reads mapped to a portion are from cancer cell nucleic acid and some of the reads mapped to the same portion are from non-cancer cell nucleic acid. In another example, reads may be obtained from a nucleic acid sample from a pregnant female bearing a fetus. In such circumstances, reads mapped to one or more portions often are reads representative of both the fetus and the mother of the fetus (e.g., a pregnant female subject). In certain embodiments some of the reads mapped to a portion are from a fetal genome and some of the reads mapped to the same portion are from a maternal genome.

Levels

In some embodiments, a value (e.g., a number, a quantitative value) is ascribed to a level. A level can be determined by a suitable method, operation or mathematical process (e.g., a processed level). A level often is, or is derived from, counts (e.g., normalized counts) for a set of portions. In some embodiments a level of a portion is substantially equal to the total number of counts mapped to a portion (e.g., counts, normalized counts). Often a level is determined from counts that are processed, transformed or manipulated by a suitable method, operation or mathematical process known in the art. In some embodiments a level is derived from counts that are processed and non-limiting examples of processed counts include weighted, removed, filtered, normalized, adjusted, averaged, derived as a mean (e.g., mean level), added, subtracted, transformed counts or combination thereof. In some embodiments a level comprises counts that are normalized (e.g., normalized counts of portions). A level can be for counts normalized by a suitable process, non-limiting examples of which are described herein. A level can comprise normalized counts or relative amounts of counts. In some embodiments a level is for counts or normalized counts of two or more portions that are averaged and the level is referred to as an average level. In some embodiments a level is for a set of portions having a mean count or mean of normalized counts which is referred to as a mean level. In some embodiments a level is derived for portions that comprise raw and/or filtered counts. In some embodiments, a level is based on counts that are raw. In some embodiments a level is associated with an uncertainty value (e.g., a standard deviation, a MAD). In some embodiments a level is represented by a Z-score or p-value.

A level for one or more portions is synonymous with a "genomic section level" herein. The term "level" as used herein is sometimes synonymous with the term "elevation." A determination of the meaning of the term "level" can be determined from the context in which it is used. For example, the term "level," when used in the context of portions, profiles, reads and/or counts often means an elevation. The term "level," when used in the context of a substance or composition (e.g., level of RNA, plexing level) often refers to an amount. The term "level," when used in the context of uncertainty (e.g., level of error, level of confidence, level of deviation, level of uncertainty) often refers to an amount.

Normalized or non-normalized counts for two or more levels (e.g., two or more levels in a profile) can sometimes be mathematically manipulated (e.g., added, multiplied, averaged, normalized, the like or combination thereof) according to levels. For example, normalized or non-normalized counts for two or more levels can be normalized according to one, some or all of the levels in a profile. In some embodiments normalized or non-normalized counts of all levels in a profile are normalized according to one level in the profile. In some embodiments normalized or non-normalized counts of a first level in a profile are normalized according to normalized or non-normalized counts of a second level in the profile.

Non-limiting examples of a level (e.g., a first level, a second level) are a level for a set of portions comprising processed counts, a level for a set of portions comprising a mean, median or average of counts, a level for a set of portions comprising normalized counts, the like or any combination thereof. In some embodiments, a first level and a second level in a profile are derived from counts of portions mapped to the same chromosome. In some embodiments, a first level and a second level in a profile are derived from counts of portions mapped to different chromosomes.

In some embodiments a level is determined from normalized or non-normalized counts mapped to one or more portions. In some embodiments, a level is determined from normalized or non-normalized counts mapped to two or more portions, where the normalized counts for each portion often are about the same. There can be variation in counts (e.g., normalized counts) in a set of portions for a level. In a set of portions for a level there can be one or more portions having counts that are significantly different than in other portions of the set (e.g., peaks and/or dips). Any suitable number of normalized or non-normalized counts associated with any suitable number of portions can define a level.

In some embodiments one or more levels can be determined from normalized or non-normalized counts of all or some of the portions of a genome. Often a level can be determined from all or some of the normalized or non-normalized counts of a chromosome, or part thereof. In some embodiments, two or more counts derived from two or more portions (e.g., a set of portions) determine a level. In some embodiments two or more counts (e.g., counts from two or more portions) determine a level. In some embodiments, counts from 2 to about 100,000 portions determine a level. In some embodiments, counts from 2 to about 50,000, 2 to about 40,000, 2 to about 30.000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 portions determine a level. In some embodiments counts from about 10 to about 50 portions determine a level. In some embodiments counts from about 20 to about 40 or more portions determine a level. In some embodiments, a level comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more portions. In some embodiments, a level corresponds to a set of portions (e.g., a set of portions of a reference genome, a set of portions of a chromosome or a set of portions of a part of a chromosome).

In some embodiments, a level is determined for normalized or non-normalized counts of portions that are contiguous. In some embodiments portions (e.g., a set of portions) that are contiguous represent neighboring regions of a genome or neighboring regions of a chromosome or gene. For example, two or more contiguous portions, when aligned by merging the portions end to end, can represent a sequence assembly of a DNA sequence longer than each portion. For example two or more contiguous portions can represent of an intact genome, chromosome, gene, intron, exon or part thereof. In some embodiments a level is determined from a collection (e.g., a set) of contiguous portions and/or non-contiguous portions.

Data Processing and Normalization

Mapped sequence reads that have been counted are referred to herein as raw data, since the data represents unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative portions or portions of a reference genome (e.g., portions of a reference genome with uninformative data, redundant mapped reads, portions with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing." Processing can render data more amenable to further analysis, and can generate an outcome in some embodiments. In some embodiments one or more or all processing methods (e.g., normalization methods, portion filtering, mapping, validation, the like or combinations thereof) are performed by a processor, a micro-processor, a computer, in conjunction with memory and/or by a microprocessor controlled apparatus.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being overrepresented when prepared using PCR-based methods. Methods described herein can reduce or eliminate the contribution of noisy data, and therefore reduce the effect of noisy data on the provided outcome.

The terms "uninformative data," "uninformative portions of a reference genome," and "uninformative portions" as used herein refer to portions, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation or genetic alteration (e.g., a copy number alteration, an aneuploidy, a microduplication, a microdeletion, a chromosomal aberration, and the like). In certain embodiments, a threshold is exceeded by results obtained by methods described herein and a subject is diagnosed with a copy number alteration. A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. In some embodiments an uncertainty value is a standard deviation, standard error, calculated variance, p-value, or mean absolute deviation (MAD). In some embodiments an uncertainty value can be calculated according to a formula described herein.

Any suitable procedure can be utilized for processing data sets described herein. Non-limiting examples of procedures suitable for use for processing data sets include filtering, normalizing, weighting, monitoring peak heights, monitoring peak areas, monitoring peak edges, peak level analysis, peak width analysis, peak edge location analysis, peak lateral tolerances, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., subject gender, subject age, subject ploidy, percent contribution of cancer cell nucleic acid, fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments one or more processing steps can comprise one or more normalization steps. Normalization can be performed by a suitable method described herein or known in the art. In certain embodiments, normalization comprises adjusting values measured on different scales to a notionally common scale. In certain embodiments, normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Normalization sometimes comprises subtraction of one or more data sets by a predetermined variable or formula. Non-limiting examples of normalization methods include portion-wise normalization, normalization by GC content, median count (median bin count, median portion count) normalization, linear and nonlinear least squares regression, LOESS, GC LOESS, LOWESS (locally weighted scatterplot smoothing), principal component normalization, repeat masking (RM), GC-normalization and repeat masking (GCRM), cQn and/or combinations thereof. In some embodiments, the determination of a presence or absence of a copy number alteration (e.g., an aneuploidy, a microduplication, a microdeletion) utilizes a normalization method (e.g., portion-wise normalization, normalization by GC content, median count (median bin count, median portion count) normalization, linear and nonlinear least squares regression, LOESS, GC LOESS, LOWESS (locally weighted scatterplot smoothing), principal component normalization, repeat masking (RM), GC-normalization and repeat masking (GCRM), cQn, a normalization method known in the art and/or a combination thereof). Described in greater detail hereafter are certain examples of normalization processes that can be utilized, such as LOESS normalization, principal component normalization, and hybrid normalization methods, for example. Aspects of certain normalization processes also are described, for example, in International Patent Application Publication No. WO2013/052913 and International Patent Application Publication No. WO2015/051163, each of which is incorporated by reference herein.

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference portions to the total number of counts mapped to the chromosome or the entire genome on which the selected portion or sections are mapped, normalizing raw count data for one or more selected portions to a median reference count for one or more portions or the chromosome on which a selected portion is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data.

Normalizing portions, or portions of a reference genome, with respect to a normalizing value sometimes is referred to as "portion-wise normalization."

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak levels, determination of peak edge locations, calculation of peak area ratios, analysis of median chromosomal level, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median levels, mean levels, count distribution within a genomic region, relative representation of nucleic acid species, the like or combinations thereof.

In some embodiments, a processing step can comprise the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include principal component analysis, decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median levels, mean levels, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principal component analysis, linear discriminant analysis, quadratic discriminant analysis, bagging, neural networks, support vector machine models, random forests, classification tree models, K-nearest neighbors, logistic regression and/or smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation/genetic alteration and/or copy number alteration, depending on the status of the reference samples (e.g., positive or negative for a selected copy number alteration). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation/genetic alteration and/or copy number alteration and/or medical condition.

After data sets have been counted, optionally filtered, normalized, and optionally weighted the processed data sets can be further manipulated by one or more filtering and/or normalizing and/or weighting procedures, in some embodiments. A data set that has been further manipulated by one or more filtering and/or normalizing and/or weighting procedures can be used to generate a profile, in certain embodiments. The one or more filtering and/or normalizing and/or weighting procedures sometimes can reduce data set complexity and/or dimensionality, in some embodiments. An outcome can be provided based on a data set of reduced complexity and/or dimensionality. In some embodiments, a profile plot of processed data further manipulated by weighting, for example, is generated to facilitate classification and/or providing an outcome. An outcome can be provided based on a profile plot of weighted data, for example.

Filtering or weighting of portions can be performed at one or more suitable points in an analysis. For example, portions may be filtered or weighted before or after sequence reads are mapped to portions of a reference genome. Portions may be filtered or weighted before or after an experimental bias for individual genome portions is determined in some embodiments. In certain embodiments, portions may be filtered or weighted before or after levels are calculated.

After data sets have been counted, optionally filtered, normalized, and optionally weighted, the processed data sets can be manipulated by one or more mathematical and/or statistical (e.g., statistical functions or statistical algorithm) manipulations, in some embodiments. In certain embodiments, processed data sets can be further manipulated by calculating Z-scores for one or more selected portions, chromosomes, or portions of chromosomes. In some embodiments, processed data sets can be further manipulated by calculating P-values. In certain embodiments, mathematical and/or statistical manipulations include one or more assumptions pertaining to ploidy and/or fraction of a minority species (e.g., fraction of cancer cell nucleic acid; fetal fraction). In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fraction of a minority species (e.g., fraction of cancer cell nucleic acid; fetal fraction).

In some embodiments, analysis and processing of data can include the use of one or more assumptions. A suitable number or type of assumptions can be utilized to analyze or process a data set. Non-limiting examples of assumptions that can be used for data processing and/or analysis include subject ploidy, cancer cell contribution, maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a nucleic acid quantification assay (e.g., fetal quantifier assay (FQA)), assumptions regarding twins (e.g., if 2 twins and only 1 is affected the effective fetal fraction is only 50% of the total measured fetal fraction (similarly for triplets, quadruplets and the like)), cell free DNA (e.g., cfDNA) uniformly covers the entire genome, the like and combinations thereof.

In those instances where the quality and/or depth of mapped sequence reads does not permit an outcome prediction of the presence or absence of a genetic variation/genetic alteration and/or copy number alteration at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

Described in greater detail hereafter are non-limiting examples of processing steps and normalization methods that can be utilized, such as normalizing to a window (static or sliding), weighting, determining bias relationship, LOESS normalization, principal component normalization, hybrid normalization, generating a profile and performing a comparison.

Normalizing to a Window (Static or Sliding)

In certain embodiments, a processing step comprises normalizing to a static window, and in some embodiments, a processing step comprises normalizing to a moving or sliding window. The term "window" as used herein refers to one or more portions chosen for analysis, and sometimes is used as a reference for comparison (e.g., used for normalization and/or other mathematical or statistical manipulation). The term "normalizing to a static window" as used herein refers to a normalization process using one or more portions selected for comparison between a test subject and reference subject data set. In some embodiments the selected portions are utilized to generate a profile. A static window generally includes a predetermined set of portions that do not change during manipulations and/or analysis. The terms "normalizing to a moving window" and "normalizing to a sliding window" as used herein refer to normalizations performed to portions localized to the genomic region (e.g., immediate surrounding portions, adjacent portion or sections, and the like) of a selected test portion, where one or more selected test portions are normalized to portions immediately surrounding the selected test portion. In certain embodiments, the selected portions are utilized to generate a profile. A sliding or moving window normalization often includes repeatedly moving or sliding to an adjacent test portion, and normalizing the newly selected test portion to portions immediately surrounding or adjacent to the newly selected test portion, where adjacent windows have one or more portions in common. In certain embodiments, a plurality of selected test portions and/or chromosomes can be analyzed by a sliding window process.

In some embodiments, normalizing to a sliding or moving window can generate one or more values, where each value represents normalization to a different set of reference portions selected from different regions of a genome (e.g., chromosome). In certain embodiments, the one or more values generated are cumulative sums (e.g., a numerical estimate of the integral of the normalized count profile over the selected portion, domain (e.g., part of chromosome), or chromosome). The values generated by the sliding or moving window process can be used to generate a profile and facilitate arriving at an outcome. In some embodiments, cumulative sums of one or more portions can be displayed as a function of genomic position. Moving or sliding window analysis sometimes is used to analyze a genome for the presence or absence of microdeletions and/or microduplications. In certain embodiments, displaying cumulative sums of one or more portions is used to identify the presence or absence of regions of copy number alteration (e.g., microdeletion, microduplication).

Weighting

In some embodiments, a processing step comprises a weighting. The terms "weighted," "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more portions or portions of a reference genome, based on the quality or usefulness of the data in the selected portion or portions of a reference genome). A weighting function can be used to increase the influence of data with a relatively small measurement variance, and/or to decrease the influence of data with a relatively large measurement variance, in some embodiments. For example, portions of a reference genome with underrepresented or low quality sequence data can be "down weighted" to minimize the influence on a data set, whereas selected portions of a reference genome can be "up weighted" to increase the influence on a data set. A non-limiting example of a weighting function is $[1/(\text{standard deviation})^2]$. Weighting portions sometimes removes portion dependencies. In some embodiments one or more portions are weighted by an eigen function (e.g., an eigenfunction). In some embodiments an eigen function comprises replacing portions with orthogonal eigen-portions. A weighting step sometimes is performed in a manner substantially similar to a normalizing step. In some embodiments, a data set is adjusted (e.g., divided, multiplied, added, subtracted) by a predetermined variable (e.g., weighting variable). In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

Bias Relationships

In some embodiments, a processing step comprises determining a bias relationship. For example, one or more relationships may be generated between local genome bias estimates and bias frequencies. The term "relationship" as use herein refers to a mathematical and/or a graphical relationship between two or more variables or values. A relationship can be generated by a suitable mathematical and/or graphical process. Non-limiting examples of a relationship include a mathematical and/or graphical representation of a function, a correlation, a distribution, a linear or non-linear equation, a line, a regression, a fitted regression, the like or a combination thereof. Sometimes a relationship comprises a fitted relationship. In some embodiments a fitted relationship comprises a fitted regression. Sometimes a relationship comprises two or more variables or values that are weighted. In some embodiments a relationship comprise a fitted regression where one or more variables or values of the relationship a weighted. Sometimes a regression is fitted in a weighted fashion. Sometimes a regression is fitted without weighting. In certain embodiments, generating a relationship comprises plotting or graphing.

In certain embodiments, a relationship is generated between GC densities and GC density frequencies. In some embodiments generating a relationship between (i) GC densities and (ii) GC density frequencies for a sample provides a sample GC density relationship. In some embodiments generating a relationship between (i) GC densities and (ii) GC density frequencies for a reference provides a reference GC density relationship.

In some embodiments, where local genome bias estimates are GC densities, a sample bias relationship is a sample GC density relationship and a reference bias relationship is a reference GC density relationship. GC densities of a reference GC density relationship and/or a sample GC density relationship are often representations (e.g., mathematical or quantitative representation) of local GC content.

In some embodiments a relationship between local genome bias estimates and bias frequencies comprises a distribution. In some embodiments a relationship between local genome bias estimates and bias frequencies comprises a fitted relationship (e.g., a fitted regression). In some embodiments a relationship between local genome bias estimates and bias frequencies comprises a fitted linear or non-linear regression (e.g., a polynomial regression). In certain embodiments a relationship between local genome bias estimates and bias frequencies comprises a weighted relationship where local genome bias estimates and/or bias frequencies are weighted by a suitable process. In some embodiments a weighted fitted relationship (e.g., a weighted fitting) can be obtained by a process comprising a quantile regression, parameterized distributions or an empirical distribution with interpolation. In certain embodiments a relationship between local genome bias estimates and bias frequencies for a test sample, a reference or part thereof, comprises a polynomial regression where local genome bias estimates are weighted. In some embodiments a weighed fitted model comprises weighting values of a distribution. Values of a distribution can be weighted by a suitable process. In some embodiments, values located near tails of a distribution are provided less weight than values closer to the median of the distribution. For example, for a distribution between local genome bias estimates (e.g., GC densities) and bias frequencies (e.g., GC density frequencies), a weight is determined according to the bias frequency for a given local genome bias estimate, where local genome bias estimates comprising bias frequencies closer to the mean of a distribution are provided greater weight than local genome bias estimates comprising bias frequencies further from the mean.

In some embodiments, a processing step comprises normalizing sequence read counts by comparing local genome bias estimates of sequence reads of a test sample to local genome bias estimates of a reference (e.g., a reference genome, or part thereof). In some embodiments, counts of sequence reads are normalized by comparing bias frequencies of local genome bias estimates of a test sample to bias frequencies of local genome bias estimates of a reference. In some embodiments counts of sequence reads are normalized by comparing a sample bias relationship and a reference bias relationship, thereby generating a comparison.

Counts of sequence reads may be normalized according to a comparison of two or more relationships. In certain embodiments two or more relationships are compared thereby providing a comparison that is used for reducing local bias in sequence reads (e.g., normalizing counts). Two or more relationships can be compared by a suitable method. In some embodiments a comparison comprises adding, subtracting, multiplying and/or dividing a first relationship from a second relationship. In certain embodiments comparing two or more relationships comprises a use of a suitable linear regression and/or a non-linear regression. In certain embodiments comparing two or more relationships comprises a suitable polynomial regression (e.g., a $3^{rd}$ order polynomial regression). In some embodiments a comparison comprises adding, subtracting, multiplying and/or dividing a first regression from a second regression. In some embodiments two or more relationships are compared by a process comprising an inferential framework of multiple regressions. In some embodiments two or more relationships are compared by a process comprising a suitable multivariate analysis. In some embodiments two or more relationships are compared by a process comprising a basis function (e.g., a blending function, e.g., polynomial bases, Fourier bases, or the like), splines, a radial basis function and/or wavelets.

In certain embodiments a distribution of local genome bias estimates comprising bias frequencies for a test sample and a reference is compared by a process comprising a polynomial regression where local genome bias estimates are weighted. In some embodiments a polynomial regression is generated between (i) ratios, each of which ratios comprises bias frequencies of local genome bias estimates of a reference and bias frequencies of local genome bias estimates of a sample and (ii) local genome bias estimates. In some embodiments a polynomial regression is generated between (i) a ratio of bias frequencies of local genome bias estimates of a reference to bias frequencies of local genome bias estimates of a sample and (ii) local genome bias estimates. In some embodiments a comparison of a distribution of local genome bias estimates for reads of a test sample and a reference comprises determining a log ratio (e.g., a log 2 ratio) of bias frequencies of local genome bias estimates for the reference and the sample. In some embodiments a comparison of a distribution of local genome bias estimates comprises dividing a log ratio (e.g., a log 2 ratio) of bias frequencies of local genome bias estimates for the reference by a log ratio (e.g., a log 2 ratio) of bias frequencies of local genome bias estimates for the sample.

Normalizing counts according to a comparison typically adjusts some counts and not others. Normalizing counts sometimes adjusts all counts and sometimes does not adjust any counts of sequence reads. A count for a sequence read sometimes is normalized by a process that comprises determining a weighting factor and sometimes the process does not include directly generating and utilizing a weighting factor. Normalizing counts according to a comparison sometimes comprises determining a weighting factor for each count of a sequence read. A weighting factor is often specific to a sequence read and is applied to a count of a specific sequence read. A weighting factor is often determined according to a comparison of two or more bias relationships (e.g., a sample bias relationship compared to a reference bias relationship). A normalized count is often determined by adjusting a count value according to a weighting factor. Adjusting a count according to a weighting factor sometimes includes adding, subtracting, multiplying and/or dividing a count for a sequence read by a weighting factor. A weighting factor and/or a normalized count sometimes are determined from a regression (e.g., a regression line). A normalized count is sometimes obtained directly from a regression line (e.g., a fitted regression line) resulting from a comparison between bias frequencies of local genome bias estimates of a reference (e.g., a reference genome) and a test sample. In some embodiments each count of a read of a sample is provided a normalized count value according to a comparison of (i) bias frequencies of a local genome bias estimates of reads compared to (ii) bias frequencies of a local genome bias estimates of a reference. In certain embodiments, counts of sequence reads obtained for a sample are normalized and bias in the sequence reads is reduced.

LOESS Normalization

In some embodiments, a processing step comprises a LOESS normalization. LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relationship between template count (e.g., sequence reads, counts) and GC composition for portions of a reference genome. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated. The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

Principal Component Analysis

In some embodiments, a processing step comprises a principal component analysis (PCA). In some embodiments, sequence read counts (e.g., sequence read counts of a test sample) is adjusted according to a principal component analysis (PCA). In some embodiments a read density profile (e.g., a read density profile of a test sample) is adjusted according to a principal component analysis (PCA). A read density profile of one or more reference samples and/or a read density profile of a test subject can be adjusted according to a PCA. Removing bias from a read density profile by a PCA related process is sometimes referred to herein as adjusting a profile. A PCA can be performed by a suitable PCA method, or a variation thereof. Non-limiting examples of a PCA method include a canonical correlation analysis (CCA), a Karhunen-Loève transform (KLT), a Hotelling transform, a proper orthogonal decomposition (POD), a singular value decomposition (SVD) of X, an eigenvalue decomposition (EVD) of XTX, a factor analysis, an Eckart-Young theorem, a Schmidt-Mirsky theorem, empirical orthogonal functions (EOF), an empirical eigenfunction decomposition, an empirical component analysis, quasiharmonic modes, a spectral decomposition, an empirical modal analysis, the like, variations or combinations thereof. A PCA often identifies and/or adjusts for one or more biases in a read density profile. A bias identified and/or adjusted for by a PCA is sometimes referred to herein as a principal component. In some embodiments one or more biases can be removed by adjusting a read density profile according to one or more principal component using a suitable method. A read density profile can be adjusted by adding, subtracting, multiplying and/or dividing one or more principal components from a read density profile. In some embodiments, one or more biases can be removed from a read density profile by subtracting one or more principal components from a read density profile. Although bias in a read density profile is often identified and/or quantitated by a PCA of a profile, principal components are often subtracted from a profile at the level of read densities. A PCA often identifies one or more principal components. In some embodiments a PCA identifies a $1^{st}$, $2^{nd}$, $3^{rd}$, $4^{th}$, $5^{th}$, $6^{th}$, $7^{th}$, $8^{th}$, $9^{th}$, and a $10^{th}$ or more principal components. In certain embodiments, 1, 2, 3, 4, 5, 6, 7, 8, 9, 10 or more principal components are used to adjust a profile. In certain embodiments, 5 principal components are used to adjust a profile. Often, principal components are used to adjust a profile in the order of appearance in a PCA. For example, where three principal components are subtracted from a read density profile, a $1^{st}$, $2^{nd}$ and $3^{rd}$ principal component are used. Sometimes a bias identified by a principal component comprises a feature of a profile that is not used to adjust a profile. For example, a PCA may identify a copy number alteration (e.g., an aneuploidy, microduplication, microdeletion, deletion, translocation, insertion) and/or a gender difference as a principal component. Thus, in some embodiments, one or more principal components are not used to adjust a profile. For example, sometimes a $1^{st}$, $2^{nd}$ and $4^{th}$ principal component are used to adjust a profile where a $3^{rd}$ principal component is not used to adjust a profile.

A principal component can be obtained from a PCA using any suitable sample or reference. In some embodiments principal components are obtained from a test sample (e.g., a test subject). In some embodiments principal components are obtained from one or more references (e.g., reference samples, reference sequences, a reference set). In certain instances, a PCA is performed on a median read density profile obtained from a training set comprising multiple samples resulting in the identification of a $1^{st}$ principal component and a $2^{nd}$ principal component. In some embodiments, principal components are obtained from a set of subjects devoid of a copy number alteration in question. In some embodiments, principal components are obtained from a set of known euploids. Principal component are often identified according to a PCA performed using one or more read density profiles of a reference (e.g., a training set). One or more principal components obtained from a reference are often subtracted from a read density profile of a test subject thereby providing an adjusted profile.

Hybrid Normalization

In some embodiments, a processing step comprises a hybrid normalization method. A hybrid normalization method may reduce bias (e.g., GC bias), in certain instances. A hybrid normalization, in some embodiments, comprises (i) an analysis of a relationship of two variables (e.g., counts and GC content) and (ii) selection and application of a normalization method according to the analysis. A hybrid normalization, in certain embodiments, comprises (i) a regression (e.g., a regression analysis) and (ii) selection and application of a normalization method according to the regression. In some embodiments counts obtained for a first sample (e.g., a first set of samples) are normalized by a different method than counts obtained from another sample (e.g., a second set of samples). In some embodiments counts obtained for a first sample (e.g., a first set of samples) are normalized by a first normalization method and counts obtained from a second sample (e.g., a second set of samples) are normalized by a second normalization method. For example, in certain embodiments a first normalization method comprises use of a linear regression and a second normalization method comprises use of a non-linear regression (e.g., a LOESS, GC-LOESS, LOWESS regression, LOESS smoothing).

In some embodiments a hybrid normalization method is used to normalize sequence reads mapped to portions of a genome or chromosome (e.g., counts, mapped counts, mapped reads). In certain embodiments raw counts are normalized and in some embodiments adjusted, weighted, filtered or previously normalized counts are normalized by a hybrid normalization method. In certain embodiments, levels or Z-scores are normalized. In some embodiments counts mapped to selected portions of a genome or chromosome are normalized by a hybrid normalization approach. Counts can refer to a suitable measure of sequence reads mapped to portions of a genome, non-limiting examples of which include raw counts (e.g., unprocessed counts), normalized counts (e.g., normalized by LOESS, principal component, or a suitable method), portion levels (e.g., average levels, mean levels, median levels, or the like), Z-scores, the like, or combinations thereof. The counts can be raw counts or processed counts from one or more samples (e.g., a test sample, a sample from a pregnant female). In some embodiments counts are obtained from one or more samples obtained from one or more subjects.

In some embodiments a normalization method (e.g., the type of normalization method) is selected according to a regression (e.g., a regression analysis) and/or a correlation coefficient. A regression analysis refers to a statistical technique for estimating a relationship among variables (e.g., counts and GC content). In some embodiments a regression is generated according to counts and a measure of GC content for each portion of multiple portions of a reference genome. A suitable measure of GC content can be used, non-limiting examples of which include a measure of guanine, cytosine, adenine, thymine, purine (GC), or pyrimidine (AT or ATU) content, melting temperature (Tm) (e.g., denaturation temperature, annealing temperature, hybridization temperature), a measure of free energy, the like or combinations thereof. A measure of guanine (G), cytosine (C), adenine (A), thymine (T), purine (GC), or pyrimidine (AT or ATU) content can be expressed as a ratio or a percentage. In some embodiments any suitable ratio or percentage is used, non-limiting examples of which include GC/AT, GC/total nucleotide, GC/A, GC/T, AT/total nucleotide, AT/GC, AT/G, AT/C, G/A, C/A, G/T, G/A, G/AT, C/T, the like or combinations thereof. In some embodiments a measure of GC content is a ratio or percentage of GC to total nucleotide content. In some embodiments a measure of GC content is a ratio or percentage of GC to total nucleotide content for sequence reads mapped to a portion of reference genome. In certain embodiments the GC content is determined according to and/or from sequence reads mapped to each portion of a reference genome and the sequence reads are obtained from a sample. In some embodiments a measure of GC content is not determined according to and/or from sequence reads. In certain embodiments, a measure of GC content is determined for one or more samples obtained from one or more subjects.

In some embodiments generating a regression comprises generating a regression analysis or a correlation analysis. A suitable regression can be used, non-limiting examples of which include a regression analysis, (e.g., a linear regression analysis), a goodness of fit analysis, a Pearson's correlation analysis, a rank correlation, a fraction of variance unexplained, Nash-Sutcliffe model efficiency analysis, regression model validation, proportional reduction in loss, root mean square deviation, the like or a combination thereof. In some embodiments a regression line is generated. In certain embodiments generating a regression comprises generating a linear regression. In certain embodiments generating a regression comprises generating a non-linear regression (e.g., an LOESS regression, an LOWESS regression).

In some embodiments a regression determines the presence or absence of a correlation (e.g., a linear correlation), for example between counts and a measure of GC content. In some embodiments a regression (e.g., a linear regression) is generated and a correlation coefficient is determined. In some embodiments a suitable correlation coefficient is determined, non-limiting examples of which include a coefficient of determination, an $R^2$ value, a Pearson's correlation coefficient, or the like.

In some embodiments goodness of fit is determined for a regression (e.g., a regression analysis, a linear regression). Goodness of fit sometimes is determined by visual or mathematical analysis. An assessment sometimes includes determining whether the goodness of fit is greater for a non-linear regression or for a linear regression. In some embodiments a correlation coefficient is a measure of a goodness of fit. In some embodiments an assessment of a goodness of fit for a regression is determined according to a correlation coefficient and/or a correlation coefficient cutoff value. In some embodiments an assessment of a goodness of fit comprises comparing a correlation coefficient to a correlation coefficient cutoff value. In some embodiments an assessment of a goodness of fit for a regression is indicative of a linear regression. For example, in certain embodiments, a goodness of fit is greater for a linear regression than for a non-linear regression and the assessment of the goodness of fit is indicative of a linear regression. In some embodiments an assessment is indicative of a linear regression and a linear regression is used to normalized the counts. In some embodiments an assessment of a goodness of fit for a regression is indicative of a non-linear regression. For example, in certain embodiments, a goodness of fit is greater for a non-linear regression than for a linear regression and the assessment of the goodness of fit is indicative of a non-linear regression. In some embodiments an assessment is indicative of a non-linear regression and a non-linear regression is used to normalized the counts.

In some embodiments an assessment of a goodness of fit is indicative of a linear regression when a correlation coefficient is equal to or greater than a correlation coefficient cutoff. In some embodiments an assessment of a goodness of fit is indicative of a non-linear regression when a correlation coefficient is less than a correlation coefficient cutoff. In some embodiments a correlation coefficient cutoff is pre-determined. In some embodiments a correlation coefficient cut-off is about 0.5 or greater, about 0.55 or greater, about 0.6 or greater, about 0.65 or greater, about 0.7 or greater, about 0.75 or greater, about 0.8 or greater or about 0.85 or greater.

In some embodiments a specific type of regression is selected (e.g., a linear or non-linear regression) and, after the regression is generated, counts are normalized by subtracting the regression from the counts. In some embodiments subtracting a regression from the counts provides normalized counts with reduced bias (e.g., GC bias). In some embodiments a linear regression is subtracted from the counts. In some embodiments a non-linear regression (e.g., a LOESS, GC-LOESS, LOWESS regression) is subtracted from the counts. Any suitable method can be used to subtract a regression line from the counts. For example, if counts x are derived from portion i (e.g., a portion i) comprising a GC content of 0.5 and a regression line determines counts y at a GC content of 0.5, then x-y=normalized counts for portion i. In some embodiments counts are normalized prior to and/or after subtracting a regression. In some embodiments, counts normalized by a hybrid normalization approach are used to generate levels, Z-scores, levels and/or profiles of a genome or a part thereof. In certain embodiments, counts normalized by a hybrid normalization approach are analyzed by methods described herein to determine the presence or absence of a genetic variation or genetic alteration (e.g., copy number alteration).

In some embodiments a hybrid normalization method comprises filtering or weighting one or more portions before or after normalization. A suitable method of filtering portions, including methods of filtering portions (e.g., portions of a reference genome) described herein can be used. In some embodiments, portions (e.g., portions of a reference genome) are filtered prior to applying a hybrid normalization method. In some embodiments, only counts of sequencing reads mapped to selected portions (e.g., portions selected according to count variability) are normalized by a hybrid normalization. In some embodiments counts of sequencing reads mapped to filtered portions of a reference genome (e.g., portions filtered according to count variability) are removed prior to utilizing a hybrid normalization method. In some embodiments a hybrid normalization method comprises selecting or filtering portions (e.g., portions of a reference genome) according to a suitable method (e.g., a method described herein). In some embodiments a hybrid normalization method comprises selecting or filtering portions (e.g., portions of a reference genome) according to an uncertainty value for counts mapped to each of the portions for multiple test samples. In some embodiments a hybrid normalization method comprises selecting or filtering portions (e.g., portions of a reference genome) according to count variability. In some embodiments a hybrid normalization method comprises selecting or filtering portions (e.g., portions of a reference genome) according to GC content, repetitive elements, repetitive sequences, introns, exons, the like or a combination thereof.

Profiles

In some embodiments, a processing step comprises generating one or more profiles (e.g., profile plot) from various aspects of a data set or derivation thereof (e.g., product of one or more mathematical and/or statistical data processing steps known in the art and/or described herein).

The term "profile" as used herein refers to a product of a mathematical and/or statistical manipulation of data that can facilitate identification of patterns and/or correlations in large quantities of data. A "profile" often includes values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a part or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a portion. In certain embodiments, a data point in a profile includes results of data manipulation for groups of portions. In some embodiments, groups of portions may be adjacent to one another, and in certain embodiments, groups of portions may be from different parts of a chromosome or genome.

Data points in a profile derived from a data set can be representative of any suitable data categorization. Non-limiting examples of categories into which data can be grouped to generate profile data points include: portions based on size, portions based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile (e.g., a genomic profile, a chromosome profile, a profile of a part of a chromosome) often is a collection of normalized or non-normalized counts for two or more portions. A profile often includes at least one level, and often comprises two or more levels (e.g., a profile often has multiple levels). A level generally is for a set of portions having about the same counts or normalized counts. Levels are described in greater detail herein. In certain embodiments, a profile comprises one or more portions, which portions can be weighted, removed, filtered, normalized, adjusted, averaged, derived as a mean, added, subtracted, processed or transformed by any combination thereof. A profile often comprises normalized counts mapped to portions defining two or more levels, where the counts are further normalized according to one of the levels by a suitable method. Often counts of a profile (e.g., a profile level) are associated with an uncertainty value.

A profile comprising one or more levels is sometimes padded (e.g., hole padding). Padding (e.g., hole padding) refers to a process of identifying and adjusting levels in a profile that are due to copy number alterations (e.g., microduplications or microdeletions in a patient's genome, maternal microduplications or microdeletions). In some embodiments, levels are padded that are due to microduplications or microdeletions in a tumor or a fetus. Microduplications or microdeletions in a profile can, in some embodiments, artificially raise or lower the overall level of a profile (e.g., a profile of a chromosome) leading to false positive or false negative determinations of a chromosome aneuploidy (e.g., a trisomy). In some embodiments, levels in a profile that are due to microduplications and/or deletions are identified and adjusted (e.g., padded and/or removed) by a process sometimes referred to as padding or hole padding.

A profile comprising one or more levels can include a first level and a second level. In some embodiments a first level is different (e.g., significantly different) than a second level. In some embodiments a first level comprises a first set of portions, a second level comprises a second set of portions and the first set of portions is not a subset of the second set of portions. In certain embodiments, a first set of portions is different than a second set of portions from which a first and second level are determined. In some embodiments a profile can have multiple first levels that are different (e.g., significantly different, e.g., have a significantly different value) than a second level within the profile. In some embodiments a profile comprises one or more first levels that are significantly different than a second level within the profile and one or more of the first levels are adjusted. In some embodiments a first level within a profile is removed from the profile or adjusted (e.g., padded). A profile can comprise multiple levels that include one or more first levels significantly different than one or more second levels and often the majority of levels in a profile are second levels, which second levels are about equal to one another. In some embodiments greater than 50%, greater than 60%, greater than 70%, greater than 80%, greater than 90% or greater than 95% of the levels in a profile are second levels.

A profile sometimes is displayed as a plot. For example, one or more levels representing counts (e.g., normalized counts) of portions can be plotted and visualized. Non-limiting examples of profile plots that can be generated include raw count (e.g., raw count profile or raw profile), normalized count, portion-weighted, z-score, p-value, area ratio versus fitted ploidy, median level versus ratio between fitted and measured minority species fraction, principal components, the like, or combinations thereof. Profile plots allow visualization of the manipulated data, in some embodiments. In certain embodiments, a profile plot can be utilized to provide an outcome (e.g., area ratio versus fitted ploidy, median level versus ratio between fitted and measured minority species fraction, principal components). The terms "raw count profile plot" or "raw profile plot" as used herein refer to a plot of counts in each portion in a region normalized to total counts in a region (e.g., genome, portion, chromosome, chromosome portions of a reference genome or a part of a chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions, e.g., assumptions described herein. In certain embodiments, a test profile often centers around a predetermined value representative of the absence of a copy number alteration, and often deviates from a predetermined value in areas corresponding to the genomic location in which the copy number alteration is located in the test subject, if the test subject possessed the copy number alteration. In test subjects at risk for, or suffering from a medical condition associated with a copy number alteration, the numerical value for a selected portion is expected to vary significantly from the predetermined value for non-affected genomic locations. Depending on starting assumptions (e.g., fixed ploidy or optimized ploidy, fixed fraction of cancer cell nucleic acid or optimized fraction of cancer cell nucleic acid, fixed fetal fraction or optimized fetal fraction, or combinations thereof) the predetermined threshold or cutoff value or threshold range of values indicative of the presence or absence of a copy number alteration can vary while still providing an outcome useful for determining the presence or absence of a copy number alteration. In some embodiments, a profile is indicative of and/or representative of a phenotype.

In some embodiments, the use of one or more reference samples that are substantially free of a copy number alteration in question can be used to generate a reference count profile (e.g., a reference median count profile), which may result in a predetermined value representative of the absence of the copy number alteration, and often deviates from a predetermined value in areas corresponding to the genomic location in which the copy number alteration is located in the test subject, if the test subject possessed the copy number alteration. In test subjects at risk for, or suffering from a medical condition associated with a copy number alteration, the numerical value for the selected portion or sections is expected to vary significantly from the predetermined value for non-affected genomic locations. In certain embodiments, the use of one or more reference samples known to carry the copy number alteration in question can be used to generate a reference count profile (a reference median count profile), which may result in a predetermined value representative of the presence of the copy number alteration, and often deviates from a predetermined value in areas corresponding to the genomic location in which a test subject does not carry the copy number alteration. In test subjects not at risk for, or suffering from a medical condition associated with a copy number alteration, the numerical value for the selected portion or sections is expected to vary significantly from the predetermined value for affected genomic locations.

By way of a non-limiting example, normalized sample and/or reference count profiles can be obtained from raw sequence read data by (a) calculating reference median counts for selected chromosomes, portions or parts thereof from a set of references known not to carry a copy number alteration, (b) removal of uninformative portions from the reference sample raw counts (e.g., filtering), (c) normalizing the reference counts for all remaining portions of a reference genome to the total residual number of counts (e.g., sum of remaining counts after removal of uninformative portions of a reference genome) for the reference sample selected chromosome or selected genomic location, thereby generating a normalized reference subject profile; (d) removing the corresponding portions from the test subject sample, and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered portions in (b), can be included between (c) and (d).

In some embodiments a read density profile is determined. In some embodiments a read density profile comprises at least one read density, and often comprises two or more read densities (e.g., a read density profile often comprises multiple read densities). In some embodiments, a read density profile comprises a suitable quantitative value (e.g., a mean, a median, a Z-score, or the like). A read density profile often comprises values resulting from one or more read densities. A read density profile sometimes comprises values resulting from one or more manipulations of read densities based on one or more adjustments (e.g., normalizations). In some embodiments a read density profile comprises unmanipulated read densities. In some embodiments, one or more read density profiles are generated from various aspects of a data set comprising read densities, or a derivation thereof (e.g., product of one or more mathematical and/or statistical data processing steps known in the art and/or described herein). In certain embodiments, a read density profile comprises normalized read densities. In some embodiments a read density profile comprises adjusted read densities. In certain embodiments a read density profile comprises raw read densities (e.g., unmanipulated, not adjusted or normalized), normalized read densities, weighted read densities, read densities of filtered portions, z-scores of read densities, p-values of read densities, integral values of read densities (e.g., area under the curve), average, mean or median read densities, principal components, the like, or combinations thereof. Often read densities of a read density profile and/or a read density profile is associated with a measure of uncertainty (e.g., a MAD). In certain embodiments, a read density profile comprises a distribution of median read densities. In some embodiments a read density profile comprises a relationship (e.g., a fitted relationship, a regression, or the like) of a plurality of read densities. For example, sometimes a read density profile comprises a relationship between read densities (e.g., read densities value) and genomic locations (e.g., portions, portion locations). In some embodiments, a read density profile is generated using a static window process, and in certain embodiments, a read density profile is generated using a sliding window process. In some embodiments a read density profile is sometimes printed and/or displayed (e.g., displayed as a visual representation, e.g., a plot or a graph).

In some embodiments, a read density profile corresponds to a set of portions (e.g., a set of portions of a reference genome, a set of portions of a chromosome or a subset of portions of a part of a chromosome). In some embodiments a read density profile comprises read densities and/or counts associated with a collection (e.g., a set, a subset) of portions. In some embodiments, a read density profile is determined for read densities of portions that are contiguous. In some embodiments, contiguous portions comprise gaps comprising regions of a reference sequence and/or sequence reads that are not included in a density profile (e.g., portions removed by a filtering). Sometimes portions (e.g., a set of portions) that are contiguous represent neighboring regions of a genome or neighboring regions of a chromosome or gene. For example, two or more contiguous portions, when aligned by merging the portions end to end, can represent a sequence assembly of a DNA sequence longer than each portion. For example two or more contiguous portions can represent an intact genome, chromosome, gene, intron, exon or part thereof. Sometimes a read density profile is determined from a collection (e.g., a set, a subset) of contiguous portions and/or non-contiguous portions. In some cases, a read density profile comprises one or more portions, which portions can be weighted, removed, filtered, normalized, adjusted, averaged, derived as a mean, added, subtracted, processed or transformed by any combination thereof.

A read density profile is often determined for a sample and/or a reference (e.g., a reference sample). A read density profile is sometimes generated for an entire genome, one or more chromosomes, or for a part of a genome or a chromosome. In some embodiments, one or more read density profiles are determined for a genome or part thereof. In some embodiments, a read density profile is representative of the entirety of a set of read densities of a sample, and in certain embodiments, a read density profile is representative of a part or subset of read densities of a sample. That is, sometimes a read density profile comprises or is generated from read densities representative of data that has not been filtered to remove any data, and sometimes a read density profile includes or is generated from data points representative of data that has been filtered to remove unwanted data.

In some embodiments a read density profile is determined for a reference (e.g., a reference sample, a training set). A read density profile for a reference is sometimes referred to herein as a reference profile. In some embodiments a reference profile comprises a read densities obtained from one or more references (e.g., reference sequences, reference samples). In some embodiments a reference profile comprises read densities determined for one or more (e.g., a set of) known euploid samples. In some embodiments a reference profile comprises read densities of filtered portions. In some embodiments a reference profile comprises read densities adjusted according to the one or more principal components.

Performing a Comparison

In some embodiments, a processing step comprises preforming a comparison (e.g., comparing a test profile to a reference profile). Two or more data sets, two or more relationships and/or two or more profiles can be compared by a suitable method. Non-limiting examples of statistical methods suitable for comparing data sets, relationships and/or profiles include Behrens-Fisher approach, bootstrapping, Fisher's method for combining independent tests of significance, Neyman-Pearson testing, confirmatory data analysis, exploratory data analysis, exact test, F-test, Z-test, T-test, calculating and/or comparing a measure of uncertainty, a null hypothesis, counternulls and the like, a chi-square test, omnibus test, calculating and/or comparing level of significance (e.g., statistical significance), a meta analysis, a multivariate analysis, a regression, simple linear regression, robust linear regression, the like or combinations of the foregoing. In certain embodiments comparing two or more data sets, relationships and/or profiles comprises determining and/or comparing a measure of uncertainty. A "measure of uncertainty" as used herein refers to a measure of significance (e.g., statistical significance), a measure of error, a measure of variance, a measure of confidence, the like or a combination thereof. A measure of uncertainty can be a value (e.g., a threshold) or a range of values (e.g., an interval, a confidence interval, a Bayesian confidence interval, a threshold range). Non-limiting examples of a measure of uncertainty include p-values, a suitable measure of deviation (e.g., standard deviation, sigma, absolute deviation, mean absolute deviation, the like), a suitable measure of error (e.g., standard error, mean squared error, root mean squared error, the like), a suitable measure of variance, a suitable standard score (e.g., standard deviations, cumulative percentages, percentile equivalents, Z-scores, T-scores, R-scores, standard nine (stanine), percent in stanine, the like), the like or combinations thereof. In some embodiments determining the level of significance comprises determining a measure of uncertainty (e.g., a p-value). In certain embodiments, two or more data sets, relationships and/or profiles can be analyzed and/or compared by utilizing multiple (e.g., 2 or more) statistical methods (e.g., least squares regression, principal component analysis, linear discriminant analysis, quadratic discriminant analysis, bagging, neural networks, support vector machine models, random forests, classification tree models, K-nearest neighbors, logistic regression and/or loss smoothing) and/or any suitable mathematical and/or statistical manipulations (e.g., referred to herein as manipulations).

In some embodiments, a processing step comprises a comparison of two or more profiles (e.g., two or more read density profiles). Comparing profiles may comprise comparing profiles generated for a selected region of a genome. For example, a test profile may be compared to a reference profile where the test and reference profiles were determined for a region of a genome (e.g., a reference genome) that is substantially the same region. Comparing profiles sometimes comprises comparing two or more subsets of portions of a profile (e.g., a read density profile). A subset of portions of a profile may represent a region of a genome (e.g., a chromosome, or region thereof). A profile (e.g., a read density profile) can comprise any amount of subsets of portions. Sometimes a profile (e.g., a read density profile) comprises two or more, three or more, four or more, or five or more subsets. In certain embodiments, a profile (e.g., a read density profile) comprises two subsets of portions where each portion represents regions of a reference genome that are adjacent. In some embodiments, a test profile can be compared to a reference profile where the test profile and reference profile both comprise a first subset of portions and a second subset of portions where the first and second subsets represent different regions of a genome. Some subsets of portions of a profile may comprise copy number alterations and other subsets of portions are sometimes substantially free of copy number alterations. Sometimes all subsets of portions of a profile (e.g., a test profile) are substantially free of a copy number alteration. Sometimes all subsets of portions of a profile (e.g., a test profile) comprise a copy number alteration. In some embodiments a test profile can comprise a first subset of portions that comprise a copy number alteration and a second subset of portions that are substantially free of a copy number alteration.

In certain embodiments, comparing two or more profiles comprises determining and/or comparing a measure of uncertainty for two or more profiles. Profiles (e.g., read density profiles) and/or associated measures of uncertainty are sometimes compared to facilitate interpretation of mathematical and/or statistical manipulations of a data set and/or to provide an outcome. A profile (e.g., a read density profile) generated for a test subject sometimes is compared to a profile (e.g., a read density profile) generated for one or more references (e.g., reference samples, reference subjects, and the like). In some embodiments, an outcome is provided by comparing a profile (e.g., a read density profile) from a test subject to a profile (e.g., a read density profile) from a reference for a chromosome, portions or parts thereof, where a reference profile is obtained from a set of reference subjects known not to possess a copy number alteration (e.g., a reference). In some embodiments an outcome is provided by comparing a profile (e.g., a read density profile) from a test subject to a profile (e.g., a read density profile) from a reference for a chromosome, portions or parts thereof, where a reference profile is obtained from a set of reference subjects known to possess a specific copy number alteration (e.g., a chromosome aneuploidy, a microduplication, a microdeletion).

In certain embodiments, a profile (e.g., a read density profile) of a test subject is compared to a predetermined value representative of the absence of a copy number alteration, and sometimes deviates from a predetermined value at one or more genomic locations (e.g., portions) corresponding to a genomic location in which a copy number alteration is located. For example, in test subjects (e.g., subjects at risk for, or suffering from a medical condition associated with a copy number alteration), profiles are expected to differ significantly from profiles of a reference (e.g., a reference sequence, reference subject, reference set) for selected portions when a test subject comprises a copy number alteration in question. Profiles (e.g., read density profiles) of a test subject are often substantially the same as profiles (e.g., read density profiles) of a reference (e.g., a reference sequence, reference subject, reference set) for selected portions when a test subject does not comprise a copy number alteration in question. Profiles (e.g., read density profiles) may be compared to a predetermined threshold and/or threshold range. The term "threshold" as used herein refers to any number that is calculated using a qualifying data set and serves as a limit of diagnosis of a copy number alteration (e.g., an aneuploidy, a microduplication, a microdeletion, and the like). In certain embodiments a threshold is exceeded by results obtained by methods described herein and a subject is diagnosed with a copy number alteration. In some embodiments, a threshold value or range of values may be calculated by mathematically and/or statistically manipulating sequence read data (e.g., from a reference and/or subject). A predetermined threshold or threshold range of values indicative of the presence or absence of a copy number alteration can vary while still providing an outcome useful for determining the presence or absence of a copy number alteration. In certain embodiments, a profile (e.g., a read density profile) comprising normalized read densities and/or normalized counts is generated to facilitate classification and/or providing an outcome. An outcome can be provided based on a plot of a profile (e.g., a read density profile) comprising normalized counts (e.g., using a plot of such a read density profile).

Decision Analysis

In some embodiments, a determination of an outcome (e.g., making a call) or a determination of the presence or absence of a copy number alteration (e.g., chromosome aneuploidy, microduplication, microdeletion) is made according to a decision analysis. Certain decision analysis features are described in International Patent Application Publication No. WO2014/190286, which is incorporated by reference herein. For example, a decision analysis sometimes comprises applying one or more methods that produce one or more results, an evaluation of the results, and a series of decisions based on the results, evaluations and/or the possible consequences of the decisions and terminating at some juncture of the process where a final decision is made. In some embodiments a decision analysis is a decision tree. A decision analysis, in some embodiments, comprises coordinated use of one or more processes (e.g., process steps, e.g., algorithms). A decision analysis can be performed by a person, a system, an apparatus, software (e.g., a module), a computer, a processor (e.g., a microprocessor), the like or a combination thereof. In some embodiments a decision analysis comprises a method of determining the presence or absence of a copy number alteration (e.g., chromosome aneuploidy, microduplication or microdeletion) with reduced false negative and reduced false positive determinations, compared to an instance in which no decision analysis is utilized (e.g., a determination is made directly from normalized counts). In some embodiments a decision analysis comprises determining the presence or absence of a condition associated with one or more copy number alterations.

In some embodiments a decision analysis comprises generating a profile for a genome or a region of a genome (e.g., a chromosome or part thereof). A profile can be generated by any suitable method, known or described herein. In some embodiments, a decision analysis comprises a segmenting process. Segmenting can modify and/or transform a profile thereby providing one or more decomposition renderings of a profile. A profile subjected to a segmenting process often is a profile of normalized counts mapped to portions in a reference genome or part thereof. As addressed herein, raw counts mapped to the portions can be normalized by one or more suitable normalization processes (e.g., LOESS, GC-LOESS, principal component normalization, or combination thereof) to generate a profile that is segmented as part of a decision analysis. A decomposition rendering of a profile is often a transformation of a profile. A decomposition rendering of a profile is sometimes a transformation of a profile into a representation of a genome, chromosome or part thereof.

In certain embodiments, a segmenting process utilized for the segmenting locates and identifies one or more levels within a profile that are different (e.g., substantially or significantly different) than one or more other levels within a profile. A level identified in a profile according to a segmenting process that is different than another level in the profile, and has edges that are different than another level in the profile, is referred to herein as a level for a discrete segment. A segmenting process can generate, from a profile of normalized counts or levels, a decomposition rendering in which one or more discrete segments can be identified. A discrete segment generally covers fewer portions than what is segmented (e.g., chromosome, chromosomes, autosomes).

In some embodiments, segmenting locates and identifies edges of discrete segments within a profile. In certain embodiments, one or both edges of one or more discrete segments are identified. For example, a segmentation process can identify the location (e.g., genomic coordinates, e.g., portion location) of the right and/or the left edges of a discrete segment in a profile. A discrete segment often comprises two edges. For example, a discrete segment can include a left edge and a right edge. In some embodiments, depending upon the representation or view, a left edge can be a 5'-edge and a right edge can be a 3'-edge of a nucleic acid segment in a profile. In some embodiments, a left edge can be a 3'-edge and a right edge can be a 5'-edge of a nucleic acid segment in a profile. Often the edges of a profile are known prior to segmentation and therefore, in some embodiments, the edges of a profile determine which edge of a level is a 5'-edge and which edge is 3'-edge. In some embodiments one or both edges of a profile and/or discrete segment is an edge of a chromosome.

In some embodiments, the edges of a discrete segment are determined according to a decomposition rendering generated for a reference sample (e.g., a reference profile). In some embodiments a null edge height distribution is determined according to a decomposition rendering of a reference profile (e.g., a profile of a chromosome or part thereof). In certain embodiments, the edges of a discrete segment in a profile are identified when the level of the discrete segment is outside a null edge height distribution. In some embodiments, the edges of a discrete segment in a profile are identified according a Z-score calculated according to a decomposition rendering for a reference profile.

In some instances, segmenting generates two or more discrete segments (e.g., two or more fragmented levels, two or more fragmented segments) in a profile. In some embodiments, a decomposition rendering derived from a segmenting process is over-segmented or fragmented and comprises multiple discrete segments. Sometimes discrete segments generated by segmenting are substantially different and sometimes discrete segments generated by segmenting are substantially similar. Substantially similar discrete segments (e.g., substantially similar levels) often refers to two or more adjacent discrete segments in a segmented profile each having a level that differs by less than a predetermined level of uncertainty. In some embodiments, substantially similar discrete segments are adjacent to each other and are not separated by an intervening segment. In some embodiments, substantially similar discrete segments are separated by one or more smaller segments. In some embodiments substantially similar discrete segments are separated by about 1 to about 20, about 1 to about 15, about 1 to about 10 or about 1 to about 5 portions where one or more of the intervening portions have a level significantly different than the level of each of the substantially similar discrete segments. In some embodiments, the level of substantially similar discrete segments differs by less than about 3 times, less than about 2 times, less than about 1 time or less than about 0.5 times a level of uncertainty. Substantially similar discrete segments, in some embodiments, comprise a median level that differs by less than 3 MAD (e.g., less than 3 sigma), less than 2 MAD, less than 1 MAD or less than about 0.5 MAD, where a MAD is calculated from a median level of each of the segments. Substantially different discrete segments, in some embodiments, are not adjacent or are separated by 10 or more, 15 or more or 20 or more portions. Substantially different discrete segments generally have substantially different levels. In certain embodiments, substantially different discrete segments comprises levels that differ by more than about 2.5 times, more than about 3 times, more than about 4 times, more than about 5 times, more than about 6 times a level of uncertainty. Substantially different discrete segments, in some embodiments, comprise a median level that differs by more than 2.5 MAD (e.g., more than 2.5 sigma), more than 3 MAD, more than 4 MAD, more than about 5 MAD or more than about 6 MAD, where a MAD is calculated from a median level of each of the discrete segments.

In some embodiments, a segmentation process comprises determining (e.g., calculating) a level (e.g., a quantitative value, e.g., a mean or median level), a level of uncertainty (e.g., an uncertainty value), Z-score, Z-value, p-value, the like or combinations thereof for one or more discrete segments in a profile or part thereof. In some embodiments a level (e.g., a quantitative value, e.g., a mean or median level), a level of uncertainty (e.g., an uncertainty value), Z-score, Z-value, p-value, the like or combinations thereof are determined (e.g., calculated) for a discrete segment.

Segmenting can be performed, in full or in part, by one or more decomposition generating processes. A decomposition generating process may provide, for example, a decomposition rendering of a profile. Any decomposition generating process described herein or known in the art may be used. Non-limiting examples of a decomposition generating process include circular binary segmentation (CBS) (see e.g., Olshen et al. (2004) Biostatistics 5(4):557-72; Venkatraman, E S, Olshen, A B (2007) Bioinformatics 23(6):657-63); Haar wavelet segmentation (see e.g., Haar, Alfred (1910) Mathematische Annalen 69(3):331-371); maximal overlap discrete wavelet transform (MODWT) (see e.g., Hsu et al. (2005) Biostatistics 6 (2):211-226); stationary wavelet (SWT) (see e.g., Y. Wang and S. Wang (2007) International Journal of Bioinformatics Research and Applications 3(2): 206-222); dual-tree complex wavelet transform (DTCWT) (see e.g., Nguyen et al. (2007) Proceedings of the 7th IEEE International Conference, Boston Mass., on Oct. 14-17, 2007, pages 137-144); maximum entropy segmentation, convolution with edge detection kernel, Jensen Shannon Divergence, Kullback-Leibler divergence, Binary Recursive Segmentation, a Fourier transform, the like or combinations thereof.

In some embodiments, segmenting is accomplished by a process that comprises one process or multiple sub-processes, non-limiting examples of which include a decomposition generating process, thresholding, leveling, smoothing, polishing, the like or combination thereof. Thresholding, leveling, smoothing, polishing and the like can be performed in conjunction with a decomposition generating process, for example.

In some embodiments, a decision analysis comprises identifying a candidate segment in a decomposition rendering. A candidate segment is determined as being the most significant discrete segment in a decomposition rendering. A candidate segment may be the most significant in terms of the number of portions covered by the segment and/or in terms of the absolute value of the level of normalized counts for the segment. A candidate segment sometimes is larger and sometimes substantially larger than other discrete segments in a decomposition rendering. A candidate segment can be identified by a suitable method. In some embodiments, a candidate segment is identified by an area under the curve (AUC) analysis. In certain embodiments, where a first discrete segment has a level and/or covers a number of portions substantially larger than for another discrete segment in a decomposition rendering, the first segment comprises a larger AUC. Where a level is analyzed for AUC, an absolute value of a level often is utilized (e.g., a level corresponding to normalized counts can have a negative value for a deletion and a positive value for a duplication). In certain embodiments, an AUC is determined as an absolute value of a calculated AUC (e.g., a resulting positive value). In certain embodiments, a candidate segment, once identified (e.g., by an AUC analysis or by a suitable method) and optionally after it is validated, is selected for a z-score calculation, or the like, to determine if the candidate segment represents a genetic variation or genetic alteration (e.g., an aneuploidy, microdeletion or microduplication).

In some embodiments, a decision analysis comprises a comparison. In some embodiments, a comparison comprises comparing at least two decomposition renderings. In some embodiments, a comparison comprises comparing at least two candidate segments. In certain embodiments, each of the at least two candidate segments is from a different decomposition rendering. For example, a first candidate segment can be from a first decomposition rendering and a second candidate segment can be from a second decomposition rendering. In some embodiments, a comparison comprises determining if two decomposition renderings are substantially the same or different. In some embodiments, a comparison comprises determining if two candidate segments are substantially the same or different. Two candidate segments can be determined as substantially the same or different by a suitable comparison method, non-limiting examples of which include by visual inspection, by comparing levels or Z-scores of the two candidate segments, by comparing the edges of the two candidate segments, by overlaying either the two candidate segments or their corresponding decomposition renderings, the like or combinations thereof.

Classifications and Uses Thereof

Methods described herein can provide an outcome indicative of a genotype and/or presence or absence of a genetic variation/alteration in a genomic region for a test sample (e.g., providing an outcome determinative of the presence or absence of a genetic variation). Methods described herein sometimes provide an outcome indicative of a phenotype and/or presence or absence of a medical condition for a test sample (e.g., providing an outcome determinative of the presence or absence of a medical condition and/or phenotype). An outcome often is part of a classification process, and a classification (e.g., classification of presence or absence of a genotype, phenotype, genetic variation and/or medical condition for a test sample) sometimes is based on and/or includes an outcome. An outcome and/or classification sometimes is based on and/or includes a result of data processing for a test sample that facilitates determining presence or absence of a genotype, phenotype, genetic variation, genetic alteration, and/or medical condition in a classification process (e.g., a statistic value (e.g., standard score (e.g., z-score)). An outcome and/or classification sometimes includes or is based on a score determinative of, or a call of, presence or absence of a genotype, phenotype, genetic variation, genetic alteration, and/or medical condition. In certain embodiments, an outcome and/or classification includes a conclusion that predicts and/or determines presence or absence of a genotype, phenotype, genetic variation, genetic alteration, and/or medical condition in a classification process.

A genotype and/or genetic variation often includes a gain, a loss and/or alteration of a region comprising one or more nucleotides (e.g., duplication, deletion, fusion, insertion, short tandem repeat (STR), mutation, single nucleotide alteration, reorganization, substitution or aberrant methylation) that results in a detectable change in the genome or genetic information for a test sample. A genotype and/or genetic variation often is in a particular genomic region (e.g., chromosome, portion of a chromosome (i.e., subchromosome region), STR, polymorphic region, translocated region, altered nucleotide sequence, the like or combinations of the foregoing). A genetic variation sometimes is a copy number alteration for a particular region, such as a trisomy or monosomy for chromosome region, or a microduplication or microdeletion event for a particular region (e.g., gain or loss of a region of about 10 megabases or less (e.g., about 9 megabases or less, 8 megabases or less, 7 megabases or less, 6 megabases or less, 5 megabases or less, 4 megabases or less, 3 megabases or less, 2 megabases or less or 1 megabase or less)), for example. A copy number alteration sometimes is expressed as having no copy or one, two, three or four or more copies of a particular region (e.g., chromosome, sub-chromosome, STR, microduplication or microdeletion region).

Presence or absence of a genotype, phenotype, genetic variation and/or medical condition can be determined by transforming, analyzing and/or manipulating sequence reads that have been mapped to genomic portions (e.g., counts, counts of genomic portions of a reference genome). In certain embodiments, an outcome and/or classification is determined according to normalized counts, read densities, read density profiles, and the like, and can be determined by a method described herein. An outcome and/or classification sometimes includes one or more scores and/or calls that refer to the probability that a particular genotype, phenotype, genetic variation, or medical condition is present or absent for a test sample. The value of a score may be used to determine, for example, a variation, difference, or ratio of mapped sequence reads that may correspond to a genotype, phenotype, genetic variation, or medical condition. For example, calculating a positive score for a selected genotype, phenotype, genetic variation, or medical condition from a data set, with respect to a reference genome, can lead to a classification of the genotype, phenotype, genetic variation, or medical condition, for a test sample.

Any suitable expression of an outcome and/or classification can be provided. An outcome and/or classification sometimes is based on and/or includes one or more numerical values generated using a processing method described herein in the context of one or more considerations of probability. Non-limiting examples of values that can be utilized include a sensitivity, specificity, standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, ploidy value, fitted minority species fraction, area ratio, median level, the like or combination thereof. In some embodiments, an outcome and/or classification comprises a read density, a read density profile and/or a plot (e.g., a profile plot). In certain embodiments, multiple values are analyzed together, sometimes in a profile for such values (e.g., z-score profile, p-value profile, chi value profile, phi value profile, result of a t-test, value profile, the like, or combination thereof). A consideration of probability can facilitate determining whether a subject is at risk of having, or has, a genotype, phenotype, genetic variation and/or medical condition, and an outcome and/or classification determinative of the foregoing sometimes includes such a consideration.

In certain embodiments, an outcome and/or classification is based on and/or includes a conclusion that predicts and/or determines a risk or probability of the presence or absence of a genotype, phenotype, genetic variation and/or medical condition for a test sample. A conclusion sometimes is based on a value determined from a data analysis method described herein (e.g., a statistics value indicative of probability, certainty and/or uncertainty (e.g., standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, sensitivity, specificity, the like or combination thereof). An outcome and/or classification sometimes is expressed in a laboratory test report (described in greater detail hereafter) for particular test sample as a probability (e.g., odds ratio, p-value), likelihood, or risk factor, associated with the presence or absence of a genotype, phenotype, genetic variation and/or medical condition. An outcome and/or classification for a test sample sometimes is provided as "positive" or "negative" with respect a particular genotype, phenotype, genetic variation and/or medical condition. For example, an outcome and/or classification sometimes is designated as "positive" in a laboratory test report for a particular test sample where presence of a genotype, phenotype, genetic variation and/or medical condition is determined, and sometimes an outcome and/or classification is designated as "negative" in a laboratory test report for a particular test sample where absence of a genotype, phenotype, genetic variation and/or medical condition is determined. An outcome and/or classification sometimes is determined and sometimes includes an assumption used in data processing.

An outcome and/or classification sometimes is based on or is expressed as a value in or out of a cluster, value over or under a threshold value, value within a range (e.g., a threshold range), and/or a value with a measure of variance or confidence. In some embodiments, an outcome and/or classification is based on or is expressed as a value above or below a predetermined threshold or cutoff value and/or a measure of uncertainty, confidence level or confidence interval associated with the value. In certain embodiments, a predetermined threshold or cutoff value is an expected level or an expected level range. In some embodiments, a value obtained for a test sample is a standard score (e.g., z-score), where presence of a genotype, phenotype, genetic variation and/or medical condition is determined when the absolute value of the score is greater than a particular score threshold (e.g., threshold between about 2 and about 5; between about 3 and about 4), and where the absence of a genotype, phenotype, genetic variation and/or medical condition is determined when the absolute value of the score is less than the particular score threshold. In certain embodiments, an outcome and/or classification is based on or is expressed as a value that falls within or outside a predetermined range of values (e.g., a threshold range) and the associated uncertainty or confidence level for that value being inside or outside the range. In some embodiments, an outcome and/or classification comprises a value that is equal to a predetermined value (e.g., equal to 1, equal to zero), or is equal to a value within a predetermined value range, and its associated uncertainty or confidence level for that value being equal or within or outside the range. An outcome and/or classification sometimes is graphically represented as a plot (e.g., profile plot). An outcome and/or classification sometimes comprises use of a reference value or reference profile, and sometimes a reference value or reference profile is obtained from one or more reference samples (e.g., reference sample(s) euploid for a selected part of a genome (e.g., region)).

In some embodiments, an outcome and/or classification is based on or includes use of a measure of uncertainty between a test value or profile and a reference value or profile for a selected region. In some embodiments, a determination of the presence or absence of a genotype, phenotype, genetic variation and/or medical condition is according to the number of deviations (e.g., sigma) between a test value or profile and a reference value or profile for a selected region (e.g., a chromosome, or part thereof). A measure of deviation often is an absolute value or absolute measure of deviation (e.g., mean absolute deviation or median absolute deviation (MAD)). In some embodiments, the presence of a genotype, phenotype, genetic variation and/or medical condition is determined when the number of deviations between a test value or profile and a reference value or profile is about 1 or greater (e.g., about 1.5, 2, 2.5, 2.6, 2.7, 2.8, 2.9, 3, 3.1, 3.2, 3.3, 3.4, 3.5, 3.6, 3.7, 3.8, 3.9, 4, 5 or 6 deviations or greater). In certain embodiments, presence of a genotype, phenotype, genetic variation and/or medical condition is determined when a test value or profile and a reference value or profile differ by about 2 to about 5 measures of deviation (e.g., sigma, MAD), or more than 3 measures of deviation (e.g., 3 sigma, 3 MAD). A deviation of greater than three between a test value or profile and a reference value or profile often is indicative of a non-euploid test subject (e.g., presence of a genetic variation (e.g., presence of trisomy, monosomy, microduplication, microdeletion) for a selected region. Test values or profiles significantly above a reference profile, which reference profile is indicative of euploidy, sometimes are determinative of a trisomy, sub-chromosome duplication or microduplication. Test values or profiles significantly below a reference profile, which reference profile is indicative of euploidy, sometimes are determinative of a monosomy, sub-chromosome deletion or microdeletion. In some embodiments, absence of a genotype, phenotype, genetic variation and/or medical condition is determined when the number of deviations between a test value or profile and reference value or profile for a selected region of a genome is about 3.5 or less (e.g., about less than about 3.4, 3.3, 3.2, 3.1, 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1 or less). In certain embodiments, absence of a genotype, phenotype, genetic variation and/or medical condition is determined when a test value or profile differs from a reference value or profile by less than three measures of deviation (e.g., 3 sigma, 3 MAD). In some embodiments, a measure of deviation of less than three between a test value or profile and reference value or profile (e.g., 3-sigma for standard deviation) often is indicative of a region that is euploid (e.g., absence of a genetic variation). A measure of deviation between a test value or profile for a test sample and a reference value or profile for one or more reference subjects can be plotted and visualized (e.g., z-score plot).

In some embodiments, an outcome and/or classification is determined according to a call zone. In certain embodiments, a call is made (e.g., a call determining presence or absence of a genotype, phenotype, genetic variation and/or medical condition) when a value (e.g., a profile, a read density profile and/or a measure of uncertainty) or collection of values falls within a pre-defined range (e.g., a zone, a call zone). In some embodiments, a call zone is defined according to a collection of values (e.g., profiles, read density profiles, measures or determination of probability and/or measures of uncertainty) obtained from a particular group of samples. In certain embodiments, a call zone is defined according to a collection of values that are derived from the same chromosome or part thereof. In some embodiments, a call zone for determining presence or absence of a genotype, phenotype, genetic variation and/or medical condition is defined according a measure of uncertainty (e.g., high level of confidence or low measure of uncertainty) and/or a quantification of a minority nucleic acid species (e.g., about 1% minority species or greater (e.g., about 2, 3, 4, 5, 6, 7, 8, 9, 10% or more minority nucleic acid species)) determined for a test sample. A minority nucleic acid species quantification sometimes is a fraction or percent of cancer cell nucleic acid or fetal nucleic acid (i.e., fetal fraction) ascertained for a test sample. In some embodiments, a call zone is defined by a confidence level or confidence interval (e.g., a confidence interval for 95% level of confidence). A call zone sometimes is defined by a confidence level, or confidence interval based on a particular confidence level, of about 90% or greater (e.g., about 91, 92, 93, 94, 95, 96, 97, 98, 99, 99.1, 99.2, 99.3, 99.4, 99.5, 99.6, 99.7, 99.8, 99.9% or greater). In some embodiments, a call is made using a call zone and additional data or information. In some embodiments, a call is made without using a call zone. In some embodiments, a call is made based on a comparison without the use of a call zone. In some embodiments, a call is made based on visual inspection of a profile (e.g., visual inspection of read densities).

In some embodiments, a classification or call is not provided for a test sample when a test value or profile is in a no-call zone. In some embodiments, a no-call zone is defined by a value (e.g., collection of values) or profile that indicates low accuracy, high risk, high error, low level of confidence, high measure of uncertainty, the like or combination thereof. In some embodiments, a no-call zone is defined, in part, by a minority nucleic acid species quantification (e.g., a minority nucleic acid species of about 10% or less (e.g., about 9, 8, 7, 6, 5, 4, 3, 2% or less minority nucleic acid species)). An outcome and/or classification generated for determining the presence or absence of a genotype, phenotype, genetic variation and/or medical condition sometimes includes a null result. A null result sometimes is a data point between two clusters, a numerical value with a standard deviation that encompasses values for both the presence and absence of a genotype, phenotype, genetic variation and/or medical condition, a data set with a profile plot that is not similar to profile plots for subjects having or free from the genetic variation being investigated). In some embodiments, an outcome and/or classification indicative of a null result is considered a determinative result, and the determination can include a conclusion of the need for additional information and/or a repeat of data generation and/or analysis for determining the presence or absence of a genotype, phenotype, genetic variation and/or medical condition.

There typically are four types of classifications generated in a classification process: true positive, false positive, true negative and false negative. The term "true positive" as used herein refers to presence of a genotype, phenotype, genetic variation, or medical condition correctly determined for a test sample. The term "false positive" as used herein refers to presence of a genotype, phenotype, genetic variation, or medical condition incorrectly determined for a test sample. The term "true negative" as used herein refers to absence of a genotype, phenotype, genetic variation, or medical condition correctly determined for a test sample. The term "false negative" as used herein refers to absence of a genotype, phenotype, genetic variation, or medical condition incorrectly determined for a test sample. Two measures of performance for a classification process can be calculated based on the ratios of these occurrences: (i) a sensitivity value, which generally is the fraction of predicted positives that are correctly identified as being positives, and (ii) a specificity value, which generally is the fraction of predicted negatives correctly identified as being negative.

In certain embodiments, a laboratory test report generated for a classification process includes a measure of test performance (e.g., sensitivity and/or specificity) and/or a measure of confidence (e.g., a confidence level, confidence interval). A measure of test performance and/or confidence sometimes is obtained from a clinical validation study performed prior to performing a laboratory test for a test sample. In certain embodiments, one or more of sensitivity, specificity and/or confidence are expressed as a percentage. In some embodiments, a percentage expressed independently for each of sensitivity, specificity or confidence level, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). A confidence interval expressed for a particular confidence level (e.g., a confidence level of about 90% to about 99.9% (e.g., about 95%)) can be expressed as a range of values, and sometimes is expressed as a range or sensitivities and/or specificities for a particular confidence level. Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome and/or classification is not due to chance) in certain embodiments is expressed as a standard score (e.g., z-score), a p-value, or result of a t-test. In some embodiments, a measured variance, confidence level, confidence interval, sensitivity, specificity and the like (e.g., referred to collectively as confidence parameters) for an outcome and/or classification can be generated using one or more data processing manipulations described herein. Specific examples of generating an outcome and/or classification and associated confidence levels are described, for example, in International Patent Application Publication Nos. WO2013/052913, WO2014/190286 and WO2015/051163, the entire content of which is incorporated herein by reference, including all text, tables, equations and drawings.

An outcome and/or classification for a test sample often is ordered by, and often is provided to, a health care professional or other qualified individual (e.g., physician or assistant) who transmits an outcome and/or classification to a subject from whom the test sample is obtained. In certain embodiments, an outcome and/or classification is provided using a suitable visual medium (e.g., a peripheral or component of a machine, e.g., a printer or display). A classification and/or outcome often is provided to a healthcare professional or qualified individual in the form of a report. A report typically comprises a display of an outcome and/or classification (e.g., a value, or an assessment or probability of presence or absence of a genotype, phenotype, genetic variation and/or medical condition), sometimes includes an associated confidence parameter, and sometimes includes a measure of performance for a test used to generate the outcome and/or classification. A report sometimes includes a recommendation for a follow-up procedure (e.g., a procedure that confirms the outcome or classification). A report sometimes includes a visual representation of a chromosome or portion thereof (e.g., a chromosome ideogram or karyogram), and sometimes shows a visualization of a duplication and/or deletion region for a chromosome (e.g., a visualization of a whole chromosome for a chromosome deletion or duplication, a visualization of a whole chromosome with a deleted region or duplicated region shown; a visualization of a portion of chromosome duplicated or deleted; a visualization of a portion of a chromosome remaining in the event of a deletion of a portion of a chromosome) identified for a test sample.

A report can be displayed in a suitable format that facilitates determination of presence or absence of a genotype, phenotype, genetic variation and/or medical condition by a health professional or other qualified individual. Non-limiting examples of formats suitable for use for generating a report include digital data, a graph, a 2D graph, a 3D graph, and 4D graph, a picture (e.g., a jpg, bitmap (e.g., bmp), pdf, tiff, gif, raw, png, the like or suitable format), a pictograph, a chart, a table, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, or combination of the foregoing.

A report may be generated by a computer and/or by human data entry, and can be transmitted and communicated using a suitable electronic medium (e.g., via the internet, via computer, via facsimile, from one network location to another location at the same or different physical sites), or by another method of sending or receiving data (e.g., mail service, courier service and the like). Non-limiting examples of communication media for transmitting a report include auditory file, computer readable file (e.g., pdf file), paper file, laboratory file, medical record file, or any other medium described in the previous paragraph. A laboratory file or medical record file may be in tangible form or electronic form (e.g., computer readable form), in certain embodiments. After a report is generated and transmitted, a report can be received by obtaining, via a suitable communication medium, a written and/or graphical representation comprising an outcome and/or classification, which upon review allows a healthcare professional or other qualified individual to make a determination as to presence or absence of a genotype, phenotype, genetic variation and/or or medical condition for a test sample.

An outcome and/or classification may be provided by and obtained from a laboratory (e.g., obtained from a laboratory file). A laboratory file can be generated by a laboratory that carries out one or more tests for determining presence or absence of a genotype, phenotype, genetic variation and/or medical condition for a test sample. Laboratory personnel (e.g., a laboratory manager) can analyze information associated with test samples (e.g., test profiles, reference profiles, test values, reference values, level of deviation, patient information) underlying an outcome and/or classification. For calls pertaining to presence or absence of a genotype, phenotype, genetic variation and/or medical condition that are close or questionable, laboratory personnel can re-run the same procedure using the same (e.g., aliquot of the same sample) or different test sample from a test subject. A laboratory may be in the same location or different location (e.g., in another country) as personnel assessing the presence or absence of a genotype, phenotype, genetic variation and/or a medical condition from the laboratory file. For example, a laboratory file can be generated in one location and transmitted to another location in which the information for a test sample therein is assessed by a healthcare professional or other qualified individual, and optionally, transmitted to the subject from which the test sample was obtained. A laboratory sometimes generates and/or transmits a laboratory report containing a classification of presence or absence of genomic instability, a genotype, phenotype, a genetic variation and/or a medical condition for a test sample. A laboratory generating a laboratory test report sometimes is a certified laboratory, and sometimes is a laboratory certified under the Clinical Laboratory Improvement Amendments (CLIA).

An outcome and/or classification sometimes is a component of a diagnosis for a subject, and sometimes an outcome and/or classification is utilized and/or assessed as part of providing a diagnosis for a test sample. For example, a healthcare professional or other qualified individual may analyze an outcome and/or classification and provide a diagnosis based on, or based in part on, the outcome and/or classification. In some embodiments, determination, detection or diagnosis of a medical condition, disease, syndrome or abnormality comprises use of an outcome and/or classification determinative of presence or absence of a genotype, phenotype, genetic variation and/or medical condition. In some embodiments, an outcome and/or classification based on counted mapped sequence reads, normalized counts and/or transformations thereof is determinative of presence or absence of a genotype and/or genetic variation. In certain embodiments, a diagnosis comprises determining presence or absence of a condition, syndrome or abnormality. In certain instances, a diagnosis comprises a determination of a genotype or genetic variation as the nature and/or cause of a medical condition, disease, syndrome or abnormality. Thus, provided herein are methods for diagnosing presence or absence of a genotype, phenotype, a genetic variation and/or a medical condition for a test sample according to an outcome or classification generated by methods described herein, and optionally according to generating and transmitting a laboratory report that includes a classification for presence or absence of the genotype, phenotype, a genetic variation and/or a medical condition for the test sample.

An outcome and/or classification sometimes is a component of health care and/or treatment of a subject. An outcome and/or classification sometimes is utilized and/or assessed as part of providing a treatment for a subject from whom a test sample was obtained. For example, an outcome and/or classification indicative of presence or absence of a genotype, phenotype, genetic variation, and/or medical condition is a component of health care and/or treatment of a subject from whom a test sample was obtained. Medical care, treatment and or diagnosis can be in any suitable area of health, such as medical treatment of subjects for prenatal care, cell proliferative conditions, cancer and the like, for example. An outcome and/or classification determinative of presence or absence of a genotype, phenotype, genetic variation and/or medical condition, disease, syndrome or abnormality by methods described herein sometimes is independently verified by further testing. Any suitable type of further test to verify an outcome and/or classification can be utilized, non-limiting examples of which include blood level test (e.g., serum test), biopsy, scan (e.g., CT scan, MRI scan), invasive sampling (e.g., amniocentesis or chorionic villus sampling), karyotyping, microarray assay, ultrasound, sonogram, and the like, for example.

A healthcare professional or qualified individual can provide a suitable healthcare recommendation based on the outcome and/or classification provided in a laboratory report. In some embodiments, a recommendation is dependent on the outcome and/or classification provided (e.g., cancer, stage and/or type of cancer, Down's syndrome, Turner syndrome, medical conditions associated with genetic variations in T13, medical conditions associated with genetic variations in T18). Non-limiting examples of recommendations that can be provided based on an outcome or classification in a laboratory report includes, without limitation, surgery, radiation therapy, chemotherapy, genetic counseling, after-birth treatment solutions (e.g., life planning, long term assisted care, medicaments, symptomatic treatments), pregnancy termination, organ transplant, blood transfusion, further testing described in the previous paragraph, the like or combinations of the foregoing. Thus, methods for treating a subject and methods for providing health care to a subject sometimes include generating a classification for presence or absence of a genotype, phenotype, a genetic variation and/or a medical condition for a test sample by a method described herein, and optionally generating and transmitting a laboratory report that includes a classification of presence or absence of a genotype, phenotype, genetic variation and/or medical condition for the test sample.

Generating an outcome and/or classification can be viewed as a transformation of nucleic acid sequence reads from a test sample into a representation of a subject's cellular nucleic acid. For example, transmuting sequence reads of nucleic acid from a subject by a method described herein, and generating an outcome and/or classification can be viewed as a transformation of relatively small sequence read templates to a representation of relatively large and complex structure of nucleic acid in the subject. In some embodiments, an outcome and/or classification results from a transformation of sequence reads from a subject into a representation of an existing nucleic acid structure present in the subject (e.g., a genome, a chromosome, chromosome segment, mixture of circulating cell-free nucleic acid templates in the subject).

In some embodiments, a method herein comprises treating a subject when the presence of a genetic alteration or genetic variation is determined for a test sample from the subject. In some embodiments, treating a subject comprises performing a medical procedure when the presence of a genetic alteration or genetic variation is determined for a test sample. In some embodiments, a medical procedure includes an invasive diagnostic procedure such as, for example, amniocentesis, chorionic villus sampling, biopsy, and the like. For example, a medical procedure comprising amniocentesis or chorionic villus sampling may be performed when the presence of a fetal aneuploidy is determined for a test sample from a pregnant female. In another example, a medical procedure comprising a biopsy may be performed when presence of a genetic alteration indicative of or associated with the presence of cancer is determined for a test sample from a subject. An invasive diagnostic procedure may be performed to confirm a determination of the presence of a genetic alteration or genetic variation and/or may be performed to further characterize a medical condition associated with a genetic alteration or genetic variation, for example. In some embodiments, a medical procedure may be performed as a treatment of a medical condition associated with a genetic alteration or genetic variation. Treatments may include one or more of surgery, radiation therapy, chemotherapy, pregnancy termination, organ transplant, cell transplant, blood transfusion, medicaments, symptomatic treatments, and the like, for example.

In some embodiments, a method herein comprises treating a subject when the absence of a genetic alteration or genetic variation is determined for a test sample from the subject. In some embodiments, treating a subject comprises performing a medical procedure when the absence of a genetic alteration or genetic variation is determined for a test sample. For example, when the absence of a genetic alteration or genetic variation is determined for a test sample, a medical procedure may include health monitoring, retesting, further screening, follow-up examinations, and the like. In some embodiments, a method herein comprises treating a subject consistent with a euploid pregnancy or normal pregnancy when the absence of a fetal aneuploidy, genetic variation or genetic alteration is determined for a test sample from a pregnant female. For example, a medical procedure consistent with a euploid pregnancy or normal pregnancy may be performed when the absence of a fetal aneuploidy, genetic variation or genetic alteration is determined for a test sample from a pregnant female. A medical procedure consistent with a euploid pregnancy or normal pregnancy may include one or more procedures performed as part of monitoring health of the fetus and/or the mother, or monitoring feto-maternal well-being. A medical procedure consistent with a euploid pregnancy or normal pregnancy may include one or more procedures for treating symptoms of pregnancy which may include, for example, one or more of nausea, fatigue, breast tenderness, frequent urination, back pain, abdominal pain, leg cramps, constipation, heartburn, shortness of breath, hemorrhoids, urinary incontinence, varicose veins and sleeping problems. A medical procedure consistent with a euploid pregnancy or normal pregnancy may include one or more procedures performed throughout the course of prenatal care for assessing potential risks, treating complications, addressing preexisting medical conditions (e.g., hypertension, diabetes), and monitoring the growth and development of the fetus, for example. Medical procedures consistent with a euploid pregnancy or normal pregnancy may include, for example, complete blood count (CBC) monitoring, Rh antibody testing, urinalysis, urine culture monitoring, rubella screening, hepatitis B and hepatitis C screening, sexually transmitted infection (STI) screening (e.g., screening for syphilis, chlamydia, gonorrhea), human immunodeficiency virus (HIV) screening, tuberculosis (TB) screening, alpha-fetoprotein screening, fetal heart rate monitoring (e.g., using an ultrasound transducer), uterine activity monitoring (e.g., using toco transducer), genetic screening and/or diagnostic testing for genetic disorders (e.g., cystic fibrosis, sickle cell anemia, hemophilia A), glucose screening, glucose tolerance testing, treatment of gestational diabetes, treatment of prenatal hypertension, treatment of preeclampsia, group B streptococci (GBS) blood type screening, group B strep culture, treatment of group B strep (e.g., with antibiotics), ultrasound monitoring (e.g., routine ultrasound monitoring, level II ultrasound monitoring, targeted ultrasound monitoring), non-stress test monitoring, biophysical profile monitoring, amniotic fluid index monitoring, serum testing (e.g., plasma protein-A (PAPP-A), alpha-fetoprotein (AFP), human chorionic gonadotropin (hCG), unconjugated estriol (uE3), and inhibin-A (inhA) testing), genetic testing, amniocentesis diagnostic testing and chorionic villus sampling (CVS) diagnostic testing.

In some embodiments, a method herein comprises treating a subject consistent with having no cancer when the absence of a genetic variation or genetic alteration is determined for a test sample from a subject. In certain embodiments, a medical procedure consistent with a healthy prognosis may be performed when absence of a genetic alteration or genetic variation associated with cancer is determined for a test sample. For example, medical procedures consistent with a healthy prognosis include without limitation monitoring health of the subject from whom a test sample was tested, performing a secondary test (e.g., a secondary screening test), performing a confirmatory test, monitoring one or more biomarkers associated with cancer (e.g., prostate specific antigen (PSA) in males), monitoring blood cells (e.g., red blood cells, white blood cells, platelets), monitoring one or more vital signs (e.g., heart rate, blood pressure), and/or monitoring one or more blood metabolites (e.g., total cholesterol, HDL (high-density lipoprotein), LDL (low-density lipoprotein), triglycerides, total cholesterol/HDL ratio, glucose, fibrinogen, hemoglobin, dehydroepiandrosterone (DHEA), homocysteine, C-reactive protein, hormones (e.g., thyroid stimulating hormone, testosterone, estrogen, estradiol), creatine, salt (e.g., potassium, calcium), and the like). In some embodiments, a method herein comprises performing no medical procedure, and sometimes no medical procedure that includes invasive sampling, when the absence of a genetic alteration or genetic variation is determined for a test sample.

Machines, Software and Interfaces

Certain processes and methods described herein (e.g., mapping, counting, normalizing, range setting, adjusting, categorizing and/or determining sequence reads, counts, levels and/or profiles) often cannot be performed without a computer, microprocessor, software, module or other machine. Methods described herein typically are computer-implemented methods, and one or more portions of a method sometimes are performed by one or more processors (e.g., microprocessors), computers, systems, apparatuses, or machines (e.g., microprocessor-controlled machine).

Computers, systems, apparatuses, machines and computer program products suitable for use often include, or are utilized in conjunction with, computer readable storage media. Non-limiting examples of computer readable storage media include memory, hard disk, CD-ROM, flash memory device and the like. Computer readable storage media generally are computer hardware, and often are non-transitory computer-readable storage media. Computer readable storage media are not computer readable transmission media, the latter of which are transmission signals per se.

Provided herein are computer readable storage media with an executable program stored thereon, where the program instructs a microprocessor to perform a method described herein. Provided also are computer readable storage media with an executable program module stored thereon, where the program module instructs a microprocessor to perform part of a method described herein. Also provided herein are systems, machines, apparatuses and computer program products that include computer readable storage media with an executable program stored thereon, where the program instructs a microprocessor to perform a method described herein. Provided also are systems, machines and apparatuses that include computer readable storage media with an executable program module stored thereon, where the program module instructs a microprocessor to perform part of a method described herein.

Also provided are computer program products. A computer program product often includes a computer usable medium that includes a computer readable program code embodied therein, the computer readable program code adapted for being executed to implement a method or part of a method described herein. Computer usable media and readable program code are not transmission media (i.e., transmission signals per se). Computer readable program code often is adapted for being executed by a processor, computer, system, apparatus, or machine.

In some embodiments, methods described herein (e.g., quantifying, counting, filtering, normalizing, transforming, clustering and/or determining sequence reads, counts, levels, profiles and/or outcomes) are performed by automated methods. In some embodiments, one or more steps of a method described herein are carried out by a microprocessor and/or computer, and/or carried out in conjunction with memory. In some embodiments, an automated method is embodied in software, modules, microprocessors, peripherals and/or a machine comprising the like, that perform methods described herein. As used herein, software refers to computer readable program instructions that, when executed by a microprocessor, perform computer operations, as described herein.

Sequence reads, counts, levels and/or profiles sometimes are referred to as "data" or "data sets." In some embodiments, data or data sets can be characterized by one or more features or variables (e.g., sequence based (e.g., GC content, specific nucleotide sequence, the like), function specific (e.g., expressed genes, cancer genes, the like), location based (genome specific, chromosome specific, portion or portion-specific), the like and combinations thereof). In certain embodiments, data or data sets can be organized into a matrix having two or more dimensions based on one or more features or variables. Data organized into matrices can be organized using any suitable features or variables. In certain embodiments, data sets characterized by one or more features or variables sometimes are processed after counting.

Machines, software and interfaces may be used to conduct methods described herein. Using machines, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations. Where a system includes two or more machines, some or all of the machines may be located at the same location as a user, some or all of the machines may be located at a location different than a user, all of the machines may be located at the same location as the user, and/or all of the machine may be located at one or more locations different than the user.

A system sometimes comprises a computing machine and a sequencing apparatus or machine, where the sequencing apparatus or machine is configured to receive physical nucleic acid and generate sequence reads, and the computing apparatus is configured to process the reads from the sequencing apparatus or machine. The computing machine sometimes is configured to determine a classification outcome from the sequence reads.

A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, machines, apparatuses, computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output components may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus or machine may serve as data that can be input via an input device. In certain embodiments, mapped sequence reads may serve as data that can be input via an input device. In certain embodiments, nucleic acid template size (e.g., length) may serve as data that can be input via an input device. In certain embodiments, output from a nucleic acid capture process (e.g., genomic region origin data) may serve as data that can be input via an input device. In certain embodiments, a combination of nucleic acid template size (e.g., length) and output from a nucleic acid capture process (e.g., genomic region origin data) may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process or part of a process described herein, and software can include one or more modules for performing such processes (e.g., sequencing module, logic processing module, data display organization module). The term "software" refers to computer readable program instructions that, when executed by a computer, perform computer operations. Instructions executable by the one or more microprocessors sometimes are provided as executable code, that when executed, can cause one or more microprocessors to implement a method described herein. A module described herein can exist as software, and instructions (e.g., processes, routines, subroutines) embodied in the software can be implemented or performed by a microprocessor. For example, a module (e.g., a software module) can be a part of a program that performs a particular process or task. The term "module" refers to a self-contained functional unit that can be used in a larger machine or software system. A module can comprise a set of instructions for carrying out a function of the module. A module can transform data and/or information. Data and/or information can be in a suitable form. For example, data and/or information can be digital or analogue. In certain embodiments, data and/or information sometimes can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to a machine, peripheral, component or another module. A module can perform one or more of the following non-limiting functions: mapping sequence reads, providing counts, assembling portions, providing or determining a level, providing a count profile, normalizing (e.g., normalizing reads, normalizing counts, and the like), providing a normalized count profile or levels of normalized counts, comparing two or more levels, providing uncertainty values, providing or determining expected levels and expected ranges (e.g., expected level ranges, threshold ranges and threshold levels), providing adjustments to levels (e.g., adjusting a first level, adjusting a second level, adjusting a profile of a chromosome or a part thereof, and/or padding), providing identification (e.g., identifying a copy number alteration, genetic variation/genetic alteration or aneuploidy), categorizing, plotting, and/or determining an outcome, for example. A microprocessor can, in certain embodiments, carry out the instructions in a module. In some embodiments, one or more microprocessors are required to carry out instructions in a module or group of modules. A module can provide data and/or information to another module, machine or source and can receive data and/or information from another module, machine or source.

Accordingly, this disclosure also provides systems for determining a sequence of nucleotides for one or more nucleic acid templates in a nucleic acid sample using the methods as described above. In one embodiment, the system comprises: one or more processors; and memory coupled to one or more processors; and the memory is encoded with a set of instructions configured to perform a process comprising: contacting double-stranded nucleic acid templates of the nucleic acid sample with partially double-stranded nonrandom oligonucleotide adapter species under ligation conditions, thereby generating adapter-ligated nucleic acid templates. Each of the nonrandom oligonucleotide adapter species may comprise a first oligonucleotide species and a second oligonucleotide species: each of the first oligonucleotide species comprises 5' to 3' a polynucleotide A and a 5'-3' polynucleotide B species and each of the second oligonucleotide species comprises 5' to 3' a polynucleotide B' species and a 5' to 3' polynucleotide A'; each of the polynucleotide B species and the polynucleotide B' species are predetermined, are non-randomly generated, are the same length, and are about 4 to about 20 consecutive nucleotides in length; there are 300 or fewer polynucleotide B species and each polynucleotide B' species is a reverse complement of a polynucleotide B species; polynucleotide A is not a reverse complement of polynucleotide A': the ratio of nucleic acid templates to polynucleotide B species is greater than 1,000 to 1; the polynucleotide B species anneal to the complementary polynucleotide B' species and the polynucleotide A' species does not anneal to the polynucleotide A species. The process further comprises amplifying the adapter-ligated nucleic acid templates, thereby generating amplicons and sequencing all or a portion of each amplicon, thereby determining a sequence of nucleotides for the one or more nucleic acid templates in the nucleic acid sample.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

Accordingly, this disclosure also provides a non-transitory computer readable storage medium storing instructions that, when executed by one or more processors of a computing system, cause the computing system to execute the methods steps disclosed herein. In one embodiment, said method steps comprise contacting double-stranded nucleic acid templates of the nucleic acid sample with partially double-stranded nonrandom oligonucleotide adapter species under ligation conditions, thereby generating adapter-ligated nucleic acid templates. Each of the nonrandom oligonucleotide adapter species may comprise a first oligonucleotide species and a second oligonucleotide species: each of the first oligonucleotide species comprises 5' to 3' a polynucleotide A and a 5'-3' polynucleotide B species and each of the second oligonucleotide species comprises 5' to 3' a polynucleotide B' species and a 5' to 3' polynucleotide A'; each of the polynucleotide B species and the polynucleotide B' species are predetermined, are non-randomly generated, are the same length, and are about 4 to about 20 consecutive nucleotides in length; there are 300 or fewer polynucleotide B species and each polynucleotide B' species is a reverse complement of a polynucleotide B species; polynucleotide A is not a reverse complement of polynucleotide A'; the ratio of nucleic acid templates to polynucleotide B species is greater than 1,000 to 1; the polynucleotide B species anneal to the complementary polynucleotide B' species and the polynucleotide A' species does not anneal to the polynucleotide A species. The process further comprises amplifying the adapter-ligated nucleic acid templates, thereby generating amplicons and sequencing all or a portion of each amplicon, thereby determining a sequence of nucleotides for the one or more nucleic acid templates in the nucleic acid sample.

A machine, in some embodiments, comprises at least one microprocessor for carrying out the instructions in a module. Sequence read quantifications (e.g., counts) sometimes are accessed by a microprocessor that executes instructions configured to carry out a method described herein. Sequence read quantifications that are accessed by a microprocessor can be within memory of a system, and the counts can be accessed and placed into the memory of the system after they are obtained. In some embodiments, a machine includes a microprocessor (e.g., one or more microprocessors) which microprocessor can perform and/or implement one or more instructions (e.g., processes, routines and/or subroutines) from a module. In some embodiments, a machine includes multiple microprocessors, such as microprocessors coordinated and working in parallel. In some embodiments, a machine operates with one or more external microprocessors (e.g., an internal or external network, server, storage device and/or storage network (e.g., a cloud)). In some embodiments, a machine comprises a module (e.g., one or more modules). A machine comprising a module often is capable of receiving and transferring one or more of data and/or information to and from other modules.

In certain embodiments, a machine comprises peripherals and/or components. In certain embodiments, a machine can comprise one or more peripherals or components that can transfer data and/or information to and from other modules, peripherals and/or components. In certain embodiments, a machine interacts with a peripheral and/or component that provides data and/or information. In certain embodiments, peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a microprocessor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like,), the world wide web (www), the internet, a computer and/or another module.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash memory devices (e.g., flash drives), RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more microprocessors in certain embodiments. A microprocessor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A microprocessor may implement software in a system. In some embodiments, a microprocessor may be programmed to automatically perform a task described herein that a user could perform. Accordingly, a microprocessor, or algorithm conducted by such a microprocessor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation or genetic alteration.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

FIG. 1 illustrates a non-limiting example of a computing environment 110 in which various systems, methods, algorithms, and data structures described herein may be implemented. The computing environment 110 is only one example of a suitable computing environment and is not intended to suggest any limitation as to the scope of use or functionality of the systems, methods, and data structures described herein. Neither should computing environment 110 be interpreted as having any dependency or requirement relating to any one or combination of components illustrated in computing environment 110. A subset of systems, methods, and data structures shown in FIG. 1 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 110 of FIG. 1 includes a general purpose computing device in the form of a computer 120, including a processing unit 121, a system memory 122, and a system bus 123 that operatively couples various system components including the system memory 122 to the processing unit 121. There may be only one or there may be more than one processing unit 121, such that the processor of computer 120 includes a single central-processing unit (CPU), or a plurality of processing units, commonly referred to as a parallel processing environment. The computer 120 may be a conventional computer, a distributed computer, or any other type of computer.

The system bus 123 may be any of several types of bus structures including a memory bus or memory controller, a peripheral bus, and a local bus using any of a variety of bus architectures. The system memory may also be referred to as simply the memory, and includes read only memory (ROM) 124 and random access memory (RAM). A basic input/output system (BIOS) 126, containing the basic routines that help to transfer information between elements within the computer 120, such as during start-up, is stored in ROM 124. The computer 120 may further include a hard disk drive interface 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media.

The hard disk drive 127, magnetic disk drive 128, and optical disk drive 130 are connected to the system bus 123 by a hard disk drive interface 132, a magnetic disk drive interface 133, and an optical disk drive interface 134, respectively. The drives and their associated computer-readable media provide nonvolatile storage of computer-readable instructions, data structures, program modules and other data for the computer 120. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 129, optical disk 131, ROM 124, or RAM, including an operating system 135, one or more application programs 136, other program modules 137, and program data 138. A user may enter commands and information into the personal computer 120 through input devices such as a keyboard 140 and pointing device 142. Other input devices (not shown) may include a microphone, joystick, game pad, satellite dish, scanner, or the like. These and other input devices are often connected to the processing unit 121 through a serial port interface 146 that is coupled to the system bus, but may be connected by other interfaces, such as a parallel port, game port, or a universal serial bus (USB). A monitor 147 or other type of display device is also connected to the system bus 123 via an interface, such as a video adapter 148. In addition to the monitor, computers typically include other peripheral output devices (not shown), such as speakers and printers.

The computer 120 may operate in a networked environment using logical connections to one or more remote computers, such as remote computer 149. These logical connections may be achieved by a communication device coupled to or a part of the computer 120, or in other manners. The remote computer 149 may be another computer, a server, a router, a network PC, a client, a peer device or other common network node, and typically includes many or all of the elements described above relative to the computer 120, although only a memory storage device 150 has been illustrated in FIG. 1. The logical connections depicted in FIG. 1 include a local-area network (LAN) 151 and a wide-area network (WAN) 152. Such networking environments are commonplace in office networks, enterprise-wide computer networks, intranets and the Internet, which all are types of networks.

When used in a LAN-networking environment, the computer 120 is connected to the local network 151 through a network interface or adapter 153, which is one type of communications device. When used in a WAN-networking environment, the computer 120 often includes a modem 154, a type of communications device, or any other type of communications device for establishing communications over the wide area network 152. The modem 154, which may be internal or external, is connected to the system bus 123 via the serial port interface 146. In a networked environment, program modules depicted relative to the personal computer 120, or portions thereof, may be stored in the remote memory storage device. It is appreciated that the network connections shown are non-limiting examples and other communications devices for establishing a communications link between computers may be used.

Transformations

As noted above, data sometimes is transformed from one form into another form. The terms "transformed," "transformation," and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion, represent the presence or absence of a variation in the physical amount of a sequence associated with medical conditions). A virtual representation sometimes is further transformed into one or more numerical values or graphical representations of the digital representation of the starting material. These methods can transform physical starting material into a numerical value or graphical representation, or a representation of the physical appearance of a test subject's nucleic acid.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, fragment size (e.g., length of CCF fragments, reads or a suitable representation thereof (e.g., FRS)), fragment sequence, identification of a copy number alteration, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principal component analysis of derived quantities, and the like or combinations thereof.

Genetic Variations/Genetic Alterations and Medical Conditions

The presence or absence of a genetic variation can be determined using a method or apparatus described herein. A genetic variation also may be referred to as a genetic alteration, and the terms are often used interchangeably herein and in the art. In certain instances, "genetic alteration" may be used to describe a somatic alteration whereby the genome in a subset of cells in a subject contains the alteration (such as, for example, in tumor or cancer cells). In certain instances, "genetic variation" may be used to describe a variation inherited from one or both parents (such as, for example, a genetic variation in a fetus).

In certain embodiments, the presence or absence of one or more genetic variations or genetic alterations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation or genetic alteration is a chromosome abnormality or copy number alteration (e.g., aneuploidy, duplication of one or more chromosomes, loss of one or more chromosomes, partial chromosome abnormality or mosaicism (e.g., loss or gain of one or more regions of a chromosome), translocation, inversion, each of which is described in greater detail herein). Non-limiting examples of genetic variations/genetic alterations include one or more copy number alterations/variations, deletions (e.g., microdeletions), duplications (e.g., microduplications), insertions, mutations (e.g., single nucleotide variations, single nucleotide alterations), polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 50,000 kilobases (kb) in length (e.g., about 10 bp, 50 bp, 100 bp, 500 bp, 1 kb, 5 kb, 10 kb, 50 kb, 100 kb, 500 kb, 1000 kb, 5000 kb or 10,000 kb in length).

A genetic variation or genetic alteration is sometime a deletion. In certain instances, a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a region of a chromosome, an allele, a gene, an intron, an exon, any non-coding region, any coding region, a part thereof or combination thereof. A deletion can comprise a microdeletion. A deletion can comprise the deletion of a single base.

A genetic variation or genetic alteration is sometimes a duplication. In certain instances, a duplication is a mutation (e.g., a genetic aberration) in which a part of a chromosome or a sequence of DNA is copied and inserted back into the genome. In certain embodiments, a genetic duplication (e.g., duplication) is any duplication of a region of DNA. In some embodiments, a duplication is a nucleic acid sequence that is repeated, often in tandem, within a genome or chromosome. In some embodiments, a duplication can comprise a copy of one or more entire chromosomes, a region of a chromosome, an allele, a gene, an intron, an exon, any non-coding region, any coding region, part thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation or genetic alteration is sometimes an insertion. An insertion is sometimes the addition of one or more nucleotide base pairs into a nucleic acid sequence. An insertion is sometimes a microinsertion. In certain embodiments, an insertion comprises the addition of a region of a chromosome into a genome, chromosome, or part thereof. In certain embodiments, an insertion comprises the addition of an allele, a gene, an intron, an exon, any non-coding region, any coding region, part thereof or combination thereof into a genome or part thereof. In certain embodiments, an insertion comprises the addition (e.g., insertion) of nucleic acid of unknown origin into a genome, chromosome, or part thereof. In certain embodiments, an insertion comprises the addition (e.g., insertion) of a single base.

As used herein a "copy number alteration" generally is a class or type of genetic variation, genetic alteration or chromosomal aberration. A copy number alteration also may be referred to as a copy number variation, and the terms are often used interchangeably herein and in the art. In certain instances, "copy number alteration" may be used to describe a somatic alteration whereby the genome in a subset of cells in a subject contains the alteration (such as, for example, in tumor or cancer cells). In certain instances, "copy number variation" may be used to describe a variation inherited from one or both parents (such as, for example, a copy number variation in a fetus). A copy number alteration can be a deletion (e.g., microdeletion), duplication (e.g., a microduplication) or insertion (e.g., a microinsertion). Often, the prefix "micro" as used herein sometimes is a region of nucleic acid less than 5 Mb in length. A copy number alteration can include one or more deletions (e.g., microdeletion), duplications and/or insertions (e.g., a microduplication, microinsertion) of a part of a chromosome. In certain embodiments, a duplication comprises an insertion. In certain embodiments, an insertion is a duplication. In certain embodiments, an insertion is not a duplication.

In some embodiments, a copy number alteration is a copy number alteration from a tumor or cancer cell. In some embodiments, a copy number alteration is a copy number alteration from a non-cancer cell. In certain embodiments, a copy number alteration is a copy number alteration within the genome of a subject (e.g., a cancer patient) and/or within the genome of a cancer cell or tumor in a subject. A copy number alteration can be a heterozygous copy number alteration where the variation (e.g., a duplication or deletion) is present on one allele of a genome. A copy number alteration can be a homozygous copy number alteration where the alteration is present on both alleles of a genome. In some embodiments, a copy number alteration is a heterozygous or homozygous copy number alteration. In some embodiments, a copy number alteration is a heterozygous or homozygous copy number alteration from a cancer cell or non-cancer cell. A copy number alteration sometimes is present in a cancer cell genome and a non-cancer cell genome, a cancer cell genome and not a non-cancer cell genome, or a non-cancer cell genome and not a cancer cell genome.

In some embodiments, a copy number alteration is a fetal copy number alteration. Often, a fetal copy number alteration is a copy number alteration in the genome of a fetus. In some embodiments, a copy number alteration is a maternal and/or fetal copy number alteration. In certain embodiments, a maternal and/or fetal copy number alteration is a copy number alteration within the genome of a pregnant female (e.g., a female subject bearing a fetus), a female subject that gave birth or a female capable of bearing a fetus. A copy number alteration can be a heterozygous copy number alteration where the alteration (e.g., a duplication or deletion) is present on one allele of a genome. A copy number alteration can be a homozygous copy number alteration where the alteration is present on both alleles of a genome. In some embodiments, a copy number alteration is a heterozygous or homozygous fetal copy number alteration. In some embodiments, a copy number alteration is a heterozygous or homozygous maternal and/or fetal copy number alteration. A copy number alteration sometimes is present in a maternal genome and a fetal genome, a maternal genome and not a fetal genome, or a fetal genome and not a maternal genome.

"Ploidy" is a reference to the number of chromosomes present in a subject. In certain embodiments, "ploidy" is the same as "chromosome ploidy." In humans, for example, autosomal chromosomes are often present in pairs. For example, in the absence of a genetic variation or genetic alteration, most humans have two of each autosomal chromosome (e.g., chromosomes 1-22). The presence of the normal complement of 2 autosomal chromosomes in a human is often referred to as euploid or diploid. "Microploidy" is similar in meaning to ploidy. "Microploidy" often refers to the ploidy of a part of a chromosome. The term "microploidy" sometimes is a reference to the presence or absence of a copy number alteration (e.g., a deletion, duplication and/or an insertion) within a chromosome (e.g., a homozygous or heterozygous deletion, duplication, or insertion, the like or absence thereof).

A genetic variation or genetic alteration for which the presence or absence is identified for a subject is associated with a medical condition in certain embodiments. Thus, technology described herein can be used to identify the presence or absence of one or more genetic variations or genetic alterations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations/genetic alterations, medical conditions and states are described hereafter.

Chromosome Abnormalities

In some embodiments, the presence or absence of a chromosome abnormality can be determined by using a method and/or apparatus described herein. Chromosome abnormalities include, without limitation, copy number alterations, and a gain or loss of an entire chromosome or a region of a chromosome comprising one or more genes. Chromosome abnormalities include monosomies, trisomies, polysomies, loss of heterozygosity, translocations, deletions and/or duplications of one or more nucleotide sequences (e.g., one or more genes), including deletions and duplications caused by unbalanced translocations. The term "chromosomal abnormality" or "aneuploidy" as used herein refer to a deviation between the structure of the subject chromosome and a normal homologous chromosome. The term "normal" refers to the predominate karyotype or banding pattern found in healthy individuals of a particular species, for example, a euploid genome (e.g., diploid in humans, e.g., 46,XX or 46,XY). As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a region of a chromosome. The term "euploid," in some embodiments, refers a normal complement of chromosomes.

The term "monosomy" as used herein refers to lack of one chromosome of the normal complement. Partial monosomy can occur in unbalanced translocations or deletions, in which only a part of the chromosome is present in a single copy. Monosomy of sex chromosomes (45, X) causes Turner syndrome, for example. The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47,XYY in Jacobs Syndrome). In some embodiments, a trisomy is a duplication of most or all of an autosome. In certain embodiments, a trisomy is a whole chromosome aneuploidy resulting in three instances (e.g., three copies) of a particular type of chromosome (e.g., instead of two instances (e.g., a pair) of a particular type of chromosome for a euploid).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Medical Disorders and Medical Conditions

Methods described herein can be applicable to any suitable medical disorder or medical condition. Non-limiting examples of medical disorders and medical conditions include cell proliferative disorders and conditions, wasting disorders and conditions, degenerative disorders and conditions, autoimmune disorders and conditions, pre-eclampsia, chemical or environmental toxicity, liver damage or disease, kidney damage or disease, vascular disease, high blood pressure, and myocardial infarction.

In some embodiments, a cell proliferative disorder or condition sometimes is a cancer, tumor, neoplasm, metastatic disease, the like or combination thereof. A cell proliferative disorder or condition sometimes is a disorder or condition of the liver, lung, spleen, pancreas, colon, skin, bladder, eye, brain, esophagus, head, neck, ovary, testes, prostate, the like or combination thereof. Non-limiting examples of cancers include hematopoietic neoplastic disorders, which are diseases involving hyperplastic/neoplastic cells of hematopoietic origin (e.g., arising from myeloid, lymphoid or erythroid lineages, or precursor cells thereof), and can arise from poorly differentiated acute leukemias (e.g., erythroblastic leukemia and acute megakaryoblastic leukemia). Certain myeloid disorders include, but are not limited to, acute promyeloid leukemia (APML), acute myelogenous leukemia (AML) and chronic myelogenous leukemia (CML). Certain lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Certain forms of malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. A cell proliferative disorder sometimes is a non-endocrine tumor or endocrine tumor. Illustrative examples of non-endocrine tumors include, but are not limited to, adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor sometimes is an islet cell tumor.

In some embodiments, a wasting disorder or condition, or degenerative disorder or condition, is cirrhosis, amyotrophic lateral sclerosis (ALS), Alzheimer's disease, Parkinson's disease, multiple system atrophy, atherosclerosis, progressive supranuclear palsy, Tay-Sachs disease, diabetes, heart disease, keratoconus, inflammatory bowel disease (IBD), prostatitis, osteoarthritis, osteoporosis, rheumatoid arthritis, Huntington's disease, chronic traumatic encephalopathy, chronic obstructive pulmonary disease (COPD), tuberculosis, chronic diarrhea, acquired immune deficiency syndrome (AIDS), superior mesenteric artery syndrome, the like or combination thereof.

In some embodiments, an autoimmune disorder or condition is acute disseminated encephalomyelitis (ADEM), Addison's disease, alopecia areata, ankylosing spondylitis, antiphospholipid antibody syndrome (APS), autoimmune hemolytic anemia, autoimmune hepatitis, autoimmune inner ear disease, bullous pemphigoid, celiac disease, Chagas disease, chronic obstructive pulmonary disease, Crohns Disease (a type of idiopathic inflammatory bowel disease "IBD"), dermatomyositis, diabetes mellitus type 1, endometriosis, Goodpasture's syndrome, Graves' disease, Guillain-Barré syndrome (GBS), Hashimoto's disease, hidradenitis suppurativa, idiopathic thrombocytopenic purpura, interstitial cystitis, Lupus erythematosus, mixed connective tissue disease, morphea, multiple sclerosis (MS), myasthenia gravis, narcolepsy, euromyotonia, pemphigus vulgaris, pernicious anaemia, polymyositis, primary biliary cirrhosis, rheumatoid arthritis, schizophrenia, scleroderma, Sjögren's syndrome, temporal arteritis (also known as "giant cell arteritis"), ulcerative colitis (a type of idiopathic inflammatory bowel disease "IBD"), vasculitis, vitiligo, Wegener's granulomatosis, the like or combination thereof.

Preeclampsia

In some embodiments, the presence or absence of preeclampsia is determined by using a method or apparatus described herein. Preeclampsia is a condition in which hypertension arises in pregnancy (e.g., pregnancy-induced hypertension) and is associated with significant amounts of protein in the urine. In certain instances, preeclampsia may be associated with elevated levels of extracellular nucleic acid and/or alterations in methylation patterns. For example, a positive correlation between extracellular fetal-derived hypermethylated RASSF1A levels and the severity of preeclampsia has been observed. In certain instances, increased DNA methylation is observed for the H19 gene in preeclamptic placentas compared to normal controls.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods, machines and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g., strain).

Use of Cell Free Nucleic Acid

In certain instances, nucleic acid from abnormal or diseased cells associated with a particular condition or disorder is released from the cells as circulating cell-free nucleic acid (CCF-NA). For example, cancer cell nucleic acid is present in CCF-NA, and analysis of CCF-NA using methods provided herein can be used to determining whether a subject has, or is at risk of having, cancer. Analysis of the presence or absence of cancer cell nucleic acid in CCF-NA can be used for cancer screening, for example. In certain instances, levels of CCF-NA in serum can be elevated in patients with various types of cancer compared with healthy patients. Patients with metastatic diseases, for example, can sometimes have serum DNA levels approximately twice as high as non-metastatic patients. Accordingly, methods described herein can provide an outcome by processing sequencing read counts obtained from CCF-NA extracted from a sample from a subject (e.g., a subject having, suspected of having, predisposed to, or suspected as being predisposed to, a particular condition or disease).

Markers

In certain instances, a polynucleotide in abnormal or diseased cells is modified with respect to nucleic acid in normal or non-diseased cells (e.g., single nucleotide alteration, single nucleotide variation, copy number alteration, copy number variation). In some instances, a polynucleotide is present in abnormal or diseased cells and not present in normal or non-diseased cells, and sometimes a polynucleotide is not present in abnormal or diseased cells and is present in normal or non-diseased cells. Thus, a marker sometimes is a single nucleotide alteration/variation and/or a copy number alteration/variation (e.g., a differentially expressed DNA or RNA (e.g., mRNA)). For example, patients with metastatic diseases may be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Accordingly, methods described herein sometimes provide an outcome based on determining the presence or absence of a particular marker, and sometimes an outcome is presence or absence of a particular type of condition (e.g., a particular type of cancer).

Certain methods described herein may be performed in conjunction with methods described, for example in International Patent Application Publication No. WO2013/052913, International Patent Application Publication No. WO2013/052907, International Patent Application Publication No. WO2013/055817, International Patent Application Publication No. WO2013/109981, International Patent Application Publication No. WO2013/177086, International Patent Application Publication No. WO2013/192562, International Patent Application Publication No. WO2014/116598, International Patent Application Publication No. WO2014/055774, International Patent Application Publication No. WO2014/190286, International Patent Application Publication No. WO2014/205401, International Patent Application Publication No. WO2015/051163, International Patent Application Publication No. WO2015/138774, International Patent Application Publication No. WO2015/054080, International Patent Application Publication No. WO2015/183872, International Patent Application Publication No. WO2016/019042, and International Patent Application Publication No. WO 2016/057901, the entire content of each is incorporated herein by reference, including all text, tables, equations and drawings.

EXAMPLES

The examples set forth below illustrate certain embodiments and do not limit the technology.

Example 1: Materials and Methods

The materials and methods set forth in this example were used, or can be used, to perform certain aspects of the methods and analysis described in Examples 2 and 3, except where otherwise noted.
DNA Extraction
Whole blood is collected, for example in Streck BCT tubes, and processed to plasma using the methods previously described (see e.g., Jensen et al. (2013) PLoS One 8(3): e57381). DNA extraction from plasma is performed using Hamilton liquid handlers.
Library Preparation
After extraction, ccf DNA is used to create sequencing libraries. This process includes the following enzymatic reactions: end repair, mono-adenylation (a-tailing), adapter ligation, and PCR. Adapters include single molecule barcodes or unique molecule identifiers. Since the ligation process occurs prior to PCR, single molecule barcodes enable the differentiation of unique template molecules and can be useful for error correction.

In one example, indexed and single molecule barcoded sequencing libraries were prepared from plasma DNA samples for sequencing on Illumina instruments using NEB-NEXT ULTRA biochemistry modified for Oncology library custom adapters. Specifically, custom single molecule barcoded library adapters were hybridized in plate format prior to preparation of sequencing libraries. Generation of Y-shaped custom single molecule barcoded library adapters was achieved by mixing custom P5 and P7 oligonucleotides in equimolar concentration in STE buffer, denaturing this mixture on a thermal cycler, and slowly ramping to room temperature. Sequencing libraries were prepared in a multi-step, automated process using the ZEPHYR liquid handler. The starting material was 40 μL of DNA extracted from plasma or 40 μL of fragmented and size selected DNA extracted from tissue or buffy coat samples. During NEB-NEXT ULTRA/Oncology library preparation, a series of enzymatic reactions were performed to modify the dsDNA fragments such that the molecules were amenable to clustering and sequencing on Illumina sequencing platforms. These included: 1) end preparation, 2) adapter ligation, and 3) PCR. Adapter ligation and PCR were each followed by a cleanup step using AMPURE XP beads to remove excess proteins and nucleotides prior to further downstream processing. These cleanup steps were automated in a 96-well plate format. In the first enzymatic step, combined End Prep Enzyme Mix (NEB) and 10× End Repair Reaction Buffer (NEB) were used to: 1) create blunt-ended, 5' phosphorylated fragments via exonuclease and polymerase activities and 2) add a single adenine nucleotide to 3' fragment ends (A-tailing) in order to minimize the incidence of template concatenation and facilitate adapter ligation. To achieve these combined activities, a brief heat inactivation step immediately after blunt-end formation substituted for a more traditional magnetic bead cleanup and catalyzed the A-tailing of DNA fragments. These 3' adenine overhangs were complementary to the thymine overhangs present on custom single molecule barcoded library adapters. The addition of double-stranded Y-shaped adapters to the A-tailed fragments was mediated by Blunt/TA Ligase Master Mix (NEB) and Ligation Enhancer (NEB) in the second enzymatic reaction. Finally, DNA fragments with adapters properly ligated at both ends were selectively amplified using universal forward and universal reverse PCR primers and NEBNEXT Hot Start High-Fidelity 2×PCR Master Mix. The library preparation process was performed in two lab spaces separated by traditional pre- and post-PCR restrictions. The final PCR cleanup step yielded stock libraries eluted in HPLC water that were suitable for dilution, QC, normalization, target capture enrichment, and sequencing on Illumina instruments.
Quantification
After library preparation, the libraries are quantified using capillary electrophoresis (e.g., CaliperGX) or PCR-based methods (e.g., droplet digital PCR, quantitative PCR). A fixed amount of library is then used as the template for target enrichment. The amount of library used for target enrichment is dependent upon the number of samples multiplexed together prior to target enrichment (e.g., 1 to 24 samples).
Target Enrichment
In order to enable for a certain level of sequencing (e.g., 30,000-fold to 50,000-fold) using as few sequencing reads as possible, hybridization capture methods are utilized to enrich for genomic regions of interest. For this process, biotinylated probes (sometimes referred to as baits) are designed to span regions of interest, manufactured, and pooled together in a single reaction well. The target enrichment process works by first denaturing the library/libraries and then hybridizing biotinylated probes to the target libraries. This process occurs at an elevated temperature (45° C. to 65° C.) for an extended period of time (4 to 72 hours). Upon completion of the hybridization process, the hybridized probe/library complex is then precipitated using streptavidin coated beads. The beads are washed and the enriched libraries are then amplified using an additional PCR reaction, similar to the PCR reaction used during library preparation. Target enrichment probes may be commercially manufactured, for example by integrated DNA technologies (IDT) and/or Roche/Nimblegen, and may be about 60 to 120 bp in length.

In one example, single molecular barcode indexed libraries were target captured using an oncology probe panel for sequencing on Illumina instruments (certain genes represented in the oncology probe panel are described in Example 4 and presented in Table 2). Specifically, single molecular indexed libraries were captured in a multi-step manual process. The starting material was an adapter ligated, cleaned library eluted in 50 μL of water prepared on the ZEPHYR liquid handler using NEBNEXT Ultra Biochemistry. During the target capture procedure, a series of steps were performed to capture desired target loci which were amenable to clustering and sequencing on Illumina's HISEQ 2500 instruments including 1) blocking of repetitive elements and adapter sequences, 2) hybridization of capture probes to target DNA, 3) bead binding of capture probes and washing, 3) PCR amplification, and 4) bead cleanup. In the first step, blocking oligos complementary to the Illumina adapters were added along with Cot-1 DNA that blocked repetitive elements in the genome. The blocked DNA was then dried in a CENTRIVAP concentrator centrifuge at 65° C. until samples were completely evaporated. The dried samples were then immediately resuspended using hybridization buffer. During hybridization, the templates were denatured and the blocking elements and biotinylated capture probes subsequently were hybridized. The bound templates were captured with streptavidin-coated magnetic beads, washed to remove unbound template, and then PCR amplified. The amplified products were then SPRI cleaned using AMPURE beads and the entire process was repeated. The final PCR cleanup step yielded stock captured libraries that were ready for dilution, QC, and normalization.

Further Quantification

After completing the target enrichment process, the enriched libraries are quantified using capillary electrophoresis (CaliperGX) or PCR-based methods (droplet digital PCR, quantitative PCR). Enriched libraries are then normalized to a fixed concentration and loaded onto a next generation sequencing instrument (e.g., Illumina HISEQ 2000/2500).

In one example, an Agilent Bioanalyzer 2100 was used to quantify sequencing libraries that were prepared from cell-free plasma DNA using NEBNEXT biochemistry and subsequently double captured with an oncology probe panel. Specifically, libraries were analyzed to determine average fragment size distribution and concentration via gel electrophoresis on a micro fluidic platform. The average fragment size of each captured library was determined using smear detection parameters and the concentration was calculated by integration of the electropherogram output. The calculated concentration was used in a subsequent normalization process prior to clustering and sequencing.

Sequencing

Sequencing by synthesis is performed using paired end sequencing, for example. Libraries are sequenced for about 100 to 150 cycles for each of the paired reads.

In one example, sequencing was performed on the Illumina HISEQ 2500 instrument. Illumina's sequencing by synthesis technology uses a reversible terminator-based approach that is able to detect single bases as they are incorporated into a growing DNA strand. A fluorescently-labeled terminator is imaged as each dNTP is added and then cleaved to allow incorporation of the next base. All four reversible terminator-bound dNTPs are present at each cycle so a natural competition between the bases minimizes incorporation bias. After each round of synthesis the clusters are excited by a laser emitting a color that identifies the newly added base. The fluorescent label and blocking group are then removed allowing for the addition of the next base. This biochemistry allows for a single base to be read each cycle. Using the HISEQ 2500 sequencer and reagent kits from Illumina for this example, the clusters on a flow cell were used as templates to generate paired 150 base pair sequencing reads of ~50 million uniquely aligned sequences per sample (when assayed in 6-plex).

Data Analysis

Sequencing reads are aligned to a reference genome with one or more distinct parameter settings. After alignment, certain processes described herein are utilized to evaluate various types of genetic alterations (e.g., single nucleotide alterations, insertions/deletions, fusions, and copy number alterations).

Example 2: De-Multiplexing, Alignment, Read Group Generation and Consensus Making In this Example, nucleotide sequence reads were de-multiplexed, aligned, and assigned to read groups. A consensus was generated as described below.

De-Multiplexing and Alignment

The purpose of the process described below is to distribute reads according to sample, extract the single molecule barcode (SMB), and to align the reads to a reference genome. This process requires a complete Illumina sequencing run as input. The output contains various FASTQ files and BAM alignment files.

In this Example, BCL convert was run on sequence read data prepared as described in Example 1 using a script provided by Illumina. This resulted in FASTQ reads. A custom Perl script was applied to match read pairs to sample IDs using the sample index read. In certain instances, de-multiplexing was performed using a custom de-multiplexing process, referred to as a "demultiplexer." The demultiplexer first parsed a sample sheet to associate index values to sample names. The demultiplexer then proceeded to read in two or three fastq files (R1, R2, R3 optional) as generated by bcltofastq1.8. It assumed that each record in R1 file, had a corresponding record in R2 in the same position, and a corresponding record in R3 in the same position for paired end data. Given this assumption, the demultiplexer processed each record from R1, R2, and R3 (optional) as a set. The demultiplexer interpreted R2 as the "index" for R1 and R3 (mate of R1), but only used part of the read as the actual index and the other part as a random barcode. The barcode (for the sample index) was appended to the header of R1 and R3 for downstream processing whereas the index part was fuzzily matched against the list of indexes as determined by the sample sheet. This was the de-multiplexing part. If a match occurred, the updated records were written to a fastq file matching the sample to which the index belongs. Otherwise, the record was placed in an undetermined_index file. The random barcode (i.e., the SMB) sequence was split from the sample index read and concatenated to the read name of both paired end reads. The barcode base quality values also were concatenated to the read names. Reads that did not pass an Illumina chastity filter were stored in separate fastq files. Trimmomatic (0.32) was applied to remove large adapter sequences remaining on each read. The trimmed reads were aligned using BWA mem (0, 7, 12) with default parameters to HG19. The alignments were converted to BAM format, then sorted and indexed using Samtools (1.1).

Read Groups

The purpose of the process described below is to mark duplicate reads and generate read groups. Read groups generally are a collection of reads with similar start (i.e., the start of the corresponding DNA template), end (i.e., the end of the corresponding DNA template), and barcode. This process requires a sorted and indexed BAM file, with SMB (single molecule barcode) as part. It is run on each chromosome independently. It generates a new BAM file with duplicate reads marked, and read group IDs associated with each read. This process also splits on-target reads, off-target reads, and ambiguous reads into separate BAM files.

In this Example, a few filters were applied on the raw aligned data provided above. Barcodes and/or indexes with ambiguous nucleotides, ambiguously aligned reads, and discordantly mapped reads were filtered out. For example, reads with an SMB or sample index having a single base with a base quality score of less than 14, or two or more bases with a base quality score of less than 21, were filtered out. Then, using a custom set of Perl scripts, PCR duplicates were identified using the random single molecule barcode (SMB) associated with each read. The SMB was parsed from each aligned read and a molecule signature was created by concatenating the SMB with the chromosome, start position of the template, and end position of the template. Reads having identical molecule signatures were flagged as duplicate reads by adjusting the bit flag in the alignment file and were given a unique read group numerical identifier. Read groups which shared the same SMB and were within 5 bases of each other from either the start or end of the template were collapsed together by marking them with the same read group identifier. Read groups with similar SMBs were checked and read groups with SMBs that have an edit distance less than two were collapsed (reads assigned to a read group have the same SMB (zero mismatches) or nearly the same SMB (edit distance of 1)). The final output from these scripts was a duplicate marked alignment file with one entry for each on-target read. Intermediary files also were outputted. One file contained signatures for each molecule and the number of times a molecule signature was observed. Another file contained the number of reads per multiplicity of read groups.

Consensus

The purpose of consensus making is to collapse SMB read groups to compile a sequence representation of the original template. This process generates a single read which will represent duplicate reads that were grouped into read groups. In other words, this process generates a consensus read representing a collection of reads in a single read group. This process uses a marked duplicate chrom file (i.e., a BAM file with the read group id as the first column) and outputs a sorted BAM file with consensus reads. A call file also is outputted which contains the nucleotide count at each position in the panel.

In this Example, consensus sequences were made for each set of read groups originating from one template in the original sample. Consensus reads were generated for each end of a template; and for each pair of consensus reads having an overlapping region, nucleotide identity agreement for each base in the overlapping region was assessed. If nucleotide identity agreement was not present for a base in the overlapping region, the base with the higher quality was selected. Then, for each position in a template covered by any of the reads, the total number and identity of the nucleotides at that position was determined, and their total qualities were assessed. If a position had >=90% of the count of the nucleotides and >=90% of the quality of the nucleotides agreeing on the same call, then that base and the mean quality for that letter was the output. Otherwise, an "N" with base quality "#" was the output. The base calls were then tallied for each position.

QC Metrics

Table 1 provides a description of certain quality control (QC) metrics assessed for each sample run. Certain terms referred to in Table1* include: panel (all positions overlapped by a capture probe); padded panel (panel with an additional 250 bases on either side of capture probes); singleton (a consensus read group that has only one read pair); doubleton (a consensus read group that has two read pairs); consensus coverage (coverage derived from sequences that are themselves a read group consensus; does not include singletons or doubletons); consensus 1-2 ton coverage (coverage derived from sequences that are themselves a read group consensus, including singletons and doubletons; and raw coverage (coverage from all input reads without consensus or duplicate marking).

An additional QC metric may be employed using the nonrandom oligonucleotide adapters of the present application. The sequences of the set of the nonrandom oligonucleotide adapters provided in the ligation reaction are known. Adapter-ligated nucleic acid templates that consist of at least one adapter having a nucleotide sequence that is not one of the known adapter set are removed from any additional sequencing or counting analysis.

The QC metrics file contains the following metrics. Values listed here are example values from an arbitrary sample and are for illustrative purposes only.

TABLE 1

| Metric | Value | Description |
| --- | --- | --- |
| Total Reads | 284312328 | Total reads input into the pipeline, typically chastity filtered reads |
| Aligned Reads | 282922663 | Number of reads that align to the genome |
| Discordant Reads | 226331 | Number of reads that are discordant |
| On-Target Reads | 245672560 | Number of reads that align and overlap the padded panel |
| Alignment Rate | 0.995112188733511 | Fraction of reads that align to the genome |
| Discordant Rate | 0.000796064671525605 | Fraction of reads that are discordant between read 1 and read 2 |
| On-Target Rate | 0.864093941082991 | Fraction of reads that align and overlap the padded panel |
| Mean Raw Coverage | 73,881.17 | Average raw panel coverage |
| Median Raw Coverage | 72,508 | Median raw panel coverage |
| 10X Raw Coverage | 0.999973028939947 | Fraction of padded panel that has at least 10X raw coverage |
| 200X Raw Coverage | 0.998783305513184 | Fraction of padded panel that has at least 200X raw coverage |
| 500X Raw Coverage | 0.998306816785589 | Fraction of padded panel that has at least 500X raw coverage |
| 1000X Raw Coverage | 0.997944205867105 | Fraction of padded panel that has at least 1000X raw coverage |
| Standard Deviation Raw Coverage | 32,948.79 | Standard deviation of raw padded panel coverage |
| Mean Consensus Coverage | 2,252.04 | Average consensus padded panel coverage |

TABLE 1-continued

| Metric | Value | Description |
|---|---|---|
| Median Consensus Coverage | 1,249 | Median consensus padded panel coverage |
| 10X Consensus Coverage | 0.938361415544044 | Fraction of padded panel with at least 10X consensus coverage |
| 200X Consensus Coverage | 0.689131411644163 | Fraction of padded panel with at least 200X consensus coverage |
| 500X Consensus Coverage | 0.604114015720306 | Fraction of padded panel with at least 500X consensus coverage |
| 1000X Consensus Coverage | 0.530249664006354 | Fraction of padded panel with at least 1000X consensus coverage |
| Standard Deviation Consensus Coverage | 2,528.09 | Standard deviation of consensus padded panel coverage |
| Mean Consensus With 1-2 ton Coverage | 2,507.85 | Average of consensus 1-2 ton padded panel coverage |
| Median Consensus With 1-2 ton Coverage | 1,406 | Median of consensus 1-2 ton padded panel coverage |
| 10X Consensus Wtih 1-2 ton Coverage | 0.948465279291839 | Fraction of panel with at least 10X consensus 1-2 ton padded panel coverage |
| 200X Consensus With 1-2 ton Coverage | 0.707896899850863 | Fraction of panel with at least 200X consensus 1-2 ton padded panel coverage |
| 500X Consensus With 1-2 ton Coverage | 0.61798674040614 | Fraction of panel with at least 500X consensus 1-2 ton padded panel coverage |
| 1000X Consensus With 1-2 ton Coverage | 0.545143932205541 | Fraction of panel with at least 1000X consensus 1-2 ton padded panel coverage |
| Standard Deviation Consensus With 1-2 ton Coverage | 2,802.25 | Standard deviation of consensus 1-2 ton padded panel coverage |
| Mean Consensus Coverage Panel | 4,936.97 | Mean consensus panel coverage |
| Median Consensus Coverage Panel | 4,786 | Median consensus panel coverage |
| 10X Consensus Coverage Panel | 0.998078022698492 | Fraction of panel with at least 10X consensus coverage |
| 200X Consensus Coverage Panel | 0.996036296032404 | Fraction of panel with at least 200X consensus coverage |
| 500X Consensus Coverage Panel | 0.991503782583054 | Fraction of panel with at least 500X consensus coverage |
| 1000X Consensus Coverage Panel | 0.981390948744278 | Fraction of panel with at least 1000X consensus coverage |
| Standard Deviation Consensus Coverage Panel | 2,225.5 | Standard deviation of panel consensus coverage |
| Mean Consensus With 1-2 ton Coverage Panel | 5,479.65 | Average of consensus 1-2 ton panel coverage |
| Median Consensus With 1-2 ton Coverage Panel | 5,307 | Median of consensus 1-2 ton panel coverage |
| 10X Consensus Wtih 1-2 ton Coverage Panel | 0.998194778328958 | Fraction of panel with at least 10X consensus 1-2 ton coverage |
| 200X Consensus With 1-2 ton Coverage Panel | 0.996551218300098 | Fraction of panel with at least 200X consensus 1-2 ton coverage |
| 500X Consensus With 1-2 ton Coverage Panel | 0.992946762426242 | Fraction of panel with at least 500X consensus 1-2 ton coverage |
| 1000X Consensus With 1-2 ton Coverage Panel | 0.984923554999386 | Fraction of panel with at least 1000X consensus 1-2 ton coverage |
| Standard Deviation Consensus With 1-2 ton Coverage Panel | 2,470.14 | Standard deviation of consensus 1-2 ton panel coverage |
| Mean Probe Unique Coverage | 2,060.08 | Average of average probe consensus 1-2 ton coverage |
| Median Probe Unique Coverage | 1,807.12 | Median of average probe consensus 1-2 ton coverage |
| Standard Deviation Probe Unique Coverage | 1,144.92 | Standard deviation of average probe consensus 1-2 ton coverage |
| Reads Per SMB | 8.10385332610447 | Average number of read pairs in a consensus read group |
| Singleton Rate | 0.0686965529607867 | Fraction of read groups that are composed of singletons |
| Doubleton Rate | 0.0314754249341031 | Fraction of read groups that are composed of doubletons |
| Median Upsample Metric | 17 | The median number of bases sampled to observe all available barcodes. This is repeated 1000 times from randomly chosen starting points. |

Example 3: Identification of Single Nucleotide Alterations

In this Example, single nucleotide alterations were detected by analyzing reads and consensus sequences generated using methods described in Examples 1 and 2, except where otherwise noted.

VCF Maker

A pileup of reads was generated post consensus to generate allelic count at each position in the probe panel described above. The count of unique bases and qualities were tallied independently for a given position. In certain instances, the position based counting information was converted to a variant call format (VCF). The overall process for VCF conversion included the following steps:
1) Tally consensus base counts at each position
2) Calculate allele depth and fraction
3) Annotate each position with external data
   a. Gene information
   b. Effect e.g. intergenic_region, intron_variant
   c. Impact e.g. modifier, low, high
   d. Amino acid change (if any)
   e. Observed population frequencies in:
      i. UK10k database
      ii. dbNSFP 1000 genomes database
      iii. dbSNP
      iv. ESP6500
4) Annotate each position with internal data
   a. List of actionable SNPs
   b. Mappability scores
   c. Homopolymer rate
5) Only positions covered by a probe reported
6) General sample level metrics embedded in the VCF header
7) True positives and false positives not identified Described below is the script used to convert position-based counting information output by the methods above into VCF (variant call format) and MAF (mutation annotation format) with position-based annotation. VCF is a text file format containing meta-information lines, a header line, and data lines containing information about a position in a genome. A MAF file (.maf) is a tab-delimited text file that lists mutations. The operation of the script itself and the external data sources used to annotate the resulting VCF are described.

Certain terms referred to in the general script algorithm include: multiplicity (the number of raw molecules that are combined to form a single consensus molecule, which is half the number of raw reads for paired end sequencing), and singleton (a consensus molecule with a multiplicity of 1).

Generally, the script tallies up all the consensus base counts at each position, and calculates total allele depth and fraction, then annotates the position based on certain external resources and outputs the results in VCF and MAF format. The primary function is reformatting the data in industry standard formats.

For certain applications. Illumina uses 8 quality bins (numbered 0 through 7) to describe base qualities. When considering consensus counts, quality bins 5, 6 and 7 are included, corresponding to quality scores of >=30. When referring to the probe panel described above, one can refer to regions that are both covered by a targeted probe (inProbe=1), or are adjacent to a probe (inProbe=0). By default an entry in the VCF and MAF files is generated for every position where inProbe=1, and no positions where inProbe=0.

The general script algorithm includes:
1) Read in external files with fixed position-based annotation:
   a. List of actionable SNPs
   b. List of mappability scores for each position in the panel
   c. List of homopolymer rate for each position in the panel
   d. List of external database annotations
      i. Gene information
      ii. Effect e.g. intergenic_region, intron_variant
      iii. Impact e.g. modifier, low, high
      iv. Amino acid change (if any)
      v. Observed population frequencies in:
         1. UK10k database
         2. dbNSFP 1000 genomes database
         3. dbSNP
         4. ESP6500
   e. Read in multiplicity weights file (if applicable, see below)
2) Read in the consensus counts file line by line
   a. Collect allele counts, fraction, total counts
   b. Simultaneously read in the bias stats file line by line
3) Generate the VCF output entry.
   a. ID is the dbSNP rsID when available, otherwise ".".
   b. REF is the reference base
   c. ALT is all non-reference bases that have a non-zero consensus count
   d. QUAL is always "."
   e. FILTER one or more of:
      i. MINCOV100: did not meet minimum coverage of 100
      ii. MINCOV500: did not meet minimum coverage of 500
      iii. MINALT2: did not meet minimum alternate depth of 2
      iv. MINALT4: did not meet minimum alternate depth of 4
      v. PASS: meets all filters
   f. INFO
      i. Contains all the information relevant to the position read in from external files in step #1 above
   g. FORMAT
      i. GT: Genotype, a "|" delimited string of indices of all present alleles
      ii. DP: Total consensus depth at that position
      iii. AD: Allele depth for ref and alt in order listed
      iv. AF: Allele fraction for ref and alt in order listed
      v. SF: Singleton fraction for ref and alt in order listed
      vi. SB: Strand bias for ref and alt in order listed
      vii. EB: End bias for ref and alt in order listed
      viii. IB: Indel bias for ref and alt in order listed
   h. <SAMPLE> entry contains the actual values for items defined in FORMAT
4) Generate the MAF output entry
   a. Hugo_Symbol: Gene
   b. Entrez_Gene_id: "."
   c. Center: SQNM
   d. HCBI_Build: hg19
   e. Chromosome
   f. Start_Position: Current position
   g. End_Position: Current position
   h. Strand: "+"
   i. Variant_Classification: Mutation severity e.g. high or low
   j. Reference_Allele: Reference allele
   k. Tumor_Seq_Allele1: Alternate allele with highest fraction (if any)
   l. Tumor_Seq_Allele2: Alternate allele with second highest fraction (if any)

m. dbSNP_RS: dnSNP rsID (if available)
n. dnSNP_Val_Status: "."
o. Tumore_Sample_Barcode: "."
p. Matched_Norm_Sample_Barcode: "."
q. Match_Norm_Seq_Allelele1: "."
r. Match_Norm_Seq_Allele2: "."
s. Tumor_Validation_Allele1: "."
t. Tumor_Validation_Allele2: "."
u. Match_Norm_Validation_Allele1: "."
v. Match_Norm_Validation_Allele2: "."
w. Verification_Status: "."
x. Validation_Status: "."
y. Mutation_Status: "."
z. Sequencing_Phase: "."
aa. Sequence_Source: "."
bb. Validation_Method: "."
cc. Score: "."
dd. BAM_File: "."
ee. Sequencer: IlluminaHiSeq
ff. Tumor_Sample_UUID: "."
gg. Matched_Norm_Sample_UUID: "."
hh. (Columns below this point are custom column additions)
ii. Tumor_Seq_Allele3: Alternate allele with third highest fraction (if any)
jj. InProbe: Whether or not the position is within a targeted probe
kk. Total_Depth: Total consensus depth at that position
ll. Reference_Depth: Depth of reference allele
mm. Alt_Depth1, Alt_Depth2, Alt_Depth3: Alternate allele depths
nn. Reference Frac: Allele fraction of reference
oo. Alt_Frac1, Alt_Frac2, Alt_Frac3: Alternate allele fractions
pp. Reference_SF, Alt_SF1, Alt_SF1, Alt_SF3: Singleton fraction of ref and alts
qq. Reference_SB, Alt_SB1, Alt_SB2, Alt_SB3: Strand bias of ref and alts
rr. Reference_EB, Alt_EB1, Alt_EB2, Alt_EB3: End bias of ref and alts
ss. Reference_IB, Alt_IB1, Alt_IB2, Alt_IB3: Indel bias of ref and alts
tt. Actionable: Annotation of actionable mutation (if any)
uu. Mappability: Calculated mappability rate at that position
vv. Homopolymer: Calculated hompolymer rate at that position
ww. Population_Frequency: Population frequency in above-mentioned databases
xx. Sample_ID: Internal sample ID of given sample
yy. Context: Reference sequence context of the position
zz. Adjacent_Variant: Whether or not the adjacent positions have non-reference allele counts
  i. m1: Only the previous position has non-reference alleles
  ii. p1: Only the next position has non-reference alleles
  iii. m1p1: Both previous and next positions have non-reference alleles
5) Calculate singleton fraction statistics considering all reference alleles with coverage >=500. This information is embedded in the header of the VCF and MAF files
  a. Average
  b. Standard deviation
  c. Median
  d. MAD A script for position variant calling is presented below:

```
rm(list=ls( ))
gc( )
library(MASS)
library(parallel)
arg=commandArgs( )
dirOut = as.character(unlist(strsplit(arg[ pmatch("--dirOut",arg)], "="))[2])
sampleNm.tr = as.character(unlist(strsplit(arg[ pmatch("--sampleNmTr",arg)], "="))[2]) # a vector of training sample names (e.g. RDSRs)
sampleNm.ts = as.character(unlist(strsplit(arg[ pmatch("--sampleNmTs",arg)], "="))[2]) # testing sample names (e.g. RDSRs)
mc_cores = as.numeric(unlist(strsplit(arg[ pmatch("--mc_cores",arg)], "="))[2]) # number of threads
outRFile = as.character(unlist(strsplit(arg[ pmatch("--outRFile",arg)], "="))[2]) # full dir to output file
inRFile = as.character(unlist(strsplit(arg[ pmatch("--inRFile",arg)], "="))[2]) # full dir to input file
load(inRFile) # load in loci (a vector of loci of interests), sampleNm.tr ( a vector of training sample names, e.g. RDSRs), sampleNm.ts (testing sample names) and x.list ( a list of loci info--each sublist corresponds to one locus. Rows are samples and columns contains at least the following info: DP, AF.alt and AD.alt obtained from vcf files.),
names(loci) = loci
nLoci = length(loci)
####### 1) Variant calling/outlier detection based on mahal distance
AF.alt.tr.max = 0.05
DP.tr.min = 100
mahal.pvalue.thld = 0.01 # pvalue threshold
loess.z.thld = 3 # zscore threshold
detOutlier.mahal = T
if(detOutlier.mahal){
    p.chisq = 1 - mahal.pvalue.thld
    df.chisq = 2
    findOutlier.mahal <- function(locus){
        x = x.list[[locus]][, c("DP", "AF.alt")]
        if(is.null(x) ) return(NULL);
        if(nrow(x)==0) return(NULL);
        selId = which(x[,"AF.alt"]<= AF.alt.tr.max & (x[,"DP"]>= DP.tr.min) )
        if (length(selId)==0) return(NULL)
        x = log10(x)
        x.tr = x[selId,][sampleNm.tr, ]
        x.ts = x[sampleNm.ts, ]
        mu = apply( x.tr, MARGIN=2, median, na.rm=T)
        sigma = cov(x.tr, use="pairwise.complete.obs")
```

-continued

```
    if ( class(try( mahalanobis(x.ts, center=mu, cov=sigma) ))=="try-error" ){
      return (NULL)
    } else {
      mahal = mahalanobis(x.ts, center=mu, cov=sigma)
    }
    mahal.pvalue = pchisq(q=mahal, df=df.chisq, lower.tail=F)
    outId = which(mahal.pvalue < mahal.pvalue.thld )
    rst = list(mahal=mahal, mahal.pvalue=mahal.pvalue, outId=outId, mu=mu, sigma=sigma)
    return(rst)
  }
  detRst.mahal = mclapply(loci, mc.cores=mc_cores, FUN=function(locus){
    detRst = findOutlier.mahal(locus)
    return(detRst)
  })
}
####### 2) Variant calling/outlier detection based on Loess regression
detOutlier.loess = T
if(detOutlier.loess){
  loess.span = 2
  min.se = 0.008
  featureNm.y = "AF.alt"
  findOutlier.loess <- function(locus, featureNm.y = "AF.alt", loess.span=2, debug=F){
    x = x.list[[locus]][, c("DP", "AF.alt", "AD.alt")]
    if(is.null(x) ) return(NULL);
    if(nrow(x)==0) return(NULL);
    x.tr = x[sampleNm.tr, ]
    x.ts = x[sampleNm.ts, ]
    xl.tr = x.tr[,"DP"]
    yl.tr = x.tr[, featureNm.y]
    names(xl.tr)=names(yl.tr)=sampleNm.tr
    xl.ts = x.ts[,"DP"]
    yl.ts = x.ts[, featureNm.y]
    names(xl.ts)=names(yl.ts)=sampleNm.ts
    selId = x.tr[,"AF.alt"]<= AF.alt.tr.max & (x.tr[,"DP"]>= DP.tr.min) & (!( is.na(xl.tr)|is.na(yl.tr) )) #
    xl.tr = xl.tr[selId]
    yl.tr = yl.tr[selId]
    if(length(xl.tr)<=1 | length(yl.tr)<=1) return(NULL);
    sortId = order(xl.tr)
    xl.tr = xl.tr[sortId]
    yl.tr = yl.tr[sortId]
    regMethod = "loess" # default
    if ( class(try( suppressWarnings( loess(yl.tr~xl.tr)) ))=="try-error" ){
      regMethod <- "rlm"
    } else {
      suppressWarnings( tmp.lo.fit <- loess(yl.tr~xl.tr, span=loess.span, degree=2))
      if ( all( is.na( tmp.lo.fit$residuals )) ) {
        regMethod <- "rlm"
      } else {
        suppressWarnings( tmp.pred.lo <-predict(tmp.lo.fit, se=T) )
        if ( all( is.na( tmp.pred.lo$se)) | any( is.infinite(tmp.pred.lo$se)) ) {
          regMethod <- "rlm"
        }
      }
    }
    if (regMethod=="rlm"){
      lm.fit = rlm( yl.tr~xl.tr )
      se <- abs(lm.fit$residuals)
      myfit <- lm.fit
    }else if (regMethod=="loess") {
      pred.lo <-predict(loess(yl.tr~xl.tr, span=loess.span, degree=2), se=T)
      se <- pred.lo$se.fit
      myfit<-pred.lo
    }
    yl.tr.mad = mad( yl.tr[xl.tr>300], na.rm=T )
    se.med = median(se, na.rm=T)
    se.med0 = se.med
    if(se.med < min.se){
      se.med <- min.se
    }
    err.tr = rep(se.med, length(xl.tr))
    err.ts = rep(se.med, length(xl.ts))
    xOutId = which( xl.ts>max(xl.tr) | xl.ts<min(xl.tr))
    err.ts[xOutId] <- se.med
    extroQuant = 0.05
    tmp <- myfit$fit; tmp.left = quantile(tmp, na.rm=T, probs=1-extroQuant); tmp.right = quantile(tmp,
na.rm=T, probs=extroQuant)
    fit.itpl = approx(xl.tr, myfit$fit, xout = xl.ts, yleft=tmp.left, yright=tmp.right)
    ci.upper.ts = fit.itpl$y + loess.z.thld * err.ts
    ci.lower.ts = fit.itpl$y - loess.z.thld * err.ts
```

```
    z.ts = (yl.ts - fit.itpl$y) / err.ts # z score for each test point
    outId = which( z.ts > loess.z.thld)
    rst = list(xl.tr=xl.tr, yl.tr=yl.tr, myfit=myfit, yl.tr.mad=yl.tr.mad,
          fit.itpl=fit.itpl, err.ts=err.ts,
          z.ts=z.ts, outId=outId)
    return(rst)
  }
  detRst.loess = mclapply(loci, mc.cores=mc_cores, FUN=function(locus){
    detRst = findOutlier.loess(locus, featureNm.y, debug=F)
    return(detRst)
  })
}
save(detRst.loess, detRst.mahal, file=outRFile)
```

Figure 9:
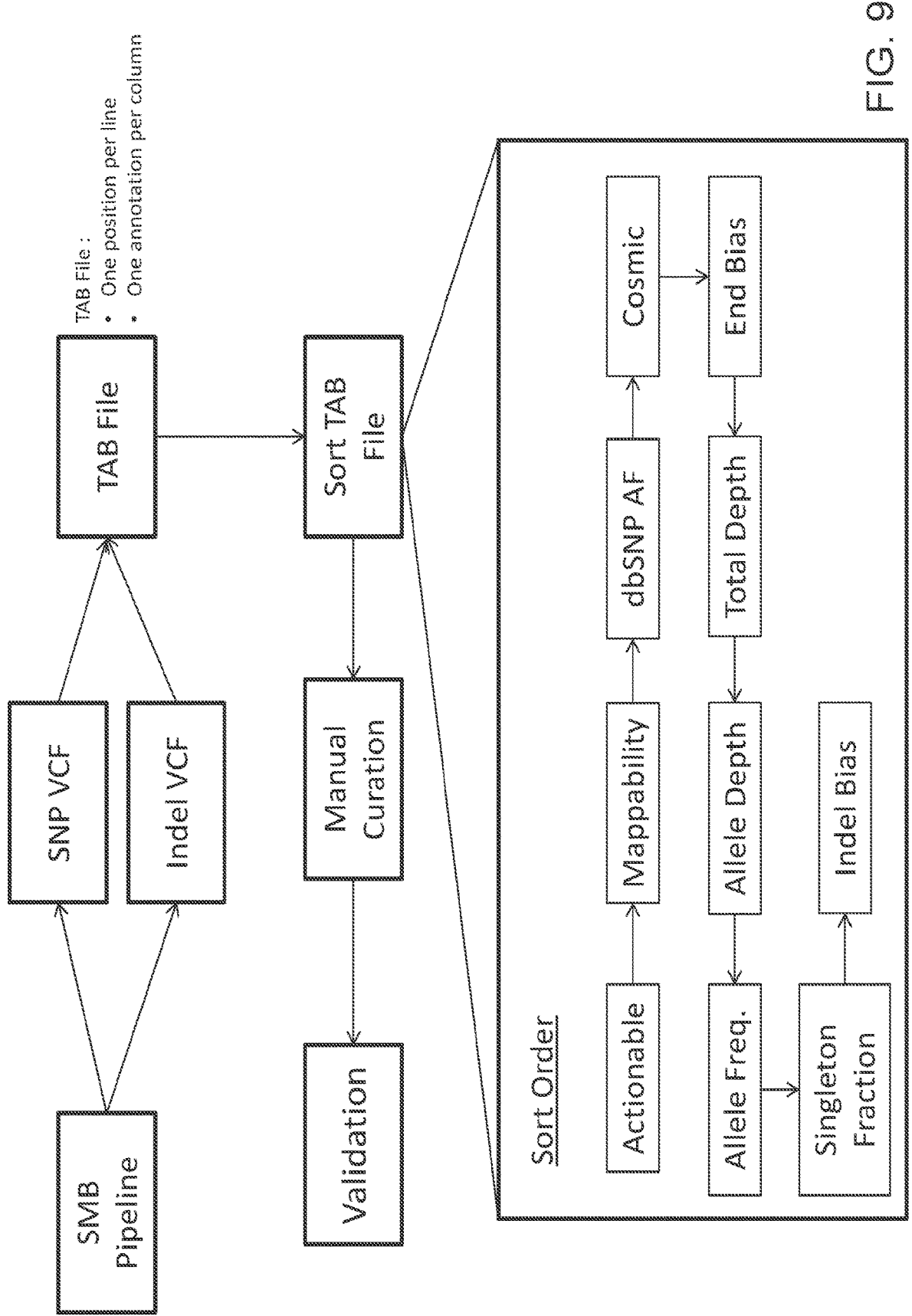
FIG. 9 shows an illustrative embodiment of a process described herein.

Certain metrics were annotated as illustrated in the flowchart presented in FIG. 9 and described below.

Mappability

Provided below is a summary of how mappability scores were calculated for individual positions in the assay panel described above. Mappability is a metric that can indicate how reliable mapping is when a sequence is mapped to a particular region of the genome. Mappability can be negatively impacted by elements such as repeat regions that make a unique alignment to the genome difficult.

Mappability scores were calculated using the following method:

1) Simulate 100 bp reads by extracting 100 bp sections of the genome.
   a. These simulated reads span the entire panel
   b. These simulated reads are staggered in 1 base increments
2) Mutate the simulated reads at every position in the following way:
   a. 1 base mismatch (all mismatch bases)
   b. 2 base mismatch (all mismatch base combinations)
   c. 1 base insertion (all possible bases)
   d. 2 base insertion (all possible base combinations)
   e. 5 base insertion (all possible base combinations)
   f. 10 base insertion (all possible base combinations)
   g. 1 base deletion
   h. 2 base deletion
   i. 5 base deletion
   j. 10 base deletion
3) Align original and mutated reads back to the genome using bwa mem, default parameters
4) Calculate the number of times the read aligned back to the original position (mapback)
5) Calculate the number of positions each read aligned to in the genome (althit)
6) Calculate mappability as mapback/althit
   a. If all mutated reads mapped back to the original position uniquely,
   mappability is calculated as N/N or "1".

Weighted Homopolyer Rate

Provided below is a summary of how weighted homopolymer rates (WHR) were calculated for individual positions in the assay panel described above. A homopolymer is a sequence of identical bases, like AAAA or TTTTTTTT, for example. The weighted homopolymer rate (WHR) of a sequence is a measure of the frequency of homopolymers in the sequence.

According to the Broad Institute definition:

$$WHR = \frac{\sum_{i=1}^{N} n_i^2}{N}$$

where N is the number of homopolymers in the sequence, and the $n_i$'s are the homopolymers' lengths, so that the summation goes from 1 to N (N is not the total length of the sequence).

For example:

TGATTCAAGCATTCGATC: This homopolymer-poor sequence has a WHR of (1+1+1+4+1+4+1+11++4+11+1+1+11)/15=1.6.

GGGTGCCCCCAAAATATT: This homopolymer-rich sequence has a WHR of (9+1+1+25+16+1+1+4)/8=7.25.

The lowest possible WHR of a sequence is 1; the highest possible is the square of the sequence length (if N=1). A randomly-generated sequence has an expected WHR of 20/9≈2.222. Most genomes have WHRs higher than the random value, due to imbalances in GC-content and the presence of junk DNA.

Indel Bias, End Bias and Strand Bias

Provided below is a summary of how indel bias, end bias and strand bias scores were calculated for the various alleles and positions.

The method below refers to overlapping mate consensus, which is a consensus base that comes from a section of the molecule where mate 1 and mate 2 strands overlap. For example, if the physical molecule is 150 bases long, and the reads are 150 bases, all of the bases should have overlapping mates. If the physical molecule is 100 bases long, and the reads are 150 bases long, only the middle 100 bases have overlapping mates. The 50 bases on either end come from a mate aligned to either the "+" or "−" strand of the genome.

Strand bias, indel bias, and end bias were calculated using the following method:

1) Strand Bias
   a. For each allele X where X is A, C, G or T:
      i. Track the number of times the consensus is formed from overlapping mates.
         1. Xboth
      ii. Track the number of times the consensus is formed from non-overlapping mates aligned to the "+" strand
         1. Xplus
      iii. Track the number of times the consensus is formed from non-overlapping mates aligned to the "−" strand
         1. Xminus b. For each allele X:
  i. Calculate a p-value indicating whether or not the relative counts of Xboth. Xplus and Xminus are different than for the other three alleles. This is performed using the fisher.test function in the R programming language.
    1. XstrandStat
2) Indel Bias
  a. For each allele X:
    i. Track the number of times the consensus base is found near an indel (within 3 bases). The tally is done in consensus space, but the proximity to indels is defined by the CIGAR strings from non-consensus aligned reads
      1. Xindel
    ii. Track the number of times the consensus base is not near an indel
      1. XnoIndel
  b. For each allele X:
    i. Calculate the fraction of consensus counts that are near an indel
      1. XindelStat
3) End Bias
  a. For each allele X:
    i. Track the number of times the consensus base is near the end of the molecule (within 5 bases). This refers to the physical molecule, which is bounded on either end by the two mates
      1. XnearEnd
    ii. Track the number of times the consensus base is not near the end of the molecule
      1. XnearMiddle
  b. For each allele X:
    i. Calculate the fraction of consensus counts that are near an end
      1. XendStat Position Specific Error Model In certain instances, a position specific variant calling algorithm is applied to position specific data generated as described above. Generally, the input to the algorithm is a list of loci (or filtered list of loci) along with historical data pertaining to the loci. Typically, the algorithm can be run after vcf generation, GATK germline filtering and/or other basic filtering. Model based position specific noise removal and signal detection is described below. Specifically, a position specific classification model which can distinguish signal from background noise by utilizing information residing in a cohort of samples is described.

Fixed thresholds often are used for variant filtering and detection. For example, one conservative criterion may include requesting all reported variants have at least 5 alternative allele depth and more than 1% allele fraction. However, each locus in the genome may have different characteristics in terms of sequence context, mappability, background noise level, etc. A position-specific threshold or position-specific model may distinguish signal or true variant from background noise. Filtering variants for each sample based on fixed thresholds also does not utilize information residing in a cohort of samples. Some true variants may fail a fixed threshold, resulting in reduced sensitivity; and false variants may pass the threshold, resulting in reduced specificity. By compiling information (e.g., allele depth, allele fraction, and the like) across multiple samples for a particular position, a position-specific background distribution is generated. For consideration of a variant, its statistics (e.g., allele depth, allele fraction) can be compared to the background to verify whether the variant is a true signal or not.

The first step is data preprocessing to parse and compile relevant information (such as AF (alternative allele fraction at a given position) and DP (consensus depth at a given position)) from input VCF files. The output is an R list variable and each sub-list contains detailed information of one locus across different samples as specified in the sample sheet.

Two algorithms were developed to calculate the variant significance for each sample based on a position-specific model developed using training data. The training data was generated using normal buff coat samples and normal plasma samples. Including buffy coat samples into the training dataset not only increased the training data size but also effectively extended the range of data observations (in terms of depth and allele frequency distribution).

The first algorithm is regression based. It was developed based on the observation that the AF distribution can be dependent on DP and the trend may vary for different positions. Therefore, for each given position (positions are processed in parallel), the algorithm tries to fit a loess model (curve) for the predictor DP and response variable AF using training data pertinent to the locus. The degree of loess smoothing level and number of model polynomials are both set to two based on empirical results. If loess fitting fails (typically due to insufficient training data for certain positions), the algorithm then switches to a robust linear fit to simplify the regression problem. Next, for each variant (one sample data point in the DP and AF classification plane of the position), its z-score is calculated as: $z=(AF-\mu)/e$, where AF is the alternative allele fraction for that sample, $\mu$ is the predicted response based on the predictor DP (depth of the sample), and e is the median standard error of the loess regression model (or median residual error of the linear regression model). A higher z-score suggests that the variant stands out from the background DP and AF distribution and is more likely to be a true mutation. In certain instances, samples may show high z-scores in a noisy position (e.g., a known dbSNP position or a position in a region that has low mappability). In such instances, visual inspection may be used to further rule out false positives with high z-scores.

The second algorithm is a 2-dimensional classification approach, which utilizes the multivariate distribution of AF and DP. The values of AF and DP are first transformed logarithmically to obtain the desired "log normal" property. Then, for each given position the algorithm calculates the distribution center and covariance of AF and DP using training data pertinent to the position. Next, for each variant (one sample data point in the DP and AF classification plane specific to the position), its mahalanobis distance from the distribution center is computed. The p value for the mahalanobis distance is then calculated as the tail probability of a chi square distribution with degree of freedom equal to 2. A smaller p value suggests that the variant stands out from the background DP and AF distribution and is more likely to be a true mutation. In certain instances, samples may show low p values in a noisy position. In such instances, visual inspection may be used to further rule out false positives with low p values. This approach can be extended to a higher dimension, incorporating more pertinent features such as end bias, indel bias and singleton fraction, which may provide different aspects for distinguishing true mutations from false positives.

Filtering

A filtering step was included in the methods discussed herein in Example 4. Described below are methods and steps for 1) annotating variants (SNV and INDEL) produced by methods described above in VCF format; 2) calling germline variants in buff coat samples in a cohort; and 3) flagging and filtering false somatic variants identified by the methods described above in plasma cfDNA. Methods described below are in the context of a study cohort which included a set of plasma cfDNA samples and their matched buffy coat.

Certain terms used in the methods below include: CNV (copy number variant); GVCF (genomic variant call format); INDEL (short insertion and deletion, e.g. <100 bp): SNV (single nucleotide variant): VCF (variant call format); and variant classification (function annotations specified by HGVS (Human Genome Variation Society) implemented in snpEff (genetic variant annotation and effect prediction toolbox). For variant annotation, open source snpEff/snpSift suite was used. For germline variant calling, GATK (genomic analysis toolkit, Broad Institute software) was used. Flagging and filtering variants was achieved using unix shell and R scripts.

Variant Annotation

For SNV annotation, a pre-computed SNV annotation file containing each position on the panel was created and used to annotate variants during the VCF making step. The pre-computed annotation file was generated using snpEff/SnpSift suite. For INDELs, annotation was done after VCF was generated by the methods above using snpEff/snpSift suite. Annotation databases (VCF format) were downloaded from public sites, sorted and indexed. These included: dbSNP, COSMIC coding mutation V68, ESP6500, UK10K, ClinVar.

Germline Variant Calling

GATK variant calling was developed. Sequential steps for variant calling include: mark duplicates, re-alignment around know INDELs, recalibrate base call, variant call by HaploTypeCaller (EMIT_ALL_SITES option). A GVCF file was generated for each sample. All samples in the cohort were jointly called using GATK "GenotypeGVCFs" to create a VCF file, and annotation was done using snpEff/snpSift suite. Variants that have DP (consensus depth at a given position) >=30, GQ (genotype quality) >=99, AD (allelic depth) >1, and AF (alternative allele fraction at a given position) >=5% were designated as germline mutations. Total coverage for each callable site was kept for somatic mutation filtering in next step.

Flag and Filter to Identify Somatic Mutation in cfDNA

Four categories of metrics were used to flag and filter variants. The first category is variant quality including total depth, allele depth, exceed sample-specific error rate, buffy coat coverage for the variant site, and site-specific noise level. The second category is variant context characteristics, which include end bias, indel bias, homopolymer rate, cluster of SNPs, reads start/stop diversity, genomic difficult regions. The third category is healthy population status; variants with >0.1% in any of the normal databases (dbSNP/1000 Genome, UK10K, ESP6500) were considered germline mutations. The fourth category of flags is classification and function annotation of the variant by snpEff/snpSift suite.

Most metrics were generated using scripts described above, and packaged into "INFO" field in VCF file output. Exceptions include site-specific noise level, buffy coat coverage, reads start/stop diversity (a customized Perl script was created to tally start/stop genomic location of a read that harbors the variant).

Cutoffs and steps are listed below:
1. Remove private germline variants that are identified in buffy coat; major alternative allele is considered.
2. Remove variant with AD<2, end bias=1, indel bias=1, homopolymer score >=20, matched buffy coat coverage <30.
3. Flag variants >0.1% in at least three normal population databases, and variants that are dbSNP-only without COSMIC records.
4. Flag variants with following fields:
    a. AF exceeds sample-specific error rate
    b. Site-specific variant call significance: p<0.05 and/or z>=3
    c. Variant classification and impact annotations by snpEff
    d. Genomic difficult regions: low complexity region, genome super duplicated region, SQNM.black list
    e. Start/stop diversity of mutation harboring reads>1

All metrics were collected into VCF and MAF file, flagging and filtering were done using R script.

Example 4: Sample Report

In this Example, certain methods described in the above Examples were used to identify single nucleotide somatic alterations in a subject.

A test designed to detect specific DNA alterations comprising single nucleotide variants, insertions and deletions, copy number variations, and fusions in 134 cancer-related genes was performed on a plasma sample from a 95 year-old subject having a diagnosis of non-small cell lung cancer. The collection of genes assayed by the test is shown in Table 2 below. Circulating cell-free DNA was isolated and purified from the plasma component of anticoagulated whole blood for detection of somatic DNA alternations. Additionally, genomic DNA was isolated and purified from the buffy coat for detection of germline DNA alterations. Genomic DNA libraries were prepared and used to determine DNA alterations by next generation sequencing (NGS). Bioinformatic methods were subsequently used to subtract the germline alterations from the somatic alterations. The assay was analytically validated in a research setting across six variant frequencies. The demonstrated sensitivity was >78% for variant allele frequencies >0.5%. Specificity was >99% for all variant levels at clinically actionable genomic loci.

TABLE 2

| Genes represented in probe panel | | | | |
|---|---|---|---|---|
| ABL2 | CDKN2A | FGFR3 | MLH3 | PIK3CG |
| AKT1 | CDKN2B | FGFR4 | MPL | PIK3R1 |
| AKT2 | CSF1R | FLT1 | MSH2 | POLE |
| AKT3 | CSF3R | FLT3 | MSH3 | PTCH1 |
| ALK | CTNNB1 | GATA3 | MSH6 | PTEN |
| APC | DDR2 | GNA11 | MTOR | RAC1 |
| AR | DNMT3A | GNAQ | MYC | RAF1 |
| ARAF | EGFR | GNAS | MYCL1 | RB1 |
| ARID1A | EML4 | HIF1A | MYCN | RET |
| ATM | EPHA2 | HNF1A | MYD88 | RHEB |
| AURKA | APHA3 | HRAS | NCOA4 | RHOA |
| AURKC | ERBB2 | IDH1 | NF1 | RIT1 |
| AXL | ERBB3 | IDH2 | NF2 | ROS1 |
| BAP1 | ERBB4 | IGF1R | NFE2L2 | SMO |
| BRAF | ESR1 | JAK3 | NKX2-1 | SETD2 |
| BRCA1 | EWSR1 | KDR | NOTCH1 | SMAD4 |
| BRCA2 | EZH2 | KEAP1 | NOTCH1 | SMARCB1 |
| BTK | FANCA | KIT | NPM1 | SRC |
| CBL | FANCD2 | KRAS | NRAS | STK11 |
| CCND1 | FBXW7 | MAP2K1 | NTRK1 | TERT |
| CCND2 | FGF3 | MAP2K2 | NTRK2 | TET2 |
| CCNE2 | FGF10 | MAP2K3 | NTRK3 | TP53 |

TABLE 2-continued

| Genes represented in probe panel | | | | |
|---|---|---|---|---|
| CD274 | FGF5 | MAPK1 | PDGFRA | TRIM33 |
| CD74 | FGF6 | MCL1 | PDGFRB | TSC1 |
| CDH1 | FGF8 | MDM2 | PIK3CA | TSCD |
| CDK4 | FGFR1 | MET | PIK3CB | VHL |
| CDK6 | FGFR2 | MLH1 | PIK3CD | |

Figure 10:
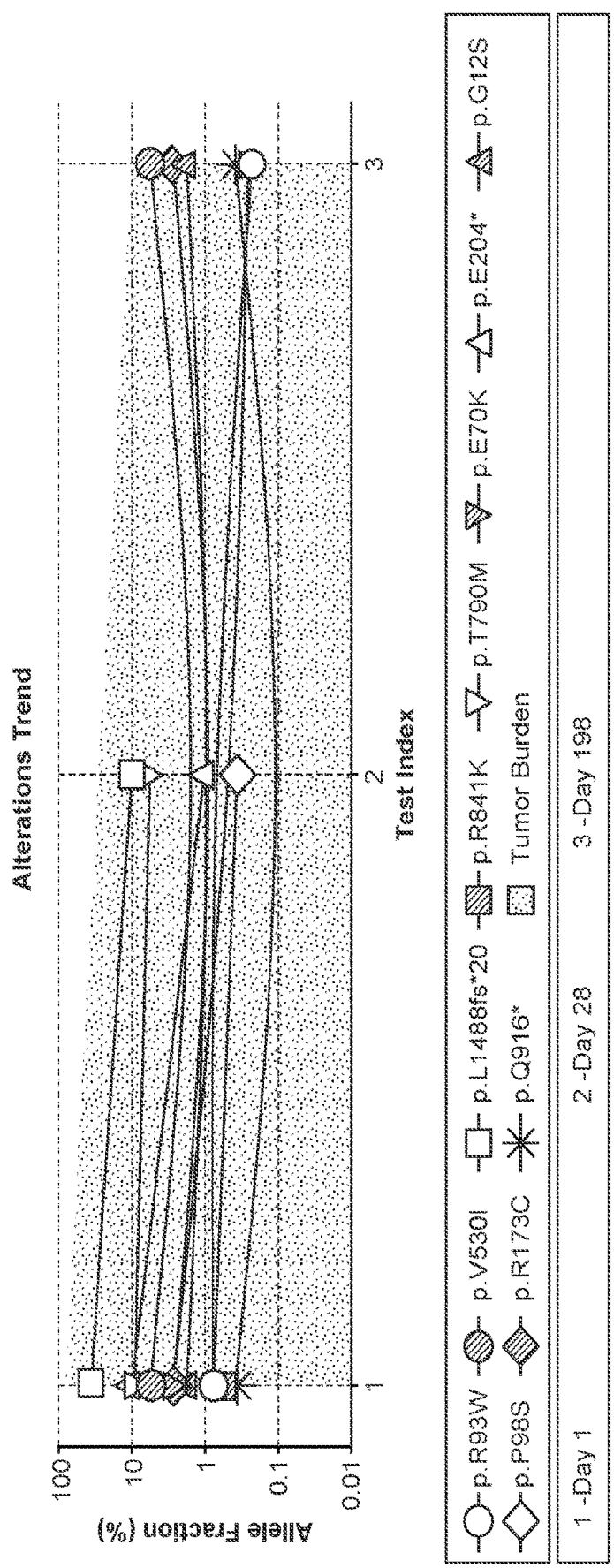
FIG. 10 shows an alterations trend over three sample collection time points for a subject.

An initial plasma sample was collected from the subject (day 1; test index 1) and subsequent collections were performed after about 1 month (day 28; test index 2) and again after about 6 months (day 198; test index 3). Alterations detected in the samples are presented in Table 3 below and an alterations trend for the different sample collections is shown in FIG. 10.

TABLE 3

| Gene | Type | Mutation | Allele fraction (%) | Functional impact |
|---|---|---|---|---|
| KIT | SNV | V530I | 5.61 | gain |
| PIK3CA | SNV | R93W | 0.23 | gain |
| HRAS | SNV | G12S | 1.78 | gain |
| PTEN | SNV | R173C | 2.69 | loss |
| TET2 | SNV | Q916* | 0.38 | loss |
| VHL | SNV | E70K | 0.26 | normal |

Descriptions of the genes provided in Table 3 are presented below.

KIT encodes a receptor tyrosine kinase that is expressed on a wide variety of cell types. The ligand for KIT is stem cell factor which activates downstream signaling pathways, including the PI3K-AKT-mTOR, RAS-RAF-MEK-ERK, and STAT3 pathways, all of which have a role in cell growth and survival. KIT mutations are found in more than 80% of gastrointestinal stromal tumors (GIST). KIT mutations also occur in approximately 20% of acute leukemias and 20% of genital tract cancers (COSMIC).

PIK3CA encodes the catalytic subunit of phosphatidylinositol 3-kinase that belongs to a family of lipid kinases. These kinases regulate a diverse range of cellular processes including cell proliferation, adhesion, survival, and migration. Mutations in PIK3CA stimulate downstream AKT-mTOR signaling pathways, thereby promoting growth-factor independent growth, cell invasion and metastasis. PIK3CA mutations may occur in multiple malignancies, including approximately 25% of gastric, 4% of lung, 25% of breast, and 20% of colorectal cancers. Germline PIK3CA mutations may occur in Cowden syndrome.

HRAS belongs to the RAS oncogene family and encodes a GTP and GDP binding protein with intrinsic GTPase activity. The protein cycles between an inactive GDP-bound and active GTP-bound form, and is involved in downstream receptor signaling critical for cell proliferation, survival and differentiation. HRAS mutations are found in multiple malignancies including approximately 12% of skin cancers, 9% of salivary gland carcinomas, 8% of cervical carcinomas, and 3% of prostate carcinomas (COSMIC). HRAS mutations are also frequent in cutaneous squamous cell carcinomas and keratoacanthomas that develop in patients treated with BRAF inhibitors. HRAS somatic mutations may occur in certain cases of acute myelogenous leukemia. Germline HRAS mutations cause Costello syndrome.

Somatic PTEN mutations may occur in a broad range of cancers, including approximately 40% of endometrial cancers, 11% of colorectal cancers, 10% of melanomas, 4% of ovarian cancer, and 3% of breast cancer (COSMIC). PTEN mutations have been found in approximately 11% of pediatric T-cell acute lymphoblastic leukemia (T-ALL) patients, and mutations are associated with a negative prognosis. Germline PTEN mutations cause PTEN hamartoma tumor syndrome and Cowden syndrome 1. PTEN encodes a phosphatidylinositol-3,4,5-triphosphate 3-phosphatase. This protein preferentially dephosphorylates phosphoinositide substrates and negatively regulates intracellular levels of phosphatidylinositol-3,4,5-triphosphate in cells. It acts as a tumor suppressor by negatively regulating the AKT-PKB signaling pathway by dephosphorylating phosphoinositides, thereby modulating cell cycle progression and survival.

Somatic TET2 gene mutations have been reported in a variety of cancers, including approximately 18% of polycythemia vera cases, 4% of endometrial carcinomas, 4% of colorectal carcinomas, and 2% of bladder carcinomas (COSMIC). TET2 mutations may occur in approximately 13% of primary acute myeloid leukemia (AML) patients, and may be associated with an unfavorable prognosis in AML patients with intermediate risk cytogenetics. In certain instances, TET2 mutations may occur in about 7% of younger AML patients, with no impact of TET2 mutations on response to therapy and survival. TET2 mutations may occur in approximately 27% of myelodysplastic syndrome patients, and may predict response to hypomethylating agents. The TET2 gene encodes the enzyme methylcytosine dioxygenase that catalyzes the conversion of the modified genomic DNA base methylcytosine to 5-hydroxymethylcytosine. Methylation of cytosine bases is an epigenetic modification that plays an important role in transcriptional regulation. The enzyme is involved in active DNA demethylation, and also in myelopoiesis.

VHL encodes a protein that is part of a complex including elongin B, elongin C, and cullin-2, and possesses ubiquitin ligase E3 activity. The protein is involved in ubiquitination and degradation of hypoxia-inducible-factor, a transcription factor involved in the regulation of gene expression by oxygen. The protein can target RNA polymerase II subunit POLR2G/RPB7. Somatic VHL mutations occur in about half of patients with hemangioblastomas, and about half of clear cell renal cell carcinomas. Germline VHL mutations cause von Hippel-Lindau syndrome, a dominantly inherited familial cancer syndrome that predisposes to a variety of tumors, including hemangioblastoma.

Example 5: Duplex Sequencing Evaluation

Figure 7:
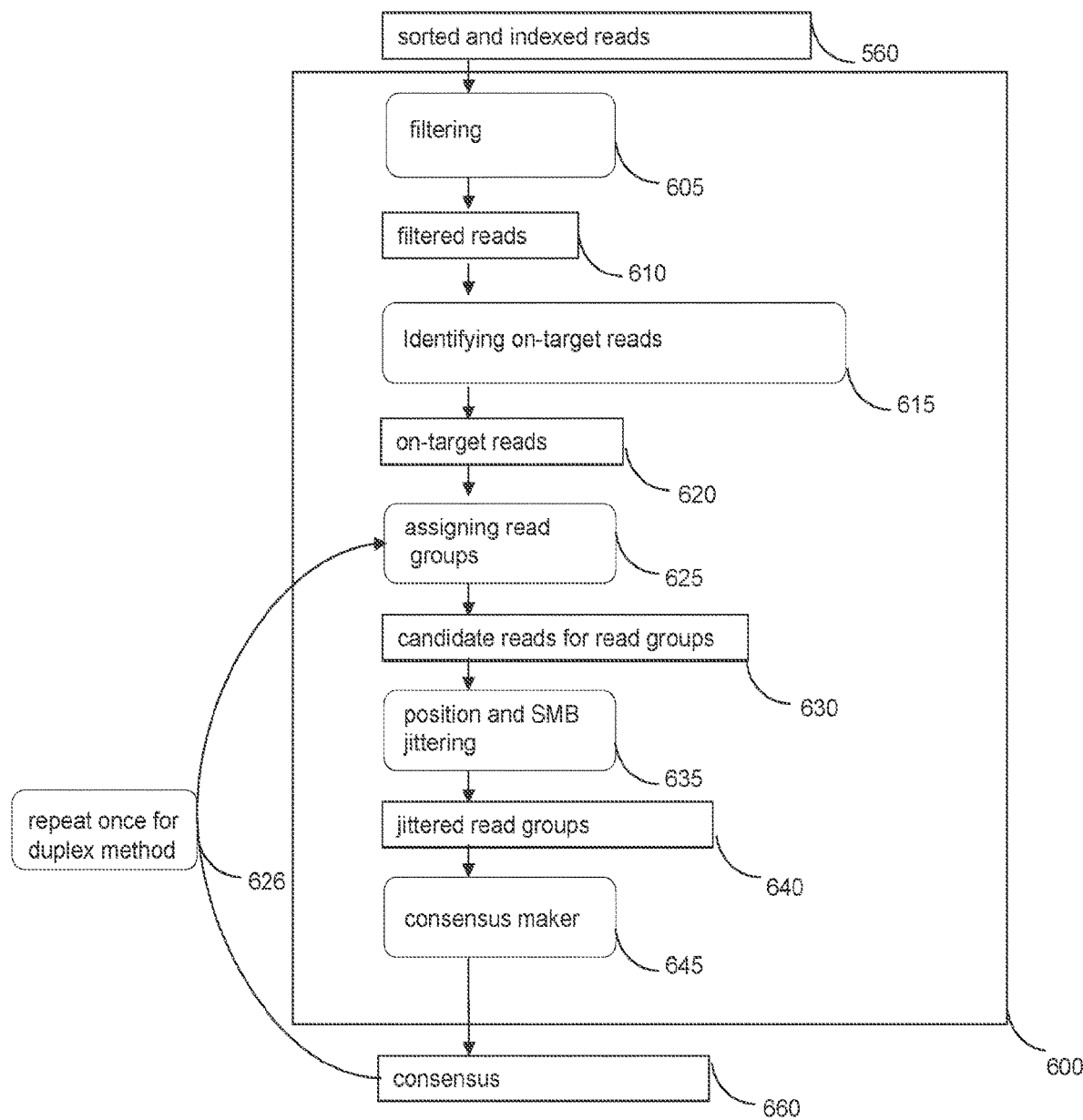
FIG. 7 shows an illustrative embodiment of a process described herein.
Figure 8:
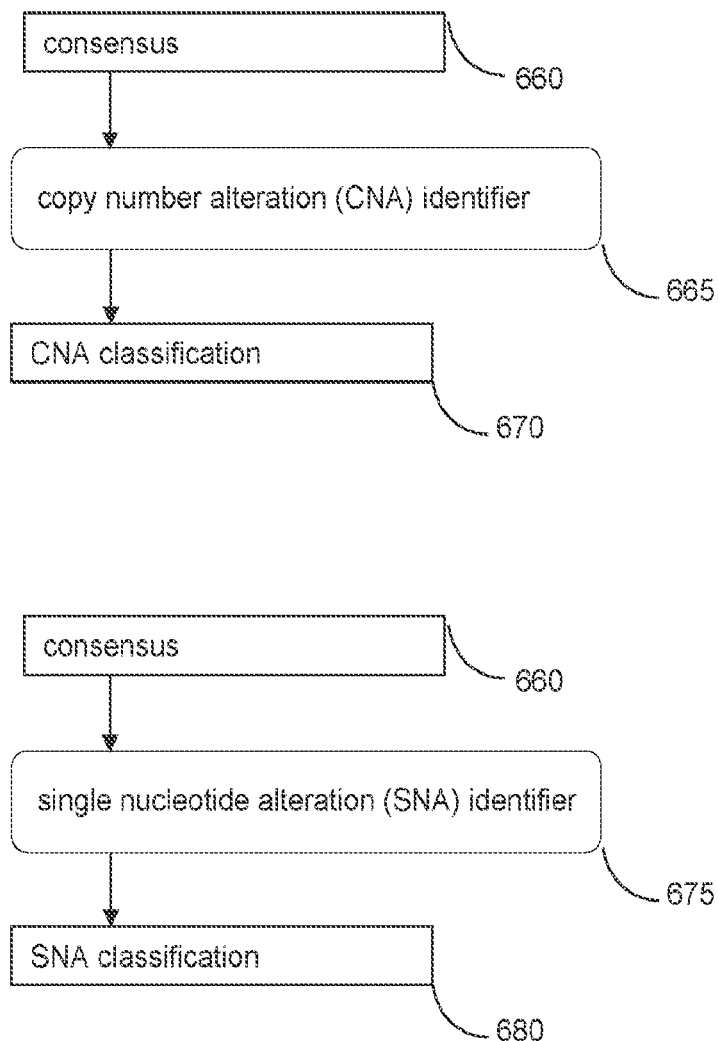
FIG. 8 shows an illustrative embodiment of a process described herein.

In this Example, certain methods described in the above Examples were applied to duplex sequencing data, and the error rates were compared to the error rates for data generated using an existing method. Duplex sequencing data was generated as described above, with the exception that adapters designed for duplex sequencing were used. The sequencing data was processed as described above, with the exception that the steps from read group to consensus were repeated, as illustrated in FIG. 7.

Error rates for single strand consensus sequence (SSCS) and duplex consensus sequence (DCS) data processed using an existing method are presented in Table 4. "Index duplex" adapter molecules refer to nonrandom oligonucleotide adapters. "Random duplex" adapter molecules refer to oligonucleotide adapter molecules comprising random base compositions. The ratios of the number of adapter molecules provided in the ligation reaction to nucleic acid templates is the same for both the index duplex and random duplex reactions. The random duplex adapters are expected to comprise approximately 1.7×10⁷ oligonucleotide species and the index duplex adapters are expected to comprise approximately 2.9×10² oligonucleotide species.

TABLE 4

| Sample | Adapter | Raw error rate | SSCS error rate | DCS error rate |
|---|---|---|---|---|
| 1 | index duplex | 8.82E−04 | 9.09E−04 | 5.27E−05 |
| 2 | index duplex | 8.63E−04 | 8.78E−04 | 5.42E−05 |
| 3 | index duplex | 8.59E−04 | 8.37E−04 | 5.34E−05 |
| 4 | random duplex | 2.20E−03 | 2.31E−03 | 2.21E−05 |
| 5 | random duplex | 2.15E−03 | 2.13E−03 | 2.21E−05 |
| 6 | random duplex | 1.83E−03 | 1.53E−03 | 2.49E−05 |

Single strand error rates were about 1.1 fold reduced relative to raw data. Indexed duplex error rates were about 15 fold reduced relative to raw data. Random duplex raw error rates were about 100 fold reduced relative to raw data (but raw error rates were much higher).

Error rates for data processed using the methods discussed herein are presented in Table 5.

TABLE 5

| Sample | Adapter | Raw error rate | SSCS error rate | DCS error rate |
|---|---|---|---|---|
| 1 | index duplex | 8.82E−04 | 4.23E−04 | 6.97E−06 |
| 2 | index duplex | 8.63E−04 | 4.18E−04 | 7.13E−06 |
| 3 | index duplex | 8.59E−04 | 3.93E−04 | 6.72E−06 |
| 4 | random duplex | 2.20E−03 | 1.11E−03 | 6.60E−06 |
| 5 | random duplex | 2.15E−03 | 1.02E−03 | 7.08E−06 |
| 6 | random duplex | 1.83E−03 | 5.81E−04 | 5.95E−06 |

SSCS error rate included only those "orphaned" SSCS data that were not included in duplexes. Thus, paired duplex reads were not used in the calculation of SSCS error rate. (Some SSCS reads were not assigned to a duplex; these unassigned SSCS reads were used for this calculation.)

Single strand error rates were about 2.5 fold reduced relative to raw data. Indexed duplex error rates were about 125 fold reduced relative to raw data. Random duplex raw error rates were about 300 fold reduced relative to raw data (but raw error rates were much higher). Accordingly, the methods described herein generated data with about 3.5× to about 7.5× lower error rates than the error rates observed for data generated using an existing method.

Figure 11:
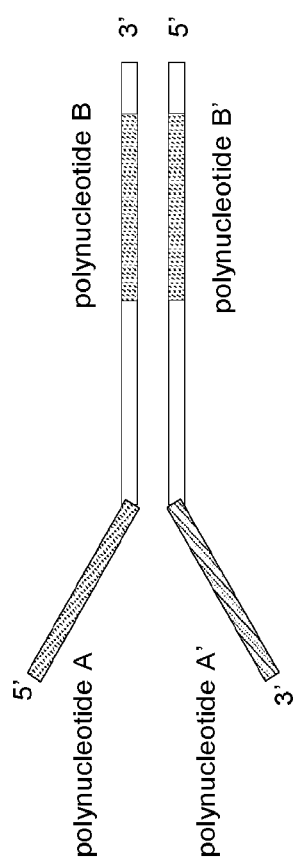
FIG. 11 provides a schematic of an example of a nonrandom oligonucleotide adapter.

Example 6: Manufacture of Sequencing Adapters Containing Predetermined Non-Randomly Generated Bar Codes Partially double-stranded Y-shaped nonrandom oligonucleotide adapters are prepared prior to ligation of the nonrandom oligonucleotide adapters to nucleic acid templates. (FIG. 11) Each strand of each nonrandom oligonucleotide adapter species may be synthesized and comprises a polynucleotide that is not complementary to the other strand, and comprises an amplification primer binding sequence; for example, one strand comprises a P5 sequence and the other strand comprises a P7 sequence. These non-complementary regions may optionally comprise an index sequence. Each strand of each nonrandom oligonucleotide adapter species also comprises a polynucleotide that has a nonrandom nucleotide sequence that is the reverse complement to the corresponding polynucleotide on the other strand. The nonrandom nucleotide sequence of the present example is 8 nucleotides long, but may be of any appropriate length, including, for example, 6, 7, 8, 9, 10, 1, 12, 13, 14, 15, 16, 17, 18, 19, or 20 nucleotides. These nonrandom nucleotide sequences may be predetermined, for example, by selection using a computer, or may be obtained by fragmentation of natural DNA. By nonrandom is meant that the nucleotide sequence is predetermined before attachment of the adapter to the nucleic acid template. The nonrandom nucleotide sequence may, however, be determined in advance using a computer program that randomly designs the sequence. The nonrandom oligonucleotide adapter sequences also have a single thymine overhang. Synthesized oligonucleotide species may be pooled based on the non-complementary polynucleotide, for example, one P5 and one P7 pool, then adapters may be prepared using, for example, the methods of Example 1.

In other examples, the nonrandom oligonucleotide adapters may be prepared by first synthesizing or obtaining a polynucleotide comprising a nonrandom nucleotide sequence, copying the nonrandom nucleotide sequence using DNA polymerase, then ligating the resulting double stranded oligonucleotide to a Y shaped tail, synthesized to comprise the non-complementary polynucleotides discussed above in this example. A single thymine overhang is also attached to the double stranded oligonucleotide opposite the Y-shaped polynucleotides.

Figure 12:
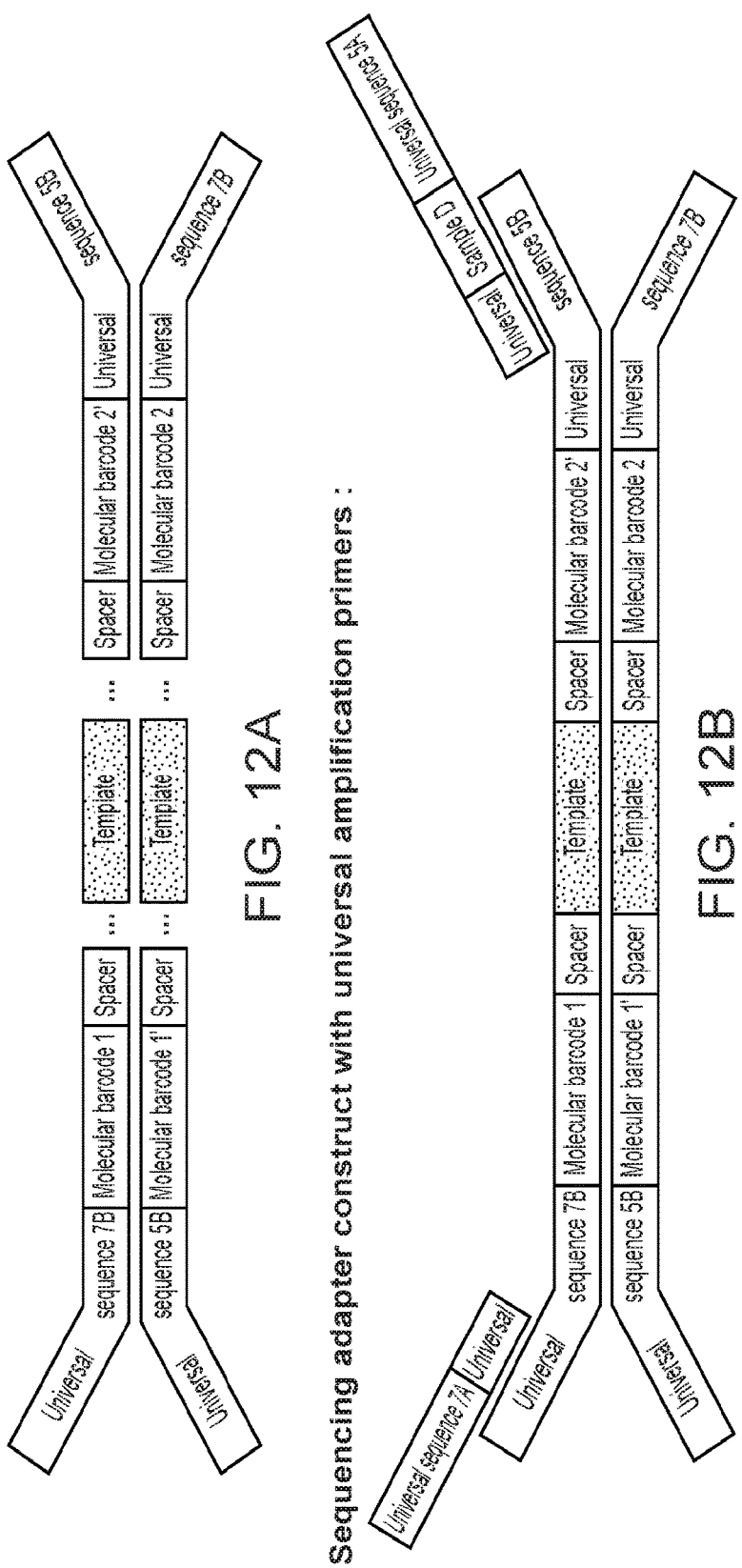
FIG. 12A provides a schematic of annealed nonrandom oligonucleotide adapters positioned adjacent to nucleic acid template DNA, where nonrandom oligonucleotide adapters are ligated to both ends of the nucleic acid template.
FIG. 12B is a schematic of the nonrandom oligonucleotide adapters of FIG. 12A, ligated to nucleic acid template DNA, and also depicts universal amplification primers annealed at each end of one of the strands of the construct.
FIG. 12C provides a schematic of the template strand 1 library construct, obtained using the nonrandom oligonucleotide adapters/nucleic acid template construct and primers of the bottom strand of FIG. 12B.
FIG. 12D provides a schematic of the template strand 2 library construct obtained using the nonrandom oligonucleotide adapters/nucleic acid template construct and primers of the top strand of FIG. 12B.

An example of a set of nonrandom oligonucleotide adapters is provided in Table 6 below. FIG. 12 provides an example of a schematic of the nonrandom oligonucleotide adapters ligated to the nucleic acid template. FIG. 12A provides a schematic of annealed nonrandom oligonucleotide adapters positioned adjacent to nucleic acid template DNA. FIG. 12B is a schematic of the nonrandom oligonucleotide adapters of FIG. 12A, ligated to nucleic acid template DNA, and also depicts universal amplification primers annealed at each end of one of the strands of the construct. FIG. 12C provides a schematic of the template strand 1 library construct, obtained using the nonrandom oligonucleotide adapters/nucleic acid template construct and primers of the bottom strand of FIG. 12B. FIG. 12D provides a schematic of the template strand 2 library construct obtained using the nonrandom oligonucleotide adapters/ nucleic acid template construct and primers of the top strand of FIG. 12B, FIG. 12B.

In some examples, the second nonrandom oligonucleotide adapter species comprises the same molecular barcode as the first nonrandom oligonucleotide adapter species. In some examples, the second nonrandom oligonucleotide adapter species comprises a different molecular barcode than the first nonrandom oligonucleotide adapter species.

In FIG. 12A and FIG. 12B, each strand of the oligonucleotides adapter includes a universal sequence at one end. For purposes of the schematic, the top strand represents a first oligonucleotide species and the bottom strand represents a second oligonucleotide species. The first oligonucleotide species comprises at one end, for example at the 5' end, a universal sequence. In the present example, the universal sequence is universal sequence 7B. The second oligonucleotide species comprises at one end, for example, the 3' end, universal sequence 5B. A portion of universal sequence 7B is not a reverse complement to a portion of universal sequence 5B, and the two portions are not annealed. In the schematic, the first oligonucleotide species comprises a first molecular barcode species (Molecular barcode 2), and the second oligonucleotide species comprises a molecular barcode species that is the reverse complement of the first molecular barcode species (Molecular barcode 2'). Each oligonucleotide species comprises a spacer region, the spacer region of the first oligonucleotide species is the reverse complement of the spacer region of the second oligonucleotide species, with the exception that one of the oligonucleotide species further comprises a ligation linker, for example, an A overhang (FIG. 12A).

FIG. 12B is a schematic of the nonrandom oligonucleotide adapters of FIG. 12A, ligated to template DNA and hybridized to universal amplification primers. The Universal sequence SA' primer also includes a sample identification barcode, shown as Sample ID'. Not shown in the drawing are the universal amplification primers that may be used in sequencing of the bottom strand, but are understood to be similar to the amplification primers shown in the top strand.

Example 7: Sequencing of Adapter-Ligated Nucleic Acid Templates

Nucleic acid templates are identified and grouped, where appropriate, by identifying identical adapter sequences at one end or both ends. Where two nucleic acid templates having different sizes or nucleotide sequences are ligated to identical adapter sequences, the nucleic acid templates are identified by mapping the position of the start and end of each template as discussed herein. Sequencing is performed essentially as discussed herein, with appropriate trimming of a number of cycles, "x cycles", as needed so that the nonrandom oligonucleotide sequence is copied with the insert (nucleic acid template sequence).

Example 8: Error Detection

Duplex sequencing using the nonrandom oligonucleotide adapters is performed essentially as discussed herein.

In some embodiments, each nucleic acid template is tagged with a nonrandom oligonucleotide adapter at one end and a standard sequencing adapter at one end. The nonrandom oligonucleotide adapter and the standard sequencing adapter may be ligated to the nucleic acid templates in the same ligation reaction, or in separate ligation reactions. Nucleic acid template sequences are grouped based on having matching nonrandom barcodes in the nonrandom oligonucleotide adapter, and, optionally on also having matching standard sequencing adapters. The sequences are aligned and compared. For each nucleic acid/nonrandom oligonucleotide adapter sequence group, there are two sets of amplified copies. One set (A) includes copies having adapters comprising a molecular barcode, B; the other set (B) includes copies having adapters comprising the complementary molecular barcode, B'. Sets (A) and (B) are paired.

In some embodiments, each nucleic acid template is tagged with a nonrandom oligonucleotide adapter at each end, adapter 1 and adapter 2. Nucleic acid template sequences are grouped based on having matching nonrandom barcodes in both adapter 1 and adapter 2. The sequences are aligned and compared. For each nucleic acid/nonrandom oligonucleotide adapter sequence group, there are two sets of amplified copies. One set (A), includes copies having the orientation adapter 1/adapter 2, and the other set (B) includes copies having the orientation adapter 2/adapter 1. For example, in set (A), adapter 1 may comprise the molecular barcode B1, and adapter 2 may comprise the molecular barcode B2', and in set B, adapter 1 may comprise the molecular barcode B1' and adapter 2 may comprise the molecular barcode B2, where B1 and B2 are B species, and B1' has the complementary nucleotide sequence to B1, and B2' has the complementary sequence to B2. Set (A) and set (B) are paired.

For embodiments that comprise two nonrandom oligonucleotide adapters, one at each end, and for embodiments that comprise one nonrandom oligonucleotide adapter and one standard sequencing adapter, sequencing calls are made by comparing the sequences within each set, and then by comparing sequences in one set to the sequences obtained in paired sets in each group. In one illustrative example, where a mutation appears in only one or a few members of one of the sets, it is likely to be a sequencing error. Where a mutation appears in most of the members of only one of the sets, for example, in set A only, but the mutation does not occur in the other set (B) of the same group, then the mutation is likely to be only an artifact of PCR amplification. Where the same mutation occurs in 90% or more of the sequences in each set of the same group, a call is made that the mutation is a true mutation. Other consensus determination methods may also be used to call the true mutation.

Example 9: Counting Adapter-Ligated Nucleic Acid Templates

In some embodiments, methods are provided of counting nucleic acid molecules, such as, nucleic acid templates. These counting methods may be used, for example, to detect a genetic disorder, where the genetic disorder is associated with a copy number alteration. Since each nucleic acid template with a nonrandom oligonucleotide adapter attached is amplified through the process of PCR as part of the library preparation process, duplicates of each template molecule are created. After sequencing and the nonrandom oligonucleotide adapter-ligated templates are mapped to a genome, templates mapped to a particular region are counted and the absolute or relative abundance of templates is used to detect copy number alterations. The nonrandom oligonucleotide adapters of the present application allow for each duplicate of a template molecule to be counted once. Without the nonrandom oligonucleotide adapters, duplicates of a template molecule might be counted multiple times, which increases the noise of the counting measurement. Duplex sequencing enables the accurate marking of original template molecules, thereby reducing the noise in counting methods by discriminating between true molecules and amplified molecules.

Provided in Table 6 below are examples of nonrandom oligonucleotide adapters described herein and their sequences.

TABLE 6

| Nonrandom oligonucleotide adapter | Oligonucleotide adapter Sequence | SEQ ID Nos. |
| --- | --- | --- |
| Duplex_p5_oligo1 | ACACTCTTTCCCTACACGACGCTCTTCCGATCTCCTTTGGCTGACT | 1 |
| Duplex_p7_oligo1 | GTCAGCCAAAGGAGATCGGAAGAGCACACGTCTGAACTCCAGTCACAC | 2 |

TABLE 6-continued

| Nonrandom oligonucleotide adapter | Oligonucleotide adapter Sequence | SEQ ID Nos. |
|---|---|---|
| Duplex_p5_oligo2 | ACACTCTTTCCCTACACGACGCTCTTCCGATCTTTGGGTACTGACT | 3 |
| Duplex_p7_oligo2 | GTCAGTACCCAAAGATCGGAAGAGCACACGTCTGAACTCCAGTCACAC | 4 |
| Duplex_p5_oligo3 | ACACTCTTTCCCTACACGACGCTCTTCCGATCTTTCAATAGTGACT | 5 |
| Duplex_p7_oligo3 | GTCACTATTGAAAGATCGGAAGAGCACACGTCTGAACTCCAGTCACAC | 6 |
| Duplex_p5_oligo4 | ACACTCTTTCCCTACACGACGCTCTTCCGATCTTCGCGCAATGACT | 7 |
| Duplex_p7_oligo4 | GTCATTGCGCGAAGATCGGAAGAGCACACGTCTGAACTCCAGTCACAC | 8 |
| Duplex_p5_oligo5 | ACACTCTTTCCCTACACGACGCTCTTCCGATCTAGGCTCCATGACT | 9 |
| Duplex_p7_oligo5 | GTCATGGAGCCTAGATCGGAAGAGCACACGTCTGAACTCCAGTCACAC | 10 |
| Duplex_p5_oligo6 | ACACTCTTTCCCTACACGACGCTCTTCCGATCTCGGTGGAATGACT | 11 |
| Duplex_p7_oligo6 | GTCATTCCACCGAGATCGGAAGAGCACACGTCTGAACTCCAGTCACAC | 12 |
| Duplex_p5_oligo7 | ACACTCTTTCCCTACACGACGCTCTTCCGATCTTCGCTACATGACT | 13 |
| Duplex_p7_oligo7 | GTCATGTAGCGAAGATCGGAAGAGCACACGTCTGAACTCCAGTCACAC | 14 |
| Duplex_p5_oligo8 | ACACTCTTTCCCTACACGACGCTCTTCCGATCTAAGATCGTTGACT | 15 |
| Duplex_p7_oligo8 | GTCAACGATCTTAGATCGGAAGAGCACACGTCTGAACTCCAGTCACAC | 16 |
| Duplex_p5_oligo9 | ACACTCTTTCCCTACACGACGCTCTTCCGATCTTCGTAAGCTGACT | 17 |
| Duplex_p7_oligo9 | GTCAGCTTACGAAGATCGGAAGAGCACACGTCTGAACTCCAGTCACAC | 18 |
| Duplex_p5_oligo10 | ACACTCTTTCCCTACACGACGCTCTTCCGATCTATTACCCATGACT | 19 |
| Duplex_p7_oligo10 | GTCATGGGTAATAGATCGGAAGAGCACACGTCTGAACTCCAGTCACAC | 20 |
| Duplex_p5_oligo11 | ACACTCTTTCCCTACACGACGCTCTTCCGATCTGTCGTCCATGACT | 21 |
| Duplex_p7_oligo11 | GTCATGGACGACAGATCGGAAGAGCACACGTCTGAACTCCAGTCACAC | 22 |
| Duplex_p5_oligo12 | ACACTCTTTCCCTACACGACGCTCTTCCGATCTTCAGGCGTTGACT | 23 |
| Duplex_p7_oligo12 | GTCAACGCCTGAAGATCGGAAGAGCACACGTCTGAACTCCAGTCACAC | 24 |
| Duplex_p5_oligo13 | ACACTCTTTCCCTACACGACGCTCTTCCGATCTCGGTACCTTGACT | 25 |
| Duplex_p7_oligo13 | GTCAAGGTACCGAGATCGGAAGAGCACACGTCTGAACTCCAGTCACAC | 26 |
| Duplex_p5_oligo14 | ACACTCTTTCCCTACACGACGCTCTTCCGATCTCAGCTTCGTGACT | 27 |
| Duplex_p7_oligo14 | GTCACGAAGCTGAGATCGGAAGAGCACACGTCTGAACTCCAGTCACAC | 28 |
| Duplex_p5_oligo15 | ACACTCTTTCCCTACACGACGCTCTTCCGATCTTCTGGAACTGACT | 29 |
| Duplex_p7_oligo15 | GTCAGTTCCAGAAGATCGGAAGAGCACACGTCTGAACTCCAGTCACAC | 30 |
| Duplex_p5_oligo16 | ACACTCTTTCCCTACACGACGCTCTTCCGATCTAGCGAGAATGACT | 31 |
| Duplex_p7_oligo16 | GTCATTCTCGCTAGATCGGAAGAGCACACGTCTGAACTCCAGTCACAC | 32 |
| Duplex_p5_oligo17 | ACACTCTTTCCCTACACGACGCTCTTCCGATCTAACCGATGTGACT | 33 |
| Duplex_p7_oligo17 | GTCACATCGGTTAGATCGGAAGAGCACACGTCTGAACTCCAGTCACAC | 34 |
| Duplex_p5_oligo18 | ACACTCTTTCCCTACACGACGCTCTTCCGATCTTTACCCGCTGACT | 35 |
| Duplex_p7_oligo18 | GTCAGCGGGTAAAGATCGGAAGAGCACACGTCTGAACTCCAGTCACAC | 36 |
| Duplex_p5_oligo19 | ACACTCTTTCCCTACACGACGCTCTTCCGATCTTTCTCTCGTGACT | 37 |
| Duplex_p7_oligo19 | GTCACGAGAGAAAGATCGGAAGAGCACACGTCTGAACTCCAGTCACAC | 38 |
| Duplex_p5_oligo20 | ACACTCTTTCCCTACACGACGCTCTTCCGATCTCTTTCCCTTGACT | 39 |
| Duplex_p7_oligo20 | GTCAAGGGAAAGAGATCGGAAGAGCACACGTCTGAACTCCAGTCACAC | 40 |

TABLE 6-continued

| Nonrandom oligonucleotide adapter | Oligonucleotide adapter Sequence | SEQ ID Nos. |
|---|---|---|
| Duplex_p5_oligo21 | ACACTCTTTCCCTACACGACGCTCTTCCGATCTGTGCGAGGTGACT | 41 |
| Duplex_p7_oligo21 | GTCACCTCGCACAGATCGGAAGAGCACACGTCTGAACTCCAGTCACAC | 42 |
| Duplex_p5_oligo22 | ACACTCTTTCCCTACACGACGCTCTTCCGATCTGACAGGTTTGACT | 43 |
| Duplex_p7_oligo22 | GTCAAACCTGTCAGATCGGAAGAGCACACGTCTGAACTCCAGTCACAC | 44 |
| Duplex_p5_oligo23 | ACACTCTTTCCCTACACGACGCTCTTCCGATCTCGGTGACCTGACT | 45 |
| Duplex_p7_oligo23 | GTCAGGTCACCGAGATCGGAAGAGCACACGTCTGAACTCCAGTCACAC | 46 |
| Duplex_p5_oligo24 | ACACTCTTTCCCTACACGACGCTCTTCCGATCTTAATCTCGTGACT | 47 |
| Duplex_p7_oligo24 | GTCACGAGATTAAGATCGGAAGAGCACACGTCTGAACTCCAGTCACAC | 48 |
| Duplex_p5_oligo25 | ACACTCTTTCCCTACACGACGCTCTTCCGATCTCGATCGAATGACT | 49 |
| Duplex_p7_oligo25 | GTCATTCGATCGAGATCGGAAGAGCACACGTCTGAACTCCAGTCACAC | 50 |
| Duplex_p5_oligo26 | ACACTCTTTCCCTACACGACGCTCTTCCGATCTACAGTTGTTGACT | 51 |
| Duplex_p7_oligo26 | GTCAACAACTGTAGATCGGAAGAGCACACGTCTGAACTCCAGTCACAC | 52 |
| Duplex_p5_oligo27 | ACACTCTTTCCCTACACGACGCTCTTCCGATCTGGCACGAATGACT | 53 |
| Duplex_p7_oligo27 | GTCATTCGTGCCAGATCGGAAGAGCACACGTCTGAACTCCAGTCACAC | 54 |
| Duplex_p5_oligo28 | ACACTCTTTCCCTACACGACGCTCTTCCGATCTGCCAATCCTGACT | 55 |
| Duplex_p7_oligo28 | GTCAGGATTGGCAGATCGGAAGAGCACACGTCTGAACTCCAGTCACAC | 56 |
| Duplex_p5_oligo29 | ACACTCTTTCCCTACACGACGCTCTTCCGATCTACCCGTTGTGACT | 57 |
| Duplex_p7_oligo29 | GTCACAACGGGTAGATCGGAAGAGCACACGTCTGAACTCCAGTCACAC | 58 |
| Duplex_p5_oligo30 | ACACTCTTTCCCTACACGACGCTCTTCCGATCTCCGACCAGTGACT | 59 |
| Duplex_p7_oligo30 | GTCACTGGTCGGAGATCGGAAGAGCACACGTCTGAACTCCAGTCACAC | 60 |
| Duplex_p5_oligo31 | ACACTCTTTCCCTACACGACGCTCTTCCGATCTCCTTCAATTGACT | 61 |
| Duplex_p7_oligo31 | GTCAATTGAAGGAGATCGGAAGAGCACACGTCTGAACTCCAGTCACAC | 62 |
| Duplex_p5_oligo32 | ACACTCTTTCCCTACACGACGCTCTTCCGATCTATCCGCAGTGACT | 63 |
| Duplex_p7_oligo32 | GTCACTGCGGATAGATCGGAAGAGCACACGTCTGAACTCCAGTCACAC | 64 |
| Duplex_p5_oligo33 | ACACTCTTTCCCTACACGACGCTCTTCCGATCTGTTGGCGTTGACT | 65 |
| Duplex_p7_oligo33 | GTCAACGCCAACAGATCGGAAGAGCACACGTCTGAACTCCAGTCACAC | 66 |
| Duplex_p5_oligo34 | ACACTCTTTCCCTACACGACGCTCTTCCGATCTTTGCGTTATGACT | 67 |
| Duplex_p7_oligo34 | GTCATAACGCAAAGATCGGAAGAGCACACGTCTGAACTCCAGTCACAC | 68 |
| Duplex_p5_oligo35 | ACACTCTTTCCCTACACGACGCTCTTCCGATCTGATGTCATTGACT | 69 |
| Duplex_p7_oligo35 | GTCAATGACATCAGATCGGAAGAGCACACGTCTGAACTCCAGTCACAC | 70 |
| Duplex_p5_oligo36 | ACACTCTTTCCCTACACGACGCTCTTCCGATCTGTGTGGCATGACT | 71 |
| Duplex_p7_oligo36 | GTCATGCCACACAGATCGGAAGAGCACACGTCTGAACTCCAGTCACAC | 72 |
| Duplex_p5_oligo37 | ACACTCTTTCCCTACACGACGCTCTTCCGATCTGTAGTAGATGACT | 73 |
| Duplex_p7_oligo37 | GTCATCTACTACAGATCGGAAGAGCACACGTCTGAACTCCAGTCACAC | 74 |
| Duplex_p5_oligo38 | ACACTCTTTCCCTACACGACGCTCTTCCGATCTGGCTTACTTGACT | 75 |
| Duplex_p7_oligo38 | GTCAAGTAAGCCAGATCGGAAGAGCACACGTCTGAACTCCAGTCACAC | 76 |
| Duplex_p5_oligo39 | ACACTCTTTCCCTACACGACGCTCTTCCGATCTTACCTGTGTGACT | 77 |
| Duplex_p7_oligo39 | GTCACACAGGTAAGATCGGAAGAGCACACGTCTGAACTCCAGTCACAC | 78 |

TABLE 6-continued

| Nonrandom oligonucleotide adapter | Oligonucleotide adapter Sequence | SEQ ID Nos. |
|---|---|---|
| Duplex_p5_oligo40 | ACACTCTTTCCCTACACGACGCTCTTCCGATCTGCTCGAAGTGACT | 79 |
| Duplex_p7_oligo40 | GTCACTTCGAGCAGATCGGAAGAGCACACGTCTGAACTCCAGTCACAC | 80 |
| Duplex_p5_oligo41 | ACACTCTTTCCCTACACGACGCTCTTCCGATCTACTGCCCGTGACT | 81 |
| Duplex_p7_oligo41 | GTCACGGGCAGTAGATCGGAAGAGCACACGTCTGAACTCCAGTCACAC | 82 |
| Duplex_p5_oligo42 | ACACTCTTTCCCTACACGACGCTCTTCCGATCTTTACACAATGACT | 83 |
| Duplex_p7_oligo42 | GTCATTGTGTAAAGATCGGAAGAGCACACGTCTGAACTCCAGTCACAC | 84 |
| Duplex_p5_oligo43 | ACACTCTTTCCCTACACGACGCTCTTCCGATCTTAGCACCTTGACT | 85 |
| Duplex_p7_oligo43 | GTCAAGGTGCTAAGATCGGAAGAGCACACGTCTGAACTCCAGTCACAC | 86 |
| Duplex_p5_oligo44 | ACACTCTTTCCCTACACGACGCTCTTCCGATCTCTAATTCTTGACT | 87 |
| Duplex_p7_oligo44 | GTCAAGAATTAGAGATCGGAAGAGCACACGTCTGAACTCCAGTCACAC | 88 |
| Duplex_p5_oligo45 | ACACTCTTTCCCTACACGACGCTCTTCCGATCTGAGGACCATGACT | 89 |
| Duplex_p7_oligo45 | GTCATGGTCCTCAGATCGGAAGAGCACACGTCTGAACTCCAGTCACAC | 90 |
| Duplex_p5_oligo46 | ACACTCTTTCCCTACACGACGCTCTTCCGATCTTACTTGCCTGACT | 91 |
| Duplex_p7_oligo46 | GTCAGGCAAGTAAGATCGGAAGAGCACACGTCTGAACTCCAGTCACAC | 92 |
| Duplex_p5_oligo47 | ACACTCTTTCCCTACACGACGCTCTTCCGATCTAATACGTCTGACT | 93 |
| Duplex_p7_oligo47 | GTCAGACGTATTAGATCGGAAGAGCACACGTCTGAACTCCAGTCACAC | 94 |
| Duplex_p5_oligo48 | ACACTCTTTCCCTACACGACGCTCTTCCGATCTAGATGATCTGACT | 95 |
| Duplex_p7_oligo48 | GTCAGATCATCTAGATCGGAAGAGCACACGTCTGAACTCCAGTCACAC | 96 |
| Duplex_p5_oligo49 | ACACTCTTTCCCTACACGACGCTCTTCCGATCTGTACATGTTGACT | 97 |
| Duplex_p7_oligo49 | GTCAACATGTACAGATCGGAAGAGCACACGTCTGAACTCCAGTCACAC | 98 |
| Duplex_p5_oligo50 | ACACTCTTTCCCTACACGACGCTCTTCCGATCTTGCGGGATTGACT | 99 |
| Duplex_p7_oligo50 | GTCAATCCCGCAAGATCGGAAGAGCACACGTCTGAACTCCAGTCACAC | 100 |
| Duplex_p5_oligo51 | ACACTCTTTCCCTACACGACGCTCTTCCGATCTCATATAGCTGACT | 101 |
| Duplex_p7_oligo51 | GTCAGCTATATGAGATCGGAAGAGCACACGTCTGAACTCCAGTCACAC | 102 |
| Duplex_p5_oligo52 | ACACTCTTTCCCTACACGACGCTCTTCCGATCTAACGCGAATGACT | 103 |
| Duplex_p7_oligo52 | GTCATTCGCGTTAGATCGGAAGAGCACACGTCTGAACTCCAGTCACAC | 104 |
| Duplex_p5_oligo53 | ACACTCTTTCCCTACACGACGCTCTTCCGATCTATGGCTGTTGACT | 105 |
| Duplex_p7_oligo53 | GTCAACAGCCATAGATCGGAAGAGCACACGTCTGAACTCCAGTCACAC | 106 |
| Duplex_p5_oligo54 | ACACTCTTTCCCTACACGACGCTCTTCCGATCTATGTTTAGTGACT | 107 |
| Duplex_p7_oligo54 | GTCACTAAACATAGATCGGAAGAGCACACGTCTGAACTCCAGTCACAC | 108 |
| Duplex_p5_oligo55 | ACACTCTTTCCCTACACGACGCTCTTCCGATCTACCAACAGTGACT | 109 |
| Duplex_p7_oligo55 | GTCACTGTTGGTAGATCGGAAGAGCACACGTCTGAACTCCAGTCACAC | 110 |
| Duplex_p5_oligo56 | ACACTCTTTCCCTACACGACGCTCTTCCGATCTTCCGAGTCTGACT | 111 |
| Duplex_p7_oligo56 | GTCAGACTCGGAAGATCGGAAGAGCACACGTCTGAACTCCAGTCACAC | 112 |
| Duplex_p5_oligo57 | ACACTCTTTCCCTACACGACGCTCTTCCGATCTTGCCCATCTGACT | 113 |
| Duplex_p7_oligo57 | GTCAGATGGGCAAGATCGGAAGAGCACACGTCTGAACTCCAGTCACAC | 114 |
| Duplex_p5_oligo58 | ACACTCTTTCCCTACACGACGCTCTTCCGATCTATTGGACATGACT | 115 |
| Duplex_p7_oligo58 | GTCATGTCCAATAGATCGGAAGAGCACACGTCTGAACTCCAGTCACAC | 116 |

TABLE 6-continued

| Nonrandom oligonucleotide adapter | Oligonucleotide adapter Sequence | SEQ ID Nos. |
|---|---|---|
| Duplex_p5_oligo59 | ACACTCTTTCCCTACACGACGCTCTTCCGATCTGCGTTCTATGACT | 117 |
| Duplex_p7_oligo59 | GTCATAGAACGCAGATCGGAAGAGCACACGTCTGAACTCCAGTCACAC | 118 |
| Duplex_p5_oligo60 | ACACTCTTTCCCTACACGACGCTCTTCCGATCTAAGTGTGGTGACT | 119 |
| Duplex_p7_oligo60 | GTCACCACACTTAGATCGGAAGAGCACACGTCTGAACTCCAGTCACAC | 120 |
| Duplex_p5_oligo61 | ACACTCTTTCCCTACACGACGCTCTTCCGATCTTCCATTTCTGACT | 121 |
| Duplex_p7_oligo61 | GTCAGAAATGGAAGATCGGAAGAGCACACGTCTGAACTCCAGTCACAC | 122 |
| Duplex_p5_oligo62 | ACACTCTTTCCCTACACGACGCTCTTCCGATCTTCATCACGTGACT | 123 |
| Duplex_p7_oligo62 | GTCACGTGATGAAGATCGGAAGAGCACACGTCTGAACTCCAGTCACAC | 124 |
| Duplex_p5_oligo63 | ACACTCTTTCCCTACACGACGCTCTTCCGATCTTTCCCGAATGACT | 125 |
| Duplex_p7_oligo63 | GTCATTCGGGAAAGATCGGAAGAGCACACGTCTGAACTCCAGTCACAC | 126 |
| Duplex_p5_oligo64 | ACACTCTTTCCCTACACGACGCTCTTCCGATCTGGACTTCCTGACT | 127 |
| Duplex_p7_oligo64 | GTCAGGAAGTCCAGATCGGAAGAGCACACGTCTGAACTCCAGTCACAC | 128 |
| Duplex_p5_oligo65 | ACACTCTTTCCCTACACGACGCTCTTCCGATCTGACGCACTTGACT | 129 |
| Duplex_p7_oligo65 | GTCAAGTGCGTCAGATCGGAAGAGCACACGTCTGAACTCCAGTCACAC | 130 |
| Duplex_p5_oligo66 | ACACTCTTTCCCTACACGACGCTCTTCCGATCTGTGTATCGTGACT | 131 |
| Duplex_p7_oligo66 | GTCACGATACACAGATCGGAAGAGCACACGTCTGAACTCCAGTCACAC | 132 |
| Duplex_p5_oligo67 | ACACTCTTTCCCTACACGACGCTCTTCCGATCTCAAGACTGTGACT | 133 |
| Duplex_p7_oligo67 | GTCACAGTCTTGAGATCGGAAGAGCACACGTCTGAACTCCAGTCACAC | 134 |
| Duplex_p5_oligo68 | ACACTCTTTCCCTACACGACGCTCTTCCGATCTTGCGTTCTTGACT | 135 |
| Duplex_p7_oligo68 | GTCAAGAACGCAAGATCGGAAGAGCACACGTCTGAACTCCAGTCACAC | 136 |
| Duplex_p5_oligo69 | ACACTCTTTCCCTACACGACGCTCTTCCGATCTTGGCACTGTGACT | 137 |
| Duplex_p7_oligo69 | GTCACAGTGCCAAGATCGGAAGAGCACACGTCTGAACTCCAGTCACAC | 138 |
| Duplex_p5_oligo70 | ACACTCTTTCCCTACACGACGCTCTTCCGATCTCACCTGTATGACT | 139 |
| Duplex_p7_oligo70 | GTCATACAGGTGAGATCGGAAGAGCACACGTCTGAACTCCAGTCACAC | 140 |
| Duplex_p5_oligo71 | ACACTCTTTCCCTACACGACGCTCTTCCGATCTAGAATCCATGACT | 141 |
| Duplex_p7_oligo71 | GTCATGGATTCTAGATCGGAAGAGCACACGTCTGAACTCCAGTCACAC | 142 |
| Duplex_p5_oligo72 | ACACTCTTTCCCTACACGACGCTCTTCCGATCTAATCCATGTGACT | 143 |
| Duplex_p7_oligo72 | GTCACATGGATTAGATCGGAAGAGCACACGTCTGAACTCCAGTCACAC | 144 |
| Duplex_p5_oligo73 | ACACTCTTTCCCTACACGACGCTCTTCCGATCTGAGTCGATTGACT | 145 |
| Duplex_p7_oligo73 | GTCAATCGACTCAGATCGGAAGAGCACACGTCTGAACTCCAGTCACAC | 146 |
| Duplex_p5_oligo74 | ACACTCTTTCCCTACACGACGCTCTTCCGATCTGTGGATAATGACT | 147 |
| Duplex_p7_oligo74 | GTCATTATCCACAGATCGGAAGAGCACACGTCTGAACTCCAGTCACAC | 148 |
| Duplex_p5_oligo75 | ACACTCTTTCCCTACACGACGCTCTTCCGATCTTCAGCGCCTGACT | 149 |
| Duplex_p7_oligo75 | GTCAGGCGCTGAAGATCGGAAGAGCACACGTCTGAACTCCAGTCACAC | 150 |
| Duplex_p5_oligo76 | ACACTCTTTCCCTACACGACGCTCTTCCGATCTGCACTGGCTGACT | 151 |
| Duplex_p7_oligo76 | GTCAGCCAGTGCAGATCGGAAGAGCACACGTCTGAACTCCAGTCACAC | 152 |
| Duplex_p5_oligo77 | ACACTCTTTCCCTACACGACGCTCTTCCGATCTCATTATGGTGACT | 153 |
| Duplex_p7_oligo77 | GTCACCATAATGAGATCGGAAGAGCACACGTCTGAACTCCAGTCACAC | 154 |

TABLE 6-continued

| Nonrandom oligonucleotide adapter | Oligonucleotide adapter Sequence | SEQ ID Nos. |
|---|---|---|
| Duplex_p5_oligo78 | ACACTCTTTCCCTACACGACGCTCTTCCGATCTACACGACTTGACT | 155 |
| Duplex_p7_oligo78 | GTCAAGTCGTGTAGATCGGAAGAGCACACGTCTGAACTCCAGTCACAC | 156 |
| Duplex_p5_oligo79 | ACACTCTTTCCCTACACGACGCTCTTCCGATCTGAATCGCCTGACT | 157 |
| Duplex_p7_oligo79 | GTCAGGCGATTCAGATCGGAAGAGCACACGTCTGAACTCCAGTCACAC | 158 |
| Duplex_p5_oligo80 | ACACTCTTTCCCTACACGACGCTCTTCCGATCTTACCGGCTTGACT | 159 |
| Duplex_p7_oligo80 | GTCAAGCCGGTAAGATCGGAAGAGCACACGTCTGAACTCCAGTCACAC | 160 |
| Duplex_p5_oligo81 | ACACTCTTTCCCTACACGACGCTCTTCCGATCTACACCTGCTGACT | 161 |
| Duplex_p7_oligo81 | GTCAGCAGGTGTAGATCGGAAGAGCACACGTCTGAACTCCAGTCACAC | 162 |
| Duplex_p5_oligo82 | ACACTCTTTCCCTACACGACGCTCTTCCGATCTCATACCGTTGACT | 163 |
| Duplex_p7_oligo82 | GTCAACGGTATGAGATCGGAAGAGCACACGTCTGAACTCCAGTCACAC | 164 |
| Duplex_p5_oligo83 | ACACTCTTTCCCTACACGACGCTCTTCCGATCTGAGACAGTTGACT | 165 |
| Duplex_p7_oligo83 | GTCAACTGTCTCAGATCGGAAGAGCACACGTCTGAACTCCAGTCACAC | 166 |
| Duplex_p5_oligo84 | ACACTCTTTCCCTACACGACGCTCTTCCGATCTAGTCGCTATGACT | 167 |
| Duplex_p7_oligo84 | GTCATAGCGACTAGATCGGAAGAGCACACGTCTGAACTCCAGTCACAC | 168 |
| Duplex_p5_oligo85 | ACACTCTTTCCCTACACGACGCTCTTCCGATCTTCCTAGGTTGACT | 169 |
| Duplex_p7_oligo85 | GTCAACCTAGGAAGATCGGAAGAGCACACGTCTGAACTCCAGTCACAC | 170 |
| Duplex_p5_oligo86 | ACACTCTTTCCCTACACGACGCTCTTCCGATCTGATATGAATGACT | 171 |
| Duplex_p7_oligo86 | GTCATTCATATCAGATCGGAAGAGCACACGTCTGAACTCCAGTCACAC | 172 |
| Duplex_p5_oligo87 | ACACTCTTTCCCTACACGACGCTCTTCCGATCTTAAATCACTGACT | 173 |
| Duplex_p7_oligo87 | GTCAGTGATTTAAGATCGGAAGAGCACACGTCTGAACTCCAGTCACAC | 174 |
| Duplex_p5_oligo88 | ACACTCTTTCCCTACACGACGCTCTTCCGATCTCTCTCATATGACT | 175 |
| Duplex_p7_oligo88 | GTCATATGAGAGAGATCGGAAGAGCACACGTCTGAACTCCAGTCACAC | 176 |
| Duplex_p5_oligo89 | ACACTCTTTCCCTACACGACGCTCTTCCGATCTCATGTGCTTGACT | 177 |
| Duplex_p7_oligo89 | GTCAAGCACATGAGATCGGAAGAGCACACGTCTGAACTCCAGTCACAC | 178 |
| Duplex_p5_oligo90 | ACACTCTTTCCCTACACGACGCTCTTCCGATCTTGCAATGGTGACT | 179 |
| Duplex_p7_oligo90 | GTCACCATTGCAAGATCGGAAGAGCACACGTCTGAACTCCAGTCACAC | 180 |
| Duplex_p5_oligo91 | ACACTCTTTCCCTACACGACGCTCTTCCGATCTCCGACTCTTGGACT | 181 |
| Duplex_p7_oligo91 | GTCAAGAGTCGGAGATCGGAAGAGCACACGTCTGAACTCCAGTCACAC | 182 |
| Duplex_p5_oligo92 | ACACTCTTTCCCTACACGACGCTCTTCCGATCTTCCCACGATGACT | 183 |
| Duplex_p7_oligo92 | GTCATCGTGGGAAGATCGGAAGAGCACACGTCTGAACTCCAGTCACAC | 184 |
| Duplex_p5_oligo93 | ACACTCTTTCCCTACACGACGCTCTTCCGATCTTCTGAATGTGACT | 185 |
| Duplex_p7_oligo93 | GTCACATTCAGAAGATCGGAAGAGCACACGTCTGAACTCCAGTCACAC | 186 |
| Duplex_p5_oligo94 | ACACTCTTTCCCTACACGACGCTCTTCCGATCTCAGCAGTCTGACT | 187 |
| Duplex_p7_oligo94 | GTCAGACTGCTGAGATCGGAAGAGCACACGTCTGAACTCCAGTCACAC | 188 |
| Duplex_p5_oligo95 | ACACTCTTTCCCTACACGACGCTCTTCCGATCTTGAATACCTGACT | 189 |
| Duplex_p7_oligo95 | GTCAGGTATTCAAGATCGGAAGAGCACACGTCTGAACTCCAGTCACAC | 190 |
| Duplex_p5_oligo96 | ACACTCTTTCCCTACACGACGCTCTTCCGATCTGATTGTGCTGACT | 191 |
| Duplex_p7_oligo96 | GTCAGCACAATCAGATCGGAAGAGCACACGTCTGAACTCCAGTCACAC | 192 |

TABLE 6-continued

| Nonrandom oligonucleotide adapter | Oligonucleotide adapter Sequence | SEQ ID Nos. |
|---|---|---|
| Duplex_p5_oligo97 | ACACTCTTTCCCTACACGACGCTCTTCCGATCTCTCCCACTTGACT | 193 |
| Duplex_p7_oligo97 | GTCAAGTGGGAGAGATCGGAAGAGCACACGTCTGAACTCCAGTCACAC | 194 |
| Duplex_p5_oligo98 | ACACTCTTTCCCTACACGACGCTCTTCCGATCTTCATGTGATGACT | 195 |
| Duplex_p7_oligo98 | GTCATCACATGAAGATCGGAAGAGCACACGTCTGAACTCCAGTCACAC | 196 |
| Duplex_p5_oligo99 | ACACTCTTTCCCTACACGACGCTCTTCCGATCTTAGTGATGTGACT | 197 |
| Duplex_p7_oligo99 | GTCACATCACTAAGATCGGAAGAGCACACGTCTGAACTCCAGTCACAC | 198 |
| Duplex_p5_oligo100 | ACACTCTTTCCCTACACGACGCTCTTCCGATCTCGATATCATGACT | 199 |
| Duplex_p7_oligo100 | GTCATGATATCGAGATCGGAAGAGCACACGTCTGAACTCCAGTCACAC | 200 |
| Duplex_p5_oligo101 | ACACTCTTTCCCTACACGACGCTCTTCCGATCTGCGCCGAATGACT | 201 |
| Duplex_p7_oligo101 | GTCATTCGGCGCAGATCGGAAGAGCACACGTCTGAACTCCAGTCACAC | 202 |
| Duplex_p5_oligo102 | ACACTCTTTCCCTACACGACGCTCTTCCGATCTTAGGGAGATGACT | 203 |
| Duplex_p7_oligo102 | GTCATCTCCCTAAGATCGGAAGAGCACACGTCTGAACTCCAGTCACAC | 204 |
| Duplex_p5_oligo103 | ACACTCTTTCCCTACACGACGCTCTTCCGATCTTCGGACAGTGACT | 205 |
| Duplex_p7_oligo103 | GTCACTGTCCGAAGATCGGAAGAGCACACGTCTGAACTCCAGTCACAC | 206 |
| Duplex_p5_oligo104 | ACACTCTTTCCCTACACGACGCTCTTCCGATCTGTTCCGGATGACT | 207 |
| Duplex_p7_oligo104 | GTCATCCGGAACAGATCGGAAGAGCACACGTCTGAACTCCAGTCACAC | 208 |
| Duplex_p5_oligo105 | ACACTCTTTCCCTACACGACGCTCTTCCGATCTATTCGGTATGACT | 209 |
| Duplex_p7_oligo105 | GTCATACCGAATAGATCGGAAGAGCACACGTCTGAACTCCAGTCACAC | 210 |
| Duplex_p5_oligo106 | ACACTCTTTCCCTACACGACGCTCTTCCGATCTCTACACAGTGACT | 211 |
| Duplex_p7_oligo106 | GTCACTGTGTAGAGATCGGAAGAGCACACGTCTGAACTCCAGTCACAC | 212 |
| Duplex_p5_oligo107 | ACACTCTTTCCCTACACGACGCTCTTCCGATCTGTCCGCAATGACT | 213 |
| Duplex_p7_oligo107 | GTCATTGCGGACAGATCGGAAGAGCACACGTCTGAACTCCAGTCACAC | 214 |
| Duplex_p5_oligo108 | ACACTCTTTCCCTACACGACGCTCTTCCGATCTACTTCGGATGACT | 215 |
| Duplex_p7_oligo108 | GTCATCCGAAGTAGATCGGAAGAGCACACGTCTGAACTCCAGTCACAC | 216 |
| Duplex_p5_oligo109 | ACACTCTTTCCCTACACGACGCTCTTCCGATCTACTGCTATTGACT | 217 |
| Duplex_p7_oligo109 | GTCAATAGCAGTAGATCGGAAGAGCAACGTCTGAACTCCAGTCACAC | 218 |
| Duplex_p5_oligo110 | ACACTCTTTCCCTACACGACGCTCTTCCGATCTCCTACATGTGACT | 219 |
| Duplex_p7_oligo110 | GTCACATGTAGGAGATCGGAAGAGCACACGTCTGAACTCCAGTCACAC | 220 |
| Duplex_p5_oligo111 | ACACTCTTTCCCTACACGACGCTCTTCCGATCTGTCAGTATTGACT | 221 |
| Duplex_p7_oligo111 | GTCAATACTGACAGATCGGAAGAGCACACGTCTGAACTCCAGTCACAC | 222 |
| Duplex_p5_oligo112 | ACACTCTTTCCCTACACGACGCTCTTCCGATCTTCTACGGCTGACT | 223 |
| Duplex_p7_oligo112 | GTCAGCCGTAGAAGATCGGAAGAGCACACGTCTGAACTCCAGTCACAC | 224 |
| Duplex_p5_oligo113 | ACACTCTTTCCCTACACGACGCTCTTCCGATCTACGTATTCTGACT | 225 |
| Duplex_p7_oligo113 | GTCAGAATACGTAGATCGGAAGAGCACACGTCTGAACTCCAGTCACAC | 226 |
| Duplex_p5_oligo114 | ACACTCTTTCCCTACACGACGCTCTTCCGATCTAGATCTATTGACT | 227 |
| Duplex_p7_oligo114 | GTCAATAGATCTAGATCGGAAGAGCACACGTCTGAACTCCAGTCACAC | 228 |
| Duplex_p5_oligo115 | ACACTCTTTCCCTACACGACGCTCTTCCGATCTAGTTCCACTGACT | 229 |
| Duplex_p7_oligo115 | GTCAGTGGAACTAGATCGGAAGAGCACACGTCTGAACTCCAGTCACAC | 230 |

TABLE 6-continued

| Nonrandom oligonucleotide adapter | Oligonucleotide adapter Sequence | SEQ ID Nos. |
|---|---|---|
| Duplex_p5_oligo116 | ACACTCTTTCCCTACACGACGCTCTTCCGATCTTTGATCCGTGACT | 231 |
| Duplex_p7_oligo116 | GTCACGGATCAAAGATCGGAAGAGCACACGTCTGAACTCCAGTCACAC | 232 |
| Duplex_p5_oligo117 | ACACTCTTTCCCTACACGACGCTCTTCCGATCTTGTTCGCCTGACT | 233 |
| Duplex_p7_oligo117 | GTCAGGCGAACAAGATCGGAAGAGCACACGTCTGAACTCCAGTCACAC | 234 |
| Duplex_p5_oligo118 | ACACTCTTTCCCTACACGACGCTCTTCCGATCTGCACACCTTGACT | 235 |
| Duplex_p7_oligo118 | GTCAAGGTGTGCAGATCGGAAGAGCACACGTCTGAACTCCAGTCACAC | 236 |
| Duplex_p5_oligo119 | ACACTCTTTCCCTACACGACGCTCTTCCGATCTGTAAGCCTTGACT | 237 |
| Duplex_p7_oligo119 | GTCAAGGCTTACAGATCGGAAGAGCACACGTCTGAACTCCAGTCACAC | 238 |
| Duplex_p5_oligo120 | ACACTCTTTCCCTACACGACGCTCTTCCGATCTTACCAATCTGACT | 239 |
| Duplex_p7_oligo120 | GTCAGATTGGTAAGATCGGAAGAGCACACGTCTGAACTCCAGTCACAC | 240 |
| Duplex_p5_oligo121 | ACACTCTTTCCCTACACGACGCTCTTCCGATCTCGGTAGTTTGACT | 241 |
| Duplex_p7_oligo121 | GTCAAACTACCGAGATCGGAAGAGCACACGTCTGAACTCCAGTCACAC | 242 |
| Duplex_p5_oligo122 | ACACTCTTTCCCTACACGACGCTCTTCCGATCTGAATATACTGACT | 243 |
| Duplex_p7_oligo122 | GTCAGTATATTCAGATCGGAAGAGCACACGTCTGAACTCCAGTCACAC | 244 |
| Duplex_p5_oligo123 | ACACTCTTTCCCTACACGACGCTCTTCCGATCTATGCCGGTTGACT | 245 |
| Duplex_p7_oligo123 | GTCAACCGGCATAGATCGGAAGAGCACACGTCTGAACTCCAGTCACAC | 246 |
| Duplex_p5_oligo124 | ACACTCTTTCCCTACACGACGCTCTTCCGATCTACTAGTTGTGACT | 247 |
| Duplex_p7_oligo124 | GTCACAACTAGTAGATCGGAAGAGCACACGTCTGAACTCCAGTCACAC | 248 |
| Duplex_p5_oligo125 | ACACTCTTTCCCTACACGACGCTCTTCCGATCTAATCGTAATGACT | 249 |
| Duplex_p7_oligo125 | GTCATTACGATTAGATCGGAAGAGCACACGTCTGAACTCCAGTCACAC | 250 |
| Duplex_p5_oligo126 | ACACTCTTTCCCTACACGACGCTCTTCCGATCTCCAAGATTTGACT | 251 |
| Duplex_p7_oligo126 | GTCAAATCTTGGAGATCGGAAGAGCACACGTCTGAACTCCAGTCACAC | 252 |
| Duplex_p5_oligo127 | ACACTCTTTCCCTACACGACGCTCTTCCGATCTGTAACCACTGACT | 253 |
| Duplex_p7_oligo127 | GTCAGTGGTTACAGATCGGAAGAGCACACGTCTGAACTCCAGTCACAC | 254 |
| Duplex_p5_oligo128 | ACACTCTTTCCCTACACGACGCTCTTCCGATCTCCAAACTCTGACT | 255 |
| Duplex_p7_oligo128 | GTCAGAGTTTGGAGATCGGAAGAGCACACGTCTGAACTCCAGTCACAC | 256 |
| Duplex_p5_oligo129 | ACACTCTTTCCCTACACGACGCTCTTCCGATCTGATAGGGCTGACT | 257 |
| Duplex_p7_oligo129 | GTCAGCCCTATCAGATCGGAAGAGCACACGTCTGAACTCCAGTCACAC | 258 |
| Duplex_p5_oligo130 | ACACTCTTTCCCTACACGACGCTCTTCCGATCTCCAGGACATGACT | 259 |
| Duplex_p7_oligo130 | GTCATGTCCTGGAGATCGGAAGAGCACACGTCTGAACTCCAGTCACAC | 260 |
| Duplex_p5_oligo131 | ACACTCTTTCCCTACACGACGCTCTTCCGATCTACGATATGTGACT | 261 |
| Duplex_p7_oligo131 | GTCACATATCGTAGATCGGAAGAGCACACGTCTGAACTCCAGTCACAC | 262 |
| Duplex_p5_oligo132 | ACACTCTTTCCCTACACGACGCTCTTCCGATCTACGTGGTTTGACT | 263 |
| Duplex_p7_oligo132 | GTCAAACCACGTAGATCGGAAGAGCACACGTCTGAACTCCAGTCACAC | 264 |
| Duplex_p5_oligo133 | ACACTCTTTCCCTACACGACGCTCTTCCGATCTCACGATGGTGACT | 265 |
| Duplex_p7_oligo133 | GTCACCATCGTGAGATCGGAAGAGCACACGTCTGAACTCCAGTCACAC | 266 |
| Duplex_p5_oligo134 | ACACTCTTTCCCTACACGACGCTCTTCCGATCTACCGTAAGTGACT | 267 |
| Duplex_p7_oligo134 | GTCACTTACGGTAGATCGGAAGAGCACACGTCTGAACTCCAGTCACAC | 268 |

TABLE 6-continued

| Nonrandom oligonucleotide adapter | Oligonucleotide adapter Sequence | SEQ ID Nos. |
|---|---|---|
| Duplex_p5_oligo135 | ACACTCTTTCCCTACACGACGCTCTTCCGATCTCCTTGGAATGACT | 269 |
| Duplex_p7_oligo135 | GTCATTCCAAGGAGATCGGAAGAGCACACGTCTGAACTCCAGTCACAC | 270 |
| Duplex_p5_oligo136 | ACACTCTTTCCCTACACGACGCTCTTCCGATCTAGTTGAGGTGACT | 271 |
| Duplex_p7_oligo136 | GTCACCTCAACTAGATCGGAAGAGCACACGTCTGAACTCCAGTCACAC | 272 |
| Duplex_p5_oligo137 | ACACTCTTTCCCTACACGACGCTCTTCCGATCTGTAATGCGTGACT | 273 |
| Duplex_p7_oligo137 | GTCACGCATTACAGATCGGAAGAGCACACGTCTGAACTCCAGTCACAC | 274 |
| Duplex_p5_oligo138 | ACACTCTTTCCCTACACGACGCTCTTCCGATCTCGCTAATCTGACT | 275 |
| Duplex_p7_oligo138 | GTCAGATTAGCGAGATCGGAAGAGCACACGTCTGAACTCCAGTCACAC | 276 |
| Duplex_p5_oligo139 | ACACTCTTTCCCTACACGACGCTCTTCCGATCTAAGGTCAATGACT | 277 |
| Duplex_p7_oligo139 | GTCATTGACCTTAGATCGGAAGAGCACACGTCTGAACTCCAGTCACAC | 278 |
| Duplex_p5_oligo140 | ACACTCTTTCCCTACACGACGCTCTTCCGATCTGAAAGAGTTGACT | 279 |
| Duplex_p7_oligo140 | GTCAACTCTTTCAGATCGGAAGAGCACACGTCTGAACTCCAGTCACAC | 280 |
| Duplex_p5_oligo141 | ACACTCTTTCCCTACACGACGCTCTTCCGATCTCGGAAACTTGACT | 281 |
| Duplex_p7_oligo141 | GTCAAGTTTCCGAGATCGGAAGAGCACACGTCTGAACTCCAGTCACAC | 282 |
| Duplex_p5_oligo142 | ACACTCTTTCCCTACACGACGCTCTTCCGATCTGCTGGTCTTGACT | 283 |
| Duplex_p7_oligo142 | GTCAAGACCAGCAGATCGGAAGAGCACACGTCTGAACTCCAGTCACAC | 284 |
| Duplex_p5_oligo143 | ACACTCTTTCCCTACACGACGCTCTTCCGATCTACCGGAGTTGACT | 285 |
| Duplex_p7_oligo143 | GTCAACTCCGGTAGATCGGAAGAGCACACGTCTGAACTCCAGTCACAC | 286 |
| Duplex_p5_oligo144 | ACACTCTTTCCCTACACGACGCTCTTCCGATCTACTCCGATTGACT | 287 |
| Duplex_p7_oligo144 | GTCAATCGGAGTAGATCGGAAGAGCACACGTCTGAACTCCAGTCACAC | 288 |
| Duplex_p5_oligo145 | ACACTCTTTCCCTACACGACGCTCTTCCGATCTTATGACGTTGACT | 289 |
| Duplex_p7_oligo145 | GTCAACGTCATAAGATCGGAAGAGCACACGTCTGAACTCCAGTCACAC | 290 |
| Duplex_p5_oligo146 | ACACTCTTTCCCTACACGACGCTCTTCCGATCTGCGATCACTGACT | 291 |
| Duplex_p7_oligo146 | GTCAGTGATCGCAGATCGGAAGAGCACACGTCTGAACTCCAGTCACAC | 292 |
| Duplex_p5_oligo147 | ACACTCTTTCCCTACACGACGCTCTTCCGATCTACGAGGAGTGACT | 293 |
| Duplex_p7_oligo147 | GTCACTCCTCGTAGATCGGAAGAGCACACGTCTGAACTCCAGTCACAC | 294 |
| Duplex_p5_oligo148 | ACACTCTTTCCCTACACGACGCTCTTCCGATCTCTGAGCTCTGACT | 295 |
| Duplex_p7_oligo148 | GTCAGAGCTCAGAGATCGGAAGAGCACACGTCTGAACTCCAGTCACAC | 296 |
| Duplex_p5_oligo149 | ACACTCTTTCCCTACACGACGCTCTTCCGATCTAGAGCGGATGACT | 297 |
| Duplex_p7_oligo149 | GTCATCCGCTCTAGATCGGAAGAGCACACGTCTGAACTCCAGTCACAC | 298 |
| Duplex_p5_oligo150 | ACACTCTTTCCCTACACGACGCTCTTCCGATCTCTAGTCGCTGACT | 299 |
| Duplex_p7_oligo150 | GTCAGCGACTAGAGATCGGAAGAGCACACGTCTGAACTCCAGTCACAC | 300 |
| Duplex_p5_oligo151 | ACACTCTTTCCCTACACGACGCTCTTCCGATCTCACTTTGGTGACT | 301 |
| Duplex_p7_oligo151 | GTCACCAAAGTGAGATCGGAAGAGCACACGTCTGAACTCCAGTCACAC | 302 |
| Duplex_p5_oligo152 | ACACTCTTTCCCTACACGACGCTCTTCCGATCTAGATTACATGACT | 303 |
| Duplex_p7_oligo152 | GTCATGTAATCTAGATCGGAAGAGCACACGTCTGAACTCCAGTCACAC | 304 |
| Duplex_p5_oligo153 | ACACTCTTTCCCTACACGACGCTCTTCCGATCTGCCTATGATGACT | 305 |
| Duplex_p7_oligo153 | GTCATCATAGGCAGATCGGAAGAGCACACGTCTGAACTCCAGTCACAC | 306 |

TABLE 6-continued

| Nonrandom oligonucleotide adapter | Oligonucleotide adapter Sequence | SEQ ID Nos. |
|---|---|---|
| Duplex_p5_oligo154 | ACACTCTTTCCCTACACGACGCTCTTCCGATCTCGAACGTCTGACT | 307 |
| Duplex_p7_oligo154 | GTCAGACGTTCGAGATCGGAAGAGCACACGTCTGAACTCCAGTCACAC | 308 |
| Duplex_p5_oligo155 | ACACTCTTTCCCTACACGACGCTCTTCCGATCTGTTTCTTGTGACT | 309 |
| Duplex_p7_oligo155 | GTCACAAGAAACAGATCGGAAGAGCACACGTCTGAACTCCAGTCACAC | 310 |
| Duplex_p5_oligo156 | ACACTCTTTCCCTACACGACGCTCTTCCGATCTAAGGGCGCTGACT | 311 |
| Duplex_p7_oligo156 | GTCAGCGCCCTTAGATCGGAAGAGCACACGTCTGAACTCCAGTCACAC | 312 |
| Duplex_p5_oligo157 | ACACTCTTTCCCTACACGACGCTCTTCCGATCTCGCTCTTATGACT | 313 |
| Duplex_p7_oligo157 | GTCATAAGAGCGAGATCGGAAGAGCACACGTCTGAACTCCAGTCACAC | 314 |
| Duplex_p5_oligo158 | ACACTCTTTCCCTACACGACGCTCTTCCGATCTTCAACCCGTGACT | 315 |
| Duplex_p7_oligo158 | GTCACGGGTTGAAGATCGGAAGAGCACACGTCTGAACTCCAGTCACAC | 316 |
| Duplex_p5_oligo159 | ACACTCTTTCCCTACACGACGCTCTTCCGATCTTCGGTGTATGACT | 317 |
| Duplex_p7_oligo159 | GTCATACACCGAAGATCGGAAGAGCACACGTCTGAACTCCAGTCACAC | 318 |
| Duplex_p5_oligo160 | ACACTCTTTCCCTACACGACGCTCTTCCGATCTGTCCGATCTGACT | 319 |
| Duplex_p7_oligo160 | GTCAGATCGGACAGATCGGAAGAGCACACGTCTGAACTCCAGTCACAC | 320 |
| Duplex_p5_oligo161 | ACACTCTTTCCCTACACGACGCTCTTCCGATCTTCCCAACCTGACT | 321 |
| Duplex_p7_oligo161 | GTCAGGTTGGGAAGATCGGAAGAGCACACGTCTGAACTCCAGTCACAC | 322 |
| Duplex_p5_oligo162 | ACACTCTTTCCCTACACGACGCTCTTCCGATCTTCTTGCGGTGACT | 323 |
| Duplex_p7_oligo162 | GTCACCGCAAGAAGATCGGAAGAGCACACGTCTGAACTCCAGTCACAC | 324 |
| Duplex_p5_oligo163 | ACACTCTTTCCCTACACGACGCTCTTCCGATCTGCCGGTACTGACT | 325 |
| Duplex_p7_oligo163 | GTCAGTACCGGCAGATCGGAAGAGCACACGTCTGAACTCCAGTCACAC | 326 |
| Duplex_p5_oligo164 | ACACTCTTTCCCTACACGACGCTCTTCCGATCTTTCTAGAGTGACT | 327 |
| Duplex_p7_oligo164 | GTCACTCTAGAAAGATCGGAAGAGCACACGTCTGAACTCCAGTCACAC | 328 |
| Duplex_p5_oligo165 | ACACTCTTTCCCTACACGACGCTCTTCCGATCTGGCCTATATGACT | 329 |
| Duplex_p7_oligo165 | GTCATATAGGCCAGATCGGAAGAGCACACGTCTGAACTCCAGTCACAC | 330 |
| Duplex_p5_oligo166 | ACACTCTTTCCCTACACGACGCTCTTCCGATCTTGCACGTGTGACT | 331 |
| Duplex_p7_oligo166 | GTCACACGTGCAAGATCGGAAGAGCACACGTCTGAACTCCAGTCACAC | 332 |
| Duplex_p5_oligo167 | ACACTCTTTCCCTACACGACGCTCTTCCGATCTGCCGTCTCTGACT | 333 |
| Duplex_p7_oligo167 | GTCAGAGACGGCAGATCGGAAGAGCACACGTCTGAACTCCAGTCACAC | 334 |
| Duplex_p5_oligo168 | ACACTCTTTCCCTACACGACGCTCTTCCGATCTATGCCTCGTGACT | 335 |
| Duplex_p7_oligo168 | GTCACGAGGCATAGATCGGAAGAGCACACGTCTGAACTCCAGTCACAC | 336 |
| Duplex_p5_oligo169 | ACACTCTTTCCCTACACGACGCTCTTCCGATCTCAGAGCTATGACT | 337 |
| Duplex_p7_oligo169 | GTCATAGCTCTGAGATCGGAAGAGCACACGTCTGAACTCCAGTCACAC | 338 |
| Duplex_p5_oligo170 | ACACTCTTTCCCTACACGACGCTCTTCCGATCTGCAATAGGTGACT | 339 |
| Duplex_p7_oligo170 | GTCACCTATTGCAGATCGGAAGAGCACACGTCTGAACTCCAGTCACAC | 340 |
| Duplex_p5_oligo171 | ACACTCTTTCCCTACACGACGCTCTTCCGATCTGTTTGCTCTGACT | 341 |
| Duplex_p7_oligo171 | GTCAGAGCAAACAGATCGGAAGAGCACACGTCTGAACTCCAGTCACAC | 342 |
| Duplex_p5_oligo172 | ACACTCTTTCCCTACACGACGCTCTTCCGATCTCCTCGGGTTGACT | 343 |
| Duplex_p7_oligo172 | GTCAACCCGAGGAGATCGGAAGAGCACACGTCTGAACTCCAGTCACAC | 344 |

TABLE 6-continued

| Nonrandom oligonucleotide adapter | Oligonucleotide adapter Sequence | SEQ ID Nos. |
|---|---|---|
| Duplex_p5_oligo173 | ACACTCTTTCCCTACACGACGCTCTTCCGATCTTGACTAATTGACT | 345 |
| Duplex_p7_oligo173 | GTCAATTAGTCAAGATCGGAAGAGCACACGTCTGAACTCCAGTCACAC | 346 |
| Duplex_p5_oligo174 | ACACTCTTTCCCTACACGACGCTCTTCCGATCTCGTAATTGTGACT | 347 |
| Duplex_p7_oligo174 | GTCACAATTACGAGATCGGAAGAGCACACGTCTGAACTCCAGTCACAC | 348 |
| Duplex_p5_oligo175 | ACACTCTTTCCCTACACGACGCTCTTCCGATCTCGAAAGCATGACT | 349 |
| Duplex_p7_oligo175 | GTCATGCTTTCGAGATCGGAAGAGCACACGTCTGAACTCCAGTCACAC | 350 |
| Duplex_p5_oligo176 | ACACTCTTTCCCTACACGACGCTCTTCCGATCTAATCACGGTGACT | 351 |
| Duplex_p7_oligo176 | GTCACCGTGATTAGATCGGAAGAGCACACGTCTGAACTCCAGTCACAC | 352 |
| Duplex_p5_oligo177 | ACACTCTTTCCCTACACGACGCTCTTCCGATCTACTGTACATGACT | 353 |
| Duplex_p7_oligo177 | GTCATGTACAGTAGATCGGAAGAGCACACGTCTGAACTCCAGTCACAC | 354 |
| Duplex_p5_oligo178 | ACACTCTTTCCCTACACGACGCTCTTCCGATCTGAGGTGGGTGACT | 355 |
| Duplex_p7_oligo178 | GTCACCCACCTCAGATCGGAAGAGCACACGTCTGAACTCCAGTCACAC | 356 |
| Duplex_p5_oligo179 | ACACTCTTTCCCTACACGACGCTCTTCCGATCTCTTCGCGGTGACT | 357 |
| Duplex_p7_oligo179 | GTCACCGCGAAGAGATCGGAAGAGCACACGTCTGAACTCCAGTCACAC | 358 |
| Duplex_p5_oligo180 | ACACTCTTTCCCTACACGACGCTCTTCCGATCTATGATGAGTGACT | 359 |
| Duplex_p7_oligo180 | GTCACTCATCATAGATCGGAAGAGCACACGTCTGAACTCCAGTCACAC | 360 |
| Duplex_p5_oligo181 | ACACTCTTTCCCTACACGACGCTCTTCCGATCTCCGAACGTTGACT | 361 |
| Duplex_p7_oligo181 | GTCAACGTTCGGAGATCGGAAGAGCACACGTCTGAACTCCAGTCACAC | 362 |
| Duplex_p5_oligo182 | ACACTCTTTCCCTACACGACGCTCTTCCGATCTTAGTGGGTTGACT | 363 |
| Duplex_p7_oligo182 | GTCAACCCACTAAGATCGGAAGAGCACACGTCTGAACTCCAGTCACAC | 364 |
| Duplex_p5_oligo183 | ACACTCTTTCCCTACACGACGCTCTTCCGATCTTAACCGAATGACT | 365 |
| Duplex_p7_oligo183 | GTCATTCGGTTAAGATCGGAAGAGCACACGTCTGAACTCCAGTCACAC | 366 |
| Duplex_p5_oligo184 | ACACTCTTTCCCTACACGACGCTCTTCCGATCTGAGCTAAGTGACT | 367 |
| Duplex_p7_oligo184 | GTCACTTAGCTCAGATCGGAAGAGCACACGTCTGAACTCCAGTCACAC | 368 |
| Duplex_p5_oligo185 | ACACTCTTTCCCTACACGACGCTCTTCCGATCTAGTCACATTGACT | 369 |
| Duplex_p7_oligo185 | GTCAATGTGACTAGATCGGAAGAGCACACGTCTGAACTCCAGTCACAC | 370 |
| Duplex_p5_oligo186 | ACACTCTTTCCCTACACGACGCTCTTCCGATCTTAACCTTCTGACT | 371 |
| Duplex_p7_oligo186 | GTCAGAAGGTTAAGATCGGAAGAGCACACGTCTGAACTCCAGTCACAC | 372 |
| Duplex_p5_oligo187 | ACACTCTTTCCCTACACGACGCTCTTCCGATCTCGATGCTGTGACT | 373 |
| Duplex_p7_oligo187 | GTCACAGCATCGAGATCGGAAGAGCACACGTCTGAACTCCAGTCACAC | 374 |
| Duplex_p5_oligo188 | ACACTCTTTCCCTACACGACGCTCTTCCGATCTATCAGAGCTGACT | 375 |
| Duplex_p7_oligo188 | GTCAGCTCTGATAGATCGGAAGAGCACACGTCTGAACTCCAGTCACAC | 376 |
| Duplex_p5_oligo189 | ACACTCTTTCCCTACACGACGCTCTTCCGATCTAGAGTGCTTGACT | 377 |
| Duplex_p7_oligo189 | GTCAAGCACTCTAGATCGGAAGAGCACACGTCTGAACTCCAGTCACAC | 378 |
| Duplex_p5_oligo190 | ACACTCTTTCCCTACACGACGCTCTTCCGATCTGGTGTGAGTGACT | 379 |
| Duplex_p7_oligo190 | GTCACTCACACCAGATCGGAAGAGCACACGTCTGAACTCCAGTCACAC | 380 |
| Duplex_p5_oligo191 | ACACTCTTTCCCTACACGACGCTCTTCCGATCTTTGCCAAGTGACT | 381 |
| Duplex_p7_oligo191 | GTCACTTGGCAAAGATCGGAAGAGCACACGTCTGAACTCCAGTCACAC | 382 |

TABLE 6-continued

| Nonrandom oligonucleotide adapter | Oligonucleotide adapter Sequence | SEQ ID Nos. |
|---|---|---|
| Duplex_p5_oligo192 | ACACTCTTTCCCTACACGACGCTCTTCCGATCTGTGACGATGACT | 383 |
| Duplex_p7_oligo192 | GTCATCGTCACAGATCGGAAGAGCACACGTCTGAACTCCAGTCACAC | 384 |
| Duplex_p5_oligo193 | ACACTCTTTCCCTACACGACGCTCTTCCGATCTTAGAGGCGTGACT | 385 |
| Duplex_p7_oligo193 | GTCACGCCTCTAAGATCGGAAGAGCACACGTCTGAACTCCAGTCACAC | 386 |
| Duplex_p5_oligo194 | ACACTCTTTCCCTACACGACGCTCTTCCGATCTGGCCAAGGTGACT | 387 |
| Duplex_p7_oligo194 | GTCACCTTGGCCAGATCGGAAGAGCACACGTCTGAACTCCAGTCACAC | 388 |
| Duplex_p5_oligo195 | ACACTCTTTCCCTACACGACGCTCTTCCGATCTTCCTCACTTGACT | 389 |
| Duplex_p7_oligo195 | GTCAAGTGAGGAAGATCGGAAGAGCACACGTCTGAACTCCAGTCACAC | 390 |
| Duplex_p5_oligo196 | ACACTCTTTCCCTACACGACGCTCTTCCGATCTACCCAGTATGACT | 391 |
| Duplex_p7_oligo196 | GTCATACTGGGTAGATCGGAAGAGCACACGTCTGAACTCCAGTCACAC | 392 |
| Duplex_p5_oligo197 | ACACTCTTTCCCTACACGACGCTCTTCCGATCTGACGGCTATGACT | 393 |
| Duplex_p7_oligo197 | GTCATAGCCGTCAGATCGGAAGAGCACACGTCTGAACTCCAGTCACAC | 394 |
| Duplex_p5_oligo198 | ACACTCTTTCCCTACACGACGCTCTTCCGATCTCGTGTAGTTGACT | 395 |
| Duplex_p7_oligo198 | GTCAACTACACGAGATCGGAAGAGCACACGTCTGAACTCCAGTCACAC | 396 |
| Duplex_p5_oligo199 | ACACTCTTTCCCTACACGACGCTCTTCCGATCTAAGCGTACTGACT | 397 |
| Duplex_p7_oligo199 | GTCAGTACGCTTAGATCGGAAGAGCACACGTCTGAACTCCAGTCACAC | 398 |
| Duplex_p5_oligo200 | ACACTCTTTCCCTACACGACGCTCTTCCGATCTATTATCGTTGACT | 399 |
| Duplex_p7_oligo200 | GTCAACGATAATAGATCGGAAGAGCACACGTCTGAACTCCAGTCACAC | 400 |
| Duplex_p5_oligo201 | ACACTCTTTCCCTACACGACGCTCTTCCGATCTCCGCATGATGACT | 401 |
| Duplex_p7_oligo201 | GTCATCATGCGGAGATCGGAAGAGCACACGTCTGAACTCCAGTCACAC | 402 |
| Duplex_p5_oligo202 | ACACTCTTTCCCTACACGACGCTCTTCCGATCTCACTAGACTGACT | 403 |
| Duplex_p7_oligo202 | GTCAGTCTAGTGAGATCGGAAGAGCACACGTCTGAACTCCAGTCACAC | 404 |
| Duplex_p5_oligo203 | ACACTCTTTCCCTACACGACGCTCTTCCGATCTAACGTCCTTGACT | 405 |
| Duplex_p7_oligo203 | GTCAAGGACGTTAGATCGGAAGAGCACACGTCTGAACTCCAGTCACAC | 406 |
| Duplex_p5_oligo204 | ACACTCTTTCCCTACACGACGCTCTTCCGATCTCTTGACGATGACT | 407 |
| Duplex_p7_oligo204 | GTCATCGTCAAGAGATCGGAAGAGCACACGTCTGAACTCCAGTCACAC | 408 |
| Duplex_p5_oligo205 | ACACTCTTTCCCTACACGACGCTCTTCCGATCTGTTCTTGGTGACT | 409 |
| Duplex_p7_oligo205 | GTCACCAAGAACAGATCGGAAGAGCACACGTCTGAACTCCAGTCACAC | 410 |
| Duplex_p5_oligo206 | ACACTCTTTCCCTACACGACGCTCTTCCGATCTCAAGCTAGTGACT | 411 |
| Duplex_p7_oligo206 | GTCACTAGCTTGAGATCGGAAGAGCACACGTCTGAACTCCAGTCACAC | 412 |
| Duplex_p5_oligo207 | ACACTCTTTCCCTACACGACGCTCTTCCGATCTCATAAGGGTGACT | 413 |
| Duplex_p7_oligo207 | GTCACCCTTATGAGATCGGAAGAGCACACGTCTGAACTCCAGTCACAC | 414 |
| Duplex_p5_oligo208 | ACACTCTTTCCCTACACGACGCTCTTCCGATCTTATGGCCATGACT | 415 |
| Duplex_p7_oligo208 | GTCATGGCCATAAGATCGGAAGAGCACACGTCTGAACTCCAGTCACAC | 416 |
| Duplex_p5_oligo209 | ACACTCTTTCCCTACACGACGCTCTTCCGATCTCCGCTACGTGACT | 417 |
| Duplex_p7_oligo209 | GTCACGTAGCGGAGATCGGAAGAGCACACGTCTGAACTCCAGTCACAC | 418 |
| Duplex_p5_oligo210 | ACACTCTTTCCCTACACGACGCTCTTCCGATCTTTAGTACGTGACT | 419 |
| Duplex_p7_oligo210 | GTCACGTACTAAAGATCGGAAGAGCACACGTCTGAACTCCAGTCACAC | 420 |

TABLE 6-continued

| Nonrandom oligonucleotide adapter | Oligonucleotide adapter Sequence | SEQ ID Nos. |
|---|---|---|
| Duplex_p5_oligo211 | ACACTCTTTCCCTACACGACGCTCTTCCGATCTTCTTGTTTTGACT | 421 |
| Duplex_p7_oligo211 | GTCAAAACAAGAAGATCGGAAGAGCACACGTCTGAACTCCAGTCACAC | 422 |
| Duplex_p5_oligo212 | ACACTCTTTCCCTACACGACGCTCTTCCGATCTTGAGTGGTTGACT | 423 |
| Duplex_p7_oligo212 | GTCAACCACTCAAGATCGGAAGAGCACACGTCTGAACTCCAGTCACAC | 424 |
| Duplex_p5_oligo213 | ACACTCTTTCCCTACACGACGCTCTTCCGATCTCAACCGAGTGACT | 425 |
| Duplex_p7_oligo213 | GTCACTCGGTTGAGATCGGAAGAGCACACGTCTGAACTCCAGTCACAC | 426 |
| Duplex_p5_oligo214 | ACACTCTTTCCCTACACGACGCTCTTCCGATCTGGACAGTGTGACT | 427 |
| Duplex_p7_oligo214 | GTCACACTGTCCAGATCGGAAGAGCACACGTCTGAACTCCAGTCACAC | 428 |
| Duplex_p5_oligo215 | ACACTCTTTCCCTACACGACGCTCTTCCGATCTATAGAGGCTGACT | 429 |
| Duplex_p7_oligo215 | GTCAGCCTCTATAGATCGGAAGAGCACACGTCTGAACTCCAGTCACAC | 430 |
| Duplex_p5_oligo216 | ACACTCTTTCCCTACACGACGCTCTTCCGATCTGTGACGTTTGACT | 431 |
| Duplex_p7_oligo216 | GTCAAACGTCACAGATCGGAAGAGCACACGTCTGAACTCCAGTCACAC | 432 |
| Duplex_p5_oligo217 | ACACTCTTTCCCTACACGACGCTCTTCCGATCTGGTCTCCTTGACT | 433 |
| Duplex_p7_oligo217 | GTCAAGGAGACCAGATCGGAAGAGCACACGTCTGAACTCCAGTCACAC | 434 |
| Duplex_p5_oligo218 | ACACTCTTTCCCTACACGACGCTCTTCCGATCTGGAAGAAGTGACT | 435 |
| Duplex_p7_oligo218 | GTCACTTCTTCCAGATCGGAAGAGCACACGTCTGAACTCCAGTCACAC | 436 |
| Duplex_p5_oligo219 | ACACTCTTTCCCTACACGACGCTCTTCCGATCTTTGAACAATGACT | 437 |
| Duplex_p7_oligo219 | GTCATTGTTCAAAGATCGGAAGAGCACACGTCTGAACTCCAGTCACAC | 438 |
| Duplex_p5_oligo220 | ACACTCTTTCCCTACACGACGCTCTTCCGATCTTGAGGACTTGACT | 439 |
| Duplex_p7_oligo220 | GTCAAGTCCTCAAGATCGGAAGAGCACACGTCTGAACTCCAGTCACAC | 440 |
| Duplex_p5_oligo221 | ACACTCTTTCCCTACACGACGCTCTTCCGATCTGGACCAAGTGACT | 441 |
| Duplex_p7_oligo221 | GTCACTTGGTCCAGATCGGAAGAGCACACGTCTGAACTCCAGTCACAC | 442 |
| Duplex_p5_oligo222 | ACACTCTTTCCCTACACGACGCTCTTCCGATCTCCTGCTTCTGACT | 443 |
| Duplex_p7_oligo222 | GTCAGAAGCAGGAGATCGGAAGAGCACACGTCTGAACTCCAGTCACAC | 444 |
| Duplex_p5_oligo223 | ACACTCTTTCCCTACACGACGCTCTTCCGATCTCCTATGCATGACT | 445 |
| Duplex_p7_oligo223 | GTCATGCATAGGAGATCGGAAGAGCACACGTCTGAACTCCAGTCACAC | 446 |
| Duplex_p5_oligo224 | ACACTCTTTCCCTACACGACGCTCTTCCGATCTCGGTCAATTGACT | 447 |
| Duplex_p7_oligo224 | GTCAATTGACCGAGATCGGAAGAGCACACGTCTGAACTCCAGTCACAC | 448 |
| Duplex_p5_oligo225 | ACACTCTTTCCCTACACGACGCTCTTCCGATCTACACCCTATGACT | 449 |
| Duplex_p7_oligo225 | GTCATAGGGTGTAGATCGGAAGAGCACACGTCTGAACTCCAGTCACAC | 450 |
| Duplex_p5_oligo226 | ACACTCTTTCCCTACACGACGCTCTTCCGATCTGGATTACGTGACT | 451 |
| Duplex_p7_oligo226 | GTCACGTAATCCAGATCGGAAGAGCACACGTCTGAACTCCAGTCACAC | 452 |
| Duplex_p5_oligo227 | ACACTCTTTCCCTACACGACGCTCTTCCGATCTTGTTGACGTGACT | 453 |
| Duplex_p7_oligo227 | GTCACGTCAACAAGATCGGAAGAGCACACGTCTGAACTCCAGTCACAC | 454 |
| Duplex_p5_oligo228 | ACACTCTTTCCCTACACGACGCTCTTCCGATCTGGTGACTATGACT | 455 |
| Duplex_p7_oligo228 | GTCATAGTCACCAGATCGGAAGAGCACACGTCTGAACTCCAGTCACAC | 456 |
| Duplex_p5_oligo229 | ACACTCTTTCCCTACACGACGCTCTTCCGATCTTGCAACTTTGACT | 457 |
| Duplex_p7_oligo229 | GTCAAAGTTGCAAGATCGGAAGAGCACACGTCTGAACTCCAGTCACAC | 458 |

TABLE 6-continued

| Nonrandom oligonucleotide adapter | Oligonucleotide adapter Sequence | SEQ ID Nos. |
|---|---|---|
| Duplex_p5_oligo230 | ACACTCTTTCCCTACACGACGCTCTTCCGATCTGCCGTTGATGACT | 459 |
| Duplex_p7_oligo230 | GTCATCAACGGCAGATCGGAAGAGCACACGTCTGAACTCCAGTCACAC | 460 |
| Duplex_p5_oligo231 | ACACTCTTTCCCTACACGACGCTCTTCCGATCTACAAGGCATGACT | 461 |
| Duplex_p7_oligo231 | GTCATGCCTTGTAGATCGGAAGAGCACACGTCTGAACTCCAGTCACAC | 462 |
| Duplex_p5_oligo232 | ACACTCTTTCCCTACACGACGCTCTTCCGATCTTATGGTACTGACT | 463 |
| Duplex_p7_oligo232 | GTCAGTACCATAAGATCGGAAGAGCACACGTCTGAACTCCAGTCACAC | 464 |
| Duplex_p5_oligo233 | ACACTCTTTCCCTACACGACGCTCTTCCGATCTAGCTCTAGTGACT | 465 |
| Duplex_p7_oligo233 | GTCACTAGAGCTAGATCGGAAGAGCACACGTCTGAACTCCAGTCACAC | 466 |
| Duplex_p5_oligo234 | ACACTCTTTCCCTACACGACGCTCTTCCGATCTCCTGGCTGTGACT | 467 |
| Duplex_p7_oligo234 | GTCACAGCCAGGAGATCGGAAGAGCACACGTCTGAACTCCAGTCACAC | 468 |
| Duplex_p5_oligo235 | ACACTCTTTCCCTACACGACGCTCTTCCGATCTGGCATTAGTGACT | 469 |
| Duplex_p7_oligo235 | GTCACTAATGCCAGATCGGAAGAGCACACGTCTGAACTCCAGTCACAC | 470 |
| Duplex_p5_oligo236 | ACACTCTTTCCCTACACGACGCTCTTCCGATCTCAATCGGCTGACT | 471 |
| Duplex_p7_oligo236 | GTCAGCCGATTGAGATCGGAAGAGCACACGTCTGAACTCCAGTCACAC | 472 |
| Duplex_p5_oligo237 | ACACTCTTTCCCTACACGACGCTCTTCCGATCTAGGTCATCTGACT | 473 |
| Duplex_p7_oligo237 | GTCAGATGACCTAGATCGGAAGAGCACACGTCTGAACTCCAGTCACAC | 474 |
| Duplex_p5_oligo238 | ACACTCTTTCCCTACACGACGCTCTTCCGATCTGAGAGATCTGACT | 475 |
| Duplex_p7_oligo238 | GTCAGATCTCTCAGATCGGAAGAGCACACGTCTGAACTCCAGTCACAC | 476 |
| Duplex_p5_oligo239 | ACACTCTTTCCCTACACGACGCTCTTCCGATCTGGAGCTCTTGACT | 477 |
| Duplex_p7_oligo239 | GTCAAGAGCTCCAGATCGGAAGAGCACACGTCTGAACTCCAGTCACAC | 478 |
| Duplex_p5_oligo240 | ACACTCTTTCCCTACACGACGCTCTTCCGATCTCCTAAACTTGACT | 479 |
| Duplex_p7_oligo240 | GTCAAGTTTAGGAGATCGGAAGAGCACACGTCTGAACTCCAGTCACAC | 480 |
| Duplex_p5_oligo241 | ACACTCTTTCCCTACACGACGCTCTTCCGATCTACCGACGCTGACT | 481 |
| Duplex_p7_oligo241 | GTCAGCGTCGGTAGATCGGAAGAGCACACGTCTGAACTCCAGTCACAC | 482 |
| Duplex_p5_oligo242 | ACACTCTTTCCCTACACGACGCTCTTCCGATCTAGACTCAGTGACT | 483 |
| Duplex_p7_oligo242 | GTCACTGAGTCTAGATCGGAAGAGCACACGTCTGAACTCCAGTCACAC | 484 |
| Duplex_p5_oligo243 | ACACTCTTTCCCTACACGACGCTCTTCCGATCTTAGTAGCATGACT | 485 |
| Duplex_p7_oligo243 | GTCATGCTACTAAGATCGGAAGAGCACACGTCTGAACTCCAGTCACAC | 486 |
| Duplex_p5_oligo244 | ACACTCTTTCCCTACACGACGCTCTTCCGATCTGCGCTGTTTGACT | 487 |
| Duplex_p7_oligo244 | GTCAAACAGCGCAGATCGGAAGAGCACACGTCTGAACTCCAGTCACAC | 488 |
| Duplex_p5_oligo245 | ACACTCTTTCCCTACACGACGCTCTTCCGATCTCTATAGACTGACT | 489 |
| Duplex_p7_oligo245 | GTCAGTCTATAGAGATCGGAAGAGCACACGTCTGAACTCCAGTCACAC | 490 |
| Duplex_p5_oligo246 | ACACTCTTTCCCTACACGACGCTCTTCCGATCTAGCGGCCTTGACT | 491 |
| Duplex_p7_oligo246 | GTCAAGGCCGCTAGATCGGAAGAGCACACGTCTGAACTCCAGTCACAC | 492 |
| Duplex_p5_oligo247 | ACACTCTTTCCCTACACGACGCTCTTCCGATCTCTCACAACTGACT | 493 |
| Duplex_p7_oligo247 | GTCAGTTGTGAGAGATCGGAAGAGCACACGTCTGAACTCCAGTCACAC | 494 |
| Duplex_p5_oligo248 | ACACTCTTTCCCTACACGACGCTCTTCCGATCTGTATAGTCTGACT | 495 |
| Duplex_p7_oligo248 | GTCAGACTATACAGATCGGAAGAGCACACGTCTGAACTCCAGTCACAC | 496 |

TABLE 6-continued

| Nonrandom oligonucleotide adapter | Oligonucleotide adapter Sequence | SEQ ID Nos. |
|---|---|---|
| Duplex_p5_oligo249 | ACACTCTTTCCCTACACGACGCTCTTCCGATCTCCATCCGCTGACT | 497 |
| Duplex_p7_oligo249 | GTCAGCGGATGGAGATCGGAAGAGCACACGTCTGAACTCCAGTCACAC | 498 |
| Duplex_p5_oligo250 | ACACTCTTTCCCTACACGACGCTCTTCCGATCTACTAATACTGACT | 499 |
| Duplex_p7_oligo250 | GTCAGTATTAGTAGATCGGAAGAGCACACGTCTGAACTCCAGTCACAC | 500 |
| Duplex_p5_oligo251 | ACACTCTTTCCCTACACGACGCTCTTCCGATCTGCGTAGAGTGACT | 501 |
| Duplex_p7_oligo251 | GTCACTCTACGCAGATCGGAAGAGCACACGTCTGAACTCCAGTCACAC | 502 |
| Duplex_p5_oligo252 | ACACTCTTTCCCTACACGACGCTCTTCCGATCTGCCTGATTTGACT | 503 |
| Duplex_p7_oligo252 | GTCAAATCAGGCAGATCGGAAGAGCACACGTCTGAACTCCAGTCACAC | 504 |
| Duplex_p5_oligo253 | ACACTCTTTCCCTACACGACGCTCTTCCGATCTTGACAACCTGACT | 505 |
| Duplex_p7_oligo253 | GTCAGGTTGTCAAGATCGGAAGAGCACACGTCTGAACTCCAGTCACAC | 506 |
| Duplex_p5_oligo254 | ACACTCTTTCCCTACACGACGCTCTTCCGATCTGATAATGTTGACT | 507 |
| Duplex_p7_oligo254 | GTCAACATTATCAGATCGGAAGAGCACACGTCTGAACTCCAGTCACAC | 508 |
| Duplex_p5_oligo255 | ACACTCTTTCCCTACACGACGCTCTTCCGATCTTAGGACGGTGACT | 509 |
| Duplex_p7_oligo255 | GTCACCGTCCTAAGATCGGAAGAGCACACGTCTGAACTCCAGTCACAC | 510 |
| Duplex_p5_oligo256 | ACACTCTTTCCCTACACGACGCTCTTCCGATCTCAACTAGATGACT | 511 |
| Duplex_p7_oligo256 | GTCATCTAGTTGAGATCGGAAGAGCACACGTCTGAACTCCAGTCACAC | 512 |
| Duplex_p5_oligo257 | ACACTCTTTCCCTACACGACGCTCTTCCGATCTCTTCCAACTGACT | 513 |
| Duplex_p7_oligo257 | GTCAGTTGGAAGAGATCGGAAGAGCACACGTCTGAACTCCAGTCACAC | 514 |
| Duplex_p5_oligo258 | ACACTCTTTCCCTACACGACGCTCTTCCGATCTTAGCTGGCTGACT | 515 |
| Duplex_p7_oligo258 | GTCAGCCAGCTAAGATCGGAAGAGCACACGTCTGAACTCCAGTCACAC | 516 |
| Duplex_p5_oligo259 | ACACTCTTTCCCTACACGACGCTCTTCCGATCTGTTCCTCCTGACT | 517 |
| Duplex_p7_oligo259 | GTCAGGAGGAACAGATCGGAAGAGCACACGTCTGAACTCCAGTCACAC | 518 |
| Duplex_p5_oligo260 | ACACTCTTTCCCTACACGACGCTCTTCCGATCTAGTGACTGTGACT | 519 |
| Duplex_p7_oligo260 | GTCACAGTCACTAGATCGGAAGAGCACACGTCTGAACTCCAGTCACAC | 520 |
| Duplex_p5_oligo261 | ACACTCTTTCCCTACACGACGCTCTTCCGATCTGGCCAGTTTGACT | 521 |
| Duplex_p7_oligo261 | GTCAAACTGGCCAGATCGGAAGAGCACACGTCTGAACTCCAGTCACAC | 522 |
| Duplex_p5_oligo262 | ACACTCTTTCCCTACACGACGCTCTTCCGATCTGCCTCAGCTGACT | 523 |
| Duplex_p7_oligo262 | GTCAGCTGAGGCAGATCGGAAGAGCACACGTCTGAACTCCAGTCACAC | 524 |
| Duplex_p5_oligo263 | ACACTCTTTCCCTACACGACGCTCTTCCGATCTAGAACACGTGACT | 525 |
| Duplex_p7_oligo263 | GTCACGTGTTCTAGATCGGAAGAGCACACGTCTGAACTCCAGTCACAC | 526 |
| Duplex_p5_oligo264 | ACACTCTTTCCCTACACGACGCTCTTCCGATCTCCTTTCACTGACT | 527 |
| Duplex_p7_oligo264 | GTCAGTGAAAGGAGATCGGAAGAGCACACGTCTGAACTCCAGTCACAC | 528 |
| Duplex_p5_oligo265 | ACACTCTTTCCCTACACGACGCTCTTCCGATCTTTGGTCTCTGACT | 529 |
| Duplex_p7_oligo265 | GTCAGAGACCAAAGATCGGAAGAGCACACGTCTGAACTCCAGTCACAC | 530 |
| Duplex_p5_oligo266 | ACACTCTTTCCCTACACGACGCTCTTCCGATCTGGCTGCATTGACT | 531 |
| Duplex_p7_oligo266 | GTCAATGCAGCCAGATCGGAAGAGCACACGTCTGAACTCCAGTCACAC | 532 |
| Duplex_p5_oligo267 | ACACTCTTTCCCTACACGACGCTCTTCCGATCTCTCGAAATTGACT | 533 |
| Duplex_p7_oligo267 | GTCAATTTCGAGAGATCGGAAGAGCACACGTCTGAACTCCAGTCACAC | 534 |

TABLE 6-continued

| Nonrandom oligonucleotide adapter | Oligonucleotide adapter Sequence | SEQ ID Nos. |
|---|---|---|
| Duplex_p5_oligo268 | ACACTCTTTCCCTACACGACGCTCTTCCGATCTAATGCGCGTGACT | 535 |
| Duplex_p7_oligo268 | GTCACGCGCATTAGATCGGAAGAGCACACGTCTGAACTCCAGTCACAC | 536 |
| Duplex_p5_oligo269 | ACACTCTTTCCCTACACGACGCTCTTCCGATCTCTTGAACCTGACT | 537 |
| Duplex_p7_oligo269 | GTCAGGTTCAAGAGATCGGAAGAGCACACGTCTGAACTCCAGTCACAC | 538 |
| Duplex_p5_oligo270 | ACACTCTTTCCCTACACGACGCTCTTCCGATCTTAATACGGTGACT | 539 |
| Duplex_p7_oligo270 | GTCACCGTATTAAGATCGGAAGAGCACACGTCTGAACTCCAGTCACAC | 540 |
| Duplex_p5_oligo271 | ACACTCTTTCCCTACACGACGCTCTTCCGATCTGACAATTCTGACT | 541 |
| Duplex_p7_oligo271 | GTCAGAATTGTCAGATCGGAAGAGCACACGTCTGAACTCCAGTCACAC | 542 |
| Duplex_p5_oligo272 | ACACTCTTTCCCTACACGACGCTCTTCCGATCTTGTACGGATGACT | 543 |
| Duplex_p7_oligo272 | GTCATCCGTACAAGATCGGAAGAGCACACGTCTGAACTCCAGTCACAC | 544 |
| Duplex_p5_oligo273 | ACACTCTTTCCCTACACGACGCTCTTCCGATCTGCCACGACTGACT | 545 |
| Duplex_p7_oligo273 | GTCAGTCGTGGCAGATCGGAAGAGCACACGTCTGAACTCCAGTCACAC | 546 |
| Duplex_p5_oligo274 | ACACTCTTTCCCTACACGACGCTCTTCCGATCTTCCATCGATGACT | 547 |
| Duplex_p7_oligo274 | GTCATCGATGGAAGATCGGAAGAGCACACGTCTGAACTCCAGTCACAC | 548 |
| Duplex_p5_oligo275 | ACACTCTTTCCCTACACGACGCTCTTCCGATCTTTCTCCATTGACT | 549 |
| Duplex_p7_oligo275 | GTCAATGGAGAAAGATCGGAAGAGCACACGTCTGAACTCCAGTCACAC | 550 |
| Duplex_p5_oligo276 | ACACTCTTTCCCTACACGACGCTCTTCCGATCTGTGGCCTATGACT | 551 |
| Duplex_p7_oligo276 | GTCATAGGCCACAGATCGGAAGAGCACACGTCTGAACTCCAGTCACAC | 552 |
| Duplex_p5_oligo277 | ACACTCTTTCCCTACACGACGCTCTTCCGATCTCTGGGAGTTGACT | 553 |
| Duplex_p7_oligo277 | GTCAACTCCCAGAGATCGGAAGAGCACACGTCTGAACTCCAGTCACAC | 554 |
| Duplex_p5_oligo278 | ACACTCTTTCCCTACACGACGCTCTTCCGATCTTTGCTGGATGACT | 555 |
| Duplex_p7_oligo278 | GTCATCCAGCAAAGATCGGAAGAGCACACGTCTGAACTCCAGTCACAC | 556 |
| Duplex_p5_oligo279 | ACACTCTTTCCCTACACGACGCTCTTCCGATCTCTTCAAGATGACT | 557 |
| Duplex_p7_oligo279 | GTCATCTTGAAGAGATCGGAAGAGCACACGTCTGAACTCCAGTCACAC | 558 |
| Duplex_p5_oligo280 | ACACTCTTTCCCTACACGACGCTCTTCCGATCTCATATCCATGACT | 559 |
| Duplex_p7_oligo280 | GTCATGGATATGAGATCGGAAGAGCACACGTCTGAACTCCAGTCACAC | 560 |
| Duplex_p5_oligo281 | ACACTCTTTCCCTACACGACGCTCTTCCGATCTAGACGTTGTGACT | 561 |
| Duplex_p7_oligo281 | GTCACAACGTCTAGATCGGAAGAGCACACGTCTGAACTCCAGTCACAC | 562 |
| Duplex_p5_oligo282 | ACACTCTTTCCCTACACGACGCTCTTCCGATCTATTCGAGCTGACT | 563 |
| Duplex_p7_oligo282 | GTCAGCTCGAATAGATCGGAAGAGCACACGTCTGAACTCCAGTCACAC | 564 |
| Duplex_p5_oligo283 | ACACTCTTTCCCTACACGACGCTCTTCCGATCTCTTGCATATGACT | 565 |
| Duplex_p7_oligo283 | GTCATATGCAAGAGATCGGAAGAGCACACGTCTGAACTCCAGTCACAC | 566 |
| Duplex_p5_oligo284 | ACACTCTTTCCCTACACGACGCTCTTCCGATCTATACAAACTGACT | 567 |
| Duplex_p7_oligo284 | GTCAGTTTGTATAGATCGGAAGAGCACACGTCTGAACTCCAGTCACAC | 568 |
| Duplex_p5_oligo285 | ACACTCTTTCCCTACACGACGCTCTTCCGATCTATGTTCCTTGACT | 569 |
| Duplex_p7_oligo285 | GTCAAGGAACATAGATCGGAAGAGCACACGTCTGAACTCCAGTCACAC | 570 |
| Duplex_p5_oligo286 | ACACTCTTTCCCTACACGACGCTCTTCCGATCTTGCACAGTTGACT | 571 |
| Duplex_p7_oligo286 | GTCAACTGTGCAAGATCGGAAGAGCACACGTCTGAACTCCAGTCACAC | 572 |

TABLE 6-continued

| Nonrandom oligonucleotide adapter | Oligonucleotide adapter Sequence | SEQ ID Nos. |
|---|---|---|
| Duplex_p5_oligo287 | ACACTCTTTCCCTACACGACGCTCTTCCGATCTACATGCACTGACT | 573 |
| Duplex_p7_oligo287 | GTCAGTGCATGTAGATCGGAAGAGCACACGTCTGAACTCCAGTCACAC | 574 |
| Duplex_p5_oligo288 | ACACTCTTTCCCTACACGACGCTCTTCCGATCTTACGGCAGTGACT | 575 |
| Duplex_p7_oligo288 | GTCACTGCCGTAAGATCGGAAGAGCACACGTCTGAACTCCAGTCACAC | 576 |

Example 10: Validation of Sequencing Adapters Containing Predetermined Non-Randomly Generated Bar Codes A series of different adapter constructs were tested for library preparation efficiency. FIG. 13 compares library preparation efficiency of duplex adapters in Y-adapter form, including those containing random base compositions (random duplex Y adapter, or "RDA-Y") and nonrandom base compositions (nonrandom duplex Y adapter "FDA-Y"), and a nonrandom duplex sequence adapter construct in hairpin-adapter form (nonrandom duplex hairpin adapter, or "FDA-hp"). FDA-Y adapters yielded the best results as indicated by the highest library concentration they produced.

Figure 14:
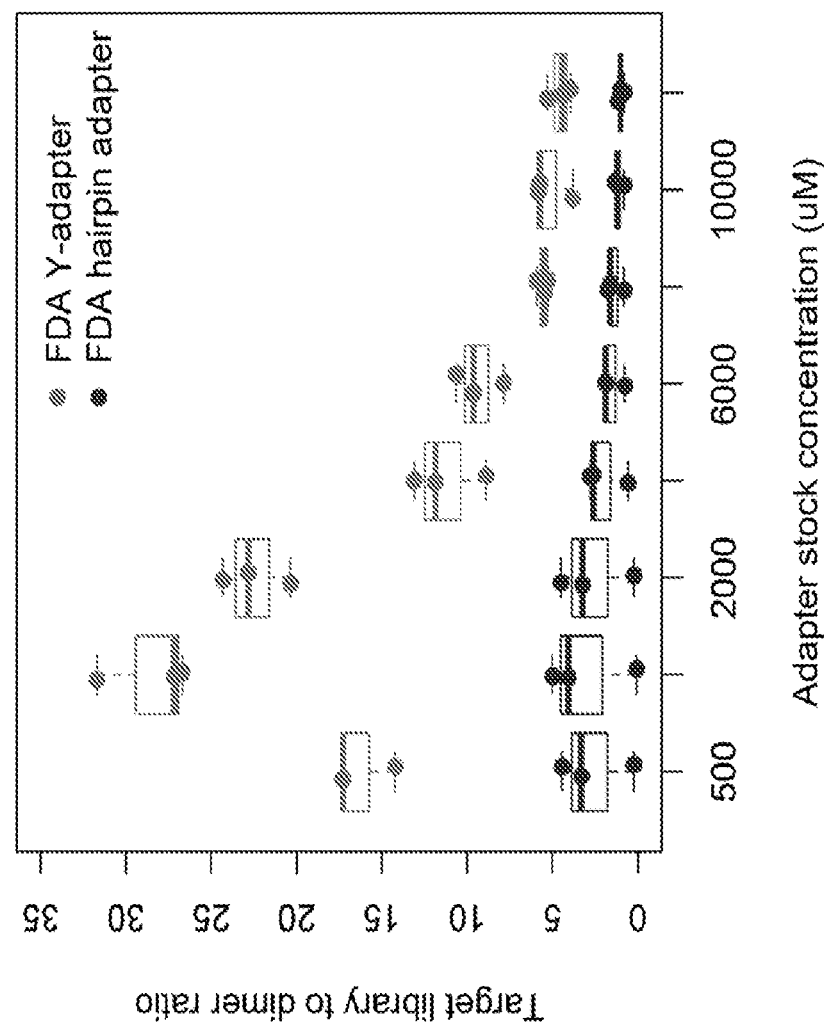
FIG. 14 shows an embodiment of confirmation of the efficiency of utilizing nonrandom duplex Y adapter (FDA-Y) adapters during library preparation and the optimization of their concentration to maximize the target library to adapter dimer ratio.

The efficiency of FDA-Y adapters was then confirmed and the input concentration optimized as shown in FIG. 14. FIG. 14 shows the ratio of target library to adapter dimer ratio at varying input concentrations of FDA-Y adapters and FDA-hp adapters. Using the ratio of target library, the desired product, to adapter dimers, an undesired product, as a response metric allowed optimization of adapter type and input concentration to maximize assay efficiency and sensitivity. Again, FDA-Y adapters yielded the best results. In FIG. 14, the X axis shows the stock concentrations of the adapters and stock solutions of the adapters were diluted 1:10,000 in ligation reaction. In this experiment, the target library used was 25-30 ng cell free DNA. The results also demonstrate that FDA-Y adapters, when used in concentrations of 50-600 nM in preparing target library, advantageously yielded products having high target library to dimer ratios, i.e., ratios in the range of 9-30. In experiments depicted in FIG. 14, 100 nM FDA-Y produced the highest target library to dimer ratio.

Figure 15:
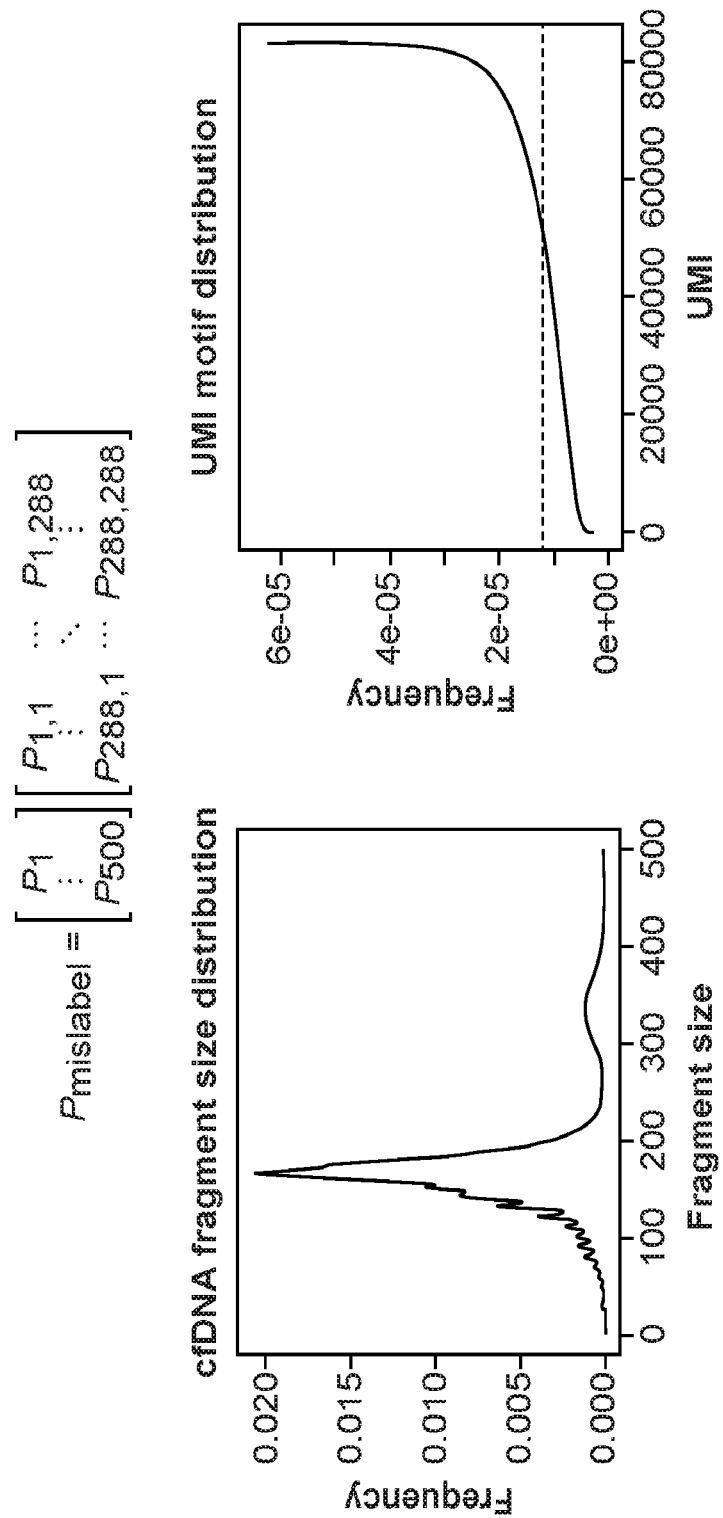
FIG. 15 shows an embodiment of modeling the likelihood of identical labeling given the likelihood of identical fragment patterns.

FIG. 15 shows the likelihood of mislabeling, i.e., the undesirable outcome of two different molecules having the same adapter and fragmentation pattern, thus negating the benefits of including unique molecule identifiers in the library preparation process. Because both cfDNA fragment size and fixed duplex adapter unique molecular index (UMI) motif diversity can be empirically determined, the likelihood value can be calculated as the product of these probability vectors. This probability vector was simulated over a hypothetical 100 kilobase (kb) panel at fixed depth of template diversity (ranging from 500 to 2500 fold unique coverage) for 1000 in silico samples at each level. As further proof of concept, FIG. 16 shows the number of incorrectly labeled molecules, unique templates indistinguishable from each other on the basis of labeling and fragmentation, tallied for each simulated sample across the 100 kb panel. On average, less than one mislabeled molecule was observed for all samples with less than 2500 fold unique depth of coverage. This shows that the method is reliable in preparing target libraries as described.

Figure 17:
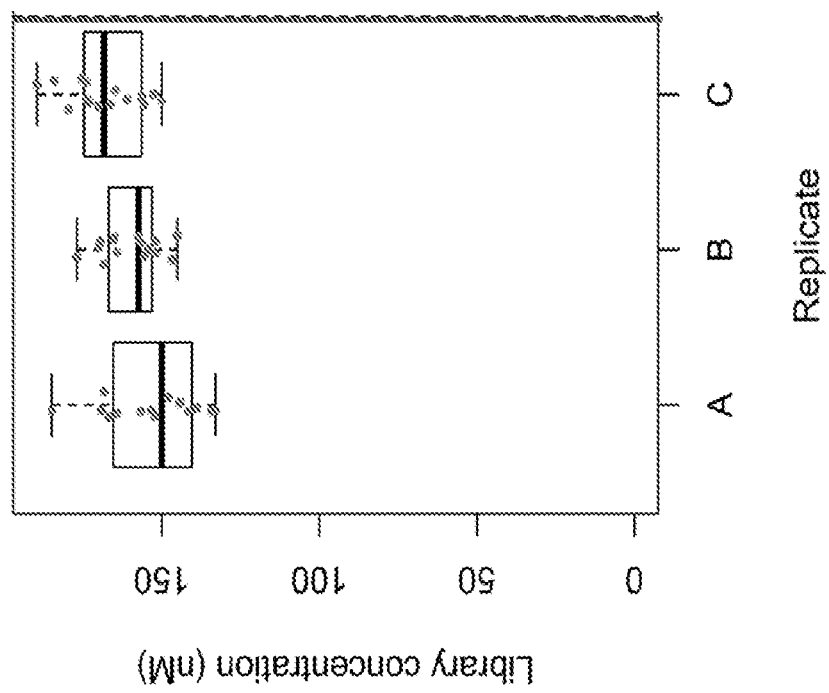
FIG. 17 shows an embodiment demonstrating that the library preparation process is consistent and reproducible over consecutive runs.

Library preparation utilizing FDA-Y adapters is consistently reproducible from run to run, as shown in FIG. 17. A series of samples were processed across three consecutive library preparations. Using library concentration as a response variable, the results were consistent from run to run—the CV of all replicates was about 8.1%. This result showed that indicating the process is reproducible over time.

Example 11: Examples of Embodiments

Provided hereafter are non-limiting examples of embodiments.

A1. A method of determining a sequence of nucleotides for one or more nucleic acid templates in a nucleic acid sample, comprising:
  contacting double-stranded nucleic acid templates of the nucleic acid sample with partially double-stranded nonrandom oligonucleotide adapter species under ligation conditions, thereby generating adapter-ligated nucleic acid templates, wherein:
  each of the nonrandom oligonucleotide adapter species comprises or consists of a first oligonucleotide species and a second oligonucleotide species; wherein optionally:
    each of the first oligonucleotide species comprises 5' to 3' a polynucleotide A and a polynucleotide B species and each of the second oligonucleotide species comprises 5' to 3' a polynucleotide B' species and a polynucleotide A';
    each of the polynucleotide B species and the polynucleotide B' species are predetermined, are nonrandomly generated, are the same length, and are about 4 to about 20 consecutive nucleotides in length;
    there are 999 or fewer polynucleotide B species and each polynucleotide B' species is a reverse complement of a polynucleotide B species;
    the ratio of nucleic acid templates to polynucleotide B species is greater than 1,000 to 1:
    polynucleotide A is not a reverse complement of polynucleotide A'; and
    the polynucleotide B species are annealed to complementary polynucleotide B' species and polynucleotide A' is not annealed to polynucleotide A; and
  amplifying the adapter-ligated nucleic acid templates, thereby generating amplicons; and
  sequencing all or a portion of each amplicon, thereby determining a sequence of nucleotides for one or more nucleic acid templates in the nucleic acid sample.

A.1.1 The method of A1 wherein each of the nonrandom oligonucleotide adapter species comprises or consists of a first oligonucleotide species and a second oligonucleotide species, wherein each of the first oligonucleotide species comprises 5' to 3' a polynucleotide A and a polynucleotide B species and each of the second oligonucleotide species comprises 5' to 3' a polynucleotide B' species and a polynucleotide A', and each of the polynucleotide B species and the polynucleotide B' species are predetermined, are nonrandomly generated and polynucleotide A is not a reverse complement of polynucleotide A'.

A1.2 The method of A1 wherein each of the polynucleotide B species are the same length, and are about 4 to about 20 consecutive nucleotides in length.

A1.3 The method of A1, wherein there are 999 or fewer polynucleotide B species and each polynucleotide B' species is a reverse complement of a polynucleotide B species.

A1.4 The method of A1, wherein the polynucleotide B species are annealed to complementary polynucleotide B' species and polynucleotide A' is not annealed to polynucleotide A A2. The method of embodiment A1, wherein the polynucleotide B species and the polynucleotide B' species are non-degenerate.

A3. The method of embodiment A1, wherein the polynucleotide B species and the polynucleotide B' species are non-semidegenerate.

A4. The method of any one of embodiments A1-A3, wherein
  each of the first oligonucleotide species comprises a polynucleotide C species between polynucleotide A and the polynucleotide B species;
  each of the second oligonucleotide species comprises a polynucleotide C' species between polynucleotide A' and the polynucleotide B' species;
  each polynucleotide C' species is the reverse complement of the polynucleotide C species; and
  the polynucleotide C species are annealed to complementary polynucleotide C' species.

A5. The method of embodiment A4, wherein each of the polynucleotide C species comprises or consists of the same nucleotide sequence.

A6. The method of embodiment A4, wherein the polynucleotide C species consist of at least two different nucleotide sequences.

A7. The method of any one of embodiments A1-A6, wherein the double-stranded nucleic acid templates are double-stranded DNA templates.

A8. The method of any one of embodiments A1-A6, wherein the double-stranded nucleic acid templates are double-stranded RNA templates.

A9. The method of any one of embodiments A1-A8, wherein:
  amplifying the adapter-ligated nucleic acid templates generates double-stranded amplicons, and
  sequencing comprises sequencing all or a portion of each strand of the amplicons.

A10. The method of any one of embodiments A1-A8, wherein the adapter-ligated nucleic acid templates are amplified by a process comprising linear amplification.

A11. The method of any one of embodiments A1-A8, wherein the adapter-ligated nucleic acid templates are amplified by a process comprising exponential amplification.

A12. The method of any one of embodiments A1-A8, wherein the adapter-ligated nucleic acid templates are amplified by a process comprising isothermal amplification.

A13 The method of any one of the previous embodiments wherein the first oligonucleotide and second oligonucleotide are partially matched reverse complement pairs selected from SEQ ID NOs: 1-576.

A14. The method of any one of embodiments A1-A13, wherein the double-stranded nucleic acid templates are blunt-ended.

A15. The method of any one of embodiments A1-A13, wherein the nucleic acid templates comprise at least one blunt end.

A116. The method of any one of embodiments A1-A13, wherein the nucleic acid templates are sheared double-stranded DNA templates.

A17. The method of any one of embodiments A1-A13, wherein the nucleic acid templates are restriction enzyme-digested double-stranded DNA templates.

A18. The method of any one of embodiments A1-A17, comprising blunt-ending the nucleic acid templates before contacting the nucleic acid templates with the nonrandom oligonucleotide adapter species.

A19. The method of any one of embodiments A14 and A18, wherein the nonrandom oligonucleotide adapter species comprise a blunt end.

A20. The method of any one of embodiments A1-A19, wherein the double-stranded nucleic acid templates comprise a ligation linker.

A21. The method of any one of embodiments A14 and A15, comprising joining a ligation linker to the blunt end of the nucleic acid template.

A22. The method of any one of embodiments A20-A21, wherein the ligation linker is selected from the group consisting of a A-overhang, T-overhang, a CG-overhang, a blunt end, or any ligatable nucleic acid sequence.

A23. The method of embodiment A22, wherein the ligation linker is an A-overhang.

A24. The method of any one of embodiments A20-A23, wherein the double-stranded nonrandom oligonucleotide adapter species comprises a ligation linker.

A24.1. The method of embodiment A24 wherein the ligation linker is selected from the group consisting of a A-overhang, T-overhang, a CG-overhang, a blunt end, or any ligatable nucleic acid sequence.

A24.2. The method of embodiment A24, wherein the ligation linker is a T-overhang.

A25. The method of any one of embodiments A1-A24.2, wherein the nucleic acid sample is obtained from a subject.

A26. The method of any one of embodiments A1-A25, wherein the nucleic acid is cell-free nucleic acid.

A27. The method of any one of embodiments A1-A25, wherein the nucleic acid sample is blood plasma, blood serum, or urine.

A28. The method of any one of embodiments A1-A25, wherein the nucleic acid sample is circulating cell-free nucleic acid.

A29. The method of any one of embodiments A1-A25, wherein the nucleic acid sample is isolated from blood plasma, blood serum, or urine.

A30. The method of any one of embodiments A1-A25, wherein the nucleic acid sample is isolated from a sample of tissue, cells, or fluid obtained from a subject.

A31. The method of any one of embodiments A1-A30, wherein the subject is human.

A32. The method of any one of embodiments A1-A31, wherein the nucleic acid sample is separated from a sample of tissue, cells, or fluid obtained from a subject.

A33. The method of any one of embodiments A1-A31, wherein the sequence of nucleotides for the one or more nucleic acid templates in the nucleic acid sample is determined in situ.

A34. The method of any one of embodiments A1-A32, comprising capturing a subset of the nucleic acid templates by hybridization to capture probes under hybridization conditions, thereby generated captured nucleic acid templates.

A35. The method of any one of embodiments A1-A32, comprising: enriching for nucleic acid templates representing one or more selected genes by means of amplifying nucleic acid templates in the nucleic acid sample that are complementary to selected genes.

A36. The method of any one of embodiments A34-A35, wherein the method of obtaining the nucleic acid sample comprises eluting captured nucleic acid templates from the capture probes.

A37. The method of any one of embodiments A34-A36, wherein the capture probes are in an array.

A37.1. The method of any one of embodiments A34-A35, wherein the capture probes are attached to beads.

A37.2. The method of any one of embodiments A1-A37.1, wherein the sequencing depth is at about 500 fold to about 150,000 fold.

A38. The method of any one of embodiments A1-A37.1, wherein the sequencing depth is at about 1,000 fold to about 100,000 fold.

A39. The method of any one of embodiments A1-A37.1, wherein the sequencing depth is at about 10,000 fold to about 70,000 fold.

A40. The method of any one of embodiments A1-A37.1, wherein the sequencing depth is at about 20,000 fold to about 60,000 fold.

A41. The method of any one of embodiments A1-A37.1, wherein the sequencing depth is at about 30,000 fold to about 50,000 fold.

A42. The method of any one of embodiments A1-A41, wherein each adapter-ligated nucleic acid template comprises or consists of one nonrandom oligonucleotide adapter at a first end and a standard sequencing adapter at a second end.

A43. The method of embodiment A42, wherein there are fewer than 999 B species, and the ratio of the number of nucleic acid templates for the nucleic acid sample to the number of polynucleotide B species in the nonrandom oligonucleotide adapters is greater than 100,000 to 1.

A44. The method of embodiment A42, wherein there are fewer than 999 B species, and the ratio of the number of nucleic acid templates for the nucleic acid sample to the number of polynucleotide B species in the nonrandom oligonucleotide adapters is greater than 500,000 to 1.

A45. The method of embodiment A42, wherein there are fewer than 999 B species, and the ratio of the number of nucleic acid templates for the nucleic acid sample to the number of polynucleotide B species in the nonrandom oligonucleotide adapters is greater than 9,000,000 to 1.

A46. The method of embodiment A42, wherein there are fewer than 999 B species, and the ratio of the number of nucleic acid templates for the nucleic acid sample to the number of polynucleotide B species in the nonrandom oligonucleotide adapters is about 1,000,000 to 1.

A47. The method of any one of embodiments A42-A46, wherein there are 500 or fewer polynucleotide B species.

A48. The method of any one of embodiments A42-A46, wherein there are 400 or fewer polynucleotide B species.

A49. The method of any one of embodiments A42-A46, wherein there are 300 or fewer polynucleotide B species.

A50. The method of any one of embodiments A42-A46, wherein there are about 200 to about 300 polynucleotide B species.

A51. The method of any one of embodiments A42-A46, wherein there are about 280 to about 290 polynucleotide B species.

A51.1. The method of any one of embodiments A42-A51, wherein less than 90% of the nonrandom oligonucleotide adapter-ligated nucleic acid templates comprise a polynucleotide B species that is different from the polynucleotide B species on the other nonrandom oligonucleotide adapter-ligated nucleic acid templates.

A51.2. The method of any one of embodiments A42-A51, wherein less than 50% of the nonrandom oligonucleotide adapter-ligated nucleic acid templates comprise a polynucleotide B species that is different from the polynucleotide B species on the other nonrandom oligonucleotide adapter-ligated nucleic acid templates.

A52. The method of any one of embodiments A42-A51.2, wherein
the presence of a single nucleotide alteration in the nucleic acid template is determined and the single nucleotide alteration is present at a frequency of 5 percent or lower.

A52.1. The method of any one of embodiments A42-A51.2, wherein
the presence of a single nucleotide alteration in the nucleic acid template is determined and the single nucleotide alteration is present at a frequency of 0.001 percent or lower.

A53. The method of any one of embodiments A42-A52, comprising providing a base call, wherein each base call represents a single nucleotide located at a single nucleotide position in the nucleic acid template.

A54. The method of embodiment A53, wherein the frequency of base call errors is lower than $1 \times 10^{-3}$.

A54.1. The method of embodiment A53, wherein the frequency of base call errors is $0.8 \times 10^{-3}$ or lower.

A54.2. The method of embodiment A53, wherein the frequency of base call errors is $0.5 \times 10^{-3}$ or lower.

A54.3. The method of embodiment A53, wherein the frequency of base call errors is $1 \times 10^{-4}$ or lower.

A54.4. The method of embodiment A53, wherein the frequency of base call errors is $0.5 \times 10^{-4}$ or lower.

A54.5. The method of embodiment A53, wherein the frequency of base call errors is $1 \times 10^{-5}$ or lower.

A55. The method of embodiment A42, wherein
the ratio of the number of nucleic acid templates for the nucleic acid sample to the number of polynucleotide B species in the nonrandom oligonucleotide adapters is greater than 1000 to 1, there are fewer than 300 B species, and
the presence of a single nucleotide alteration in the nucleic acid template is determined and the single nucleotide alteration is present at a frequency of 1 percent or lower.

A56. The method of embodiment A42, wherein
the ratio of the number of nucleic acid templates for the nucleic acid sample to the number of polynucleotide B species in the nonrandom oligonucleotide adapters is greater than 10,000 to 1, there are fewer than 300 B species, and
the presence of a single nucleotide alteration in the nucleic acid template is determined and the single nucleotide alteration is present at a frequency of 1 percent or lower.

A57. The method of embodiment A42, wherein
the ratio of the number of nucleic acid templates for the nucleic acid sample to the number of polynucleotide B species in the nonrandom oligonucleotide adapters is greater than 1000 to 1, there are fewer than 500 B species, and the presence of a single nucleotide alteration in the nucleic acid template is determined and the single nucleotide alteration is present at a frequency of 1 percent or lower.

A58. The method of embodiment A42, wherein
the ratio of the number of nucleic acid templates for the nucleic acid sample to the number of polynucleotide B species in the nonrandom oligonucleotide adapters is greater than 1,000,000 to 1, there are fewer than 300 B species, and
the presence of a single nucleotide alteration in the nucleic acid template is determined and the single nucleotide alteration is present at a frequency of 1 percent or lower.

A59. The method of embodiment A42, wherein
the method comprises base calls, wherein each base call represents a single nucleotide in the nucleic acid template;
the ratio of the number of nucleic acid templates for the nucleic acid sample to the number of polynucleotide B species in the nonrandom oligonucleotide adapters is greater than 1,000,000 to 1; and
the frequency of base call errors is lower than $1 \times 10^{-3}$.

A59.1. The method of embodiment A42, wherein
the method comprises base calls, wherein each base call represents a single nucleotide in the nucleic acid template;
the ratio of the number of nucleic acid templates for the nucleic acid sample to the number of polynucleotide B species in the nonrandom oligonucleotide adapters is greater than 1,000,000 to 1; and
the frequency of base call errors is $0.8 \times 10^{-3}$ or lower.

A59.2. The method of embodiment A42, wherein
the method comprises base calls, wherein each base call represents a single nucleotide in the nucleic acid template;
the ratio of the number of nucleic acid templates for the nucleic acid sample to the number of polynucleotide B species in the nonrandom oligonucleotide adapters is greater than 1,000,000 to 1; and
the frequency of base call errors is $0.5 \times 10^{-3}$ or lower.

A59.3. The method of embodiment A42, wherein
the method comprises base calls, wherein each base call represents a single nucleotide in the nucleic acid template;
the ratio of the number of nucleic acid templates for the nucleic acid sample to the number of polynucleotide B species in the nonrandom oligonucleotide adapters is greater than 1,000,000 to 1; and
the frequency of base call errors is $1 \times 10^{-4}$ or lower.

A59.4. The method of embodiment A42, wherein
the method comprises base calls, wherein each base call represents a single nucleotide in the nucleic acid template;
the ratio of the number of nucleic acid templates for the nucleic acid sample to the number of polynucleotide B species in the nonrandom oligonucleotide adapters is greater than 1,000,000 to 1; and
the frequency of base call errors is $0.5 \times 10^{-4}$ or lower.

A59.5. The method of embodiment A42, wherein
the method comprises base calls, wherein each base call represents a single nucleotide in the nucleic acid template;
the ratio of the number of nucleic acid templates for the nucleic acid sample to the number of polynucleotide B species in the nonrandom oligonucleotide adapters is greater than 1,000,000 to 1; and
the frequency of base call errors is $1 \times 10^{-5}$ or lower.

A60. The method of embodiment A42, wherein
the presence of a single nucleotide alteration in the nucleic acid is determined;
there are 500 or fewer polynucleotide B species; and
the single nucleotide alteration is present at a frequency of 1 percent or lower.

A61. The method of embodiment A42, wherein
the presence of a single nucleotide alteration in the nucleic acid is determined;
there are 400 or fewer polynucleotide B species; and
the single nucleotide alteration is present at a frequency of 1 percent or lower.

A62. The method of embodiment A42, wherein
the presence of a single nucleotide alteration in the nucleic acid is determined;
there are about 200 to about 300 polynucleotide B species; and
the single nucleotide alteration is present at a frequency of 1 percent or lower.

A63. The method of embodiment A42, wherein
the presence of a single nucleotide alteration in the nucleic acid is determined;
there are 300 or fewer polynucleotide B species; and
the single nucleotide alteration is present at a frequency of 1 percent or lower.

A64. The method of embodiment A42, wherein
the presence of a single nucleotide alteration in the nucleic acid is determined;
there are about 280 to about 290 polynucleotide B species; and
the single nucleotide alteration is present at a frequency of 1 percent or lower.

A64.1. The method of any one of embodiments A42-A64, further comprising the steps of
(a) obtaining a list of B species and B' species of the nonrandom oligonucleotide adapters provided for ligation with the nucleic acid templates;
(b) determining the sequence of the B species or B' species of the nonrandom oligonucleotide adapter-ligated nucleic acid templates;
(c) comparing the sequence of the B species or B' species of step (b) to the sequences of the B and B' species on the list of step (a); and
(d) removing from the determination of the sequence nucleic acid sequences of adapter-ligated nucleic acid templates that comprise B species or B' species sequences that are not identical to a B species or B' species sequence on the list of step (a).

A64.2. The method of any one of embodiments A42-A64, further comprising the steps of
(a) obtaining a list of B species and B' species of the nonrandom oligonucleotide adapters provided for ligation with the nucleic acid templates;
(b) determining the sequence of the B species or B' species of the nonrandom oligonucleotide adapter-ligated nucleic acid templates;
(c) comparing the sequence of the B species or B' species of step (b) to the sequences of the B and B' species on the list of step (a); and
(d) assigning a weight to the nonrandom oligonucleotide adapter-ligated nucleic acid template sequences, where the assigned weight is considered in the determination of at least one base call.

A64.3. The method of embodiment A64.2, wherein
(a) nonrandom oligonucleotide adapter-ligated nucleic acid sequences comprising a B species sequence or a B' species sequence that is identical to a B species sequence or a B' species sequence provided in the list of step (a) are assigned a weight of 1;
(b) nonrandom oligonucleotide adapter-ligated nucleic acid sequences comprising a B species sequence or a B' species sequence that comprises or consists of one nucleotide difference from a B species sequence or B' species sequence provided in the list of step (a) are assigned a weight of 0.5 and
(c) nonrandom oligonucleotide adapter-ligated nucleic acid sequences comprising a B species sequence or a B' species sequence that comprise more than one nucleotide difference from a B species sequence or a B' species sequence provided in the list of step (a) are assigned a weight of 0.

A65. The method of any one of embodiments A1-A41, wherein each of the adapter-ligated nucleic acid templates comprises a first nonrandom oligonucleotide adapter at a first end and a second nonrandom oligonucleotide adapter at a second end.

A66. The method of embodiment A65, wherein the B species for at least two adapter-ligated nucleic acid templates comprise or consist of the same nucleotide sequence.

A67. The method of embodiment A65, wherein the B species for at least two adapter-ligated nucleic acid template comprise or consist of a different nucleotide sequence.

A68. The method of embodiment A65, wherein the B' species at each end of the adapter-ligated nucleic templates are the same or different.

A69. The method of any one of embodiments A65-A68, wherein copies of a first double-stranded adapter species comprising a first B species and a first B' species are ligated to at least two double-stranded nucleic acid template species.

A70. The method of any one of embodiments A1-A69, wherein
copies of a first double-stranded adapter species comprising a first B species and a first B' species are ligated to the first end of the at least two double-stranded nucleic acid templates; and
copies of a second double-stranded adapter species comprising a second B species and a second B' species are ligated to the second end of the at least two double-stranded nucleic acid templates.

A71. The method of any one of embodiments A69 or A70, wherein the at least two double-stranded nucleic acid templates comprise nucleotide sequences that differ by at least one nucleotide.

A72. The method of any one of embodiments A69 or A70, wherein the at least two double-stranded nucleic acid templates consist of nucleotide sequences that differ by at least one nucleotide.

A73. The method of any one of embodiments A65-A72, wherein there are fewer than 999 B species and the ratio of the number of nucleic acid templates for the nucleic acid sample to the number of polynucleotide B species in the nonrandom oligonucleotide adapters is greater than 100,000 to 1.

A74. The method of any one of embodiments A65-A72, wherein there are fewer than 999 B species and the ratio of the number of nucleic acid templates for the nucleic acid sample to the number of polynucleotide B species in the nonrandom oligonucleotide adapters is greater than 500,000 to 1.

A75. The method of any one of embodiments A65-A72, wherein there are fewer than 999 B species, and the ratio of the number of nucleic acid templates for the nucleic acid sample to the number of polynucleotide B species in the nonrandom oligonucleotide adapters is greater than 900,000 to 1.

A76. The method of any one of embodiments A65-A72, wherein there are fewer than 999 B species, and the ratio of the number of nucleic acid templates for the nucleic acid sample to the number of polynucleotide B species in the nonrandom oligonucleotide adapters is about 1,000,000 to 1.

A77. The method of any one of embodiments A65-A72, wherein there are 500 or fewer polynucleotide B species.

A78. The method of any one of embodiments A65-A72, wherein there are 400 or fewer polynucleotide B species.

A79. The method of any one of embodiments A65-A72, wherein there are 300 or fewer polynucleotide B species.

A80. The method of any one of embodiments A65-A72, wherein there are about 200 to about 300 polynucleotide B species.

A81. The method of any one of embodiments A65-A72, wherein there are about 280 to about 290 polynucleotide B species.

A81.1. The method of any one of embodiments A65-A81, wherein less than 90% of the nonrandom oligonucleotide adapter-ligated nucleic acid templates comprise a polynucleotide B species that is different from the polynucleotide B species on the other nonrandom oligonucleotide adapter-ligated nucleic acid templates.

A81.2. The method of any one of embodiments A65-A81, wherein less than 50% of the nonrandom oligonucleotide adapter-ligated nucleic acid templates comprise a polynucleotide B species that is different from the polynucleotide B species on the other nonrandom oligonucleotide adapter-ligated nucleic acid templates.

A82. The method of any one of embodiments A65-A81.2, wherein the presence of a single nucleotide alteration in the nucleic acid template is determined and the single nucleotide alteration is present at a frequency of 1 percent or lower.

A83. The method of any one of embodiments A65-A81.2, wherein the method comprises base calls, wherein each base call represents a single nucleotide in the nucleic acid template.

A84. The method of embodiment A83, wherein the frequency of base call errors is lower than $1 \times 10^{-3}$.

A84.1. The method of embodiment A83, wherein the frequency of base call errors is $0.8 \times 10^{-3}$ or lower.

A84.2. The method of embodiment A83, wherein the frequency of base call errors is $0.5 \times 10^{-3}$ or lower.

A84.3. The method of embodiment A83, wherein the frequency of base call errors is $1 \times 10^{-4}$ or lower.

A84.4. The method of embodiment A83, wherein the frequency of base call errors is $0.5 \times 10^{-4}$ or lower.

A84.5. The method of embodiment A83, wherein the frequency of base call errors is $1 \times 10^{-5}$ or lower.

A84.6. The method of embodiment A83, wherein the frequency of base call errors is $0.5 \times 10^{-5}$ or lower.

A84.7. The method of embodiment A83, wherein the frequency of base call errors is $1 \times 10^{-6}$ or lower.

A84.8. The method of embodiment A83, wherein the frequency of base call errors is $0.5 \times 10^{-6}$ or lower.

A84.9. The method of embodiment A83, wherein the frequency of base call errors is $1 \times 10^{-7}$ or lower.

A85. The method of any one of embodiments A65-A84.9, wherein
the ratio of the number of nucleic acid templates for the nucleic acid sample to the number of polynucleotide B species in the nonrandom oligonucleotide adapters is greater than 1000 to 1, there are fewer than 300 B species, and the presence of a single nucleotide alteration in the nucleic acid template is determined and the single nucleotide alteration is present at a frequency of 1 percent or lower.

A86. The method of any one of embodiments A65-A84.9, wherein the ratio of the number of nucleic acid templates for the nucleic acid sample to the number of polynucleotide B species in the nonrandom oligonucleotide adapters is greater than 10,000 to 1, there are fewer than 300 B species, and the presence of a single nucleotide alteration in the nucleic acid template is determined and the single nucleotide alteration is present at a frequency of 1 percent or lower.

A87. The method of any one of embodiments A65-A84.9, wherein the ratio of the number of nucleic acid templates for the nucleic acid sample to the number of polynucleotide B species in the nonrandom oligonucleotide adapters is greater than 1000 to 1, there are fewer than 500 B species, and the presence of a single nucleotide alteration in the nucleic acid template is determined and the single nucleotide alteration is present at a frequency of 1 percent or lower.

A88. The method of any one of embodiments A65-A84.9, wherein the ratio of the number of nucleic acid templates for the nucleic acid sample to the number of polynucleotide B species in the nonrandom oligonucleotide adapters is greater than 1,000,000 to 1, there are fewer than 300 B species, and the presence of a single nucleotide alteration in the nucleic acid template is determined and the single nucleotide alteration is present at a frequency of 1 percent or lower.

A89. The method of any one of embodiments A65-A88, wherein the method comprises base calls, wherein each base call represents a single nucleotide in the nucleic acid template;

the ratio of the number of nucleic acid templates for the nucleic acid sample to the number of polynucleotide B species in the nonrandom oligonucleotide adapters is greater than 1,000,000 to 1; and the frequency of base call errors is $1 \times 10^{-6}$ or lower.

A89.1. The method of any one of embodiments A65-A88, wherein the method comprises base calls, wherein each base call represents a single nucleotide in the nucleic acid template;

the ratio of the number of nucleic acid templates for the nucleic acid sample to the number of polynucleotide B species in the nonrandom oligonucleotide adapters is greater than 1,000,000 to 1; and the frequency of base call errors is $1 \times 10'$ or lower.

A90. The method of embodiment A65, wherein the presence of a single nucleotide alteration in the nucleic acid is determined;

there are 500 or fewer polynucleotide B species; and the single nucleotide alteration is present at a frequency of 1 percent or lower.

A91. The method of embodiment A65, wherein the presence of a single nucleotide alteration in the nucleic acid is determined;

there are 400 or fewer polynucleotide B species; and the single nucleotide alteration is present at a frequency of 1 percent or lower.

A92. The method of embodiment A65, wherein the presence of a single nucleotide alteration in the nucleic acid is determined, there are about 300 to about 400 polynucleotide B species: and the single nucleotide alteration is present at a frequency of 1 percent or lower.

A93. The method of embodiment A65, wherein the presence of a single nucleotide alteration in the nucleic acid is determined, there are 300 or fewer polynucleotide B species; and the single nucleotide alteration is present at a frequency of 1 percent or lower.

A94. The method of embodiment A65, wherein the presence of a single nucleotide alteration in the nucleic acid is determined, there are about 280 to about 290 polynucleotide B species; and the single nucleotide alteration is present at a frequency of 1 percent or lower.

A94.1. The method of any one of embodiments A65-A94, further comprising the steps of (a) obtaining a list of B species and B' species of the nonrandom oligonucleotide adapters provided for ligation with the nucleic acid templates;

(b) determining the sequence of the B species or B' species of the nonrandom oligonucleotide adapter-ligated nucleic acid templates;

(c) comparing the sequence of the B species or B' species of step (b) to the sequences of the B and B' species on the list of step (a); and (d) removing from the determination of the count of nucleic acid templates, nonrandom oligonucleotide adapter-ligated nucleic acid templates that comprise B species or B' species sequences that are not identical to a B species or B' species sequence on the list of step (a).

A94.2. The method of any one of embodiments A65-A94.1, further comprising the steps of (a) obtaining a list of B species and B' species of the nonrandom oligonucleotide adapters provided for ligation with the nucleic acid templates;

(b) determining the sequence of the B species or B' species of the nonrandom oligonucleotide adapter-ligated nucleic acid templates;

(c) comparing the sequence of the B species or B' species of step (b) to the sequences of the B and B' species on the list of step (a); and (d) assigning a weight to the nonrandom oligonucleotide adapter-ligated nucleic acid templates, where the assigned weight is considered in the determination of the count of at least one nucleic acid template.

A94.3. The method of embodiment A94.2, wherein (a) nonrandom oligonucleotide adapter-ligated nucleic acid templates comprising a B species sequence or a B' species sequence that is identical to a B species sequence or a B' species sequence provided in the list of step (a) are assigned a weight of 1;

(b) nonrandom oligonucleotide adapter-ligated nucleic acid templates comprising a B species sequence or a B' species sequence that comprises or consists of one nucleotide difference from a B species sequence or B' species sequence provided in the list of step (a) are assigned a weight of 0.5 and (c) nonrandom oligonucleotide adapter-ligated nucleic acid templates comprising a B species sequence or a B' species sequence that comprise more than one nucleotide difference from a B species sequence or a B' species sequence provided in the list of step (a) are assigned a weight of 0.

A95. The method of any one of embodiments A1-A94.3 wherein the sequence of at least one polynucleotide B species and the sequence of at least one polynucleotide B' species are determined and are utilized to identify one or more errors.

A96. The method of embodiment A95, wherein the errors are sequencing errors and/or amplification errors.

A97. The method of any one of embodiments A1-A96, wherein the sequencing generates sequence reads and the sequence reads are mapped to regions of a reference genome.

A98. The method of any one of embodiments A1-A64, comprising reviewing the sequence of nucleotides for the one or more nucleic acid templates in the nucleic acid sample, comprising
 (a) identifying a set of amplicon duplicates, wherein the amplicon duplicates comprise amplified adapter-ligated nucleic acid templates comprising a polynucleotide B species at one end; and
 (b) determining the sequence of nucleotides for the one or more nucleic acid templates in the nucleic acid sample by removing from the determination of the sequence nucleic acid sequences having one or more nucleotide positions that disagree with the nucleotide position determined in 95% of the nucleic acid sequences of the set of amplicon duplicates.

A99. The method of embodiment A98, comprising the step of selecting amplicons having the same length for the set of amplicon duplicates.

A100. The method of any one of embodiments A65-A97, comprising reviewing the sequence of nucleotides for the one or more nucleic acid templates in the nucleic acid sample, comprising
 (a) identifying a first set of amplicon duplicates, wherein the amplicon duplicates comprise amplified adapter-ligated nucleic acid templates comprising a first polynucleotide B species at a first end and a second polynucleotide B species at the second end;
 (b) identifying a second set of amplicon duplicates, wherein the second set of amplicon duplicates comprise amplified adapter-ligated nucleic acid templates comprising the B' species that are the reverse complement of the first and second B species of step (a); and
 (c) determining the sequence of nucleotides for the one or more nucleic acid templates in the nucleic acid sample by removing from the determination of the sequence nucleic acid sequences having one or more nucleotide positions where the first single strand consensus sequence and the second single strand consensus sequence disagree at one or more nucleotide positions.

A100.1. The method of embodiment A100, comprising the step of selecting amplicons having the same length for the first and second set of amplicon duplicates.

A100.2. The method of any one of embodiments A1-A100.1, comprising determining whether a nucleic acid template is ligated to a nonrandom oligonucleotide adapter comprising a polynucleotide B or polynucleotide B' species, before sequencing the nucleic acid template.

A101. The method of any one of embodiments A1-A100.2, comprising counting the nucleic acid templates for the nucleic acid sample, comprising
 (a) identifying a set of amplicon duplicates, wherein the amplicon duplicates comprise amplified adapter-ligated nucleic acid templates comprising a polynucleotide B species; and
 (b) determining the number of amplicon duplicates comprising the polynucleotide B species.

A101.1 The method of embodiment A101, comprising comparing the number of first amplicon duplicates comprising a first polynucleotide B species with the number of second amplicon duplicates comprising a second polynucleotide B species.

A101.2. The method of embodiment A101.1, wherein the first amplicon duplicates comprise copies of a first nucleic acid template of a first chromosome and the second amplicon duplicates comprise copies of a second nucleic acid template of a second chromosome.

A101.3. The method of any one of embodiments A1-A100.2, comprising counting the number of unique nucleic acid templates for the nucleic acid sample, comprising
 (a) identifying the nonrandom oligonucleotide adapter species ligated to each nucleic acid template, and
 (b) counting the number of nonrandom oligonucleotide adapter species ligated to the nucleic acid templates for the nucleic acid sample.

A101.4. The method of any one of embodiments A1-A100.2, comprising counting the nucleic acid templates for the nucleic acid sample, comprising
 (a) identifying a set of amplicon duplicates, wherein the amplicon duplicates comprise amplified adapter-ligated nucleic acid templates comprising a first polynucleotide B species and a second polynucleotide B species at a second end, wherein the first and second polynucleotide B species may or may not consist of the same nucleotide sequence, and
 (b) determining the number of amplicon duplicates comprising both the first and the second polynucleotide B species.

A101.5 The method of embodiment A101, comprising comparing the number of first amplicon duplicates comprising the first and second polynucleotide B species with the number of second amplicon duplicates, wherein the second amplicon duplicates comprise amplified adapter-ligated nucleic acid templates comprising a third polynucleotide B species and a fourth polynucleotide species, wherein the third and fourth polynucleotide B species may or may not consist of the same nucleotide sequence.

A101.6. The method of embodiment A101.5, wherein the first amplicon duplicates comprise copies of a first nucleic acid template of a first chromosome and the second amplicon duplicates comprise copies of a second nucleic acid template of a second chromosome.

A101.7. The method of any one of embodiments A1-A100.2, comprising counting the number of unique nucleic acid templates for the nucleic acid sample, comprising
 (a) identifying the nonrandom oligonucleotide adapter species pair, wherein the nonrandom oligonucleotide adapter species pair comprises or consists of the nonrandom oligonucleotide adapter ligated to the first end of the nucleic acid template and the nonrandom oligonucleotide adapter ligated to the second end of the nucleic acid template; and (b) counting the number of nonrandom oligonucleotide adapter species pairs.

A102. The method of any one of embodiments A1-A100.2, comprising determining a base call of at least one nucleotide of a nucleic acid template, comprising
(a) identifying a set of amplicon duplicates, wherein the amplicon duplicates comprise amplified adapter-ligated nucleic acid templates comprising a polynucleotide B species at one end;
(b) identifying the at least one nucleotide in each amplicon of the set of amplicon duplicates;
(c) determining the base call of the at least one nucleotide where the identity of the at least one nucleotide is the same in at least 95% of the amplicons in the set of amplicon duplicates.

A102.1. The method of embodiment A102, comprising counting the nucleic acid templates for the nucleic acid sample that comprise the base call of the at least one nucleotide.

A103. The method of any one of embodiments A1-A100.2, comprising the step of selecting amplicons having the same length for the set of amplicon duplicates.

A104. The method of any one of embodiments A65-A97, comprising determining a base call of at least one nucleotide of a nucleic acid template, comprising
(a) identifying a first set of amplicon duplicates, wherein the amplicon duplicates comprise amplified adapter-ligated nucleic acid templates comprising a first polynucleotide B species and a second polynucleotide B species;
(b) identifying a second set of amplicon duplicates, wherein the second set of amplicon duplicates comprise amplified adapter-ligated nucleic acid templates comprising the B' species that are the reverse complement of the first and second B species of step (a);
(c) identifying the at least one nucleotide in each amplicon of the first set, and identifying the at least one nucleotide at the complementary position in the second set of amplicon duplicates;
(d) determining the base call of the at least one nucleotide where
the identity of the at least one nucleotide is the same in at least 95% of the amplicons in the first set or the second set of amplicon duplicates; and
the identity of the at least one nucleotide in the first set of amplicon duplicates is the complement to the identity of the at least one nucleotide in the complementary position in the second set of amplicon duplicates.

A105. The method of embodiment A104, comprising the step of selecting amplicons having the same length for the first and second set of amplicon duplicates.

B1. A method for manufacturing a set of 500 or fewer nonrandom nucleic acid sequencing adapters, for use in determining a sequence of nucleotides for one or more nucleic acid templates in a nucleic acid sample, wherein the ratio of the nonrandom nucleic acid sequencing adapters to nucleic acid templates of the nucleic acid sample is greater than 50 to 1, comprising or consisting essentially of:
providing first oligonucleotide species and second oligonucleotide species; wherein optionally:
each of the first oligonucleotide species comprises 5' to 3' a polynucleotide A and a polynucleotide B species and each of the second oligonucleotide species comprises 5' to 3' a polynucleotide B' species and a polynucleotide A';
each of the polynucleotide B species and the polynucleotide B' species are predetermined, are non-randomly generated, are the same length, and are about 4 to about 20 consecutive nucleotides in length;
there are 999 or fewer polynucleotide B species and each polynucleotide B' species is a reverse complement of a polynucleotide B species;
the ratio of nucleic acid templates to polynucleotide B species is greater than 1,000 to 1;
polynucleotide A is not a reverse complement of polynucleotide A'; and
each of the first oligonucleotide species and each of the second oligonucleotide species has been synthesized separately; and
in separate pairs contacting each first oligonucleotide species with each second oligonucleotide species comprising the reverse complement polynucleotide B' species under annealing conditions, thereby generating partially double-stranded adapter species; wherein the polynucleotide B species are annealed to complementary polynucleotide B' species and polynucleotide A' is not annealed to polynucleotide A.

B.1.1 The method of B1 wherein each of the nonrandom oligonucleotide adapter species comprises or consists of a first oligonucleotide species and a second oligonucleotide species, wherein each of the first oligonucleotide species comprises 5' to 3' a polynucleotide A and a polynucleotide B species and each of the second oligonucleotide species comprises 5' to 3' a polynucleotide B' species and a polynucleotide A', and each of the polynucleotide B species and the polynucleotide B' species are predetermined, are non-randomly generated and polynucleotide A is not a reverse complement of polynucleotide A'.

B1.2 The method of B1 wherein each of the polynucleotide B species are the same length, and are about 4 to about 20 consecutive nucleotides in length.

B1.3 The method of B1, wherein there are 999 or fewer polynucleotide B species and each polynucleotide B' species is a reverse complement of a polynucleotide B species.

B1.4 The method of B1, wherein the polynucleotide B species are annealed to complementary polynucleotide B' species and polynucleotide A' is not annealed to polynucleotide A B2. The method of embodiment B1, wherein the ratio of the nucleic acid sequencing adapters to nucleic acid templates of the nucleic acid sample is greater than 10,000 to 1, B3. The method of embodiment B1, wherein the ratio of the nucleic acid sequencing adapters to nucleic acid templates of the nucleic acid sample is greater than 100,000 to 1, B4. The method of embodiment B1, wherein the ratio of the nucleic acid sequencing adapters to nucleic acid templates of the nucleic acid sample is greater than 900,000 to 1, B5. The method of any one of embodiments B1-B4, wherein the set of nucleic acid sequencing adapters are combined in a vessel.

B6. The method of any one of embodiments B1-B5, wherein the polynucleotide B species and the polynucleotide B' species are non-degenerate polynucleotides.

B7. The method of any one of embodiments B1-B5, wherein the polynucleotide B species and the polynucleotide B' species are non-degenerate non-semidegenerate polynucleotides.

B8. The method of any one of embodiments B1-B7, wherein the polynucleotide B species and the polynucleotide B' species are about 6 to about 10 consecutive nucleotide bases in length.

B9. The method of embodiment B8, wherein the polynucleotide B species and the polynucleotide B' species are about 8 consecutive nucleotide bases in length.

B10. The method of any one of embodiments B1-B9, wherein there are 400 or fewer polynucleotide B species.

B11. The method of any one of embodiments B1-B9, wherein there are 300 or fewer polynucleotide B species.

B12. The method of any one of embodiments B1-B9, wherein there are about 200 to about 300 polynucleotide B species.

B13. The method of any one of embodiments B1-B9, wherein there are about 280 to about 290 polynucleotide B species.

B14. The method of any one of embodiments B1-B13, wherein each polynucleotide B species comprises a nucleotide sequence that differs from the other polynucleotide B species in the set by at least two nucleotides.

B15. The method of any one of B1-B14, wherein the first and second oligonucleotide species are partially matched reverse complement pairs selected from SEQ ID NOs: 1-576.

C1. A method of counting nucleic acid templates for a nucleic acid sample, comprising
  contacting double-stranded nucleic acid templates of the nucleic acid sample with partially double-stranded nonrandom oligonucleotide adapter species under ligation conditions, thereby generating adapter-ligated nucleic acid templates, wherein optionally:
    each of the nonrandom oligonucleotide adapter species comprises or consists of a first oligonucleotide species and a second oligonucleotide species;
    each of the first oligonucleotide species comprises 5' to 3' a polynucleotide A and a polynucleotide B species and each of the second oligonucleotide species comprises 5' to 3' a polynucleotide B' species and a polynucleotide A';
    each of the polynucleotide B species and the polynucleotide B' species are predetermined, are non-randomly generated, are the same length, and are about 4 to about 20 consecutive nucleotides in length,
    there are 999 or fewer polynucleotides B species and each polynucleotide B' species is a reverse complement of a polynucleotide B species;
    the ratio of nucleic acid templates to polynucleotide B species is greater than 1,000 to 1;
    polynucleotide A is not a reverse complement of polynucleotide A'; and
    the polynucleotide B species are annealed to complementary polynucleotide B' species and polynucleotide A' is not annealed to polynucleotide A; and
  amplifying the adapter-ligated nucleic acid templates, thereby generating amplicons; and
  identifying a set of amplicon duplicates, wherein the amplicon duplicates comprise amplified adapter-ligated nucleic acid templates comprising a polynucleotide B species at one end; and
  determining the number of amplicon duplicates comprising the polynucleotide B species.

C.1.1 The method of C1 wherein each of the nonrandom oligonucleotide adapter species comprises or consists of a first oligonucleotide species and a second oligonucleotide species, wherein each of the first oligonucleotide species comprises 5' to 3' a polynucleotide A and a polynucleotide B species and each of the second oligonucleotide species comprises 5' to 3' a polynucleotide B' species and a polynucleotide A', and each of the polynucleotide B species and the polynucleotide B' species are predetermined, are non-randomly generated and polynucleotide A is not a reverse complement of polynucleotide A'.

C1.2 The method of C1 wherein each of the polynucleotide B species are the same length, and are about 4 to about 20 consecutive nucleotides in length.

C1.3 The method of C1, wherein there are 999 or fewer polynucleotide B species and each polynucleotide B' species is a reverse complement of a polynucleotide B species.

C1.4 The method of C1, wherein the polynucleotide B species are annealed to complementary polynucleotide B' species and polynucleotide A' is not annealed to polynucleotide A C2. The method of embodiment C1, wherein the polynucleotide B species and the polynucleotide B' species are non-degenerate.

C3. The method of embodiment C1, wherein the polynucleotide B species and the polynucleotide B' species are non-semidegenerate.

C4. The method of any one of embodiments C1-C3, wherein
  each of the first oligonucleotide species comprises a polynucleotide C species between polynucleotide A and the polynucleotide B species;
  each of the second oligonucleotide species comprises a polynucleotide C' species between polynucleotide A' and the polynucleotide B' species;
  each polynucleotide C' species is the reverse complement of the polynucleotide C species; and
  the polynucleotide C species are annealed to complementary polynucleotide C' species.

C5. The method of embodiment C4, wherein each of the polynucleotide C species comprises or consists of the same nucleotide sequence.

C6. The method of embodiment C4, wherein the polynucleotide C species consist of at least two different nucleotide sequences.

C7. The method of any one of embodiments C1-C6, wherein the double-stranded nucleic acid templates are double-stranded DNA templates.

C8. The method of any one of embodiments C1-C6, wherein the double-stranded nucleic acid templates are double-stranded RNA templates.

C9. The method of any one of C1-C8, wherein the first oligonucleotide species and the second oligonucleotide species are partially matched reverse complement pairs selected from SEQ ID Nos: 1-576.

C10. The method of any one of embodiments C1-C8, wherein the adapter-ligated nucleic acid templates are amplified by a process comprising linear amplification.

C11. The method of any one of embodiments C1-C8, wherein the adapter-ligated nucleic acid templates are amplified by a process comprising exponential amplification.

C12. The method of any one of embodiments C1-C8, wherein the adapter-ligated nucleic acid templates are amplified by a process comprising isothermal amplification.

C13. The method of C1-C12, wherein 288 unique B species are used.

C14. The method of any one of embodiments C1-C12, wherein the double-stranded nucleic acid templates are blunt-ended.

C15. The method of any one of embodiments C1-C12, wherein the nucleic acid templates comprise at least one blunt end.

C16. The method of any one of embodiments C1-C12, wherein the nucleic acid templates are sheared double-stranded DNA templates.

C17. The method of any one of embodiments C1-C12, wherein the nucleic acid templates are restriction enzyme-digested double-stranded DNA templates.

C18. The method of any one of embodiments C1-C17, comprising blunt-ending the nucleic acid templates before contacting the nucleic acid templates with the nonrandom oligonucleotide adapter species.

C19. The method of any one of embodiments C14 and C18, wherein the nonrandom oligonucleotide adapter species comprise a blunt end.

C20. The method of any one of embodiments C1-C19, wherein the double-stranded nucleic acid templates comprise a ligation linker.

C21. The method of any one of embodiments C14 and C15, comprising joining a ligation linker to the blunt end of the nucleic acid template.

C22. The method of any one of embodiments C20-C21, wherein the ligation linker is selected from the group consisting of a A-overhang, T-overhang, a CG-overhang, a blunt end, or any ligatable nucleic acid sequence.

C23. The method of embodiment C22, wherein the ligation linker is an A-overhang.

C24. The method of any one of embodiments C20-C23, wherein the double-stranded nonrandom oligonucleotide adapter species comprises a ligation linker.

C24.1. The method of embodiment C24 wherein the ligation linker is selected from the group consisting of a A-overhang, T-overhang, a CG-overhang, a blunt end, or any ligatable nucleic acid sequence.

C24.2. The method of embodiment C24, wherein the ligation linker is a T-overhang.

C25. The method of any one of embodiments C1-C24.2, wherein the nucleic acid sample is obtained from a subject.

C26. The method of any one of embodiments C1-C25, wherein the nucleic acid is cell-free nucleic acid.

C27. The method of any one of embodiments C1-C25, wherein the nucleic acid sample is blood plasma, blood serum, or urine.

C28. The method of any one of embodiments C1-C25, wherein the nucleic acid sample is circulating cell-free nucleic acid.

C29. The method of any one of embodiments C1-C25, wherein the nucleic acid sample is isolated from blood plasma, blood serum, or urine.

C30. The method of any one of embodiments C1-C25, wherein the nucleic acid sample is isolated from a sample of tissue, cells, or fluid obtained from a subject.

C31. The method of any one of embodiments C1-C30, wherein the subject is human.

C32. The method of any one of embodiments C1-C31, wherein the nucleic acid sample is separated from a sample of tissue, cells, or fluid obtained from a subject.

C33. The method of any one of embodiments C1-C31, wherein the sequence of nucleotides for one or more nucleic acid templates in the nucleic acid sample is determined in situ.

C34. The method of any one of embodiments C1-C32, comprising capturing a subset of the nucleic acid templates by hybridization to capture probes under hybridization conditions, thereby generated captured nucleic acid templates.

C35. The method of any one of embodiments C1-C32, comprising: enriching for nucleic acid templates representing one or more selected genes by means of amplifying nucleic acid templates in the nucleic acid sample that are complementary to selected genes.

C36. The method of any one of embodiments C34-C35, wherein the method of obtaining the nucleic acid sample comprises eluting captured nucleic acid templates from the capture probes.

C37. The method of any one of embodiments C34-C36, wherein the capture probes are in an array.

C37.1. The method of any one of embodiments C34-C35, wherein the capture probes are attached to beads.

C37.2. The method of any one of embodiments C1-C37.1, wherein the sequencing depth is at about 500 fold to about 150,000 fold.

C38. The method of any one of embodiments C1-C37.1, wherein the sequencing depth is at about 1,000 fold to about 100,000 fold.

C39. The method of any one of embodiments C1-C37.1, wherein the sequencing depth is at about 10,000 fold to about 70,000 fold.

C40. The method of any one of embodiments C1-C37.1, wherein the sequencing depth is at about 20,000 fold to about 60,000 fold.

C41. The method of any one of embodiments C1-C37.1, wherein the sequencing depth is at about 30,000 fold to about 50,000 fold.

C42. The method of any one of embodiments C1-C41, wherein each adapter-ligated nucleic acid template comprises or consists of one nonrandom oligonucleotide adapter at a first end and a standard sequencing adapter at a second end.

C43. The method of embodiment C42, wherein the ratio of the number of nucleic acid templates for the nucleic acid sample to the number of polynucleotide B species in the nonrandom oligonucleotide adapters is greater than 100,000 to 1.

C44. The method of embodiment C42, wherein the ratio of the number of nucleic acid templates for the nucleic acid sample to the number of polynucleotide B species in the nonrandom oligonucleotide adapters is greater than 500,000 to 1.

C45. The method of embodiment C42, wherein the ratio of the number of nucleic acid templates for the nucleic acid sample to the number of polynucleotide B species in the nonrandom oligonucleotide adapters is greater than 9,000,000 to 1.

C46. The method of embodiment C42, wherein the ratio of the number of nucleic acid templates for the nucleic acid sample to the number of polynucleotide B species in the nonrandom oligonucleotide adapters is about 1,000,000 to 1.

C47. The method of any one of embodiments C42-C46, wherein there are 500 or fewer polynucleotide B species.

C48. The method of any one of embodiments C42-C46, wherein there are 400 or fewer polynucleotide B species.

C49. The method of any one of embodiments C42-C46, wherein there are 300 or fewer polynucleotide B species.

C50. The method of any one of embodiments C42-C46, wherein there are about 200 to about 300 polynucleotide B species.

C51. The method of any one of embodiments C42-C46, wherein there are about 280 to about 290 polynucleotide B species.

C51.1. The method of any one of embodiments C42-C51, wherein less than 90% of the nonrandom oligonucleotide adapter-ligated nucleic acid templates comprise a polynucleotide B species that is different from the polynucleotide B species on the other nonrandom oligonucleotide adapter-ligated nucleic acid templates.

C51.2. The method of any one of embodiments C42-C51, wherein less than 50% of the nonrandom oligonucleotide adapter-ligated nucleic acid templates comprise a polynucleotide B species that is different from the polynucleotide B species on the other nonrandom oligonucleotide adapter-ligated nucleic acid templates.

C65. The method of any one of embodiments C1-C41, wherein each of the adapter-ligated nucleic acid templates comprises a first nonrandom oligonucleotide adapter at a first end and a second nonrandom oligonucleotide adapter at a second end.

C66. The method of embodiment C65, wherein
the B species for at least two adapter-ligated nucleic acid templates consist of the same nucleotide sequence.

C67. The method of embodiment C65, wherein
the B species for at least two adapter-ligated nucleic acid template consist of a different nucleotide sequence.

C68. The method of embodiment C65, wherein the B' species at each end of the adapter-ligated nucleic templates are the same or different.

C69. The method of any one of embodiments C65-C68, wherein copies of a first double-stranded adapter species comprising a first B species and a first B' species are ligated to at least two double-stranded nucleic acid templates.

C70. The method of any one of embodiments C1-C69, wherein
copies of a first double-stranded adapter species comprising a first B species and a second B' species are ligated to the first end of the at least two double-stranded nucleic acid template species; and
copies of a second double-stranded adapter species comprising a second B species and a second B' species are ligated to the second end of the at least two double-stranded nucleic acid templates.

C71. The method of any one of embodiments C69 or C70, wherein the at least two double-stranded nucleic acid templates comprise nucleotide sequences that differ by at least one nucleotide.

C72. Reserved.

C73. The method of any one of embodiments C65-C71, wherein the ratio of the number of nucleic acid templates for the nucleic acid sample to the number of polynucleotide B species in the nonrandom oligonucleotide adapters is greater than 100,000 to 1.

C74. The method of any one of embodiments C65-C71, wherein the ratio of the number of nucleic acid templates for the nucleic acid sample to the number of polynucleotide B species in the nonrandom oligonucleotide adapters is greater than 500,000 to 1.

C75. The method of any one of embodiments C65-C71, wherein the ratio of the number of nucleic acid templates for the nucleic acid sample to the number of polynucleotide B species in the nonrandom oligonucleotide adapters is greater than 900,000 to 1.

C76. The method of any one of embodiments C65-C71, wherein the ratio of the number of nucleic acid templates for the nucleic acid sample to the number of polynucleotide B species in the nonrandom oligonucleotide adapters is about 1,000,000 to 1.

C77. The method of any one of embodiments C65-C71, wherein there are 500 or fewer polynucleotide B species.

C78. The method of any one of embodiments C65-C721, wherein there are 400 or fewer polynucleotide B species.

C79. The method of any one of embodiments C65-C71, wherein there are 300 or fewer polynucleotide B species.

C80. The method of any one of embodiments C65-C71, wherein there are about 200 to about 300 polynucleotide B species.

C81. The method of any one of embodiments C65-C71, wherein there are about 280 to about 290 polynucleotide B species.

C81.1. The method of any one of embodiments C65-C81, wherein less than 90% of the nonrandom oligonucleotide adapter-ligated nucleic acid templates comprise a polynucleotide B species that is different from the polynucleotide B species on the other nonrandom oligonucleotide adapter-ligated nucleic acid templates.

C81.2. The method of any one of embodiments C65-C81, wherein less than 50% of the nonrandom oligonucleotide adapter-ligated nucleic acid templates comprise a polynucleotide B species that is different from the polynucleotide B species on the other nonrandom oligonucleotide adapter-ligated nucleic acid templates.

C82.-C100. Reserved.

C101. The method of any one of embodiments C1-C64, comprising counting the nucleic acid templates for the nucleic acid sample, comprising
(a) identifying a set of amplicon duplicates, wherein the amplicon duplicates comprise amplified adapter-ligated nucleic acid templates comprising a polynucleotide B species; and
(b) determining the number of amplicon duplicates comprising the polynucleotide B species.

C101.1 The method of embodiment C101, comprising comparing the number of first amplicon duplicates comprising a first polynucleotide B species with the number of second amplicon duplicates comprising a second polynucleotide B species.

C101.2. The method of embodiment C101.1, wherein a ratio of the number of first amplicon duplicates to the number of second amplicon duplicates is determined.

C101.3. A method for detecting the presence of a genetic disease or disorder comprising determining the ratio of the number of first amplicon duplicates to the number of second amplicon duplicates of embodiment C101.2.

C101.4. The method of any one of embodiments C101.1 to C101.3, wherein the first amplicon duplicates are mapped to a first chromosome and the second amplicon duplicates are mapped to a second chromosome.

C101.5. The method of any one of embodiments C101 to C101.3, wherein the first amplicon duplicates are mapped to a first location on a chromosome and the second amplicon duplicates are mapped to a second location on the chromosome.

C101.6. The method of any one of embodiments C101.4 or C101.5, wherein the ratio of the number of first amplicon duplicates to the number of second amplicon duplicates is compared to the ratio determined from a patient, or patients who have been diagnosed with the genetic disease or disorder.

C101.7. The method of any one of embodiments C101.4 to C101.6, wherein the ratio of the number of first amplicon duplicates to the number of second amplicon duplicates is compared to the ratio determined from a patient, or patients who have not been diagnosed with the genetic disease or disorder.

C101.8. The method of any one of embodiments C1-C81.2, comprising counting the number of unique nucleic acid templates for the nucleic acid sample, comprising
(a) identifying the nonrandom oligonucleotide adapter species ligated to each nucleic acid template, and
(b) counting the number of nonrandom oligonucleotide adapter species ligated to the nucleic acid templates for the nucleic acid sample.

C101.9. The method of any one of embodiments C1-C81.2, comprising counting the nucleic acid templates for the nucleic acid sample, comprising
(a) identifying a set of amplicon duplicates, wherein the amplicon duplicates comprise amplified adapter-ligated nucleic acid templates comprising a first polynucleotide B species and a second polynucleotide B species, wherein the first and second polynucleotide B species may or may not consist of the same nucleotide sequence; and
(b) determining the number of amplicon duplicates comprising both the first and the second polynucleotide B species.

C101.10 The method of embodiment C101, comprising comparing the number of first amplicon duplicates comprising the first and second polynucleotide B species with the number of second amplicon duplicates, wherein the second amplicon duplicates comprise amplified adapter-ligated nucleic acid templates comprising a third polynucleotide B species and a fourth polynucleotide species, wherein the third and fourth polynucleotide B species may or may not consist of the same nucleotide sequence.

C101.11. The method of embodiment C101.10, wherein the first amplicon duplicates comprise copies of a first nucleic acid template of a first chromosome and the second amplicon duplicates comprise copies of a second nucleic acid template of a second chromosome.

C101.12. The method of any one of embodiments C1-C81.2, comprising counting the number of unique nucleic acid templates for the nucleic acid sample, comprising
(a) identifying the nonrandom oligonucleotide adapter species pair, wherein the nonrandom oligonucleotide adapter species pair comprises or consists of the nonrandom oligonucleotide adapter ligated to the nucleic acid template and the nonrandom oligonucleotide adapter ligated to the nucleic acid template; and
(b) counting the number of nonrandom oligonucleotide adapter species pairs.

C102. The method of any one of embodiments C1-C101.12, comprising determining whether a nucleic acid template is ligated to a nonrandom oligonucleotide adapter comprising a polynucleotide B or polynucleotide B' species, before counting the nucleic acid template.

C103. The method of any one of embodiments C1-C102, further comprising the steps of
(a) obtaining a list of B species and B' species of the nonrandom oligonucleotide adapters provided for ligation with the nucleic acid templates;
(b) determining the sequence of the B species or B' species of the nonrandom oligonucleotide adapter-ligated nucleic acid templates;
(C) comparing the sequence of the B species or B' species of step (b) to the sequences of the B and B' species on the list of step (a), and
(d) removing from the determination of the number of nucleic acid templates, adapter-ligated nucleic acid templates that comprise B species or B' species sequences that are not identical to a B species or B' species sequence on the list of step (a).

C104. The method of any one of embodiments C1-C102, further comprising the steps of
(a) obtaining a list of B species and B' species of the nonrandom oligonucleotide adapters provided for ligation with the nucleic acid templates;
(b) determining the sequence of the B species or B' species of the nonrandom oligonucleotide adapter-ligated nucleic acid templates;
(c) comparing the sequence of the B species or B' species of step (b) to the sequences of the B and B' species on the list of step (a); and
(d) assigning a weight to the nonrandom oligonucleotide adapter-ligated nucleic acid template sequences, where the assigned weight is considered in the determination of the number of nucleic acid templates.

C105. The method of embodiment C104, wherein
(a) nonrandom oligonucleotide adapter-ligated nucleic acid sequences comprising a B species sequence or a B' species sequence that is identical to a B species sequence or a B' species sequence provided in the list of step (a) are assigned a weight of 1;
(b) nonrandom oligonucleotide adapter-ligated nucleic acid sequences comprising a B species sequence or a B' species sequence that comprises or consists of one nucleotide difference from a B species sequence or B' species sequence provided in the list of step (a) are assigned a weight of 0.5; and
(c) nonrandom oligonucleotide adapter-ligated nucleic acid sequences comprising a B species sequence or a B' species sequence that comprise more than one nucleotide difference from a B species sequence or a B' species sequence provided in the list of step (a) are assigned a weight of 0.

D1. A method for determining a sequence of nucleotides for one or more nucleic acid templates in a nucleic acid sample, comprising:
contacting double-stranded nucleic acid templates of the nucleic acid sample with partially double-stranded nonrandom oligonucleotide adapter species under ligation conditions, thereby generating adapter-ligated nucleic acid templates, wherein:
each of the nonrandom oligonucleotide adapter species comprises or consists of a first oligonucleotide species and a second oligonucleotide species;
each of the first oligonucleotide species comprises 5' to 3' a polynucleotide A and a polynucleotide B species and each of the second oligonucleotide species comprises 5' to 3' a polynucleotide B' species and a polynucleotide A';
each of the polynucleotide B species and the polynucleotide B' species are predetermined, are non-randomly generated, are the same length, and are about 4 to about 20 consecutive nucleotides in length;
there are 300 or fewer polynucleotide B species and each polynucleotide B' species is a reverse complement of a polynucleotide B species;
polynucleotide A is not a reverse complement of polynucleotide A';
the ratio of nucleic acid templates to polynucleotide B species is greater than 1,000 to 1; and the polynucleotide B species are annealed to complementary polynucleotide B' species and polynucleotide A is not annealed to polynucleotide A; and amplifying the adapter-ligated nucleic acid templates, thereby generating amplicons; and sequencing all or a portion of each amplicon, thereby determining a sequence of nucleotides for the one or more nucleic acid templates in the nucleic acid sample.

D2. The method of embodiment D1, wherein the partially double stranded nonrandom oligonucleotide adapter species is a Y adapter.

D3. The method of embodiment D1, wherein the partially double stranded nonrandom oligonucleotide adapter species is a hairpin adapter.

D4. The method of any one of embodiments D1-D3, wherein the polynucleotide B species and the polynucleotide B' species are non-degenerate.

D5. The method of any one of embodiments D1-D4, wherein each of the first oligonucleotide species comprises a polynucleotide C species between polynucleotide A and the polynucleotide B species;

each of the second oligonucleotide species comprises a polynucleotide C' species between polynucleotide A' and the polynucleotide B' species;

each polynucleotide C' species is the reverse complement of the polynucleotide C species; and the polynucleotide C species are annealed to complementary polynucleotide C' species.

D6. The method of embodiment D5, wherein each of the polynucleotide C species comprises or consists of the same nucleotide sequence or wherein the polynucleotide C species consist of at least two different nucleotide sequences.

D7. The method of embodiment D1, wherein the double-stranded nucleic acid templates are double-stranded DNA templates or RNA templates.

D8. The method of any one of embodiments D1-D7, wherein:

amplifying the adapter-ligated nucleic acid templates generates double-stranded amplicons, and sequencing comprises sequencing all or a portion of each strand of the amplicons.

D9. The method of any one of embodiments D1-D8, wherein the adapter-ligated nucleic acid templates are amplified by a process comprising linear amplification, exponential amplification, or isothermal amplification.

D10. The method of any one of embodiments D1-D9, wherein each adapter-ligated nucleic acid template comprises or consists of one nonrandom oligonucleotide adapter at a first end and a standard sequencing adapter at a second end.

D11. The method of any of embodiments D1 and D7-D10, wherein the double-stranded nucleic acid templates are blunt-ended.

D12. The method of any of embodiments D1 and D7-D10, wherein the nucleic acid templates comprise at least one blunt end.

D113. The method of any of embodiments D1 and D7-D10, wherein the nucleic acid templates are sheared double-stranded DNA templates.

D14. The method of any of embodiments D1-D13, comprising blunt-ending the nucleic acid templates before contacting the nucleic acid templates with the nonrandom oligonucleotide adapter species.

D15. The method of any of embodiments D1-D14, wherein the nonrandom oligonucleotide adapter species comprise a blunt end.

D16. The method of any of embodiments D1-D14, wherein the double-stranded nucleic acid templates comprise a ligation linker.

D17. The method of any of embodiments D1-D15, wherein the double-stranded nonrandom oligonucleotide adapter species comprises a ligation linker.

D18. The method of embodiment D16 or D17, wherein the ligation linker is selected from the group consisting of a A-overhang, T-overhang, a CG-overhang, a blunt end, or any ligatable nucleic acid sequence.

D19. The method of any of embodiments D1-D18, wherein the presence of a single nucleotide alteration in the nucleic acid template is determined and the single nucleotide alteration is present at a frequency of 5 percent or lower.

D20. The method of any of embodiments D1-D19, comprising providing a base call, wherein each base call represents a single nucleotide located at a single nucleotide position in the nucleic acid template.

D21. The method of any one of embodiments D1-D20, wherein the nucleic acid sample is isolated from blood plasma, blood serum, or urine.

D22. The method of any one of embodiments D1-D20, wherein the nucleic acid sample is cell-free DNA.

D23. The method of any one of embodiments D1-D20, wherein the nucleic acid sample is isolated from a sample of tissue, cells, or fluid obtained from a subject.

D24. The method of embodiment D1, wherein the sequence of the nucleotides for the one or more nucleic acid templates in the nucleic acid sample is determined in situ.

D25. The method of embodiment D1 and D24, wherein the sequencing depth is at about 500 fold to about 150,000 fold.

D26. The method of any of embodiments D1-D25, wherein each of the adapter-ligated nucleic acid templates comprises a first nonrandom oligonucleotide adapter at a first end and a second nonrandom oligonucleotide adapter at a second end.

D27. The method of any of embodiments D1-D26, further comprising the steps of (e) obtaining a list of B species and B' species of the nonrandom oligonucleotide adapters provided for ligation with the nucleic acid templates;

(f) determining the sequence of the B species or B' species of the nonrandom oligonucleotide adapter-ligated nucleic acid templates;

(g) comparing the sequence of the B species or B' species of step (b) to the sequences of the B and B' species on the list of step (a); and (h) removing from the determination of the count of nucleic acid templates, nonrandom oligonucleotide adapter-ligated nucleic acid templates that comprise B species or B' species sequences that are not identical to a B species or B' species sequence on the list of step (a).

D28. The method of any of embodiments D1-D26, further comprising the steps of (a) obtaining a list of B species and B' species of the nonrandom oligonucleotide adapters provided for ligation with the nucleic acid templates;

(b) determining the sequence of the B species or B' species of the nonrandom oligonucleotide adapter-ligated nucleic acid templates;

(c) comparing the sequence of the B species or B' species of step (b) to the sequences of the B and B' species on the list of step (a); and (d) assigning a weight to the nonrandom oligonucleotide adapter-ligated nucleic acid template sequences, where the assigned weight is considered in the determination of the number of nucleic acid templates.

D29. The method of any one of embodiments D1-D28, comprising counting the number of unique nucleic acid templates for the nucleic acid sample, comprising
(c) identifying the nonrandom oligonucleotide adapter species ligated to each nucleic acid template; and
(d) counting the number of nonrandom oligonucleotide adapter species ligated to the nucleic acid templates for the nucleic acid sample.

D30. The method of any one of embodiments D1-D29, comprising counting the nucleic acid templates for the nucleic acid sample, comprising
(a) identifying a set of amplicon duplicates, wherein the amplicon duplicates comprise amplified adapter-ligated nucleic acid templates comprising a first polynucleotide B species and a second polynucleotide B species at a second end, wherein the first and second polynucleotide B species may or may not consist of the same nucleotide sequence; and
(b) determining the number of amplicon duplicates comprising both the first and the second polynucleotide B species.

D31. The method of any one of embodiments D1-D30, comprising determining a base call of at least one nucleotide of a nucleic acid template, comprising
(a) identifying a set of amplicon duplicates, wherein the amplicon duplicates comprise amplified adapter-ligated nucleic acid templates comprising a polynucleotide B species at one end;
(b) identifying the at least one nucleotide in each amplicon of the set of amplicon duplicates;
(c) determining the base call of the at least one nucleotide where the identity of the at least one nucleotide is the same in at least 95% of the amplicons in the set of amplicon duplicates.

D32. A method for manufacturing a set of 500 or fewer nonrandom nucleic acid sequencing adapters, for use in determining a sequence of nucleotides for one or more nucleic acid templates in a nucleic acid sample, wherein the ratio of the nonrandom nucleic acid sequencing adapters to nucleic acid templates of the nucleic acid sample is greater than 50 to 1, consisting essentially of:
providing first oligonucleotide species and second oligonucleotide species; wherein:
each of the first oligonucleotide species comprises 5' to 3' a polynucleotide A and a polynucleotide B species and each of the second oligonucleotide species comprises 5' to 3' a polynucleotide B' species and a polynucleotide A';
each of the polynucleotide B species and the polynucleotide B' species are predetermined, are non-randomly generated, are the same length, and are about 4 to about 20 consecutive nucleotides in length;
there are 999 or fewer polynucleotide B species and each polynucleotide B' species is a reverse complement of a polynucleotide B species;
the ratio of nucleic acid templates to polynucleotide B species is greater than 1,000 to 1;
polynucleotide A is not a reverse complement of polynucleotide A'; and
each of the first oligonucleotide species and each of the second oligonucleotide species has been synthesized separately: and
in separate pairs contacting each first oligonucleotide species with each second oligonucleotide species comprising the reverse complement polynucleotide B' species under annealing conditions, thereby generating partially double-stranded adapter species; wherein the polynucleotide B species are annealed to complementary polynucleotide B' species and polynucleotide A' is not annealed to polynucleotide A.

D33. The method of embodiment D32, wherein the polynucleotide B species and the polynucleotide B' species are non-degenerate polynucleotides.

D34. A method of counting nucleic acid templates for a nucleic acid sample, comprising
contacting double-stranded nucleic acid templates of the nucleic acid sample with partially double-stranded nonrandom oligonucleotide adapter species under ligation conditions, thereby generating adapter-ligated nucleic acid templates, wherein:
each of the nonrandom oligonucleotide adapter species comprises or consists of a first oligonucleotide species and a second oligonucleotide species;
each of the first oligonucleotide species comprises 5' to 3' a polynucleotide A and a polynucleotide B species and each of the second oligonucleotide species comprises 5' to 3' a polynucleotide B' species and a polynucleotide A';
each of the polynucleotide B species and the polynucleotide B' species are predetermined, are non-randomly generated, are the same length, and are about 4 to about 20 consecutive nucleotides in length;
there are 999 or fewer polynucleotide B species and each polynucleotide B' species is a reverse complement of a polynucleotide B species;
the ratio of nucleic acid templates to polynucleotide B species is greater than 1,000 to 1;
polynucleotide A is not a reverse complement of polynucleotide A'; and
the polynucleotide B species are annealed to complementary polynucleotide B' species and polynucleotide A' is not annealed to polynucleotide A; and
amplifying the adapter-ligated nucleic acid templates, thereby generating amplicons; and
identifying a set of amplicon duplicates, wherein the amplicon duplicates comprise amplified adapter-ligated nucleic acid templates comprising a polynucleotide B species at one end; and
determining the number of amplicon duplicates comprising the polynucleotide B species.

D35. The method of embodiment D34, wherein the polynucleotide B species and the polynucleotide B' species are non-degenerate.

D36. The method of embodiment D34 or D35, wherein each of the first oligonucleotide species comprises a polynucleotide C species between polynucleotide A and the polynucleotide B species;
each of the second oligonucleotide species comprises a polynucleotide C' species between polynucleotide A' and the polynucleotide B' species;
each polynucleotide C' species is the reverse complement of the polynucleotide C species; and
the polynucleotide C species are annealed to complementary polynucleotide C' species.

D37. The method of embodiment D36, wherein each of the polynucleotide C species comprises or consists of the same nucleotide sequence or wherein the polynucleotide C species consist of at least two different nucleotide sequences.

D38. The method of embodiment D34, wherein the double-stranded nucleic acid templates are double-stranded DNA templates or RNA templates.

D39. The method of embodiments D34 or D38, wherein the double-stranded nucleic acid templates comprise a ligation linker.

D40. The method of embodiment D34-D37, wherein the double-stranded nonrandom oligonucleotide adapter species comprises a ligation linker.

D41. The method of either of embodiments D39 or D40, wherein the ligation linker is selected from the group consisting of a A-overhang, T-overhang, a CG-overhang, a blunt end, or any ligatable nucleic acid sequence.

D42. The method of any one of embodiments D34-D41, wherein each of the adapter-ligated nucleic acid templates comprises a first nonrandom oligonucleotide adapter at a first end and a second nonrandom oligonucleotide adapter at a second end.

D43. The method of any one of embodiments D34-D42, comprising counting the nucleic acid templates for the nucleic acid sample, comprising
(a) identifying a set of amplicon duplicates, wherein the amplicon duplicates comprise amplified adapter-ligated nucleic acid templates comprising a polynucleotide B species, and
(b) determining the number of amplicon duplicates comprising the polynucleotide B species.

D44. The method of embodiment D43, comprising comparing the number of first amplicon duplicates comprising a first polynucleotide B species with the number of second amplicon duplicates comprising a second polynucleotide B species.

D45. A method of embodiment D44, comprising detecting the presence of a genetic disease or disorder comprising determining a ratio of the number of first amplicon duplicates to the number of second amplicon duplicates.

D46. A method for determining a sequence of nucleotides for one or more nucleic acid templates in a nucleic acid sample, comprising:
contacting double-stranded nucleic acid templates of the nucleic acid sample with partially double-stranded nonrandom oligonucleotide adapter species under ligation conditions, thereby generating adapter-ligated nucleic acid templates, wherein:
each of the nonrandom oligonucleotide adapter species comprises or consists of a first oligonucleotide species and a second oligonucleotide species;
each of the first oligonucleotide species comprises 5' to 3' a polynucleotide A and a polynucleotide B species and each of the second oligonucleotide species comprises 5' to 3' a polynucleotide B' species and a polynucleotide A';
each of the polynucleotide B species and the polynucleotide B' species are predetermined, are non-randomly generated, are the same length, and are about 4 to about 20 consecutive nucleotides in length;
there are 300 or fewer polynucleotide B species and each polynucleotide B' species is a reverse complement of a polynucleotide B species;
polynucleotide A is not a reverse complement of polynucleotide A';
the ratio of nucleic acid templates to polynucleotide B species is greater than 1,000,000 to 1; and
the polynucleotide B species are annealed to complementary polynucleotide B' species and polynucleotide A' is not annealed to polynucleotide A; and
amplifying the adapter-ligated nucleic acid templates, thereby generating amplicons; and
sequencing all or a portion of each amplicon, thereby determining a sequence of nucleotides for the one or more nucleic acid templates in the nucleic acid sample.

D47. The method of any of embodiments D1-D3, wherein generating adapter-ligated nucleic acid templates is performed by contacting 20-40 ng double-stranded nucleic acid templates of the nucleic acid sample with 50-500 nM partially double-stranded nonrandom oligonucleotide adapter species under ligation conditions.

D48. The method of any one of D1-D47, wherein the first oligonucleotide and the second oligonucleotide are partially matched reverse complement pairs selected from SEQ ID NOs: 1-576.

E1. A composition comprising a plurality of partially double-stranded nonrandom oligonucleotide adapter molecules, wherein:
each of the nonrandom oligonucleotide adapter species comprises a first oligonucleotide species and a second oligonucleotide species, wherein each of the first oligonucleotide species comprises 5' to 3' a polynucleotide A and a polynucleotide B species and each of the second oligonucleotide species comprises 5' to 3' a polynucleotide B' species and a polynucleotide A', and wherein each of the polynucleotide B species and the polynucleotide B' species are the reverse complement of each other and each of the polynucleotide A species is not a reverse complement of polynucleotide A' species.

E2. The composition of claim E1, wherein the B and B' species are predetermined sequences and are non-randomly generated.

E3. The composition of claim E1, wherein the individual pairs of B and B' species are the same length.

E4. The composition of claim E1, wherein the individual pairs of B and B' species are the same length but different B and B' pairs may have different lengths than each other.

E5. The composition of claim E1, wherein the B and B' species are about 4 to about 20 nucleotides in length.

E6. The composition of claim E1, wherein there are 300 or fewer polynucleotide B species.

E7. The composition of claim E1, wherein the polynucleotide B species are annealed to complementary polynucleotide B' species and polynucleotide A' is not annealed to polynucleotide A.

E8. The composition of claim E1, wherein the composition is prepared for a sequencing reaction wherein the ratio of nucleic acid templates to polynucleotide B species is greater than 1,000 to 1.

E9. The composition of any one of E1-E8, The first oligonucleotide species and the second oligonucleotide species are partially matched reverse complement pairs selected from SEQ ID Nos: 1-576.

F1. A system for determining a sequence of nucleotides for one or more nucleic acid templates in a nucleic acid sample and/or performing any of the methods and/or using any of the compositions of any of the previous embodiments, comprising:
one or more processors; and memory coupled to one or more processors, the memory encoded with a set of instructions configured to perform a process comprising:

contacting double-stranded nucleic acid templates of the nucleic acid sample with partially double-stranded nonrandom oligonucleotide adapter species under ligation conditions, thereby generating adapter-ligated nucleic acid templates, wherein:

each of the nonrandom oligonucleotide adapter species comprises a first oligonucleotide species and a second oligonucleotide species;

each of the first oligonucleotide species comprises 5' to 3' a polynucleotide A and a 5'-3' polynucleotide B species and each of the second oligonucleotide species comprises 5' to 3' a polynucleotide B' species and a 5' to 3' polynucleotide A';

each of the polynucleotide B species and the polynucleotide B' species are predetermined, are non-randomly generated, are the same length, and are about 4 to about 20 consecutive nucleotides in length;

there are 300 or fewer polynucleotide B species and each polynucleotide B' species is a reverse complement of a polynucleotide B species;

polynucleotide A is not a reverse complement of polynucleotide A';

the ratio of nucleic acid templates to polynucleotide B species is greater than 1,000 to 1;

the polynucleotide B species anneal to the complementary polynucleotide B' species and the polynucleotide A' species does not anneal to the polynucleotide A species;

amplifying the adapter-ligated nucleic acid templates, thereby generating amplicons; and sequencing all or a portion of each amplicon, thereby determining a sequence of nucleotides for the one or more nucleic acid templates in the nucleic acid sample.

F2. A non-transitory computer readable storage medium storing instructions for determining a sequence of nucleotides for one or more nucleic acid templates in a nucleic acid sample and/or performing any of the methods and/or using any of the compositions of any of the previous embodiments and that, when executed by one or more processors of a computing system, cause the computing system to execute method steps comprising:

contacting double-stranded nucleic acid templates of the nucleic acid sample with partially double-stranded nonrandom oligonucleotide adapter species under ligation conditions, thereby generating adapter-ligated nucleic acid templates, wherein:

each of the nonrandom oligonucleotide adapter species comprises a first oligonucleotide species and a second oligonucleotide species;

each of the first oligonucleotide species comprises 5' to 3' a polynucleotide A and a 5'-3' polynucleotide B species and each of the second oligonucleotide species comprises 5' to 3' a polynucleotide B' species and a 5' to 3' polynucleotide A';

each of the polynucleotide B species and the polynucleotide B' species are predetermined, are non-randomly generated, are the same length, and are about 4 to about 20 consecutive nucleotides in length;

there are 300 or fewer polynucleotide B species and each polynucleotide B' species is a reverse complement of a polynucleotide B species;

polynucleotide A is not a reverse complement of polynucleotide A';

the ratio of nucleic acid templates to polynucleotide B species is greater than 1,000 to 1;

the polynucleotide B species anneal to the complementary polynucleotide B' species and the polynucleotide A' species does not anneal to the polynucleotide A species;

amplifying the adapter-ligated nucleic acid templates, thereby generating amplicons; and sequencing all or a portion of each amplicon, thereby determining a sequence of nucleotides for the one or more nucleic acid templates in the nucleic acid sample.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The terms "method" and "process" are used interchangeably herein. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for determining the sequence of double-stranded nucleic acid templates in a nucleic acid sample, wherein the nucleic acid templates are of different double-stranded nucleic acid template species, the method comprising:
   (a) contacting the double-stranded nucleic acid templates with a predetermined discrete set of partially double-stranded nonrandom oligonucleotide adapter species under ligation conditions, thereby generating nonrandom oligonucleotide adapter-ligated nucleic acid templates, wherein:
   each of the nonrandom oligonucleotide adapter species comprises a first oligonucleotide species and a second oligonucleotide species;
   each of the first oligonucleotide species comprises a polynucleotide A species and a polynucleotide B species and each of the second oligonucleotide species comprises a polynucleotide B' species and a polynucleotide A' species;
   each of the polynucleotide B species and the polynucleotide B' species are predetermined, are non-randomly generated and are about 4 to about 20 consecutive nucleotides in length;
   there are 999 or fewer polynucleotide B species and each polynucleotide B' species is a reverse complement of a polynucleotide B species;
   each polynucleotide A species is not a reverse complement of polynucleotide A' species;
   the ratio of the double-stranded nucleic acid template species to the polynucleotide B species is greater than 1,000 to 1;
   the polynucleotide B species anneal to the complementary polynucleotide B' species and the polynucleotide A' species does not anneal to the polynucleotide A species;
   (b) amplifying the adapter-ligated nucleic acid templates, thereby generating amplicons; and sequencing all or a portion of each amplicon using a sequencer, thereby generating thousands to millions of sequence reads;
   (c) obtaining a list of polynucleotide B species and polynucleotide B' species of the nonrandom oligonucleotide adapter species provided for ligation with the nucleic acid template species;
   (d) from the thousands to millions of sequence reads, determining the sequence of the polynucleotide B species or polynucleotide B' species of the nonrandom oligonucleotide adapter-ligated nucleic acid templates;
   (e) comparing the sequence of the polynucleotide B species or polynucleotide B' species of step (d) to the sequences of the polynucleotide B and the polynucleotide B' species on the list obtained from step (c); and
   (f) removing from the determination of the count of nucleic acid template species, nonrandom oligonucleotide adapter-ligated nucleic acid templates that comprise B species or B' species sequences that are not identical to a polynucleotide B species or polynucleotide B' species sequence on the obtained list, or
   assigning a weight to the nonrandom oligonucleotide adapter-ligated nucleic acid template based on the identity of the polynucleotide B species or polynucleotide B' species in the adapter-ligated nucleic acid templates as compared to the B species or B' species sequence on the obtained list, where the assigned weight is considered in determining at least one base call;
   thereby determining the sequence of the double-stranded nucleic acid templates in the nucleic acid sample.

2. The method of claim 1, wherein the partially double stranded double-stranded nonrandom oligonucleotide adapter species is a Y adapter or a hairpin adapter.

3. The method of claim 1, wherein the polynucleotide B species and the polynucleotide B' species are non-degenerate.

4. The method of claim 1, wherein
   each of the first oligonucleotide species comprises a polynucleotide C species between polynucleotide A and the polynucleotide B species;
   each of the second oligonucleotide species comprises a polynucleotide C' species between polynucleotide A' and the polynucleotide B' species;
   each polynucleotide C' species is the reverse complement of the polynucleotide C species; and
   the polynucleotide C species anneal to complementary polynucleotide C' species.

5. The method of claim 4, wherein each of the polynucleotide C species comprises the same nucleotide sequence or wherein the polynucleotide C species comprises at least two different nucleotide sequences.

6. The method of claim 1, wherein amplifying the nonrandom oligonucleotide adapter-ligated nucleic acid templates generates double-stranded amplicons, and sequencing comprises sequencing all or a portion of each strand of the amplicons.

7. The method of claim 1, wherein the nonrandom oligonucleotide adapter-ligated nucleic acid templates are amplified by a process comprising at least one of linear amplification, exponential amplification, or isothermal amplification.

8. The method of claim 1, wherein each adapter-ligated nucleic acid template comprises one nonrandom oligonucleotide adapter at a first end and a standard sequencing adapter at a second end, or
   wherein the each of the adapter-ligated nucleic acid templates comprises a first nonrandom oligonucleotide adapter at a first end and a second nonrandom oligonucleotide adapter at a second end.

9. The method of claim 1, wherein the nucleic acid templates comprise at least one blunt end, or
   wherein the nucleic acid templates are sheared double-stranded DNA templates.

10. The method of claim 1, comprising blunt-ending the nucleic acid templates before contacting the nucleic acid templates with the nonrandom oligonucleotide adapter species.

11. The method of claim 1, wherein the nonrandom oligonucleotide adapter species comprise a blunt end.

12. The method of claim 1, wherein the double-stranded nucleic acid templates or the partially double-stranded nonrandom oligonucleotide adapter species comprise a ligation linker.

13. The method of claim 1,
wherein the method further comprises detecting presence of a single nucleotide alteration in the nucleic acid template from the thousands to millions of sequence reads, wherein the single nucleotide alteration is present at a frequency of 5 percent or lower.

14. The method of claim 1, comprising providing a base call, wherein each base call represents a single nucleotide located at a single nucleotide position in the nucleic acid template.

15. The method of claim 1, wherein generating nonrandom oligonucleotide adapter-ligated nucleic acid templates is performed by contacting 20-40 ng double-stranded nucleic acid templates of the nucleic acid sample with 50-500 nM partially double-stranded nonrandom oligonucleotide adapter species under ligation conditions.

16. A method for counting the number of nucleic acid template species for a nucleic acid sample, comprising:
   (a) contacting double-stranded nucleic acid templates of the nucleic acid sample with a predetermined discrete set of partially double-stranded nonrandom oligonucleotide adapter species under ligation conditions, wherein the double-stranded nucleic acid templates are of different double-stranded nucleic acid template species, thereby generating nonrandom oligonucleotide adapter-ligated nucleic acid templates, wherein:
   each of the nonrandom oligonucleotide adapter species comprises a first oligonucleotide species and a second oligonucleotide species;
   each of the first oligonucleotide species comprises a polynucleotide A species and a polynucleotide B species and each of the second oligonucleotide species comprises a polynucleotide B' species and a polynucleotide A' species;
   each of the polynucleotide B species and the polynucleotide B' species are predetermined, are non-randomly generated and are about 4 to about 20 consecutive nucleotides in length;
   there are 999 or fewer polynucleotide B species and each polynucleotide B' species is a reverse complement of a polynucleotide B species;
   each polynucleotide A species is not a reverse complement of a polynucleotide A' species;
   the ratio of nucleic acid template species to polynucleotide B species is greater than 1,000 to 1;
   the polynucleotide B species anneal to the complementary polynucleotide B' species and the polynucleotide A' species does not anneal to the polynucleotide A species;
   (b) amplifying the nonrandom oligonucleotide adapter-ligated nucleic acid templates, thereby generating amplicons; and sequencing all or a portion of each amplicon using a sequencer, thereby generating thousands to millions of sequence reads,
   (c) from the thousands to millions of sequence reads, counting the number of nucleic acid template species for the nucleic acid sample, wherein the counting comprises:
   (i) identifying the nonrandom oligonucleotide adapter species ligated to each nucleic acid template species; and
   (ii) counting the number of nonrandom oligonucleotide adapter species ligated to the nucleic acid template species in the nucleic acid sample; or
   (iii) identifying a set of amplicon duplicates, wherein the amplicon duplicates comprise amplified nonrandom oligonucleotide adapter-ligated nucleic acid templates, wherein each amplified nonrandom oligonucleotide adapter-ligated nucleic acid template comprises a first polynucleotide B species and a second polynucleotide B species at a second end, wherein the first and second polynucleotide B species may or may not comprise the same nucleotide sequence; and
   (iv) determining the number of amplicon duplicates comprising both the first and the second polynucleotide B species.

17. The method of claim 16, wherein the partially double-stranded nonrandom oligonucleotide adapter species is a Y adapter or a hairpin adapter.

18. The method of claim 16, wherein the polynucleotide B species and the polynucleotide B' species are non-degenerate.

19. The method of claim 16, wherein
each of the first oligonucleotide species comprises a polynucleotide C species between the polynucleotide A species and the polynucleotide B species;
each of the second oligonucleotide species comprises a polynucleotide C' species between polynucleotide A' species and the polynucleotide B' species;
each polynucleotide C' species is the reverse complement of the polynucleotide C species; and
the polynucleotide C species anneal to complementary polynucleotide C' species.

20. The method of claim 19, wherein the polynucleotide C species in the nonrandom oligonucleotide adapter species share the same nucleotide sequence or wherein the polynucleotide C species in the nonrandom oligonucleotide adapter species comprise at least two different nucleotide sequences.

21. The method of claim 16, wherein amplifying the adapter-ligated nucleic acid templates generates double-stranded amplicons, and sequencing comprises sequencing all or a portion of each strand of the amplicons.

22. The method of claim 16, wherein the adapter-ligated nucleic acid templates are amplified by a process comprising at least one of linear amplification, exponential amplification, or isothermal amplification.

23. The method of claim 16, wherein each adapter-ligated nucleic acid template comprises one nonrandom oligonucleotide adapter at a first end and a standard sequencing adapter at a second end, or
wherein the each of the adapter-ligated nucleic acid templates comprises a first nonrandom oligonucleotide adapter at a first end and a second nonrandom oligonucleotide adapter at a second end.

24. The method of claim 16, wherein the nucleic acid templates each comprise at least one blunt end, or
wherein the nucleic acid templates are sheared double-stranded DNA templates.

25. The method of claim 16, comprising blunt-ending the nucleic acid templates before contacting the nucleic acid templates with the nonrandom oligonucleotide adapter species.

26. The method of claim 16, wherein the nonrandom oligonucleotide adapter species comprise a blunt end.

27. The method of claim 16, wherein the double-stranded nucleic acid templates or the partially double-stranded nonrandom oligonucleotide adapter species comprise a ligation linker.

28. The method of claim 16, wherein the method further comprises detecting presence of a single nucleotide alteration in the nucleic acid templates from the thousands to millions of sequence reads, wherein the single nucleotide alteration is present at a frequency of 5 percent or lower.

29. The method of claim 16, comprising providing a base call, wherein each base call represents a single nucleotide located at a single nucleotide position in the nucleic acid templates.

30. A method for determining the sequences of double-stranded nucleic acid templates in a nucleic acid sample, wherein the nucleic acid templates are of different double-stranded nucleic acid template species, the method comprising:
   (a) contacting double-stranded nucleic acid templates with a predetermined discrete set of partially double-stranded nonrandom oligonucleotide adapter species under ligation conditions, thereby generating nonrandom oligonucleotide adapter-ligated nucleic acid templates, wherein:
      each of the nonrandom oligonucleotide adapter species comprises a first oligonucleotide species and a second oligonucleotide species;
      each of the first oligonucleotide species comprises a polynucleotide A species and a polynucleotide B species and each of the second oligonucleotide species comprises a polynucleotide B' species and a polynucleotide A' species;
      each of the polynucleotide B species and the polynucleotide B' species are predetermined, are non-randomly generated and are about 4 to about 20 consecutive nucleotides in length;
      there are 999 or fewer polynucleotide B species and each polynucleotide B' species is a reverse complement of a polynucleotide B species;
      each polynucleotide A species is not a reverse complement of a polynucleotide A' species;
      the ratio of double-stranded nucleic acid template species to polynucleotide B species is greater than 1,000 to 1;
      the polynucleotide B species anneal to the complementary polynucleotide B' species and the polynucleotide A' species does not anneal to the polynucleotide A species;
   (b) amplifying the nonrandom oligonucleotide adapter-ligated nucleic acid templates, thereby generating amplicons; and sequencing all or a portion of each amplicon using a sequencer, which generates thousands to millions of sequence reads,
   (c) determining a base call of at least one nucleotide of a nucleic acid template from the thousands to millions of sequence reads, wherein the determining comprises
      identifying a set of amplicon duplicates, wherein the amplicon duplicates comprise amplified nonrandom oligonucleotide adapter-ligated nucleic acid templates;
      identifying the at least one nucleotide in each amplicon of the set of amplicon duplicates; and
      determining the base call of the at least one nucleotide where the identity of the at least one nucleotide is the same in at least 95% of the amplicons in the set of amplicon duplicates, thereby determining the sequences of the double-stranded nucleic acid templates in the nucleic acid sample.

31. The method of claim 30, wherein the partially double-stranded nonrandom oligonucleotide adapter species is a Y adapter or a hairpin adapter.

32. The method of claim 30, wherein the polynucleotide B species and the polynucleotide B' species are non-degenerate.

33. The method of claim 30, wherein
   each of the first oligonucleotide species comprises a polynucleotide C species between the polynucleotide A species and the polynucleotide B species;
   each of the second oligonucleotide species comprises a polynucleotide C' species between polynucleotide A' species and the polynucleotide B' species;
   each polynucleotide C' species is the reverse complement of the polynucleotide C species; and
   the polynucleotide C species anneal to complementary polynucleotide C' species.

34. The method of claim 33, wherein the polynucleotide C species shares the same nucleotide sequence or wherein the polynucleotide C species comprise at least two different nucleotide sequences.

35. The method of claim 30, wherein amplifying the nonrandom oligonucleotide adapter-ligated nucleic acid templates generates double-stranded amplicons, and sequencing comprises sequencing all or a portion of each strand of the amplicons.

36. The method of claim 30, wherein the nonrandom oligonucleotide adapter-ligated nucleic acid templates are amplified by a process comprising at least one of linear amplification, exponential amplification, or isothermal amplification.

37. The method of claim 30, wherein each adapter-ligated nucleic acid template comprises one nonrandom oligonucleotide adapter at a first end and a standard sequencing adapter at a second end, or wherein each adapter-ligated nucleic acid template comprises a first nonrandom oligonucleotide adapter at a first end and a second nonrandom oligonucleotide adapter at a second end.

38. The method of claim 30, wherein the nucleic acid templates each comprise at least one blunt end, or wherein the nucleic acid templates are sheared double-stranded DNA.

39. The method of claim 30, comprising blunt-ending the nucleic acid templates before contacting the nucleic acid templates with the nonrandom oligonucleotide adapter species.

40. The method of claim 30, wherein the nonrandom oligonucleotide adapter species comprise a blunt end.

41. The method of claim 30, wherein the double-stranded nucleic acid templates or the partially double-stranded nonrandom oligonucleotide adapter species comprise a ligation linker.

* * * * *